United States Patent
Jackson et al.

(10) Patent No.: US 11,874,280 B2
(45) Date of Patent: Jan. 16, 2024

(54) USE OF DIVALENT METALS FOR ENHANCEMENT OF FLUORESCENT SIGNALS

(71) Applicant: SONY GROUP CORPORATION, Tokyo (JP)

(72) Inventors: Melissa Jackson, New York, NY (US); Christopher Boyce, New York, NY (US); Eriko Matsui, New York, NY (US); Michael Vanbrunt, Covington, WA (US); Sharat Singh, Rancho Santa Fe, CA (US); Tracy Matray, Snohomish, WA (US)

(73) Assignee: Sony Group Corporation, Tokyo (JP)

( * ) Notice: Subject to any disclaimer, the term of this patent is extended or adjusted under 35 U.S.C. 154(b) by 398 days.

(21) Appl. No.: 16/982,341

(22) PCT Filed: Mar. 8, 2019

(86) PCT No.: PCT/US2019/021323
§ 371 (c)(1),
(2) Date: Sep. 18, 2020

(87) PCT Pub. No.: WO2019/182765
PCT Pub. Date: Sep. 26, 2019

(65) Prior Publication Data
US 2021/0109104 A1    Apr. 15, 2021

Related U.S. Application Data

(60) Provisional application No. 62/645,121, filed on Mar. 19, 2018.

(51) Int. Cl.
*G01N 33/58* (2006.01)
*G01N 33/533* (2006.01)

(52) U.S. Cl.
CPC ......... *G01N 33/582* (2013.01); *G01N 33/533* (2013.01)

(58) Field of Classification Search
CPC .................... G01N 33/582; G01N 33/533
See application file for complete search history.

(56) References Cited

U.S. PATENT DOCUMENTS

| | | | |
|---|---|---|---|
| 4,450,305 A | 5/1984 | Kamhi | |
| 4,476,229 A | 10/1984 | Fino et al. | |
| 4,778,753 A | 10/1988 | Yamanishi et al. | |
| 5,053,054 A | 10/1991 | Kirchanski | |
| 5,268,486 A | 12/1993 | Waggoner et al. | |
| 5,318,894 A | 6/1994 | Pugia | |
| 5,582,977 A | 12/1996 | Yue et al. | |
| 5,994,143 A | 11/1999 | Bieniarz et al. | |
| 6,140,480 A | 10/2000 | Kool | |
| 6,171,859 B1 | 1/2001 | Herrnstadt et al. | |
| 6,218,108 B1 | 4/2001 | Kool | |
| 6,365,730 B1 | 4/2002 | Jennings et al. | |
| 6,380,431 B1 | 4/2002 | Whipple et al. | |
| 6,479,650 B1 | 11/2002 | Kool | |
| 6,514,700 B1 | 2/2003 | Singh | |
| 6,534,041 B1 | 3/2003 | Licha et al. | |
| 6,627,400 B1 | 9/2003 | Singh et al. | |
| 6,670,193 B2 | 12/2003 | Kool | |
| 6,716,452 B1 | 4/2004 | Piccariello et al. | |
| 6,852,709 B2 | 2/2005 | Leong et al. | |
| 7,038,063 B2 | 5/2006 | Lee et al. | |
| 7,060,708 B2 | 6/2006 | Piccariello et al. | |
| 7,172,907 B2 | 2/2007 | Chen et al. | |
| 7,423,133 B2 | 9/2008 | Kool et al. | |
| 7,667,024 B2 | 2/2010 | Mao et al. | |
| 7,897,684 B2 | 3/2011 | Bazan et al. | |
| 8,008,522 B2 | 8/2011 | Lukhtanov et al. | |
| 8,101,776 B2 | 1/2012 | Berens et al. | |
| 8,153,706 B2 | 4/2012 | Vasudevan | |
| 8,217,389 B2 | 7/2012 | Nakano et al. | |
| 8,293,700 B2 | 10/2012 | Arranz | |
| 8,349,308 B2 | 1/2013 | Yurkovetskiy et al. | |
| 8,354,515 B2 | 1/2013 | Ueno et al. | |
| 8,431,545 B2 | 4/2013 | Kataoka et al. | |
| 8,491,993 B2 | 7/2013 | Nguyen et al. | |
| 8,546,590 B2 | 10/2013 | Gall | |
| 8,632,947 B2 | 1/2014 | Bentley et al. | |
| 8,802,738 B2 | 8/2014 | Emrick | |
| 8,895,023 B2 | 11/2014 | Rademacher et al. | |
| 8,906,603 B2 | 12/2014 | Castro et al. | |
| 8,946,394 B2 | 2/2015 | Na et al. | |

(Continued)

FOREIGN PATENT DOCUMENTS

| | | |
|---|---|---|
| CA | 2263671 A1 | 2/1998 |
| CN | 102174078 A | 9/2011 |

(Continued)

OTHER PUBLICATIONS

"What is an Analyte?," Google Search, dated Mar. 22, 2018, retrieved from https://www.google.com/search?q=what+is+an+analyte&rlz=1CIGCEB_enUS775US775&oq=what+is+an+analyte&aqs=chrome..69i57j015.3231j0j7&s . . . 2 pages.
Arian et al., "1,9-Dialkoxyanthracene as a $^1O_2$-Sensitive Linker," *J. Am. Chem. Soc.* 133:3972-3980, 2011.
Avirah et al., "Infrared Absorbing Croconaine Dyes: Synthesis and Metal Ion Binding Properties," *J. Org. Chem.* 73(1):274-279, 2008.
Bergstrom et al., "A NaPi2b Antibody-Drug Conjugate Induces Durable Complete Tumor Regressions in Patient-Derived Xenograft Models of NSCLC," *IASLC 17th World Conference on Lung Cancer*, Vienna, Austria, Dec. 4-7, 2016 (8 pages).

(Continued)

*Primary Examiner* — Shafiqul Haq
*Assistant Examiner* — Nam P Nguyen
(74) *Attorney, Agent, or Firm* — Seed IP Law Group LLP

(57) ABSTRACT

Compositions comprising fluorescent or colored dyes and methods of using the same in combination with divalent metal salts to analyze samples are disclosed.

23 Claims, 27 Drawing Sheets

(56) References Cited

U.S. PATENT DOCUMENTS

| | | |
|---|---|---|
| 9,029,537 B2 | 5/2015 | Koch |
| 9,085,799 B2 | 7/2015 | Bazan et al. |
| 9,150,782 B2 | 10/2015 | Lee et al. |
| 9,400,273 B1 | 7/2016 | Liu et al. |
| 9,545,447 B2 | 1/2017 | Wooley et al. |
| 9,649,389 B2 | 5/2017 | Groves et al. |
| 9,687,291 B2 | 6/2017 | Shimizu et al. |
| 9,689,877 B2 | 6/2017 | Matray et al. |
| 9,696,310 B2 | 7/2017 | Margulies et al. |
| 9,714,946 B2 | 7/2017 | Bradner et al. |
| 9,765,220 B2 | 9/2017 | Matray et al. |
| 9,822,134 B2 | 11/2017 | Segev |
| 9,851,359 B2 | 12/2017 | Matray et al. |
| 9,884,070 B2 | 2/2018 | Denardo et al. |
| 9,910,051 B2 | 3/2018 | Beacham et al. |
| 9,913,992 B2 | 3/2018 | Demarest et al. |
| 9,932,578 B2 | 4/2018 | Feinstein et al. |
| 9,939,454 B2 | 4/2018 | Dzubay et al. |
| 10,036,754 B2 | 7/2018 | Matray et al. |
| 10,191,060 B2 | 1/2019 | Chiu et al. |
| 10,435,563 B2 | 10/2019 | Matray et al. |
| 10,617,670 B2 | 4/2020 | Sapra et al. |
| 10,709,791 B2 | 7/2020 | Stayton et al. |
| 10,834,091 B2 | 11/2020 | Deninno et al. |
| 10,865,310 B2 | 12/2020 | Matray et al. |
| 10,866,244 B2 | 12/2020 | Matray et al. |
| 10,954,391 B2 | 3/2021 | Matray et al. |
| 10,989,715 B2 | 4/2021 | Matray et al. |
| 11,013,756 B2 | 5/2021 | Haruta et al. |
| 11,084,932 B2 | 8/2021 | Battrell et al. |
| 11,142,647 B2 | 10/2021 | Matray et al. |
| 11,312,736 B1 | 4/2022 | Matray et al. |
| 11,352,502 B2 | 6/2022 | Matray et al. |
| 11,370,922 B2 | 6/2022 | Matray et al. |
| 11,377,563 B2 | 7/2022 | Matray et al. |
| 11,390,754 B2 | 7/2022 | Singh et al. |
| 11,434,374 B2 | 9/2022 | Matray et al. |
| 11,434,377 B2 | 9/2022 | Matray et al. |
| 11,453,783 B2 | 9/2022 | Matray et al. |
| 11,685,835 B2 | 6/2023 | Matray |
| 2001/0018503 A1 | 8/2001 | Whipple et al. |
| 2002/0012947 A1 | 1/2002 | Bevers et al. |
| 2002/0045263 A1 | 4/2002 | Kam |
| 2002/0099013 A1 | 7/2002 | Piccariello et al. |
| 2003/0054361 A1 | 3/2003 | Heller |
| 2003/0207208 A1 | 11/2003 | Uenishi |
| 2003/0207264 A1 | 11/2003 | Packard et al. |
| 2004/0014981 A1 | 1/2004 | Lugade et al. |
| 2004/0138467 A1 | 7/2004 | French et al. |
| 2004/0224372 A1 | 11/2004 | Li et al. |
| 2004/0241768 A1 | 12/2004 | Whitten et al. |
| 2005/0054024 A1 | 3/2005 | Lawrence |
| 2005/0123935 A1 | 6/2005 | Haugland et al. |
| 2006/0008822 A1 | 1/2006 | Manoharan et al. |
| 2006/0035302 A1 | 2/2006 | Lee |
| 2006/0063186 A1 | 3/2006 | Benson et al. |
| 2007/0042398 A1 | 2/2007 | Peng et al. |
| 2007/0077549 A1 | 4/2007 | Buller et al. |
| 2007/0148094 A1 | 6/2007 | Uzgiris |
| 2007/0269902 A1 | 11/2007 | Beechem et al. |
| 2008/0227939 A1 | 9/2008 | Mizoshita et al. |
| 2009/0253792 A1 | 10/2009 | Mickle et al. |
| 2009/0299070 A1 | 12/2009 | Berens et al. |
| 2010/0039684 A1 | 2/2010 | Kolb et al. |
| 2010/0092386 A1 | 4/2010 | Segev |
| 2010/0129800 A1 | 5/2010 | Aymami Bofarull et al. |
| 2010/0192312 A1 | 8/2010 | Cremer et al. |
| 2011/0144065 A1 | 6/2011 | Denardo et al. |
| 2011/0224516 A1 | 9/2011 | Romey et al. |
| 2012/0021454 A1 | 1/2012 | Bikker et al. |
| 2012/0116079 A1 | 5/2012 | Lukhtanov et al. |
| 2013/0059343 A1 | 3/2013 | Cheung |
| 2013/0102021 A1 | 4/2013 | Beacham et al. |
| 2013/0119363 A1 | 5/2013 | Sasaki et al. |
| 2013/0137755 A1 | 5/2013 | Segev |
| 2013/0202536 A1 | 8/2013 | Mustaev et al. |
| 2013/0244891 A1 | 9/2013 | Waggoner et al. |
| 2014/0023590 A1 | 1/2014 | Gao et al. |
| 2015/0030541 A1 | 1/2015 | Rogers |
| 2015/0110715 A1 | 4/2015 | Eder et al. |
| 2015/0159198 A1 | 6/2015 | McGall et al. |
| 2015/0232615 A1 | 8/2015 | Kwiatkowski |
| 2015/0258217 A1 | 9/2015 | Caravan |
| 2016/0039850 A1 | 2/2016 | Segev |
| 2016/0176903 A1 | 6/2016 | Segev |
| 2016/0264737 A1 | 9/2016 | Bartholomew et al. |
| 2016/0327859 A1 | 11/2016 | Idei et al. |
| 2016/0347907 A1 | 12/2016 | Dose |
| 2017/0292957 A1 | 10/2017 | Matray |
| 2017/0326233 A1 | 11/2017 | Demeule et al. |
| 2018/0065998 A1 | 3/2018 | Battrell et al. |
| 2018/0079909 A1 | 3/2018 | Matray et al. |
| 2018/0092993 A1 | 4/2018 | Desai et al. |
| 2018/0141935 A1 | 5/2018 | Josel et al. |
| 2018/0163052 A1 | 6/2018 | Matray et al. |
| 2018/0164322 A1 | 6/2018 | Matray et al. |
| 2018/0237641 A1 | 8/2018 | Matray et al. |
| 2018/0312468 A1 | 11/2018 | Zhang et al. |
| 2019/0016898 A1 | 1/2019 | Matray et al. |
| 2019/0136065 A1 | 5/2019 | Singh et al. |
| 2019/0144678 A1 | 5/2019 | Matray et al. |
| 2019/0153232 A1 | 5/2019 | Matray et al. |
| 2019/0177549 A1 | 6/2019 | Matray et al. |
| 2019/0300716 A1 | 10/2019 | Matray et al. |
| 2020/0109287 A1 | 4/2020 | Matray et al. |
| 2020/0164085 A1 | 5/2020 | Brandish et al. |
| 2020/0222554 A1 | 7/2020 | Matray et al. |
| 2020/0284798 A1 | 9/2020 | Matray et al. |
| 2020/0330610 A1 | 10/2020 | Desai et al. |
| 2020/0353089 A1 | 11/2020 | Matray |
| 2020/0353094 A1 | 11/2020 | Matray |
| 2020/0360526 A1 | 11/2020 | Matray |
| 2020/0392345 A1 | 12/2020 | Matray et al. |
| 2021/0032277 A1 | 2/2021 | Matray et al. |
| 2021/0032474 A1 | 2/2021 | Matray et al. |
| 2021/0095130 A1 | 4/2021 | Matray et al. |
| 2021/0096135 A1 | 4/2021 | Matray et al. |
| 2021/0109104 A1 | 4/2021 | Jackson et al. |
| 2021/0128591 A1 | 5/2021 | Matray |
| 2021/0128739 A1 | 5/2021 | Matray |
| 2021/0253864 A1 | 8/2021 | Matray et al. |
| 2021/0261782 A1 | 8/2021 | Matray et al. |
| 2021/0285953 A1 | 9/2021 | Matray et al. |
| 2021/0340380 A1 | 11/2021 | Matray et al. |
| 2021/0395530 A1 | 12/2021 | Matray et al. |
| 2022/0160887 A1 | 5/2022 | Matray et al. |
| 2022/0168433 A1 | 6/2022 | Matray et al. |
| 2022/0168435 A1 | 6/2022 | Matray et al. |
| 2022/0175951 A1 | 6/2022 | Boitano et al. |
| 2022/0220314 A1 | 7/2022 | Singh et al. |
| 2022/0227794 A1 | 7/2022 | Matray et al. |
| 2022/0305127 A1 | 9/2022 | Thomas et al. |
| 2022/0372297 A1 | 11/2022 | Matray et al. |
| 2022/0380603 A1 | 12/2022 | Matray et al. |
| 2022/0402963 A1 | 12/2022 | Matray et al. |
| 2023/0012304 A1 | 1/2023 | Matray et al. |
| 2023/0129481 A1 | 4/2023 | Matray et al. |

FOREIGN PATENT DOCUMENTS

| | | |
|---|---|---|
| CN | 103319378 A | 9/2013 |
| CN | 104072727 A | 10/2014 |
| CN | 106589005 A | 4/2017 |
| CN | 107106685 A | 8/2017 |
| CN | 109071961 A | 12/2018 |
| CN | 109153860 A | 1/2019 |
| GB | 2 372 256 A | 8/2002 |
| JP | S61207395 A | 9/1986 |
| JP | 4-282391 A | 10/1992 |
| JP | 2000017183 A | 1/2000 |
| JP | 2014527071 A | 10/2014 |
| JP | 2017537266 A | 5/2016 |
| JP | 2017124994 A | 7/2017 |
| JP | 2018507863 A | 3/2018 |

(56) References Cited

FOREIGN PATENT DOCUMENTS

| | | |
|---|---|---|
| KR | 101041446 B1 | 6/2011 |
| KR | 10-2015-0007795 A | 1/2015 |
| KR | 10-2020-0133374 A | 11/2020 |
| SU | 1121931 A | 4/1988 |
| WO | 95/02700 A1 | 1/1995 |
| WO | WO 9832463 A2 | 7/1998 |
| WO | WO 0173123 A2 | 10/2001 |
| WO | 02/22883 A1 | 3/2002 |
| WO | WO 02083954 A1 | 10/2002 |
| WO | WO 2004007751 A2 | 1/2004 |
| WO | WO 2007094135 A1 | 8/2007 |
| WO | WO 2009113645 A1 | 9/2009 |
| WO | 2010/026957 A1 | 3/2010 |
| WO | WO-2011088193 A2 | 7/2011 |
| WO | 2013/012687 A2 | 1/2013 |
| WO | WO 2014043289 A2 | 3/2014 |
| WO | 2014/147642 A1 | 9/2014 |
| WO | WO 2015091953 A1 | 6/2015 |
| WO | WO-2016183185 A1 * | 11/2016 |
| WO | WO 2017003639 A2 | 1/2017 |
| WO | WO 2017062271 A2 | 4/2017 |
| WO | WO 2017089890 A1 | 6/2017 |
| WO | WO 2017094897 A1 | 6/2017 |
| WO | 2017/173348 A1 | 10/2017 |
| WO | 2017/177065 A2 | 10/2017 |
| WO | WO 2017173355 A1 | 10/2017 |
| WO | WO-2018045278 A1 | 3/2018 |
| WO | 2018/060722 A1 | 4/2018 |
| WO | 2019/071208 A1 | 4/2019 |
| WO | WO 2019126691 A1 | 6/2019 |
| WO | WO 2019182765 A1 | 9/2019 |
| WO | WO 2020006285 A1 | 1/2020 |
| WO | 2020/210689 A1 | 10/2020 |
| WO | 2020/210692 A1 | 10/2020 |
| WO | 2020/210694 A1 | 10/2020 |
| WO | WO 2020219959 A1 | 10/2020 |
| WO | WO 2021062176 A2 | 4/2021 |
| WO | WO 2021067483 A1 | 4/2021 |

OTHER PUBLICATIONS

Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015, 1 page.

Bergstrom et al., "Potent Promise," *Innovations in Pharmaceutical Technology* 49:16-20, 2014.

Bergstrom et al., "XMT-1522 induces tumor regressions in preclinical models representing HER2-positive and HER2 low-expressing breast cancer," Mersana Therapeutics, Abstract P4-14-28, 2015.

Braeckmans et al., "Three-dimensional fluorescence recovery after photobleaching with the confocal scanning laser microscope," *Biophysical Journal* 85:2240-2252, 2003.

Braga et al., "Intracellular macromolecular mobility measured by fluorescence recovery after photobleaching with confocal laser scanning microscopes," *Molecular Biology of the Cell* 15:4749-4760, 2004.

Brinkley, "A brief survey of methods for preparing protein conjugates with dyes, haptens and crosslinking reagents," *Bioconjugate Chem* 3:2-13, 1992.

CAPLUS Accession No. 1975: 171341, Holy, "Nucleic acid components and their analogs. CLXXII. Aliphatic analogs of nucleosides, nucleotides, and oligonucleotides," *Collection of Czechoslovak Chemical Communications* 40(1):187-214, 1975. (1 page).

Chattopadhyay et al., "Brilliant Violet Fluorophores: A New Class of Ultrabright Fluorescent Compounds for Immunofluorescence Experiments," *Cytometry Part A* 81A:456-466, 2012.

Chong et al., "Oxygen Quenching of Pyrene-Lipid Fluorescence in Phosphatidylcholine Vesicles—A Probe for Membrane Organization," *Biophys. J.* 47:613-621, 1985.

Cuppoletti et al., "Oligomeric fluorescent labels for DNA," *Bioconjug. Chem.* 16(3):528-534, 2005.

Dai et al., "DNA-polyfluorophore excimers as sensitive reporters for esterases and lipases," *Chemical Communications* 46:1221-1223, 2010.

Daniels et al., "Fluorescence of the Purine and Pyrimidine Bases of the Nucleic Acids in Neutral Aqueous Solution at 300° K," *Science* 171(3972):675-677, 1971.

Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.

DiVittorio et al., "Synthetic peptides with selective affinity for apoptotic cells," *Organic & Biomolecular Chemistry* 4:1966-1976, 2006.

Dörwald, *Side Reactions in Organic Synthesis—A Guide to Successful Synthesis Design*, Wiley-VCH Verlag GmbH & Co. KGaA, Weinheim, Germany, 2005, p. IX (4 pages).

Dubrovsky, "Semiconductor nanoparticles as reporters in multiplexed immunoassay and cell analysis," *International Journal of Nanoscience* 8(1 & 2):163-167, 2009.

Gao et al., "Libraries of Composite Polyfluors Built from Fluorescent Deoxyribosides," *Journal of the American Chemical Society* 124:11590-11591, 2002.

Gao et al., "Modified DNA Analogues That Sense Light Exposure with Color Changes," *Journal of the American Chemical Society* 126:12748-12749, 2004.

Gordon et al., "Analysis of simulated and experimental fluorescence recovery after photobleaching. Data for two diffusing components," *Biophysical Journal* 68:766-778, 1995.

Hanhela et al., "Synthesis and Evaluation of Fluorescent Materials for Colour Control of Peroxyoxalate Chemiluminescence. III. Yellow and Red Fluorescent Emitters," *Australian Journal of Chemistry* 34:1701-1717, 1981.

Haraguchi, "Live Cell Imaging: Approaches for Studying Protein Dynamics in Living Cells," *Cell Structure and Function* 27:333-334, 2002.

Jain et al. "Current ADC Linker Chemistry," *Pharm. Res.* 32:3526-3540, 2015.

Koo et al., "Fluorescent DNA chemosensors: identification of bacterial species by their volatile metabolites," *Chemical Communications* 47:11435-11437, 2011.

Kozma et al., "Fluorescent Ligands for Adenosine Receptors," *Bioorganic & Medicinal Chemistry Letters* 23: 26-36, 2013.

Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.

Leung et al., "7-Amino-4-Methyl-6-Sulfocoumarin-3-Acetic Acid: A Novel Blue Fluorescent Dye for Protein Labeling," *Bioorganic & Medicinal Chemistry Letters* 9: 2229-2232, 1999.

Li et al., "Polymeric Drugs: Advances in the development of pharmacologically active polymers," *Journal of Controlled Release* 219:360-382, 2015.

Li et al., "Responsive nanogel-based dual fluorescent sensors for temperature and $Hg^{2+}$ ions with enhanced detection sensitivity," *J. Mater. Chem.* 20:10716-10723, 2010.

Liu et al., "Detection of prostate-specific membrane antigen on HUVECs in response to breast tumor-conditioned medium," *International Journal of Oncology* 38:1349-1355, 2011.

Liu et al., "DNA-Based Micelles: Synthesis, Micellar Properties and Size-Dependent Cell Permeability," *Chem. Eur. J.* 16:3791-3797, 2010 (14 Pages).

Luo et al., "Sensitive and rapid quantification of C-reactive protein using quantum dot-labeled microplate immunoassay," *Journal of Translational Medicine* 10(24):1-9, 2012.

Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.

Mersana Therapeutics, URL= http://www.mersana.com, download date Jan. 3, 2019, 9 pages.

(56) References Cited

OTHER PUBLICATIONS

Molotkovsky et al., "Perylenoyl- and Anthrylvinyl-Labeled Lipids as Membrane Probes," *Biochimica et Biophysica Acta* 778:281-288, 1984.
Nussbaumer et al., "Amplification of Chirality by Supramolecular Polymerization of Pyrene Oligomers," *Angewandte Chemie International Edition* 50:5490-5494, 2011.
Paris et al., "Probing DNA sequences in solution with a monomer-excimer fluorescence color change," *Nucleic Acids Research* 26(16):3789-3793, 1998.
Petreus et al., "Polyester imides containing main-chain phosphorus," *Revue Roumaine de Chimie* 34(8):971-978, 1994 (with English Abstract).
Pownall et al., "Kinetics of Spontaneous and Plasma-Stimulated Sphingomyelin Transfer," *Biochimica et Biophysica Acta* 712:169-176, 1982.
Pubchem, "U.S. Pat. No. 20100012929A1-20100121-C00010_4," SID No. 140452858, retrieved Mar. 29, 2016 from URL https://pubchem.ncbi.nlm.nih.gov/substance/140452858#sectio . . . , 6 pages.
Ren et al., "An Antisense Oligodeoxynucleotide-Doxorubicin Conjugate: Preparation and Its Reversal Multidrug Resistance of Human Carcinoma Cell Line In Vitro," *Nucleosides, Nucleotides & Nucleic Acids* 23(10):1595-1607, 2004.
RN 230952-79-1, Registry Database Compound, 1999.
Singh et al., "Multiplexed measurement of membrane protein populations," *Caplus* 2003:769075, 2003. (2 pages).
Stewart et al., "The Fluorescence of a Chelating Two-Photon-Absorbing Dye is Enhanced with the Addition of Transition Metal Ions but Quenched in the Presence of Acid," *Proc. of SPIE* 9939:993904, 2016. (10 pages).
Stuart et al., "Site-Specific DNA-Doxorubicin Conjugates Display Enhanced Cytotoxicity to Breast Cancer Cells," *Bioconjugate Chemistry* 25:406-413, 2014.
Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 25, 2010, 23 pages).
Tram et al., "Oligonucleotide Labeling Using BODIPY Phosphoramidite," *Nucleosides, Nucleotides & Nucleic Acids* 30(1):1-11, 2011.
Wang et al., "Cruciforms: Assembling Single Crystal Micro- and Nanostructures from One to Three Dimensions and Their Applications in Organic Field-Effect Transistors," *Chem. Mater.* 21:2840-2845, 2009.
Wang et al., "DNA Polyfluorophores for Real-Time Multicolor Tracking of Dynamic Biological Systems," *Angew. Chem. Int. Ed.* 51:7176-7180, 2012.
Wilson et al., "Efficient Quenching of Oligomeric Fluorophores on a DNA Backbone," *Journal of the American Chemical Society* 129(50):15426-15427, 2007.
Wilson et al., "Oligodeoxyfluorosides: Strong Sequence of Dependence of Fluorescence Emission," *Tetrahedron* 63(17):3427-3433, 2007 (18 Pages).
Yurkovetskiy et al., "Advantages of Polyacetal Polymer-based Antibody Drug Conjugates: Application to Low Expression Targets," Mersana Therapeutics, technical paper #2645, 2014, 1 page.
Zhang et al., "FRET Imaging of Enzyme-Responsive HPMA Copolymer Conjugate," *Macromolecular Bioscience* 17:1600215, 2017 (8 pages).
Babitskaya et al., "Bromacyl Analogues of Phosphatidycholine with Intramolecular Fluorescence Quenching and Their Use as Substrates for Continuous Monitoring of Phospholipase A2 Activity," *Applied Biochemistry and Microbiology* 40(4):351-356, 2004.
Beaucage et al., "The Functionalization of Oligonucleotides via Phosphoramidite Derivatives," *Tetrahedron* 49(10):1925-1963, 1993.
Becker et al., "New Thermotropic Dyes on Amino-Substituted Perylendicarboximides," *Chem. Eur. J.* 6(21):3984-3990, 2000.
Doi et al., "Hetero-Selective DNA-Like Duplex Stabilized by Donor-Acceptor Interactions," *Chem. Eur. J.* 21:15974-15980, 2015.
Johansson, "Choosing Reporter-Quencher Pairs for Efficient Quenching Through Formation of Intramolecular Dimers," *Methods in Molecular Biology* 335:17-29, 2006.
Saito et al., "Dual-labelled oligonucleotide probe for sensing adenosine via FRET: A novel alternative to SNPs genotyping," *Chem. Commun*:2133-2135, 2007.
Alexander M. Breul et al, "Fluorescent monomers as building blocks for dye labeled polymers: synthesis and application in energy conversion, biolabeling and sensors", Chemical Society Reviews, vol. 42, No. 12, Jan. 1, 2013 (Jan. 1, 2013), p. 5366, XP055591811.
Nicholas Rupcich et al: "Quenching of Fluorophore-Labeled DNA Oligonucleotides by Divalent Metal Ions: Implications for Selection, Design, and Applications of Signaling Aptamers and Signaling Deoxyribozymes", Journal of the American Chemical Society, vol. 128, No. 3, Jan. 1, 2006 (Jan. 1, 2006), pp. 780-790, XP055591815.
Aviñó et al., "Solid-phase synthesis of oligomers carrying several chromophore units linked by phosphodiester backbones," *Bioorganic & Medicinal Chemistry Letters* 18:2306-2310, 2008.
Bag et al., "Triazolyl-donor-acceptor chromophore-decorated unnatural amino acids and peptides: FRET events in a β-turn conformation," *Chem. Commun.* 50:433-435, 2014.
Boldyrev et al., "Synthesis and Characteristics of New Fluorescent Probes Based on Cardiolipin," *Russian Journal of Bioorganic Chemistry* 35(2):219-224, 2009.
Breul et al., "Fluorescent monomers as building blocks for dye labeled polymers: synthesis and application in energy conversion, biolabeling and sensors," Chem. Soc. Rev. 42(12):5366-5407, 2013.
Buckhout-White et al., "Assembling programmable FRET-based photonic networks using designer DNA scaffolds," *Nature Communications* 5:5615, Dec. 11, 2014. (16 pages).
CAS Registry No. 862288-26-4, American Chemical Society, 2021. (1 page).
Chang et al., "A General Approach for Generating Fluorescent Probes to Visualize Piconewton Forces at the Cell Surface," *J. Am. Chem. Soc.* 138:2901-2904, 2016. (4 pages).
Damian et al., "Synthesis and DNA Interaction of Platinum Complex/Peptide Chimera as Potential Drug Candidates," *Eur. J. Org. Chem.* 6161-6170, 2010.
De Vos et al., "New Non Nucleosidic Phosphoramidites for the Solid Phase Multi-Labelling of Oligonucleotides: Comb- and Multifork-Like Structures," *Nucleosides & Nucleotides* 13(10):2245-2265, 1994.
Drescher et al., "General Synthesis and Aggregation Behaviour of New Single-Chain Bolaphospholipids: Variations in Chain and Headgroup Structures," *Chemistry—A European Journal* 14(22):6796-6804, 2008.
Dropulic et al., "Update on New Antivirals Under Development for the Treatment of Double-Stranded DNA Virus Infections," Clinical Pharmacology & Therapeutics 88(5):610-619, Nov. 2010.
Finniss et al., "A versatile acid-labile linker for antibody-drug conjugates," Med. Chem, Commun; 5; Apr. 1, 2014, 4 pages.
Franceschin et al., "Synthesis of a Dibromoperylene Phosphoramidite Building Block and Its Incorporation at the 5' End of a G-Quadruplex Forming Oligonucleotide: Spectroscopic Properties and Structural Studies of the Resulting Dibromoperylene Conjugate," *Bioconjugate Chem* 22:1309-1319, 2011.
Griesang et al., "Four-Color, Enzyme-Free Interrogation of DNA Sequences with Chemically Activated, 3'-Fluorphore-Labeled Nucleotides," *Angew. Chem. Int. Ed.* 45:6144-6148, 2006.
Guryev et al., "Control of the Fluorescence of Dye-Antibody Conjugates by (2-Hydroxypropyl)-β-cyclodextrin in Fluorescence Microscopy and Flow Cytometry," *Analytical Chemistry* 83:7109-7114, Aug. 16, 2011.
Irani et al., "Molecular properties of human IgG subclasses and their implications for designing therapeutic monoclonal antibodies against infectious diseases," *Molecular Immunology* 67:171-182, 2015.
Kashida et al., "A Cationic Dye Triplet as a Unique "Glue" That Can Connect Fully Matched Termini of DNA Duplexes," *Chem. Eur. J.* 17:2614-2622, 2011.
Krueger at al., "Fluorescent Amino Acids: Modular Building Blocks for the Assembly of New Tools for Chemical Biology," *ChemBioChem* 14:788-799, 2013.

(56) References Cited

OTHER PUBLICATIONS

Lapeyre et al., "Aryldithioethyloxycarbonyl (Ardec): A New Family of Amine Protecting Groups Removable under Mild Reducing Conditions and Their Applications to Peptide Synthesis," *Chem. Eur. J.* 12:3655-3671, 2006.

Lewis et al., "Orientation Control of Fluorescence Resonance Energy Transfer Using DNA as a Helical Scaffold," *J. Am. Chem. Soc.* 127(28):10002-10003, 2005.

Masuko et al., "Fluorescence resonance energy transfer from pyrene to perylene labels for nucleic acid hybridization assays under homogenous solution conditions," *Nucleic Acids Research* 28(8):e34, 2000 (8 pages).

McKinlay et al., "Cell-Penetrating, Guanidinium-Rich Oligophosphoesters: Effective and Versatile Molecular Transporters for Drug and Probe Delivery," *J. Am. Chem. Soc.* 138:3510-3517, Feb. 22, 2016.

Moss, "Nomenclature of Fused and Bridged Fused Ring Systems," *Pure & Appl. Chem.* 70(1):143-216, 1998.

Mthembu et al., "Breaking a Couple: Disulfide Reducing Agents," *ChemBioChem 21*, 2020. (10 pages).

Nolting, "Linker Technology for Antibody-Drug Conjugates," in Ducry (ed.), *Antibody-Drug Conjugates*, Humana Press, Totowa, NJ, 2013, Ch. 5, pp. 71-100.

Pelegrin et al., "Antiviral Monoclonal Antibodies: Can They Be More Than Simple Neutralizing Agents?" *Trends in Microbiology* 23(10):653-665, Oct. 2015.

Phares et al., "Improving the Stability and Sensing of Electrochemical Biosensors by Employing Trithiol-Anchoring Groups in a Six-Carbon Self-Assembled Monolayer," *Anal. Chem.* 81(3):1095-1100, Feb. 1, 2009.

Poupart et al., "Aminopropargyl derivative of terpyridine-bis(methylenamine) tetraacetic acid chelate of europium (Eu (TMT)-AP3): a new reagent for fluorescent labelling of proteins and peptides," *Org. Biomol. Chem.* 4:4165-4177, Oct. 2006.

Rochat et al., "Water-Soluble Cationic Conjugated Polymers: Response to Electron-Rich Bioanalytes," *J. Am. Chem. Soc.* 135:17703-17706, 2013.

Rupcich et al., "Quenching of Fluorophore-Labeled DNA Oligonucleotides by Divalent Metal Ions: Implications for Selection, Design, and Applications of Signaling Aptamers and Signaling Deoxyribozymes," J. Am. Chem. Soc. 126(3):780-790, 2006.

Shuman et al., "Bacterial DNA repair by non-homologous end joining," *Nature Reviews Microbiology* 5:852-861, Nov. 2007.

Sun et al., "Dual-Color Fluorescence Imaging of Magnetic Nanoparticles in Live Cancer Cells Using Conjugated Polymer Probes," *Scientific Reports* 6:22368, 2016. (12 pages).

Sun et al., "High yield production of high molecular weight poly(ethylene glycol)/ α-cyclodextrin polyrotaxanes by aqueous one-pot approach," *Polymer* 53:2884-2889, 2012.

Sun et al., "Ultrabright and Multicolorful Fluorescence of Amphiphilic Polyethyleneimine Polymer Dots for Efficiently Combined Imaging and Therapy," *Scientific Reports* 3:3036, 2013. (6 pages).

Takakusa et al., "Design and Synthesis of an Enzyme-Cleavable Sensor Molecule for Phosphodiesterase Activity Based on Fluorescence Resonance Energy Transfer," *J. Am. Chem. Soc.* 124(8):1653-1657, 2002.

Teyssot et al., "Aromatic Nitrogen Donors for Efficient Copper(I)-NHC CuAAC under Reductant-Free Conditions," *Eur. J. Org. Chem.* 3507-3515, 2010.

Vinogradov et al., "Total synthesis and biochemical characterization of mirror image barnase," *Chem Sci.* 6: 2997-3002, 2015.

Vybornyi et al., "Formation of Two-Dimensional Supramolecular Polymers by Amphiphilic Pyrene Oligomers," *Angew. Chem. Int. Ed.* 52:114488-11493, 2013.

Wang et al., "Fluorescence-Based Evaluation of the Partitioning of Lipids and Lipidated Peptides into Liquid-Ordered Lipid Microdomains: A Model for Molecular Partitioning into Lipid Rafts," *Biophysical Journal* 79:919-933, Aug. 2000.

Winiger et al., "Long-Distance Electronic Energy Transfer in Light-Harvesting Supramolecular Polymers," *Angew. Chem. Int. Ed.* 53:13609-13613, 2014.

Yu et al., "Targeted Delivery of an Anti-Inflammatory PDE4 Inhibitor to Immune Cells via an Antibody-drug Conjugate," Molecular Therapy 24(12):2078-2089, Dec. 2016.

Zhao et al., "Mussel-Inspired One-Pot Synthesis of a Fluorescent and Water-Soluble Polydopamine-Polyethyleneimine Copolymer," Macromol. Rapid Commun. 36:909-915, 2015.

Samal et al., "Cationic polymers and their therapeutic potential," *Chemical Society Reviews* 41:7147-7194, Aug. 2012. (48 pages).

Sun et al., "Self-assembled biodegradable micellar nanoparticles of amphiphilic and cationic block copolymer for siRNA delivery," *Biomaterials* 29:4348-4355, available online Aug. 2008. (8 pages).

Tabujew et al., "Chapter One: Functionalization of Cationic Polymers for Drug Delivery Applications," *RSC Polymer Chemistry Series* 13, 2015. (29 pages).

Wu Yi et al., "$^{Py}$A-Modified Oligodeoxyadenylates: Expanded Fluorescence Phenomena and Structural Formation," *Chemistry-An Asian Journal* 7:60-63, Nov. 2011. (4 pages).

\* cited by examiner

Conjugation Efficiency, Recovered at Conjugation
[Actual degree of labeling measured / Theoretical degree of labeling] in M. Equivalents of polymer-dye *100 = % recovered.

| Statistic | No MgCl₂ (C-E-S-) | MgCl₂ (C-E-S-) | MgCl₂ (C-E-S-) | MgCl₂ (C-E-S-) |
|---|---|---|---|---|
| Mean (%) | 27.4 | 52.1 | 58.5 | 63.0 |
| STDEV | 3.9 | 12.2 | 21.8 | 10.8 |
| CV% | 14.2 | 23.4 | 37.3 | 17.1 |
| N fractions | 6 | 13 | 12 | 13 |

| Statistic | No MgCl₂ (C-E-S-) | MgCl₂ (C-E-S-) | MgCl₂ (C-E-S-) | MgCl₂ (C-E-S-) |
|---|---|---|---|---|
| % improved recovery at conjugation | baseline | 90% | 114% | 130% |

FIG. 26

USE OF DIVALENT METALS FOR ENHANCEMENT OF FLUORESCENT SIGNALS

BACKGROUND

Field

The present invention is generally directed to dimeric and polymeric fluorescent or colored dyes having spacing groups, and methods for their use in combination with divalent or trivalent metal salts in various analytical methods.

Description of the Related Art

Fluorescent and/or colored dyes are known to be particularly suitable for applications in which a highly sensitive detection reagent is desirable. Dyes that are able to preferentially label a specific ingredient or component in a biological sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed. Since analysis of biomolecules typically occurs in an aqueous environment, the focus has been on development and use of water soluble dyes.

Highly fluorescent or colored dyes are desirable since use of such dyes increases the signal to noise ratio and provides other related benefits. Accordingly, attempts have been made to increase the signal from known fluorescent and/or colored moieties. For example, dimeric and polymeric compounds comprising two or more fluorescent and/or colored moieties have been prepared in anticipation that such compounds would result in brighter dyes. However, as a result of intramolecular fluorescence quenching, the known dimeric and polymeric dyes have not achieved the desired increase in brightness.

There is thus a need in the art for methods of using water soluble dyes having an increased molar brightness. Ideally, methods of using such dyes and biomarkers should be intensely colored or fluorescent and should be available in a variety of colors and fluorescent wavelengths. The present invention fulfills this need and provides further related advantages.

BRIEF SUMMARY

In brief, embodiments of the present invention are generally directed to compositions and methods of using fluorescent and/or colored dyes and/or probes that enable visual detection of analyte molecules, such as biomolecules, as well as reagents for their preparation. Methods for visually detecting analyte molecules using the dyes are also described.

In embodiments, the present disclosure provides for a composition comprising: a) a polymeric dye comprises: i) two or more fluorescent or colored moieties; ii) at least one negatively charged group; and iii) a reactive group Q; and b) a divalent or trivalent metal salt. Any suitable polymeric dye may be used in any methods or compositions of the disclosure.

In embodiments, the present disclosure provides for methods for forming a covalent conjugate of a polymeric dye and a targeting moiety, the method comprising preparing a mixture comprising the polymeric dye, the targeting moiety, and a divalent or trivalent metal salt, and allowing the mixture to age for a time and at a temperature sufficient to form the covalent conjugate, wherein: a) the polymeric dye comprises: i) two or more fluorescent or colored moieties; ii) at least one negatively charged group; and iii) a reactive group Q capable of forming a covalent bond with a complementary reactive group Q' on the targeting moiety; and b) the targeting moiety has affinity for a target analyte and comprises the complementary reactive group Q'.

In some embodiments, the present disclosure provides for methods for detecting a target analyte, the method comprising: a) associating a covalent conjugate with the target analyte to form an analyte-targeting moiety complex in the presence of a divalent or trivalent metal salt, the covalent conjugate comprising: i) a targeting moiety that has affinity for the target analyte and comprises a reactive group Q'covalent bond to a polymeric dye; ii) the polymeric dye comprising: A) two or more fluorescent or colored moieties; B) at least one negatively charged group; and C) a covalent bond to the targeting moiety complementary reactive group Q covalently bonded with the reactive group Q'; and b) detecting a fluorescent or colored signal from the analyte-targeting moiety complex.

In some embodiments, the present disclosure provides for methods for detecting a target analyte, the method comprising: a) associating a covalent conjugate with the target analyte to form an analyte-targeting moiety complex, the covalent conjugate comprising: i) a targeting moiety that has affinity for the target analyte and comprises a reactive group Q' covalent bond to a polymeric dye; and ii) a the polymeric dye comprising: A) two or more fluorescent or colored moieties; B) at least one negatively charged group; and C) a complementary reactive group Q covalently bonded with the reactive group Q' on a covalent bond to the targeting moiety; b) treating the analyte-targeting moiety complex with a wash solution comprising a divalent or trivalent metal salt; c) detecting a fluorescent or colored signal from the analyte-targeting moiety complex.

These and other aspects of the invention will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

FIG. 21 shows additional example of findings as histograms of S/N response to antibody concentration. CD3 fluorescence resolution in two configurations is shown. S/N is enhanced by inclusion of divalent cations when $MgCl_2$ included in conjugation process steps for 10× I-16 UCHT1. Data is derived from flow cytometry and potassium buffered ammonium chloride (ACK) red cell lysed WBC when $MgCl_2$ is included in the conjugation in two configurations of I-16 UCHT1 for detection of surface CD3: (C+E+S+) and (C+E-S-) and compared to a previous trial of (C+E+S+). Results were compared to UCHT1 FITC. The assay was incubated and washed with a buffer not containing cations.

Figure 22:
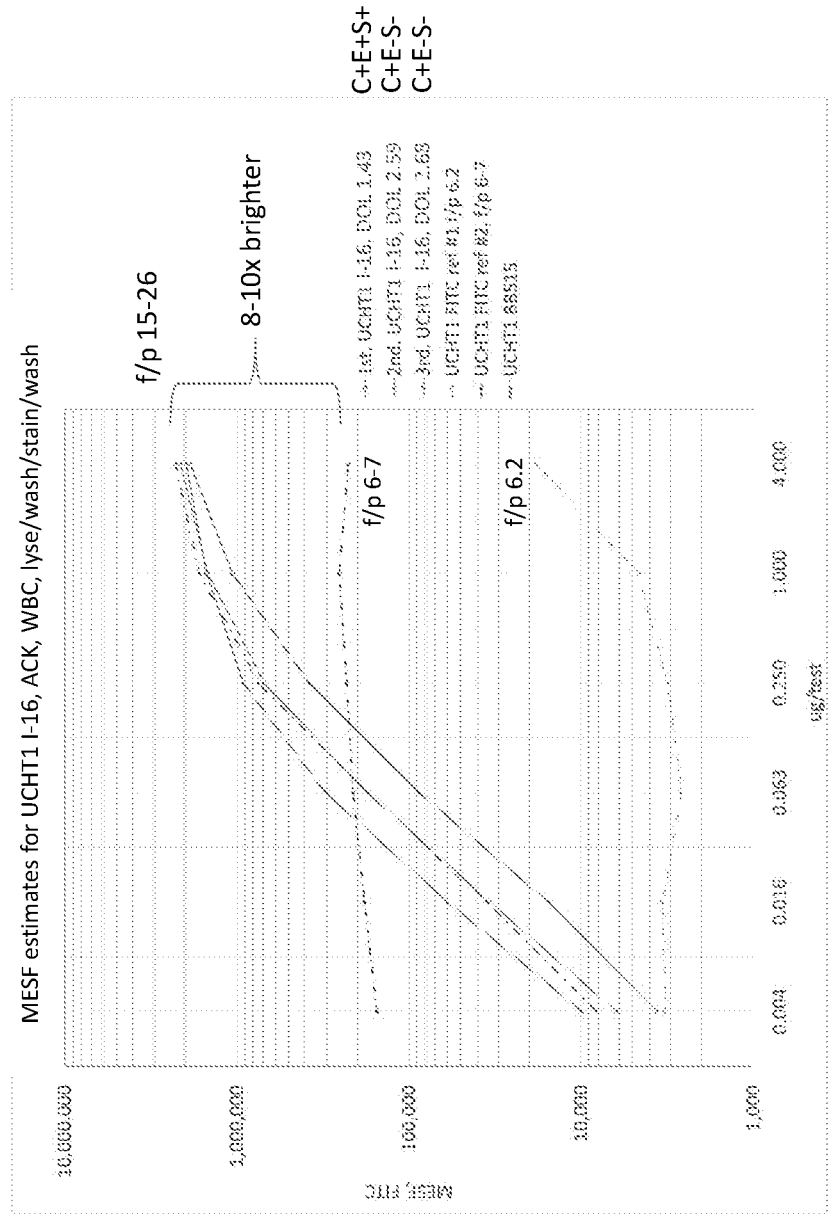

FIG. 22 shows fluorescence intensity response curves correlated to bead controls by flow cytometry measuring Molecules of Equivalent Soluble Fluorophores (MESF). Fluorescence in two configurations is shown. S/N is enhanced by inclusion of divalent cations when $MgCl_2$ included in conjugation process steps for 10× I-16 UCHT1. Data is derived from flow cytometry of potassium buffered ammonium chloride (ACK) red cell lysed WBC when $MgCl_2$ is included in the conjugation in two configurations of I-16 UCHT1 for detection of surface CD3: (C+E+S+) and (C+E-S-). Results were compared to BD Horizon™ Brilliant Blue 515 UCHT1 and two lots of FITC UCHT1. The assay was incubated and washed with a buffer not containing cations.

Figure 23:
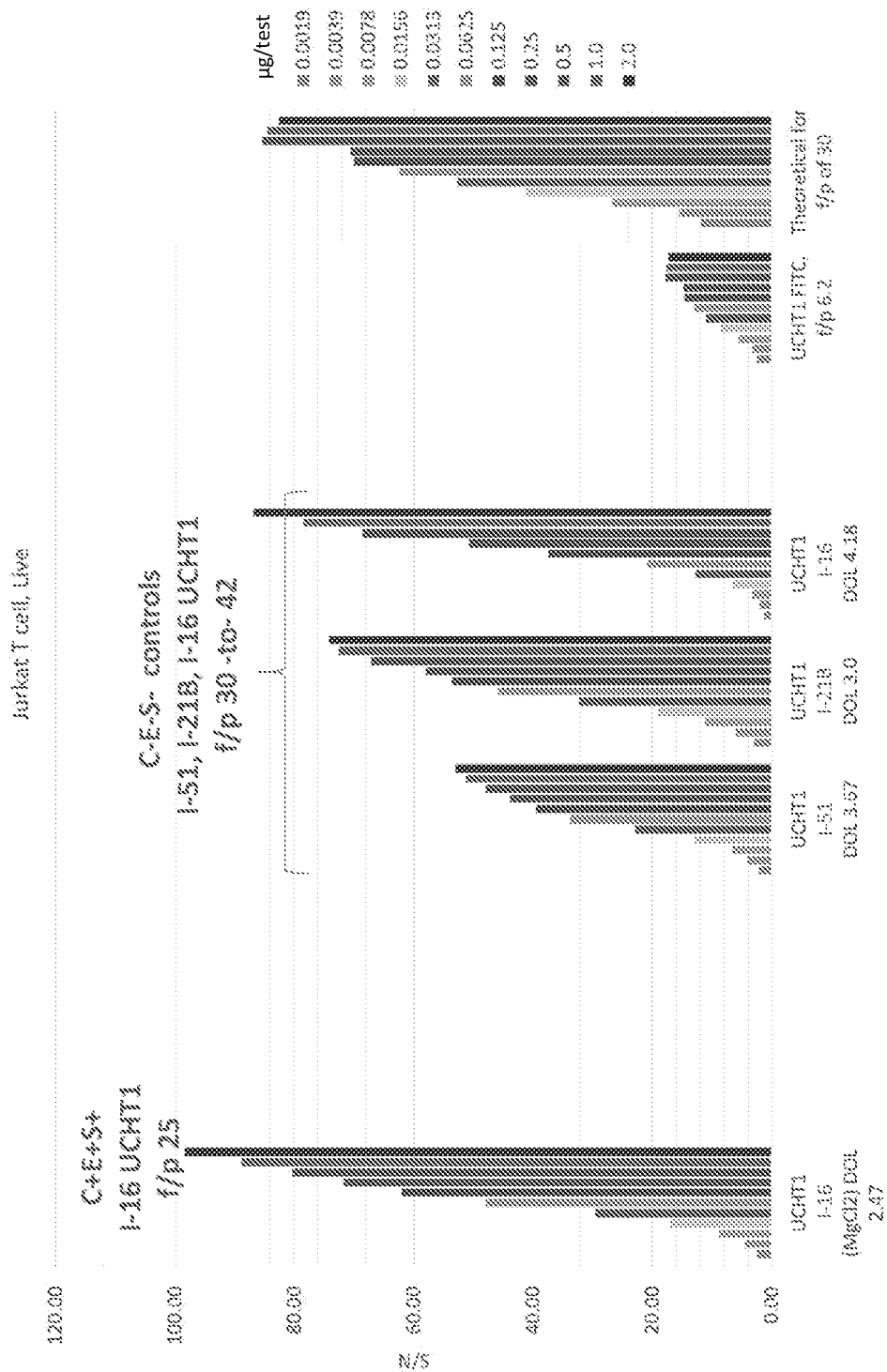

FIG. 23 shows histograms of S/N response to antibody concentration. Data is derived from flow cytometry of live Jurkat T cells when $MgCl_2$ is included in the conjugation in two configurations of I-16 UCHT1 for detection of surface CD3: (C+E+S+) and (C+E-S-) Results were compared to FITC UCHT1. In this case, other targeting moieties I-32, I-21B, I-16 UCHT1 were included as negative controls (no cations C-E-S). The assay was incubated and washed with a buffer not containing cations. CD3 fluorescence resolution in two systems shows S/N is enhanced by inclusion of divalent cations when $MgCl_2$ included in conjugation process steps for 10× I-16 UCHT1.

Figure 24:
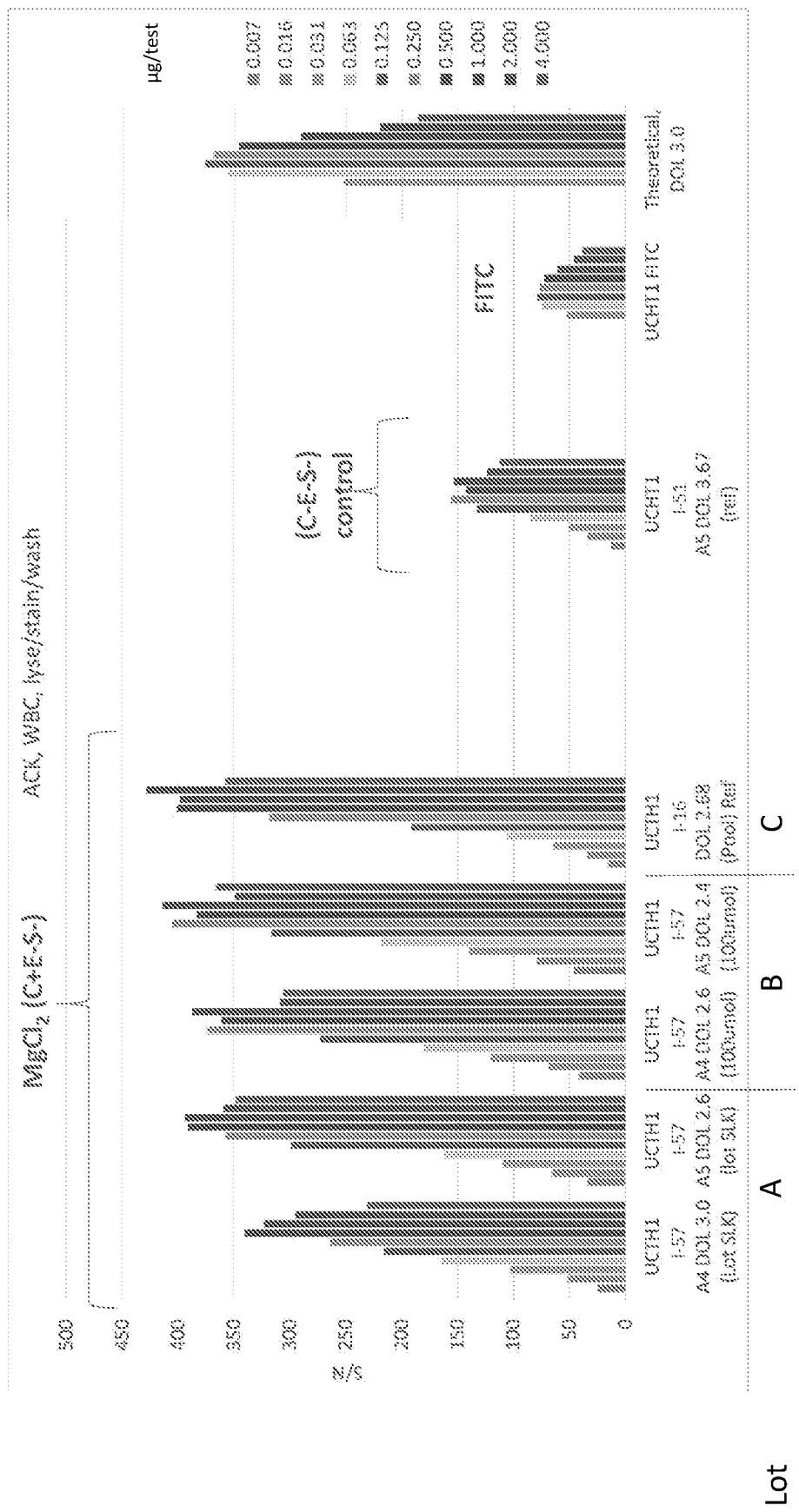

FIG. 24 show histograms of S/N response to antibody concentration in WBC. Three lots of targeting moiety configurations (C+E-S-) that are I-51-like (I-49 and I-16 UCHT1) are used to demonstrate elution and storage may not be necessary. Data is derived from flow cytometry of potassium buffered ammonium chloride (ACK) red cell lysed WBC when $MgCl_2$ is included in the conjugation of I-16 UCHT1 for detection of surface CD3. Results were compared to I-51 UCHT1 and FITC UCHT1. The assay was incubated and washed with a buffer not containing cations. Extracellular CD3 fluorescence resolution in C+E-S System and three lot shows fluorescence efficiency is enhanced by inclusion of divalent cations when $MgCl_2$ is included in conjugation process for 10× I-16 UCHT1.

Figure 25A:
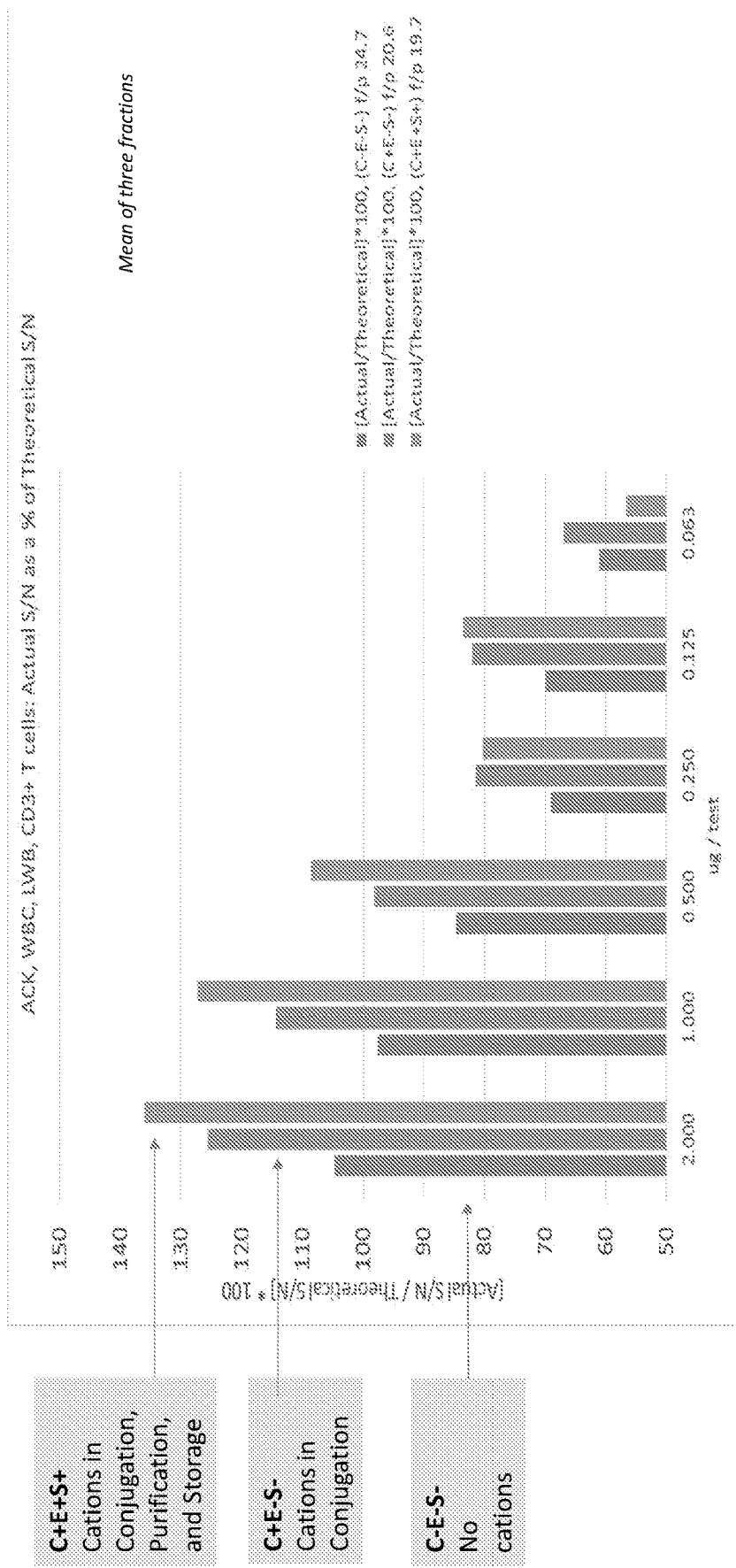

FIG. 25A show comparisons of three cation configurations using 10× I-16 UCHT1 for detection of surface CD3: (C+E+S+, C+E-S-, and control C-E-S). Data is expressed as fluorescence efficiency [Actual Signal-to-Noise/Theoretical S/N]*100. Data is derived from flow cytometry of potassium buffered ammonium chloride (ACK) red cell lysed WBC when $MgCl_2$ is included in the conjugation process. The assay was incubated and washed with a buffer not containing cations. Extracellular CD3 expression in three configurations shows fluorescence efficiency is enhanced by inclusion of divalent cations when $MgCl_2$ is included in conjugation process steps for 10× I-16 UCHT1.

Figure 25B:
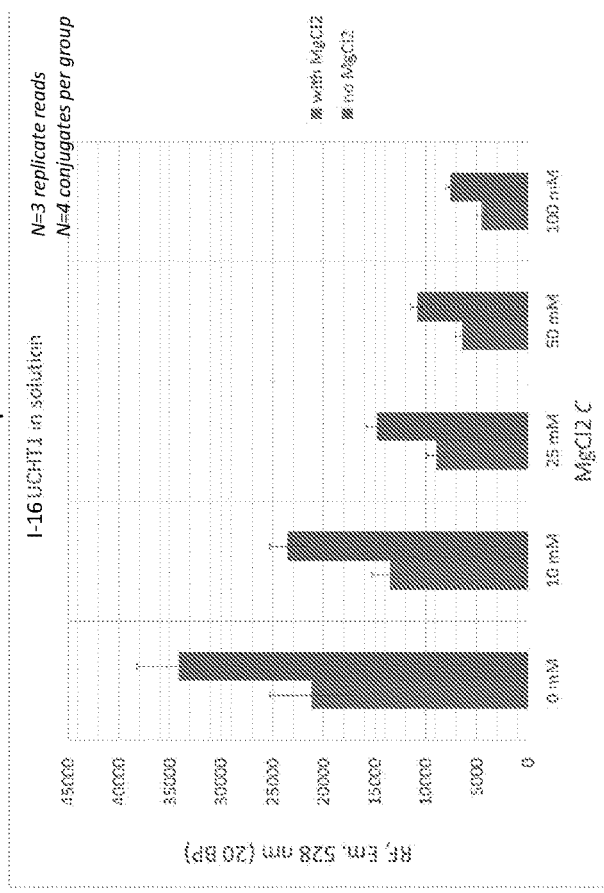
Figure 25B:
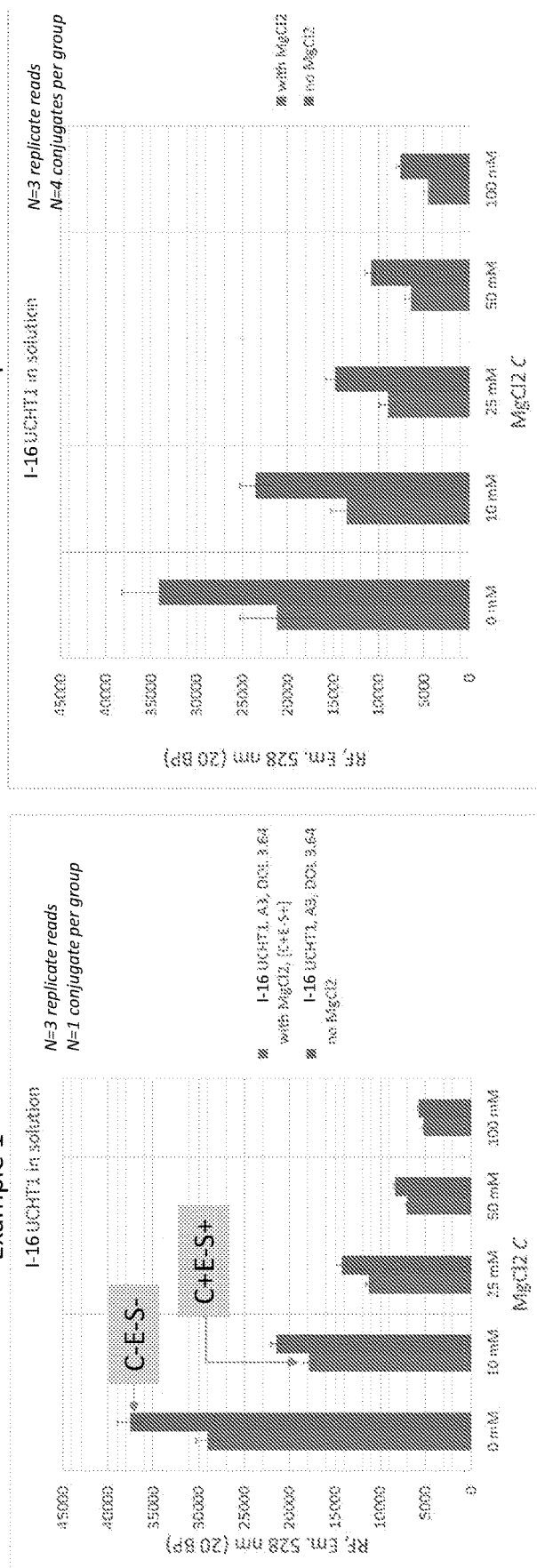

FIG. 25B shows two example analyses from two experiments using multiple conjugates results to demonstrate quenching pattern in solution when interacting with the process configurations. Targeting moieties were processed with $MgCl_2$ and without $MgCl_2$ in various cation configurations (I-51 UCHT1-like moeiteis), and then compared to $MgCl_2$ titration (at pH 7.4) of 0-100 mM at visualization. Targeting moieties processed with $MgCl_2$ are pre-quenched while titrations of $MgCl_2$ divalent cations quench all configurations. In the first example, N=3 replicate reads, and N=1 conjugate per group is plotted and the (C+E-S+) is interrogated. In the second example, N=3 replicate reads N=4 conjugates per group were analyzed and multiple process configurations were grouped into those with $MgCl_2$, and those without. Error bars represent 1SDEV.

FIG. 26 conjugation Efficiency, the polymer-dye moiety Recovered at Conjugation is observed to be higher when $MgCl_2$ is included in the process of building I-16 UCHT1 using $MgCl_2$ configurations C+E+S+, and C+E-S-. Data is expressed as [Actual degree of labeling measured/Theoretical degree of labeling] in M. Equivalents of polymer-dye*100=% recovered. The percent improvement in recovery over baseline process is noted. Data is derived from in vitro measurements of fluorescence using NanoDrop™ spectrophotometer, and compiled from three conjugations and the application of Beer-Lambert law to quantify dye concentrations.

Figure 27A:
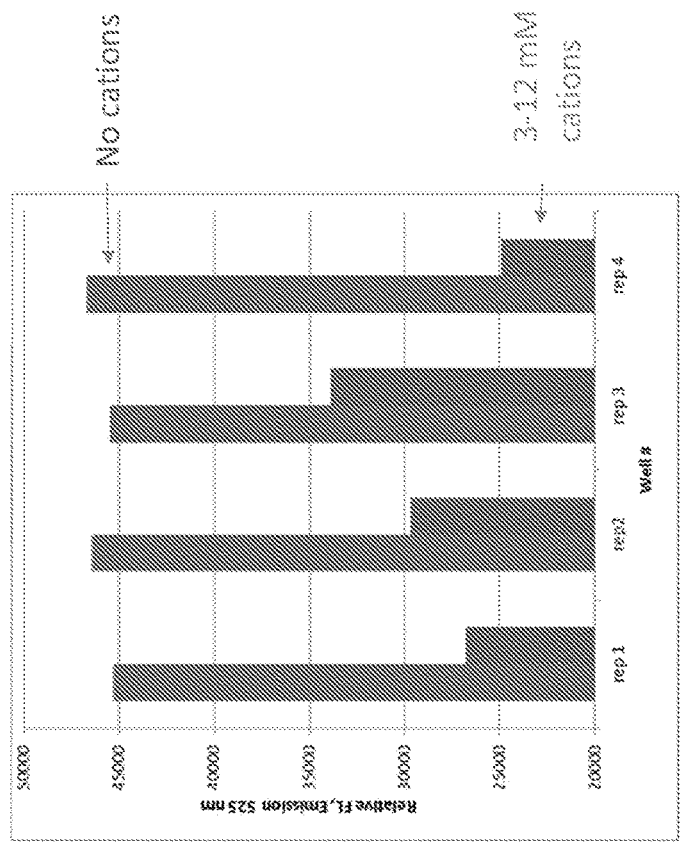
Figure 27B:
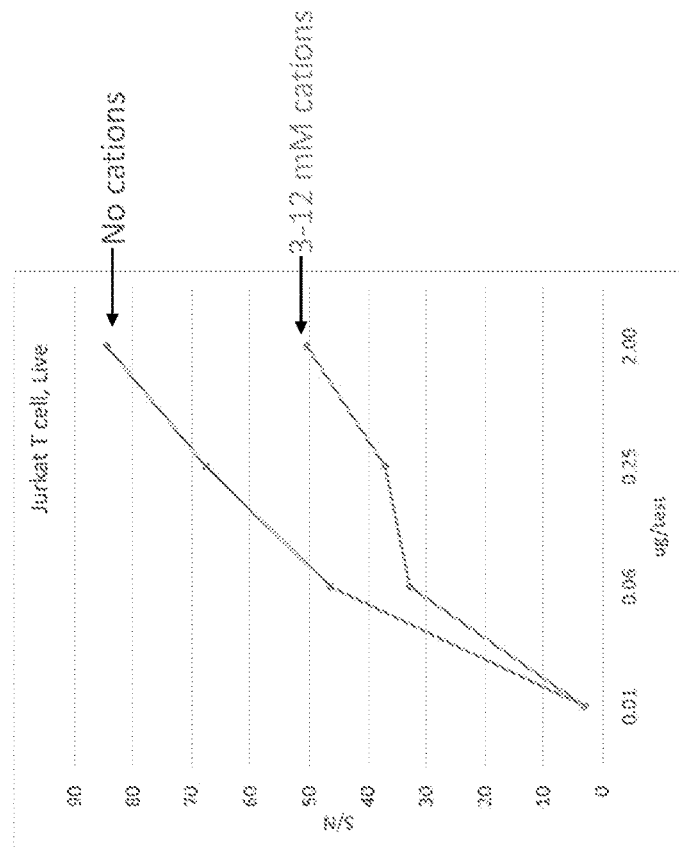
Figure 28:
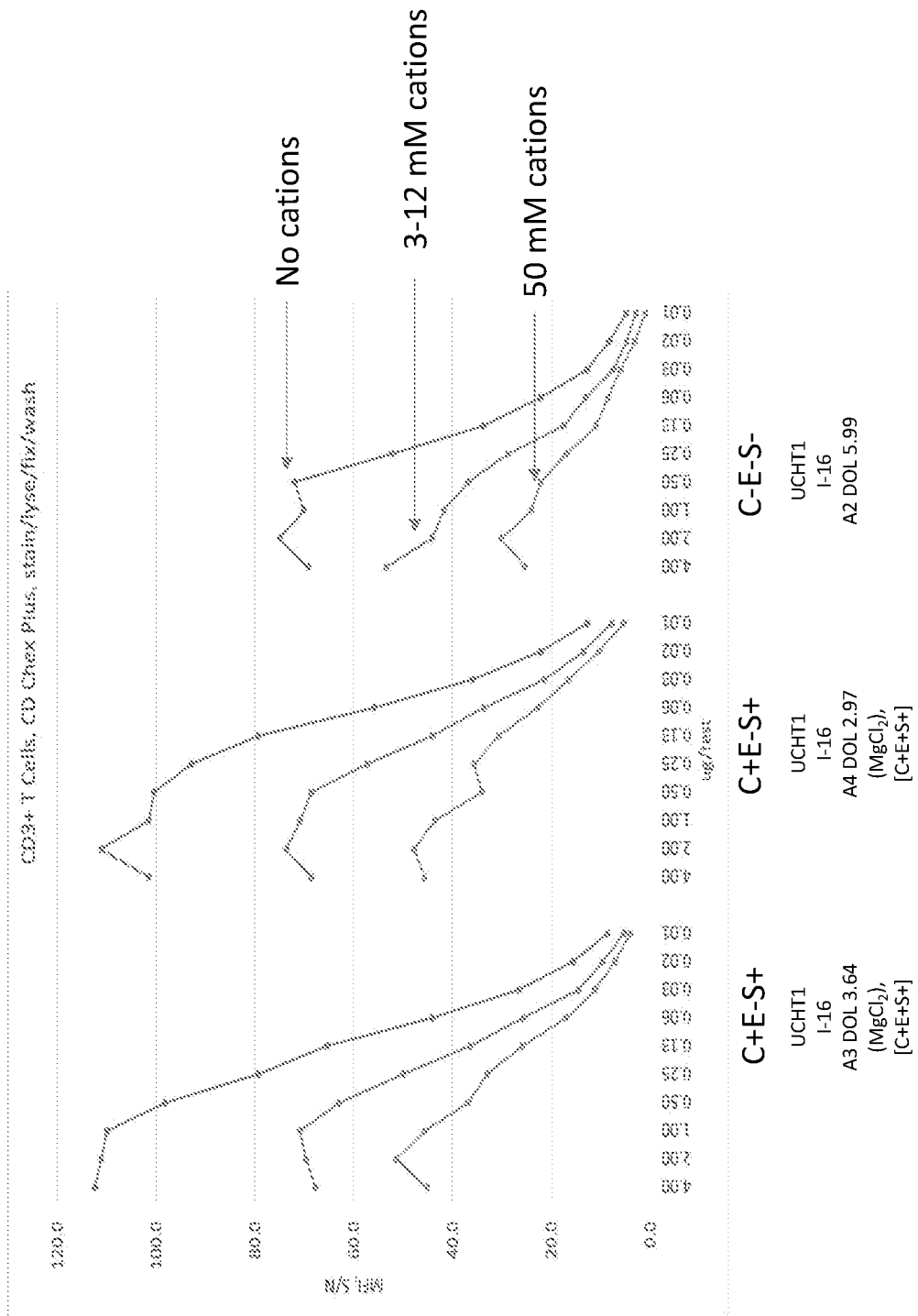

FIG. 27A and FIG. 27B show extracellular CD3 fluorescence resolution enhanced by exclusion of divalent cations during acquisition (visualization) of Jurkat T cells in flow cytometry, 10× I-51 UCHT1. FIG. 27A shows Jurkat T Cells staining by flow cytometry and the S/N enhanced by exclusion of divalent cations during data acquisition (fluorescence visualization) compared to a buffered solution containing trace amounts of calcium and magnesium (at pH 7.4). FIG. 27B shows fluorescence emission intensity in solution enhanced by exclusion of divalent cations or quenched when containing trace amounts of calcium and magnesium during plate read (fluorescence visualization). 10× I-51 UCHT1 was used for this analyses FIG. 28 show results of the quenching pattern when using buffers with cations (at pH 7.4). Two $MgCl_2$ process configurations were used (two lots of C+E-S+, and one lot of C-E-S-) in an experiment with 10× I-16 UCHT1. Data is expressed as S/N derived from median fluorescence intensity in flow cytometry of CD Chex Plus™ stabilized whole blood cells (fixed) and red cells lysed with a lysis fixation solution, washed, and visualized in different buffers. All specimens were identically handled until the end of the assay, then split into three samples, washed and re-suspended in three typical flow cytometry buffers containing either no cations, trace cations, or 50 mM of cations. Extracellular CD3 fluorescence resolution enhanced by exclusion of divalent cations during acquisition (visualization) $MgCl_2$ and 10× I-16 UCHT1 (three lots)

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ group.
"Carboxy" refers to the —CO$_2$H group.
"Cyano" refers to the —CN group.
"Formyl" refers to the —C(═O)H group.
"Hydroxy" or "hydroxyl" refers to the —OH group.
"Imino" refers to the ═NH group.
"Nitro" refers to the —NO$_2$ group.
"Oxo" refers to the ═O substituent group.
"Sulfhydryl" refers to the —SH group.
"Thioxo" refers to the ═S group.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(═$R_a$)($R_b$)$R_c$, wherein each of $R_a$, $R_b$ and $R_c$ is as defined for compounds of structure (I).

"Alkoxy" refers to a group of the formula —O$R_a$ where $R_a$ is an alkyl group as defined above containing one to twelve carbon atoms. Unless stated otherwise specifically in the specification, an alkoxy group is optionally substituted.

"Alkoxyalkylether" refers to a group of the formula —O$R_a R_b$ where $R_a$ is an alkylene group as defined above containing one to twelve carbon atoms, and $R_b$ is an alkylether group as defined herein. Unless stated otherwise specifically in the specification, an alkoxyalkylether group is optionally substituted, for example substituted with an alcohol or —OP(═$R_a$)($R_b$)$R_c$, wherein each of $R_a$, $R_b$ and $R_c$ is as defined for compounds of structure (I).

"Heteroalkyl" refers to an alkyl group, as defined above, comprising at least one heteroatom (e.g., N, O, P or S) within the alkyl group or at a terminus of the alkyl group. In some embodiments, the heteroatom is within the alkyl group (i.e., the heteroalkyl comprises at least one carbon-[heteroatom]$_x$-carbon bond, where x is 1, 2 or 3). In other embodiments, the heteroatom is at a terminus of the alkyl group and thus serves to join the alkyl group to the remainder of the molecule (e.g., M1-H-A), where M1 is a portion of the molecule, H is a heteroatom and A is an alkyl group). Unless stated otherwise specifically in the specification, a heteroalkyl group is optionally substituted. Exemplary heteroalkyl groups include ethylene oxide (e.g., polyethylene oxide), optionally including phosphorous-oxygen bonds, such as phosphodiester bonds.

"Heteroalkoxy" refers to a group of the formula —O$R_a$ where $R_a$ is a heteroalkyl group as defined above containing one to twelve carbon atoms. Unless stated otherwise specifically in the specification, a heteroalkoxy group is optionally substituted.

"Heteroalkylene" refers to an alkylene group, as defined above, comprising at least one heteroatom (e.g., N, O, P or S) within the alkylene chain or at a terminus of the alkylene chain. In some embodiments, the heteroatom is within the alkylene chain (i.e., the heteroalkylene comprises at least one carbon-[heteroatom]-carbon bond, where x is 1, 2 or 3). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. Exemplary heteroalkylene groups include ethylene oxide (e.g., polyethylene oxide) and the "C" linking group illustrated below:

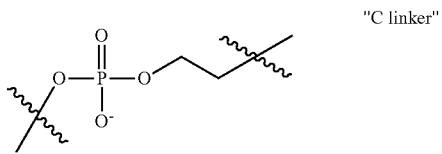 [SMILES: *CCOP(=O)([O-])O*]

"C linker"

Multimers of the above C-linker are included in various embodiments of heteroalkylene linkers.

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatoms. Exemplary heteroatomic linkers include single atoms selected from the group consisting of O, N, P and S, and multiple heteroatoms for example a linker having the formula —P(O⁻)(=O)O— or —OP(O⁻)(=O)O— and multimers and combinations thereof.

"Phosphate" refers to the —OP(=O)(R$_a$)R$_b$ group, wherein R$_a$ is OH, O⁻ or OR$_c$; and R$_b$ is OH, O⁻, OR$_c$, a thiophosphate group or a further phosphate group, wherein R$_c$ is a counter ion (e.g., Na+ and the like).

"Phosphoalkyl" refers to the —OP(=O)(R$_a$)R$_b$ group, wherein R$_a$ is OH, O⁻ or OR$_c$; and R$_b$ is —Oalkyl, wherein R$_c$ is a counter ion (e.g., Na+ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Phosphoalkylether" refers to the —OP(=O)(R$_a$)R$_b$ group, wherein R$_a$ is OH, O⁻ or OR$_c$; and R$_b$ is —Oalkylether, wherein R$_c$ is a counter ion (e.g., Na+ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)(R$_c$, wherein each of R$_a$, R$_b$ and R$_c$ is as defined for compounds of structure (I).

"Thiophosphate" refers to the —OP(=R$_a$)(R$_b$)R$_c$ group, wherein R$_a$ is O or S, R$_b$ is OH, O⁻, S⁻, OR$_d$ or SR$_d$; and R$_c$ is OH, SH, O⁻, S⁻, OR$_d$, SR$_d$, a phosphate group or a further thiophosphate group, wherein R$_d$ is a counter ion (e.g., Na+ and the like) and provided that: i) R$_a$ is S; ii) R$_b$ is S" or SR$_d$; iii)R$_c$ is SH, S⁻ or SR$_d$; or iv) a combination of i), ii) and/or iii).

"Thiophosphoalkyl" refers to the —OP(=R$_a$)(R$_b$)R$_c$ group, wherein R$_a$ is O or S, R$_b$ is OH, O⁻, S⁻, OR$_d$ or SR$_d$; and R$_c$ is —Oalkyl, wherein R$_d$ is a counter ion (e.g., Na+ and the like) and provided that: i) R$_a$ is S; ii) R$_b$ is S⁻ or SR$_d$; or iii)R$_a$ is S and R$_b$ is S⁻ or SR$_d$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Thiophosphoalkylether" refers to the —OP(=R$_a$)(R$_b$)R$_c$ group, wherein R$_a$ is O or S, R$_b$ is OH, O⁻, S⁻, OR$_d$ or SR$_d$; and R$_c$ is —Oalkylether, wherein R$_d$ is a counter ion (e.g., Na+ and the like) and provided that: i) R$_a$ is S; ii) R$_b$ is S⁻ or SR$_d$; or iii)R$_a$ is S and R$_b$ is S⁻ or SR$_d$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptly, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl.

Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-c]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tertracyclic, and the like.

The term "substituted" used herein means any of the above groups (e.g., alkyl, alkylene, alkenylene, alkynylene, heteroalkylene, heteroalkenylene, heteroalkynylene, alkoxy, alkylether, alkoxyalkylether, heteroalkyl, heteroalkoxy, phosphoalkyl, phosphoalkylether, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atoms such as: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_B$, —$SO_2R_g$, —$OSO_2R_g$, —$SO_2O$ $R_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In some embodiments, the optional substituent is —$OP(=R_a)(R_b)R_c$, wherein each of $R_a$, $R_b$ and $R_c$ is as defined for compounds of structure (I). In addition, each of the foregoing substituents may also be optionally substituted with one or more of the above substituents.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1, 3-butadine has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

The term "biomolecule" refers to any of a variety of biological materials, including nucleic acids, carbohydrates, amino acids, polypeptides, glycoproteins, hormones, aptamers and mixtures thereof. More specifically, the term is intended to include RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the invention (e.g., compounds of structure (I) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A "reactive group" is a moiety capable of reacting with a second reactive groups (e.g., a "complementary reactive group") to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin, thiirane and the like.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}$ $cm^{-1}$. The compounds of the invention may be detected by observation with the naked eye, or with the aid of an optically based detection device, including, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the invention, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable molecules of various embodiments of the invention are useful for a wide variety of analytical applications, such as biochemical and biomedical applications, in which there is a need to determine the presence, location, or quantity of a particular analyte (e.g., biomolecule). In another aspect, therefore, the invention provides a method for visually detecting a biomolecule, comprising: (a) providing a biological system with a visually detectable biomolecule comprising the compound of structure (I) linked to a biomolecule; and (b) detecting the biomolecule by its visible properties. For purposes of the invention, the phrase "detecting the biomolecule by its visible properties" means that the biomolecule, without illumination or chemical or enzymatic activation, is observed with the naked eye, or with the aid of a optically based detection device, including absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Examples of such biological systems include cells, cell extracts, tissue specimens, electrophoretic gels, assay mixtures, and hybridization reaction mixtures.

"Solid support" refers to any solid substrate known in the art for solid-phase support of molecules, for example a "microparticle" refers to any of a number of small particles useful for attachment to compounds of the invention, including glass beads, magnetic beads, polymeric beads, nonpolymeric beads, and the like. In certain embodiments, a microparticle comprises polystyrene beads.

A "solid support reside" refers to the functional group remaining attached to a molecule when the molecule is cleaved from the solid support. Solid support residues are known in the art and can be easily derived based on the structure of the solid support and the group linking the molecule thereto.

A "targeting moiety" is a moiety that selectively binds or associates with a particular target, such as an analyte molecule. "Selectively" binding or associating means a targeting moiety preferentially associates or binds with the desired target relative to other targets. In some embodiments the compounds disclosed herein include linkages to targeting moieties for the purpose of selectively binding or associating the compound with an analyte of interest (i.e., the target of the targeting moiety), thus allowing detection of the analyte. Exemplary targeting moieties include antibodies, antigens, nucleic acid sequences, enzymes, proteins, cell surface receptor antagonists, and the like. In some embodiments, the targeting moiety is a moiety, such as an antibody, that selectively binds or associates with a target feature on or in a cell, for example a target feature on a cell membrane or other cellular structure, thus allowing for detection of cells of interest. Small molecules that selectively bind or associate with a desired analyte are also contemplated as targeting moieties in certain embodiments. One of skill in the art will understand other analytes, and the corresponding targeting moiety, that will be useful in various embodiments.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Examples of base pairing moieties are RNA and DNA bases such adenosine, guanosine, thymidine, cytosine and uridine and analogues thereof.

Embodiments of the invention disclosed herein are also meant to encompass all compounds of structure (I) or (II) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively.

Isotopically-labeled compounds of structure (I) or (II) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include sodium, potassium, lithium, ammonium, calcium, magnesium, iron, zinc, copper, manganese, aluminum salts and the like. Salts derived from organic bases include salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds described herein. Embodiments of the present invention include all solvates of the described compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

Embodiments of the compounds of the invention (e.g., compounds of structure I or II), or their salts, tautomers or solvates may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

As noted above, in one embodiment of the present invention, compounds useful as fluorescent and/or colored dyes in various analytical methods are provided. In other embodiments, compounds useful as synthetic intermediates for preparation of compounds useful as fluorescent and/or colored dyes are provided. In general terms, embodiments of the present invention are directed to dimers and higher polymers of fluorescent and/or colored moieties. The fluorescent and or colored moieties are linked by a linking moiety. Without wishing to be bound by theory, it is believed the linker helps to maintain sufficient spatial distance between the fluorescent and/or colored moieties such that intramolecular quenching is reduced or eliminated, thus resulting in a dye compound having a high molar "brightness" (e.g., high fluorescence emission).

Compositions comprising any of the foregoing compounds and one or more analyte molecules (e.g., biomolecules) are provided in various other embodiments. In some embodiments, use of such compositions in analytical methods for detection of the one or more analyte molecules are also provided.

Advantageously, the inventors have discovered that divalent or trivalent metal salts (e.g., $MgCl_2$) can be used in combination with particular polymeric dyes for charge shielding and stabilizing. Under certain conditions, the combination of one or more divalent or trivalent metal salts and a polymeric dye of the disclosure improves affinity of a targeting moiety when used in conjugation, elution, storage, or during incubation. Surprisingly, the inventors have found that divalent or trivalent metal salts may quench such polymeric dyes in solution and when present during sample acquisition.

Without wishing to be bound by theory, divalent or trivalent metal salts (e.g., $MgCl_2$) may alter affinity of the dye and/or the targeting moiety when present, thus improving antibody conjugation efficiency of a polymeric dye of the disclosure and improving assay results (resolution) when used in conjugation, elution, storage, incubation, or as a washing tool.

Conjugation of a polymeric dye to a targeting moiety (e.g., an antibody) generally has three steps, conjugation, elution, and storage. In embodiments, one or more divalent or trivalent metal salts (e.g., $MgCl_2$) are present during conjugation of a polymeric dye and a targeting moiety. In embodiments, one or more divalent or trivalent metal salts are present during elution of a conjugated polymeric dye and a targeting moiety. In embodiments, or more divalent or trivalent metal salts are present during storage of a conjugated polymeric dye and a targeting moiety. In embodiments, or more divalent or trivalent metal salts are present during conjucation and elution of a polymeric dye and a targeting moiety. In embodiments, or more divalent or trivalent metal salts are present during elution and storage of a conjugated polymeric dye and a targeting moiety. In embodiments, or more divalent or trivalent metal salts are present during conjugation and storage of a polymeric dye and a targeting moiety. In embodiments, or more divalent or trivalent metal salts are present during conjugation, elution, and storage of a polymeric dye and a targeting moiety. Optionally, conjugation processes may include a step of reconstitution of a dye. Cation configurations as performed during antibody conjugation (building the targeting moiety) may be expressed, for example, as C+E-S- (i.e. in conjugation, but not in elution, and not in storage).

Immunofluorescence staining methods generally include at least three steps, incubation, washing, and visualization. In embodiments, one or more divalent or trivalent metal salts are present during inclubation of an analyte-targeting moiety complex. In embodiments, or more divalent or trivalent metal salts are present during washing of an analyte-targeting moiety complex. In embodiments, or more divalent or trivalent metal salts are present during incubation and washing of an analyte-targeting moiety complex. In embodiments, one or more divalent or trivalent metal salts are not present during visualization.

Figure 12:
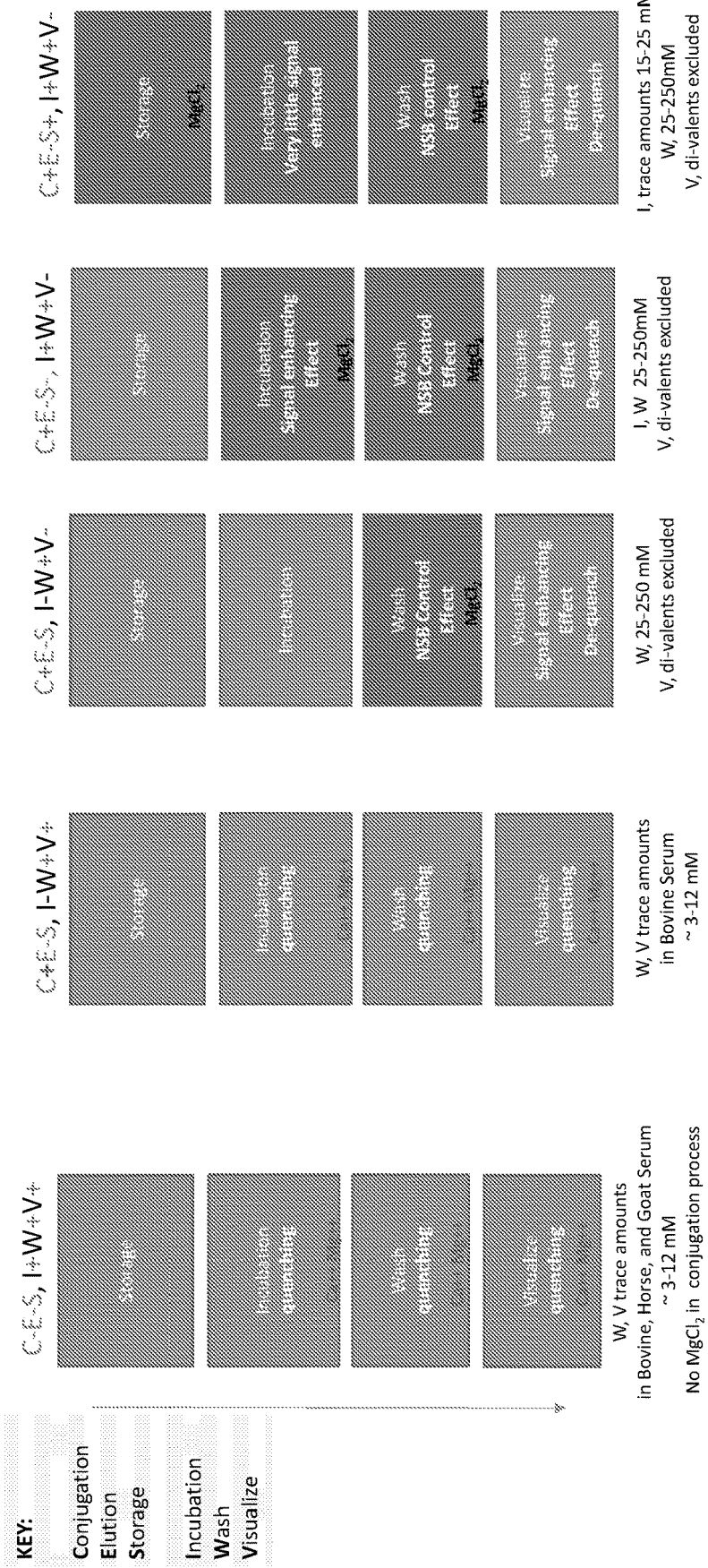
FIG. 12 diagrams divalent metal cation configurations as related to signal enhancement and quenching. The diagrams are coded in the method steps in which cations are present in the reagent or method (i.e. conjugation, elution, storage, incubation, wash, or when visualizing) example S+, I+W+, V−. These methods are contrasted against a standard method whereby divalent cations presence is either unknown, or known to be in trace amounts contributing to quenching.
Figure 13:
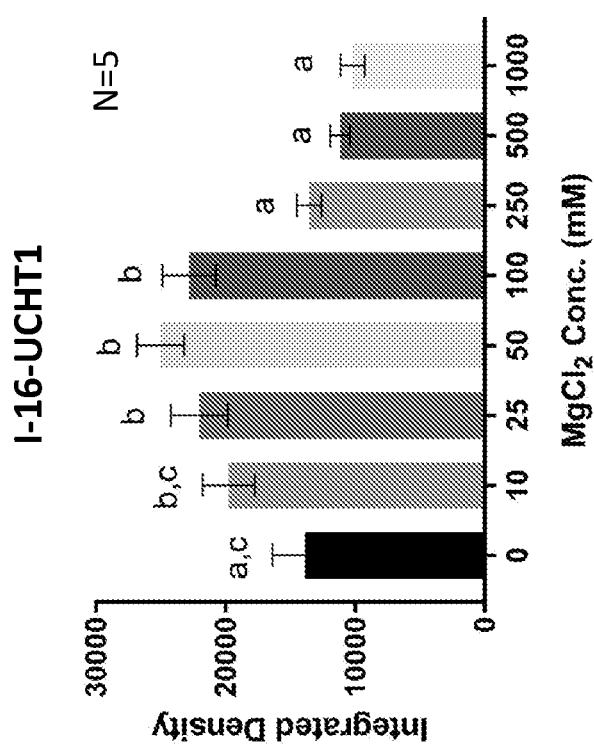
FIG. 13 shows a summary of findings, fixed and permeabilized human PBMC in microscopy: extracellular and intracellular CD3 fluorescence resolution is enhanced (and then quenched) by incubation with divalent cations, $MgCl_2$ Gradient, 10× I-16 UCHT1. A summary of analyses using one-way ANOVA statistical analyses of five fluorescence microscopy experiments for I-16 UCHT1 for detection of surface and intracellular CD3 is shown. Data is shown as integrated density (arbitrary units) of representative CD3 expression in the presence of $MgCl_2$ titration (at pH 7.4) (range 0-1000 mM). Statistical significance is indicated by shared or different letters, for example; 250 mM (a) is significantly different from 50 mM (b), while 1000 mM (a) is not significantly different from 0 mM (a, c). N=5 is described as an individual experiment performed in two days on the same specimen, twice in day one, and three times in day two.

Particular embodiments of various methods described herein are visualized in FIGS. 12 and 13. FIG. 12 shows generalized methods. FIG. 13 shows more specific illustrative methods. The left-most column of FIG. 12 and FIG. 13 show an example of the currently used methods.

In embodiments, the Signal to Noise (S/N) is enhanced in immunofluorescence when targeting moiety is incubated with divalent cations and cells, then washed off.

In some embodiments, there are process enhancements when the antibody conjugate is processed with divalent cations.

In embodiments, the S/N is enhanced at the end of the assay when antibody conjugate is visualized in final buffer without cations (at pH 7.4).

In embodiments, the S/N is enhanced when antibody conjugate is washed with a buffer (at pH 7.4) containing divalent cations, but visualized with a buffer not containing ions. In embodiments, the divalent cation wash interrupts the non-specific binding and the quenching caused by substrate tissues, but with the visualization buffer (at pH 7.5) without cations to enhance signals: (I–W+V–) or (I+W+V–).

In embodiments, the present disclosure provides for a composition comprising:
  a) a polymeric dye comprising:
    i) two or more fluorescent or colored moieties;
    ii) at least one negatively charged group; and
    iii) a reactive group Q; and
  b) a divalent or trivalent metal salt.

Any suitable polymeric dye may be used in any methods or compositions of the disclosure.

In embodiments, methods of the current disclosure include a method for forming a covalent conjugate of a polymeric dye and a targeting moiety, the method comprising preparing a mixture comprising the polymeric dye, the targeting moiety, and a divalent or trivalent metal salt, and allowing the mixture to age for a time and at a temperature sufficient to form the covalent conjugate, wherein:
  a) the polymeric dye comprises:
    i) two or more fluorescent or colored moieties;
    ii) at least one negatively charged group; and
    iii) a reactive group Q capable of forming a covalent bond with a complementary reactive group Q' on the targeting moiety; and
  b) the targeting moiety has affinity for a target analyte and comprises the complementary reactive group Q'.

In some embodiments, methods of the current disclosure include a method for detecting a target analyte, the method comprising:
  a) associating a covalent conjugate with the target analyte to form an analyte-targeting moiety complex in the presence of a divalent or trivalent metal salt, the covalent conjugate comprising:
    i) a targeting moiety that has affinity for the target analyte and comprises a reactive group Q'covalent bond to a polymeric dye;
    ii) a the polymeric dye comprising:
      A) two or more fluorescent or colored moieties;
      B) at least one negatively charged group; and
      C) a covalent bond to the targeting moiety complementary reactive group Q covalently bonded with the reactive group Q; and
  b) detecting a fluorescent or colored signal from the analyte-targeting moiety complex.

In embodiments, the methods further comprise treating the analyte-targeting moiety complex with a wash solution comprising a divalent or trivalent metal salt.

In some embodiments, methods of the current disclosure include a method for detecting a target analyte, the method comprising:

a) associating a covalent conjugate with the target analyte to form an analyte-targeting moiety complex, the covalent conjugate comprising:
   i) a targeting moiety that has affinity for the target analyte and comprises a reactive group Q' covalent bond to a polymeric dye; and
   ii) a the polymeric dye comprising:
      A) two or more fluorescent or colored moieties;
      B) at least one negatively charged group; and
      C) a complementary reactive group Q covalently bonded with the reactive group Q' on a covalent bond to the targeting moiety;
b) treating:
   i) the covalent conjugate and the target analyte with a divalent or trivalent metal salt during the associating the covalent conjugate and the target analyte; and/or
   ii) the analyte-targeting moiety complex with a wash solution comprising a divalent or trivalent metal salt after the associating the covalent conjugate and the target analyte; and
c) detecting a fluorescent or colored signal from the analyte-targeting moiety complex.

In embodiments, associating the covalent conjugate with the target analyte is performed in the presence of a divalent or trivalent metal salt. In embodiments, the methods further comprise substantially removing all of the divalent or trivalent salt from the analyte-targeting moiety complex before detecting the fluorescent or colored signal. In embodiments, the divalent or trivalent metal salt is removed from a buffer comprising the analyte-targeting moiety complex.

In embodiments, the methods further comprise forming the covalent conjugate. In embodiments, the polymeric dye and a divalent or trivalent salt have been admixed to form a composition comprising the polymeric dye and the divalent or trivalent salt prior to forming the covalent conjugate. In embodiments, the methods further comprise aging the composition comprising the polymeric dye and the divalent or trivalent salt prior to forming the covalent conjugate. In embodiments, divalent or trivalent salts are substantially absent while forming the covalent conjugate.

In embodiments, a composition of the disclosure comprises a covalent conjugate and a divalent or trivalent salt, the covalent conjugate comprising:
   i) a targeting moiety comprising a covalent bond to a polymeric dye;
   ii) the polymeric dye comprising:
      a) two or more fluorescent or colored moieties;
      b) at least one negatively charged group; and
      c) a covalent bond to the targeting moiety.

In embodiments, the targeting moiety has affinity for a target analyte. In embodiments, the targeting moiety comprises an antibody. In embodiments, the divalent or trivalent salt is a divalent salt. In embodiments, the divalent salt is a magnesium salt. In embodiments, the magnesium salt is magnesium chloride.

In embodiments, the fluorescent or colored moiety is a fluorescent moiety. In embodiments, the fluorescent or colored moiety is, at each occurrence, independently selected from the group consisting of a pyrene, perylene, perylene monoimide, and 6-FAM moiety. In embodiments, fluorescent or colored moiety is, at each occurrence, independently has one of the following structures:

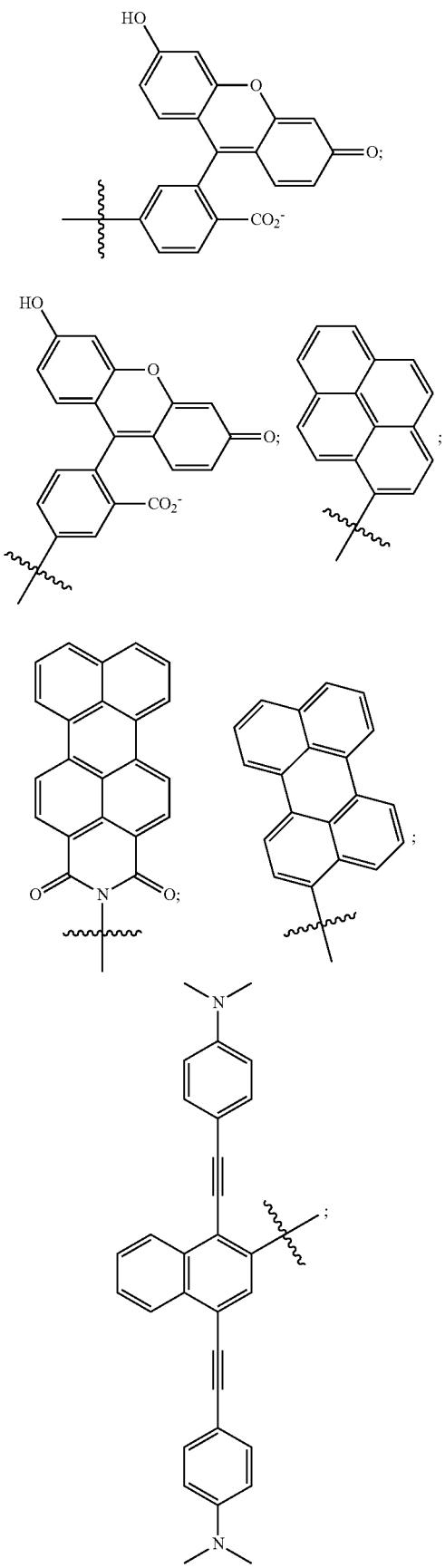

-continued

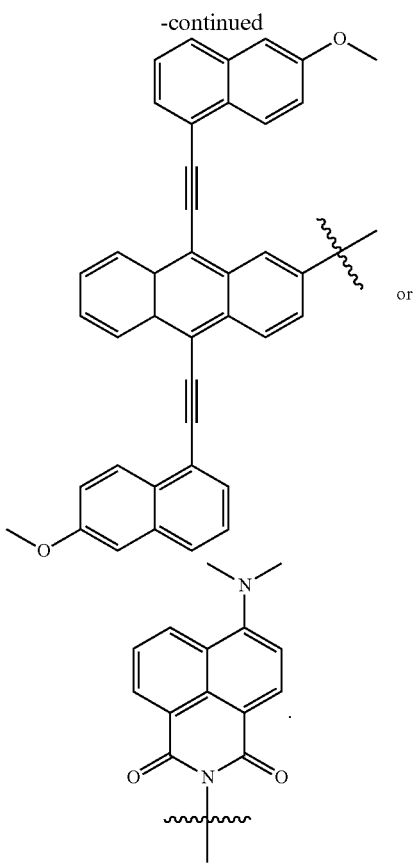

In embodiments, the polymeric dye comprises a plurality of negatively charged groups. In embodiments, the polymeric dye comprises two or more fluorescent or colored moieties, each of the two or more fluorescent or colored moieties joined to an adjacent fluorescent or colored moiety via a linker comprising the at least one negatively charged group.

In embodiments, the linker further comprises one or more alkylene or alkylene oxide moieties. In embodiments, the alkylene oxide moieties comprise polyethylene oxide moieties. In embodiments, the negatively charged group is a phosphate. In embodiments, the polymeric dye comprises from 2 to 100 fluorescent or colored moieties, the fluorescent or colored moieties being joined to an adjacent fluorescent or colored moiety via a linker comprising the at least one negatively charged group. In embodiments, the polymeric dye comprises from 2 to 10 fluorescent or colored moieties, the fluorescent or colored moieties being joined to an adjacent fluorescent or colored moiety via a linker comprising the at least one negatively charged group.

In embodiments, the methods further comprise purifying the covalent conjugate. In embodiments, purifying the covalent conjugate comprises substantially removing all of the divalent or trivalent salt from the covalent conjugate.

In embodiments, the covalent conjugate has a fluorescent extinction coefficient at least 1.1 times higher than a corresponding conjugate prepared in the absence of the divalent or trivalent salt. In embodiments, the covalent conjugate has a fluorescent extinction coefficient at least 1.2 times higher than a corresponding conjugate prepared in the absence of the divalent or trivalent salt.

In embodiments, the targeting moiety is an antibody.

In any of the embodiments above, the polymeric dye may be a compound of the structure (I) or structure (II).

In various embodiments, detecting the fluorescent or colored signal comprises the use of flow cytometry using techniques that are understood by one of skill in the art.

In embodiments, the compounds are useful in various analytical methods. For example, in certain embodiments the disclosure provides a method of staining a sample, the method comprising adding to said sample a compound of structure (I), for example wherein one of $R^2$ or $R^3$ is a linker comprising a covalent bond to an analyte molecule (e.g., biomolecule) or microparticle, and the other of $R^2$ or $R^3$ is H, OH, alkyl, alkoxy, alkylether or —OP(=$R_a$)($R_b$)$R_c$, in an amount sufficient to produce an optical response when said sample is illuminated at an appropriate wavelength.

In some embodiments of the foregoing methods, $R^2$ is a linker comprising a covalent linkage to an analyte molecule, such as a biomolecule. For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, $R^2$ is a linker comprising a covalent linkage to a solid support such as a microparticle. For example, in some embodiments the microparticle is a polymeric bead or nonpolymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, such as a biomolecule, comprising:
(a) providing a compound of structure (I), for example, wherein one of $R^2$ or $R^3$ is a linker comprising a covalent bond to the analyte molecule, and the other of $R^2$ or $R^3$ is H, OH, alkyl, alkoxy, alkylether or —OP(=$R_a$)($R_b$)$R_c$; and
(b) detecting the compound by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In other embodiments, a method for visually detecting an analyte molecule, such as a biomolecule is provided, the method comprising:
(a) admixing any of the foregoing compounds with one or more analyte molecules; and
(b) detecting the compound by its visible properties.

In other embodiments is provided a method for visually detecting an analyte molecule, the method comprising:
(a) admixing the compound of claim 1, wherein $R^2$ or $R^3$ is Q or a linker comprising a covalent bond to Q, with the analyte molecule;
(b) forming a conjugate of the compound and the analyte molecule; and
(c) detecting the conjugate by its visible properties.

Other exemplary methods include a method for detecting an analyte, the method comprising:

(a) providing a compound of structure (I), wherein $R^2$ or $R^3$ comprises a linker comprising a covalent bond to a targeting moiety having specificity for the analyte;

(b) admixing the compound and the analyte, thereby associating the targeting moiety and the analyte; and (c) detecting the compound, for example by its visible or fluorescent properties.

In certain embodiments of the foregoing methods, the analyte is a particle, such as a cell, and the method includes use of flow cytometry. For example, the compound may be provided with a targeting moiety, such as an antibody, for selectively associating with the desired cell, thus rendering the cell detectable by any number of techniques, such as visible or fluorescence detection. Appropriate antibodies can be selected by one of ordinary skill in the art depending on the desired end use. Exemplary antibodies for use in certain embodiments include UCHT1 and MOPC-21.

Embodiments of the present compounds thus find utility in any number of methods, including: cell counting; cell sorting; biomarker detection; quantifying apoptosis; determining cell viability; identifying cell surface antigens; determining total DNA and/or RNA content; identifying specific nucleic acid sequences (e.g., as a nucleic acid probe); and diagnosing diseases, such as blood cancers.

In addition to the above methods, embodiments of the compounds of structure (I) find utility in various disciplines and methods, including: imaging in endoscopy procedures for identification of cancerous and other tissues; single-cell and/or single molecule analytical methods, for example detection of polynucleotides with little or no amplification; cancer imaging, for example by including a targeting moiety, such as an antibody or sugar or other moiety that preferentially binds cancer cells, in a compound of structure (I); imaging in surgical procedures; binding of histones for identification of various diseases; drug delivery, for example by replacing the M moiety in a compound of structure (I) with an active drug moiety; and/or contrast agents in dental work and other procedures, for example by preferential binding of the compound of structure (I) to various flora and/or organisms.

It is understood that any embodiment of the compounds of structure (I), as set forth above, and any specific choice set forth herein for a $R^1$, $R^2$, $R^3$, $R^4$, $R^5$, $L^1$, $L^1$, $L^2$, $L^3$, $L^4$, M, m and/or n variable in the compounds of structure (I), as set forth above, may be independently combined with other embodiments and/or variables of the compounds of structure (I) to form embodiments of the invention not specifically set forth above. In addition, in the event that a list of choices is listed for any particular $R^1$, $R^2$, $R^3$, $R^4$, $R^5$, L', $L^1$, $L^2$, $L^3$, $L^4$, M, m and/or n variable in a particular embodiment and/or claim, it is understood that each individual choice may be deleted from the particular embodiment and/or claim and that the remaining list of choices will be considered to be within the scope of the invention.

In further embodiments of the present invention, the fluorescent and/or colored dyes used in various methods and compositions described herein may be dimers and higher polymers of fluorescent and/or colored moieties. The fluorescent and/or colored moieties are linked by linkers having multiple positively charged moieties or multiple negatively charges moieties at the pH at which an assay is conducted.

Accordingly, in some embodiments the compounds have the following structure (A):

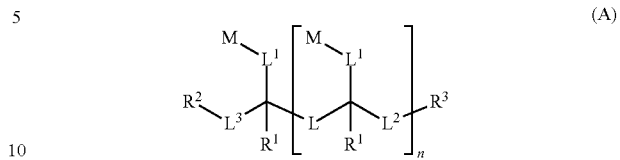

wherein L is a linker sufficient to maintain spatial separation between one or more (e.g., each) M group so that intramolecular quenching is reduced or eliminated, and $R^1$, $R^2$, $R^3$, $L^1$, $L^2$, $L^3$ and n are as defined for structure (I). In some embodiments of structure (A), L is a linker comprising one or more ethylene glycol or polyethylene glycol moieties.

In other embodiments is provided a compound having the following structure (I):

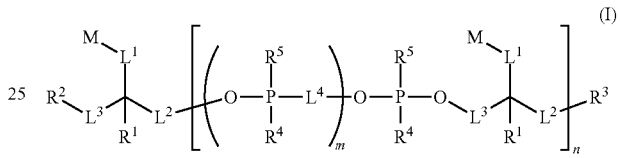

or a stereoisomer, salt or tautomer thereof, wherein:
M is, at each occurrence, independently a moiety comprising two or more carbon-carbon double bonds and at least one degree of conjugation;

$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently a heteroalkylene, heteroalkenylene or heteroalkynylene linker of greater than three atoms in length, wherein the heteroatoms in the heteroalkylene, heteroalkenylene and heteroalkynylene linker are selected from O, N and S;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q or L';

$R^4$ is, at each occurrence, independently OH, SH, O$^-$, S$^-$, O$R_d$ or S$R_d$;

$R^5$ is, at each occurrence, independently oxo, thioxo or absent;

$R_a$ is O or S;

$R_b$ is OH, SH, O$^-$, S$^-$, O$R_d$ or S$R_d$;

$R_c$ is OH, SH, O$^-$, S$^-$, O$R_d$, OL', S$R_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected analogue thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater, provided that at least one occurrence of m is an integer of one or greater; and n is an integer of one or greater.

In different embodiments of the compound of structure (I):

M is, at each occurrence, independently a moiety comprising two or more carbon-carbon double bonds and at least one degree of conjugation;

$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently a heteroalkylene, heteroalkenylene or heteroalkynylene linker of greater than three atoms in length, wherein the heteroatoms in the heteroalkylene, heteroalkenylene and heteroalkynylene linker are selected from O, N and S;

$R^1$ is, at each occurrence, independently H, alkyl or alkoxy;

$R^2$ and $R^3$ are each independently H, OH, SH, alkyl, alkoxy, alkylether, $-OP(=R_a)(R_b)R_c$, Q, a linker comprising a covalent bond to Q, a linker comprising a covalent bond to an analyte molecule, a linker comprising a covalent bond to a solid support or a linker comprising a covalent bond to a further compound of structure (I), wherein: $R_a$ is O or S; $R_b$ is OH, SH, O$^-$, S$^-$, OR$_d$ or SR$_d$; $R_c$ is OH, SH, O$^-$, S$^-$, OR$_d$, SR$_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;

$R^4$ is, at each occurrence, independently OH, SH, O$^-$, S$^-$, OR$_d$ or SR$_d$;

$R^5$ is, at each occurrence, independently oxo, thioxo or absent;

Q is, at each occurrence, independently a moiety comprising a reactive group capable of forming a covalent bond with an analyte molecule, a solid support or a complementary reactive group Q;

m is, at each occurrence, independently an integer of zero or greater, provided that at least one occurrence of m is an integer of one or greater; and n is an integer of one or greater.

The various linkers and substituents (e.g., M, Q, $R^1$, $R^2$, $R^3$, $R^c$, $L^1$, $L^2$, $L^3$ and $L^4$) in the compound of structure (I) are optionally substituted with one more substituent. For example, in some embodiments the optional substituent is selected to optimize the water solubility or other property of the compound of structure (I). In certain embodiments, each alkyl, alkoxy, alkylether, alkoxyalkylether, phosphoalkyl, thiophosphoalkyl, phosphoalkylether and thiophosphoalkyl-ether in the compound of structure (I) is optionally substituted with one more substituent selected from the group consisting of hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether. In certain embodiments the optional substituent is $-OP(=R_a)(R_b)R_c$, where $R_a$, $R_b$ and $R_c$ are as defined for the compound of structure (I).

In some embodiments, $L^1$ is at each occurrence, independently an optional alkylene, alkenylene, alkynylene, heteroalkylene, heteroalkenylene, heteroalkynylene or heteroatomic linker. In other embodiments, $L^1$ is at each occurrence, independently a linker comprising a functional group capable of formation by reaction of two complementary reactive groups, for example a Q group.

In some embodiments, $L^4$ is at each occurrence, independently a heteroalkylene linker. In other more specific embodiments, $L^4$ is at each occurrence, independently an alkylene oxide linker.

In embodiments, the polymeric dye has the following structure (I):

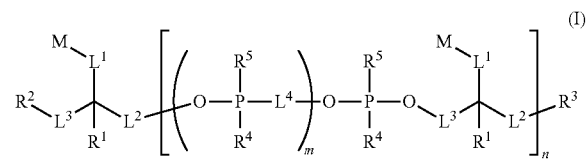

or a stereoisomer, salt or tautomer thereof, wherein:

M is, at each occurrence, independently a moiety comprising the fluorescent or colored moiety;

$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently an alkylene or alkylene oxide linker;

$R^1$ is, at each occurrence, independently H, alkyl or alkoxy;

$R^2$ and $R^3$ are each independently H, OH, SH, alkyl, alkoxy, alkylether, heteroalkyl, $-OP(=R_a)(R_b)R_c$, Q, or a protected form thereof, or L';

$R^4$ is, at each occurrence, independently OH, SH, O$^-$, S$^-$, OR$_d$ or SR$_d$;

$R^5$ is, at each occurrence, independently oxo, thioxo or absent;

$R_a$ is O or S;

$R_b$ is OH, SH, O$^-$, S$^-$, OR$_d$ or SR$_d$;

$R_c$ is OH, SH, O$^-$, S$^-$, OR$_d$, OL', SR$_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

L' is, at each occurrence, independently a linker comprising a covalent bond to Q, a linker comprising a covalent bond to the targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater, provided that at least one occurrence of m is an integer of one or greater, such that the compound includes at least one $L^4$; and n is an integer of one or greater.

For example, in some embodiments $L^4$ is polyethylene oxide, and the compound has the following structure (IA):

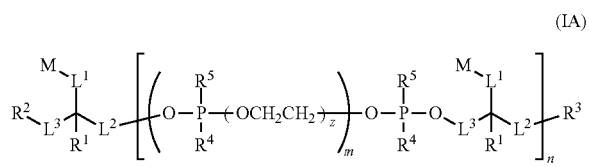

(IA)

wherein z is an integer from 2 to 100. In some embodiments of (IA), z is an integer from 2-30, for example from about 20 to 25, or about 23. In some embodiments, z is an integer from 2 to 10, for example from 3 to 6. In some embodiments, z is 3. In some embodiments, z is 4. In some embodiments, z is 5. In some embodiments, z is 6.

The optional linker $L^1$ can be used as a point of attachment of the M moiety to the remainder of the compound. For example, in some embodiments a synthetic precursor to the compound of structure (I) is prepared, and the M moiety is attached to the synthetic precursor using any number of facile methods known in the art, for example methods referred to as "click chemistry." For this purpose any reaction which is rapid and substantially irreversible can be used to attach M to the synthetic precursor to form a compound of structure (I). Exemplary reactions include the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2]cycloaddition, alkene and tetrazine inverse-demand Diels-Alder, alkene and tetrazole photoreaction and various displacement reactions, such as displacement of a leaving group by nucleophilic attack on an electrophilic atom. Exemplary displacement reactions include reaction of an amine with: an activated ester; an N-hydroxysuccinimide ester; an isocyanate; an isothioscyanate or the like. In some embodiments the reaction to form $L^1$ may be performed in an aqueous environment.

Accordingly, in some embodiments $L^1$ is at each occurrence a linker comprising a functional group capable of formation by reaction of two complementary reactive groups, for example a functional group which is the product of one of the foregoing "click" reactions. In various embodiments, for at least one occurrence of the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester (e.g., N-hydroxysuccinimide ester), ketone, α,β-unsaturated carbonyl, alkene, maleimide, α-haloimide, epoxide, aziridine, tetrazine, tetrazole, phosphine, biotin or thiirane functional group with a complementary reactive group. For example, reaction of an amine with an N-hydroxysuccinimide ester or isothiocyanate.

In other embodiments, for at least one occurrence of $L^1$, the functional group can be formed by reaction of an alkyne and an azide. In other embodiments, for at least one occurrence of $L^1$, the functional group can be formed by reaction of an amine (e.g., primary amine) and an N-hydroxysuccinimide ester or isothiocyanate.

In more embodiments, for at least one occurrence of $L^1$, the functional group comprises an alkene, ester, amide, thioester, disulfide, carbocyclic, heterocyclic or heteroaryl group. In more embodiments, for at least one occurrence of $L^1$, the functional group comprises an alkene, ester, amide, thioester, thiourea, disulfide, carbocyclic, heterocyclic or heteroaryl group. In other embodiments, the functional group comprises an amide or thiourea. In some more specific embodiments, for at least one occurrence of $L^1$, $L^1$ is a linker comprising a triazolyl functional group. While in other embodiments, for at least one occurrence of $L^1$, $L^1$ is a linker comprising an amide or thiourea functional group.

In still other embodiments, for at least one occurrence of $L^1$, $L^1$-M has the following structure:

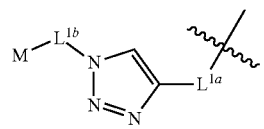

wherein $L^{1a}$ and $L^{1b}$ are each independently optional linkers.

In different embodiments, for at least one occurrence of $L^1$, $L^1$-M has the following structure:

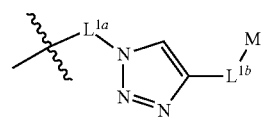

wherein $L^{1a}$ and $L^{1b}$ are each independently optional linkers.

In various embodiments of the foregoing, $L^{1a}$ or $L^{1b}$, or both, is absent. In other embodiments, $L^{1a}$ or $L^{1b}$, or both, is present.

In some embodiments $L^{1a}$ and $L^{1b}$, when present, are each independently alkylene or heteroalkylene. For example, in some embodiments $L^{1a}$ and $L^{1b}$, when present, independently have one of the following structures:

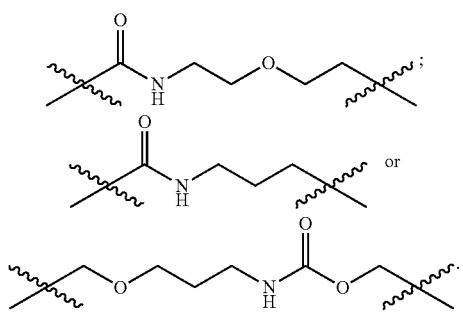

In still other different embodiments of structure (I), $L^1$ is at each occurrence, independently an optional alkylene or heteroalkylene linker. In certain embodiments, $L^1$ has one of the following structures:

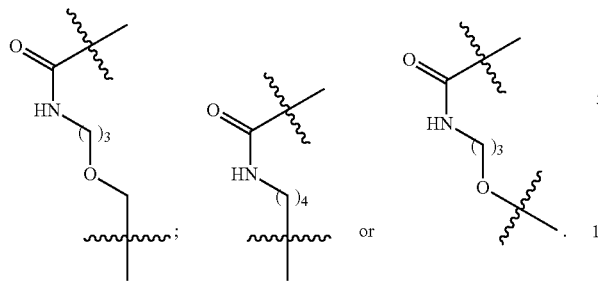

In more embodiments, $L^2$ and $L^3$ are, at each occurrence, independently $C_1$-$C_6$ alkylene, $C_2$-$C_6$ alkenylene or $C_2$-$C_6$ alkynylene. For example, in some embodiments the compound has the following structure (IB):

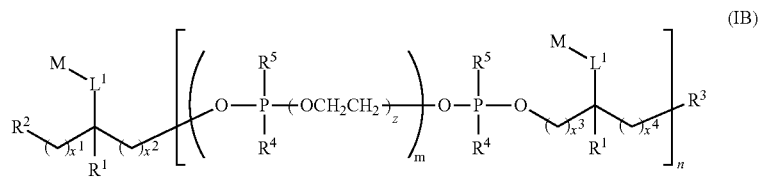

(IB)

wherein:

$x^1$, $x^2$, $x^3$ and $x^4$ are, at each occurrence, independently an integer from 0 to 6; and z is an integer from 2 to 100, for example from 3 to 6.

In certain embodiments of the compound of structure (IB), at least one occurrence of $x^1$, $x^2$, $x^3$ or $x^4$ is 1. In other embodiments, $x^1$, $x^2$, $x^3$ and $x^4$ are each 1 at each occurrence. In other embodiments, $x^1$ and $x^3$ are each 0 at each occurrence. In some embodiments, $x^2$ and $x^4$ are each 1 at each occurrence. In still other embodiments, $x^1$ and $x^3$ are each 0 at each occurrence, and $x^2$ and $x^4$ are each 1 at each occurrence.

In some more specific embodiments of the compound of structure (TB), $L^1$, at each occurrence, independently comprises a triazolyl functional group. In some other specific embodiments of the compound of structure (TB), $L^1$, at each occurrence, independently comprises an amide or thiourea functional group. In other embodiments of the compound of structure (IB), $L^1$, at each occurrence, independently an optional alkylene or heteroalkylene linker.

In still other embodiments of any of the compounds of structure (I), $R^4$ is, at each occurrence, independently OH, $O^-$ or $OR_d$. It is understood that "$OR_d$" and "$SR_d$" are intended to refer to $O^-$ and $S^-$ associated with a cation. For example, the disodium salt of a phosphate group may be represented as:

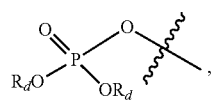

where $R_d$ is sodium ($Na^+$).

In other embodiments of any of the compounds of structure (I), $R^5$ is, at each occurrence, oxo.

In some different embodiments of any of the foregoing compounds, le is H.

In other various embodiments, $R^2$ and $R^3$ are each independently OH or —OP(=$R_a$)($R_b$)$_c$. In some different embodiments, $R^2$ or $R^3$ is OH or —OP(=$R_a$)($R_b$)$R_c$, and the other of $R^2$ or $R^3$ is Q or a linker comprising a covalent bond to Q.

In still more different embodiments of any of the foregoing compounds of structure (I), $R^2$ and $R^3$ are each independently —OP(=$R_a$)($R_b$)$_c$. In some of these embodiments, $R_c$ is OL'.

In other embodiments, $R^2$ and $R^3$ are each independently —OP(=$R_a$)($R_b$)OL', and L' is an alkylene or heteroalkylene linker to: Q, a targeting moiety, an analyte (e.g., analyte molecule), a solid support, a solid support residue, a nucleoside or a further compound of structure (I).

The linker L' can be any linker suitable for attaching Q, a targeting moiety, an analyte (e.g., analyte molecule), a solid support, a solid support residue, a nucleoside or a further compound of structure (I) to the compound of structure (I). Advantageously certain embodiments include use of L' moieties selected to increase or optimize water solubility of the compound. In certain embodiments, L' is a heteroalkylene moiety. In some other certain embodiments, L' comprises an alkylene oxide or phosphodiester moiety, or combinations thereof.

In certain embodiments, L' has the following structure:

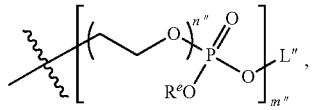

wherein:

m" and n" are independently an integer from 1 to 10;

$R^e$ is H, an electron pair or a counter ion;

L" is $R^e$ or a direct bond or linkage to: Q, a targeting moiety, an analyte (e.g., analyte molecule), a solid support, a solid support residue, a nucleoside or a further compound of structure (I).

In some embodiments, m" is an integer from 4 to 10, for example 4, 6 or 10. In other embodiments n" is an integer from 3 to 6, for example 3, 4, 5 or 6.

In some other embodiments, L" is an alkylene or heteroalkylene moiety. In some other certain embodiments, L" comprises an alkylene oxide, phosphodiester moiety, sulfhydryl, disulfide or maleimide moiety or combinations thereof.

In certain of the foregoing embodiments, the targeting moiety is an antibody or cell surface receptor antagonist.

In other more specific embodiments of any of the foregoing compounds of structure (I), $R^2$ or $R^3$ has one of the following structures:

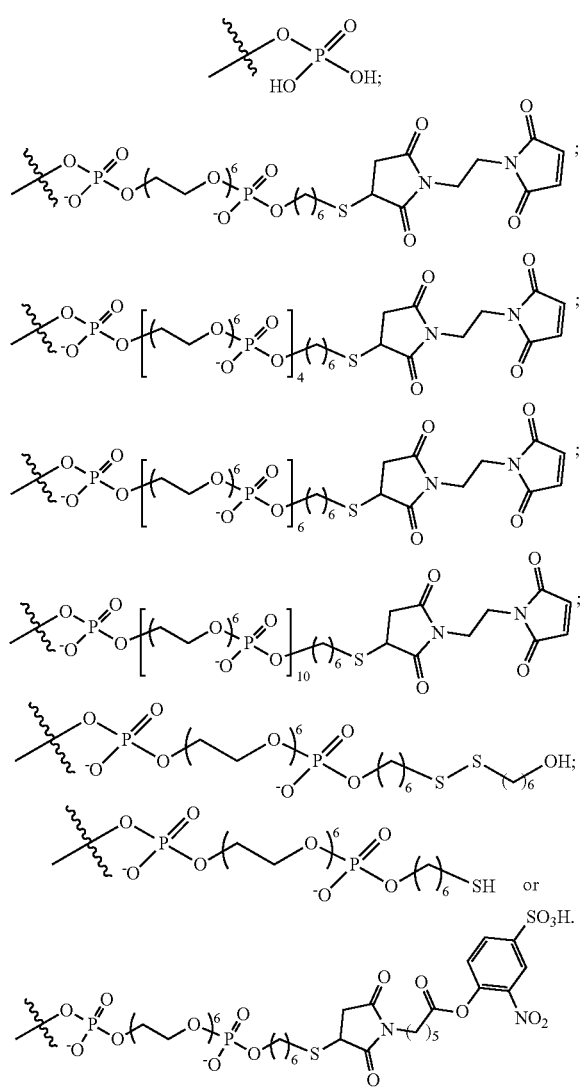

Certain embodiments of compounds of structure (I) can be prepared according to solid-phase synthetic methods analogous to those known in the art for preparation of oligonucleotides. Accordingly, in some embodiments, L' is a linkage to a solid support, a solid support residue or a nucleoside. Solid supports comprising an activated deoxythymidine (dT) group are readily available, and in some embodiments can be employed as starting material for preparation of compounds of structure (I). Accordingly, in some embodiments $R^2$ or $R^3$ has the following structure:

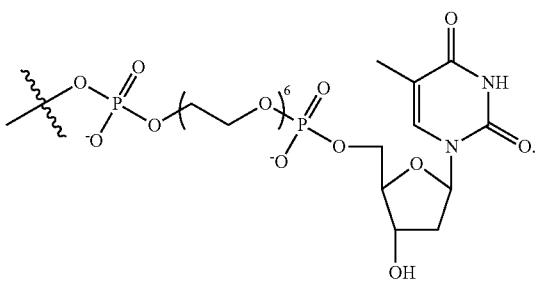

One of skill in the art will understand that the dT group depicted above is included for ease of synthesis and economic efficiencies only, and is not required. Other solid supports can be used and would result in a different nucleoside or solid support residue being present on L', or the nucleoside or solid support residue can be removed or modified post synthesis.

In still other embodiments, Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (I) (e.g., in the $R^2$ or $R^3$ position), and Q and Q' comprise complementary reactive groups such that reaction of the compound of structure (I) and the further compound of structure (I) results in covalently bound dimer of the compound of structure (I). Multimer compounds of structure (I) can also be prepared in an analogous manner and are included within the scope of embodiments of the invention.

The type of Q group and connectivity of the Q group to the remainder of the compound of structure (I) is not limited, provided that Q comprises a moiety having appropriate reactivity for forming the desired bond.

In certain embodiments, Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (I) comprise Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

The Q groups can be conveniently provided in protected form to increase storage stability or other desired properties, and then the protecting group removed at the appropriate time for conjugation with, for example, a targeting moiety or analyte. Accordingly, Q groups include "protected forms" of a reactive group, including any of the reactive groups described above and in the Table 1 below. A "protected form" of Q refers to a moiety having lower reactivity under predetermined reaction conditions relative to Q, but which can be converted to Q under conditions, which preferably do not degrade or react with other portions of the compound of structure (I). One of skill in the art can derive appropriate protected forms of Q based on the particular Q and desired end use and storage conditions. For example, when Q is SH, a protected form of Q includes a disulfide, which can be reduce to reveal the SH moiety using commonly known techniques and reagents.

Exemplary Q moieties are provided in Table 1 below.

TABLE 1

| Exemplary Q Moieties | |
|---|---|
| Structure | Class |
| —SH | Sulfhydryl |
| —N=C=S | Isothiocyanate |
| (methyl imidoester, NH$_2^+$Cl$^-$) | Imidoester |
| (acyl azide structure) | Acyl Azide |
| (tetrafluorophenyl ester) | Activated Ester |
| (pentafluorophenyl ester) | Activated Ester |
| (sulfo-nitrophenyl ester) | Activated Ester |
| (thiosuccinimide-linked sulfo-nitrophenyl ester) | Activated Ester |
| (NHS ester) | Activated Ester |

TABLE 1-continued

| Exemplary Q Moieties | |
|---|---|
| Structure | Class |
| (sulfo-NHS ester) | Activated Ester |
| —S(O)$_2$—X, X = halo | Sulfonyl halide |
| (maleimide) | Maleimide |
| (thiosuccinimide-ethyl-maleimide) | Maleimide |
| (SMCC-type cyclohexyl maleimide amide) | Maleimide |
| —NHC(O)CH$_2$X, X = halo | α-haloimide |
| (pyridyl disulfide) | Disulfide |
| (phosphine, Staudinger reagent with PPh$_2$) | Phosphine |
| —N$_3$ | Azide |

TABLE 1-continued

Exemplary Q Moieties

| Structure | Class |
|---|---|
| (alkyne structure) | Alkyne |
| (biotin structure) | Biotin |
| (diene structure) | Diene |
| (alkene structure) | Alkene/dienophile |
| (alkene with EWG) | Alkene/dienophile |
| —NH$_2$ | Amino |

EWG = electron withdrawing group

In embodiments, Q is a moiety selected from Table 1.

It should be noted that in some embodiments, wherein Q is SH, the SH moiety will tend to form disulfide bonds with another sulfhydryl group, for example on another compound of structure (I). Accordingly, some embodiments include compounds of structure (I), which are in the form of disulfide dimers, the disulfide bond being derived from SH Q groups.

Also included within the scope of certain embodiments are compounds of structure (I), wherein one, or both, of R$^2$ and R$^3$ comprises a linkage to a further compound of structure (I). For example, wherein one or both of R$^2$ and R$^3$ are —OP($=$R$_a$)(R$_b$)R$_c$, and R$_c$ is OL', and L' is a linker comprising a covalent bond to a further compound of structure (I). Such compounds can be prepared by preparing a first compound of structure (I) having for example about 10 "M" moieties (i.e., n=9) and having an appropriate "Q" for reaction with a complementary Q' group on a second compound of structure (I). In this manner, compounds of structure (I), having any number of "M" moieties, for example 100 or more, can be prepared without the need for sequentially coupling each monomer. Exemplary embodiments of such compounds of structure (I) have the following structure (I')

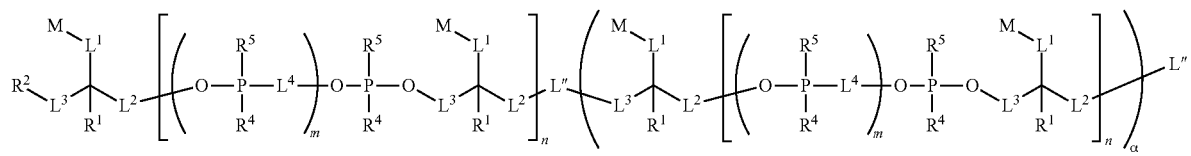

(I')

wherein:
each occurrence of R$^1$, R$^2$, R$^3$, R$^4$, R$^5$, L$^1$, L$^2$, L$^3$, L$^4$, M, m and n are independently as defined for a compound of structure (I);
L" is a linker comprising a functional group resulting from reaction of a Q moiety with a corresponding Q' moiety; and
α is an integer greater than 1, for example from 1 to 100, or 1 to 10.

An exemplary compound of structure (I') is provided in Example 5. Other compounds of structure (I') are derivable by those of ordinary skill in the art, for example by dimerizing or polymerizing compounds of structure (I) provided herein.

In other embodiments, the Q moiety is conveniently masked (e.g., protected) as a disulfide moiety, which can later be reduced to provide an activated Q moiety for binding to a desired analyte molecule or targeting moiety. For example, the Q moiety may be masked as a disulfide having the following structure:

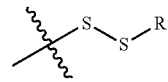

wherein R is an optionally substituted alkyl group. For example, in some embodiments, Q is provided as a disulfide moiety having the following structure:

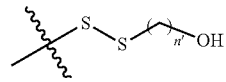

where n is an integer from 1 to 10, for example 6.

In some other embodiments, one of R$^2$ or R$^3$ is OH or —OP($=$R$_a$)(R$_b$)R$_c$, and the other of R$^2$ or R$^3$ is a linker comprising a covalent bond to an analyte molecule or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In still different embodiments, the solid support is a polymeric bead or nonpolymeric bead.

The value for m is another variable that can be selected based on the desired fluorescence and/or color intensity. In some embodiments, m is, at each occurrence, independently an integer from 1 to 10. In other embodiments, m is, at each occurrence, independently an integer from 1 to 5, for example 1, 2, 3, 4 or 5.

In other embodiments, m is, at each occurrence, independently an integer greater than 2, and z is an integer from 3 to 10, for example in some embodiment m is, at each occurrence, independently an integer greater than 2, such as 3, 4, 5 or 6, and z is an integer from 3 to 6.

The fluorescence intensity can also be tuned by selection of different values of n. In certain embodiments, n is an integer from 1 to 100. In other embodiments, n is an integer from 1 to 10. In some embodiments n is 1. In some embodiments n is 2. In some embodiments n is 3. In some embodiments n is 4. In some embodiments n is 5. In some embodiments n is 6. In some embodiments n is 7. In some embodiments n is 8. In some embodiments n is 9. In some embodiments n is 10.

M is selected based on the desired optical properties, for example based on a desired color and/or fluorescence emission wavelength. In some embodiments, M is the same at each occurrence; however, it is important to note that each occurrence of M need not be an identical M, and certain embodiments include compounds wherein M is not the same at each occurrence. For example, in some embodiments each M is not the same and the different M moieties are selected to have absorbance and/or emissions for use in fluorescence resonance energy transfer (FRET) methods. For example, in such embodiments the different M moieties are selected such that absorbance of radiation at one wavelength causes emission of radiation at a different wavelength by a FRET mechanism. Exemplary M moieties can be appropriately selected by one of ordinary skill in the art based on the desired end use. Exemplary M moieties for FRET methods include fluorescein and 5-TAMRA (5-carboxytetramethylrhodamine, succinimidyl ester) dyes.

M may be attached to the remainder of the molecule from any position (i.e., atom) on M. One of skill in the art will recognize means for attaching M to the remainder of molecule. Exemplary methods include the "click" reactions described herein.

In some embodiments, M is a fluorescent or colored moiety. In embodiments, M is a fluorescent moiety. In embodiments, M is a colored moiety. Any fluorescent and/or colored moiety may be used, for examples those known in the art and typically employed in colorimetric, UV, and/or fluorescent assays may be used. Examples of M moieties which are useful in various embodiments of the invention include: Xanthene derivatives (e.g., fluorescein, rhodamine, Oregon green, eosin or Texas red); Cyanine derivatives (e.g., cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary M moieties include: Cyanine dyes, xanthate dyes (e.g., Hex, Vic, Nedd, Joe or Tet); Yakima yellow; Redmond red; tamra; texas red and Alexa Fluor® dyes.

In still other embodiments of any of the foregoing, M comprises three or more aryl or heteroaryl rings, or combinations thereof, for example four or more aryl or heteroaryl rings, or combinations thereof, or even five or more aryl or heteroaryl rings, or combinations thereof. In some embodiments, M is, at each occurrence, independently a moiety comprising four or more aryl or heteroaryl rings, or combinations thereof. In some embodiments, M comprises six aryl or heteroaryl rings, or combinations thereof. In further embodiments, the rings are fused. For example in some embodiments, M comprises three or more fused rings, four or more fused rings, five or more fused rings, or even six or more fused rings. In embodiments, M, at each occurrence, independently comprises a fused-multicyclic aryl moiety comprising at least four fused rings.

In some embodiments, M is cyclic. For example, in some embodiments M is carbocyclic. In other embodiment, M is heterocyclic. In still other embodiments of the foregoing, M, at each occurrence, independently comprises an aryl moiety. In some of these embodiments, the aryl moiety is multicyclic. In other more specific examples, the aryl moiety is a fused-multicyclic aryl moiety, for example which may comprise at least 3, at least 4, or even more than 4 aryl rings.

In other embodiments of any of the foregoing compounds of structure (I), (IA), (IB) or (I'), M, at each occurrence, independently comprises at least one heteroatom. For example, in some embodiments, the heteroatom is nitrogen, oxygen or sulfur.

In still more embodiments of any of the foregoing, M, at each occurrence, independently comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, M, at each occurrence, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorobora-diaza-indacene)phenyl, quaterphenyl, bi-benzothiazole, ter-benzothiazole, bi-naphthyl, bi-anthracyl, squaraine, squarylium, 9,10-ethynylanthracene or ter-naphthyl moiety. In other embodiments, M is, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, M is, at each occurrence, independently a coumarin dye, resorufin dye, dipyrromethenboron difluoride dye, ruthenium bipyridyl dye, energy transfer dye, thiazole orange dye, polymethine or N-aryl-1,8-naphthalimide dye.

In still more embodiments of any of the foregoing, M at each occurrence is the same. In other embodiments, each M is different. In still more embodiments, one or more M is the same and one or more M is different.

In some embodiments, M is pyrene, perylene, perylene monoimide or 6-FAM or a derivative thereof. In some other embodiments, M has one of the following structures:

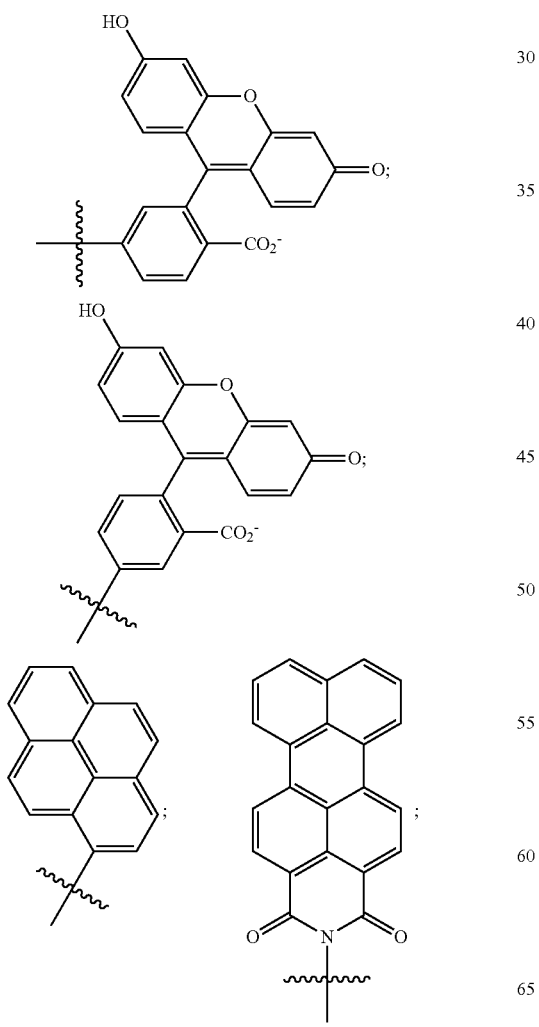

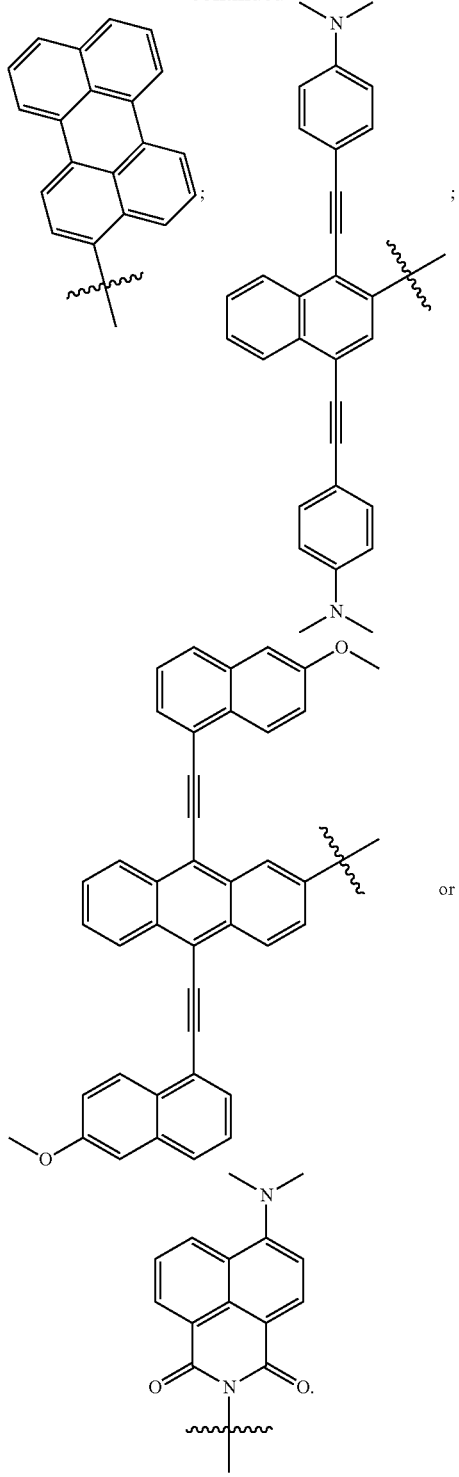

Although M moieties comprising carboxylic acid groups are depicted in the anionic form ($CO_2^-$) above, one of skill in the art will understand that this will vary depending on pH, and the protonated form ($CO_2H$) is included in various embodiments.

In some specific embodiments, the compound is a compound selected from Table 2. The compounds in Table 2 were prepared according to the procedures set forth in the Examples and their identity confirmed by mass spectrometry.

TABLE 2

Exemplary Compounds of Structure I

| No. | MW. Found Calc. | Structure |
|---|---|---|
| I-1 | 1364.6 1365.2 | 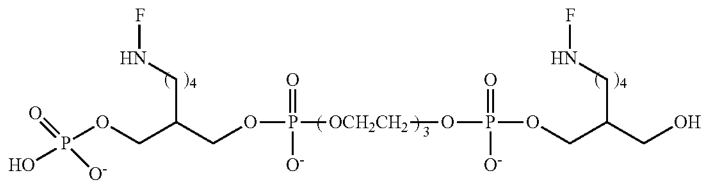 |
| I-2 | 1576.2 1577.3 | 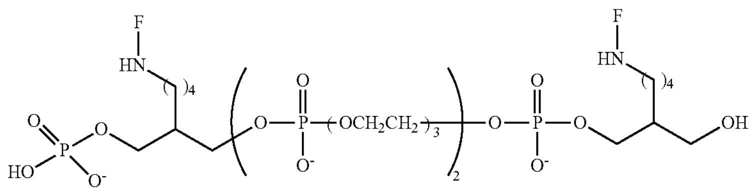 |
| I-3 | 1497.4 1497.3 | 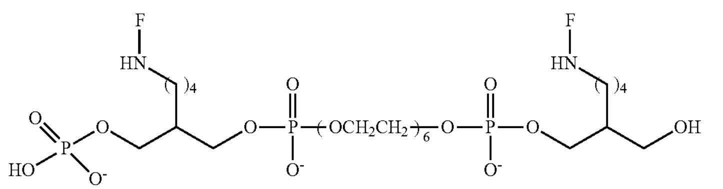 |
| I-4 | 1841.4 1841.6 | 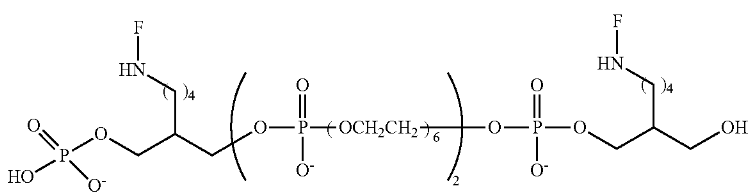 |
| I-5 | 2185.8 2185.9 | 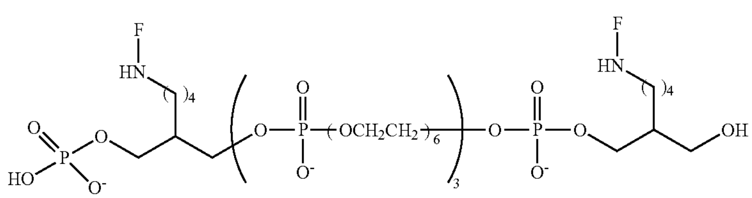 |
| I-6 | 2532.2 2530.2 | 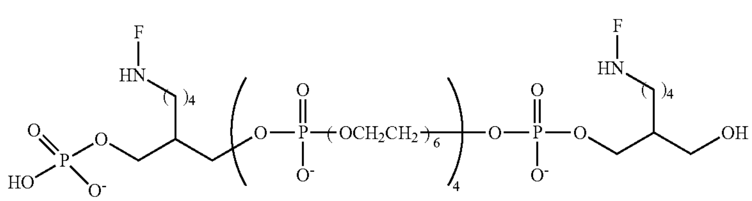 |
| I-7 | 1789.6 1789.5 | 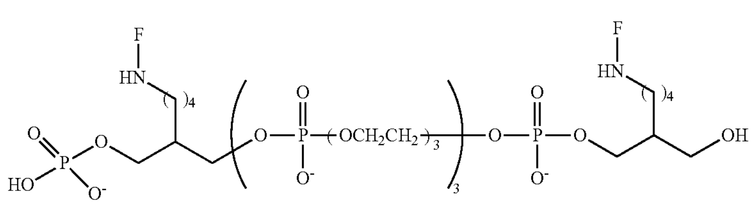 |

TABLE 2-continued

Exemplary Compounds of Structure I

| No. | MW. Found Calc. | Structure |
|---|---|---|
| I-8 | 2001.6 / 2001.6 | 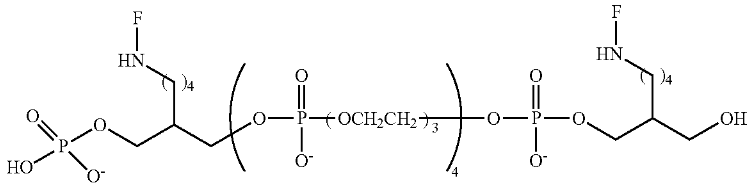 |
| I-9 | 2213.5 / 2213.8 | 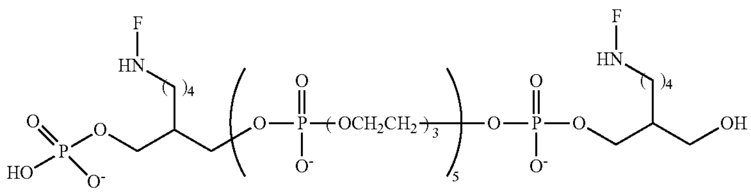 |
| I-10 | 4481.6 / 4480.9 | 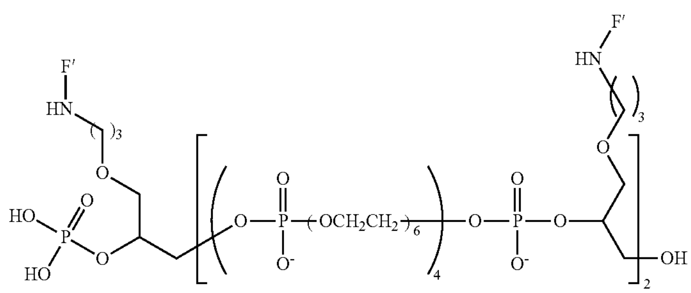 |
| I-11 | 8375.9 / 8374.3 | 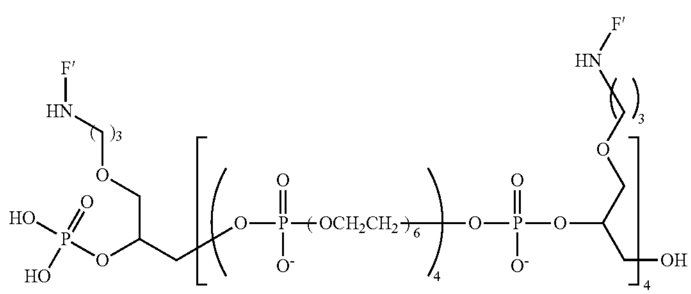 |
| I-12 | TBD | z = 3, 4, 5 or 6; m = 2, 3, 4 or 5; n = 1-10 |
| I-13 | TBD | 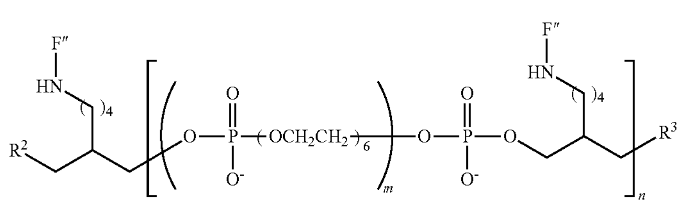 |

TABLE 2-continued
Exemplary Compounds of Structure I
| No. | MW. Found Calc. | Structure |
|---|---|---|
| I-14 | TBD | 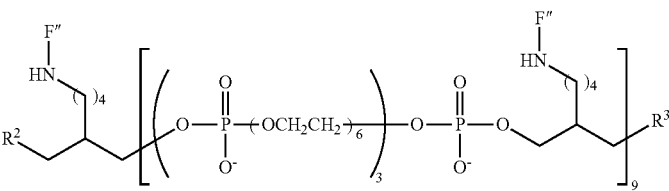 |
| I-15 | TBD | 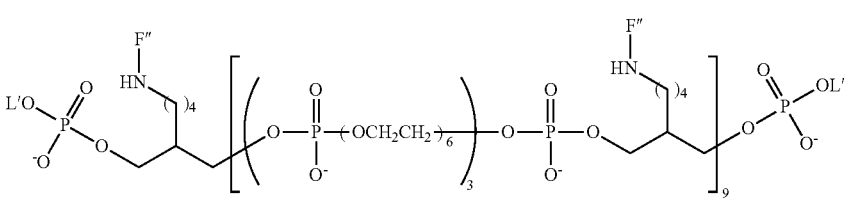 |
| I-16 | TBD | 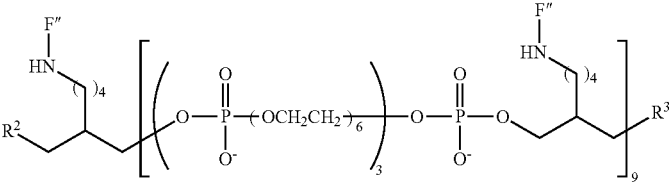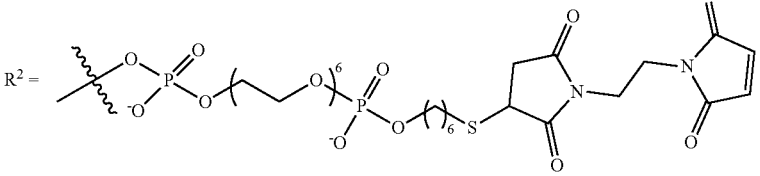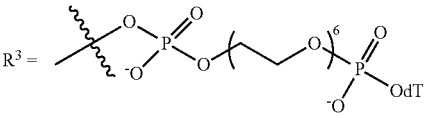 |
| I-17 | 15684.6<br>15681.5 | 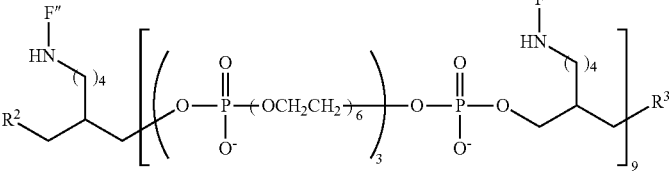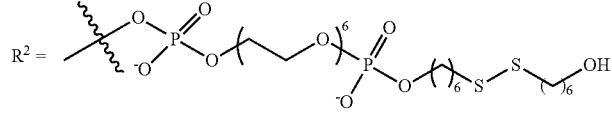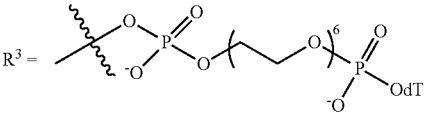 |

TABLE 2-continued

Exemplary Compounds of Structure I

| No. | MW. Found Calc. | Structure |
|---|---|---|
| I-18 | TBD | |
| I-19 | TBD | |
| I-20 | TBD | |

A = antibody (for I-19)

TABLE 2-continued
Exemplary Compounds of Structure I
| No. | MW. Found Calc. | Structure |
|---|---|---|
| I-21 | TBD | 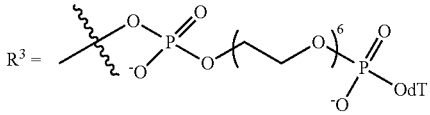 |
| I-22 | TBD | 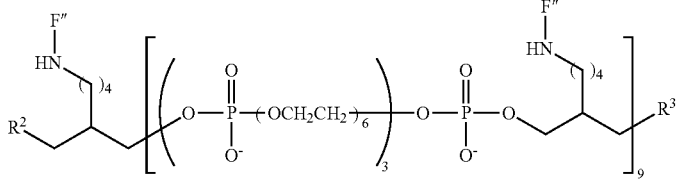 |
| I-23 | TBD | 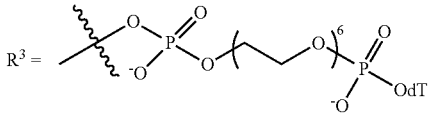 |
m″ = 4 (I-21A)
m″ = 10 (I-21B)
m″ = 4 or 10
A = antibody TABLE 2-continued Exemplary Compounds of Structure I

| No. | MW. Found Calc. | Structure |
|---|---|---|
| I-24 | TBD | 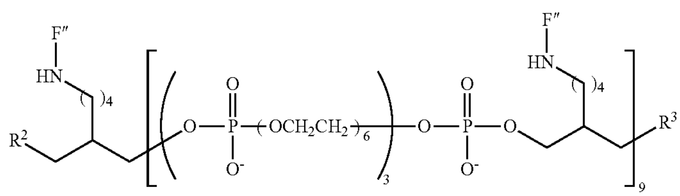 |
| I-25 | TBD | 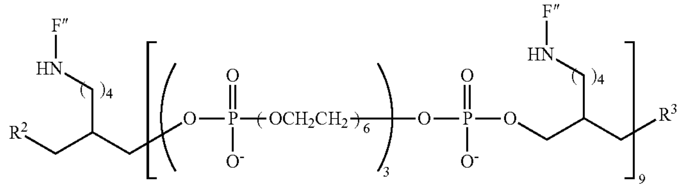 |

TABLE 2-continued
Exemplary Compounds of Structure I
| No. | MW. Found Calc. | Structure |
|---|---|---|
| I-26 | TBD | 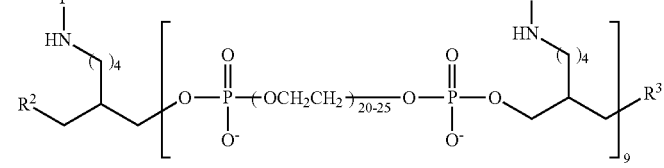 |
| I-27 | TBD | 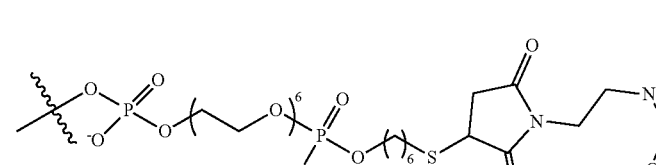 |
| I-28 | TBD | 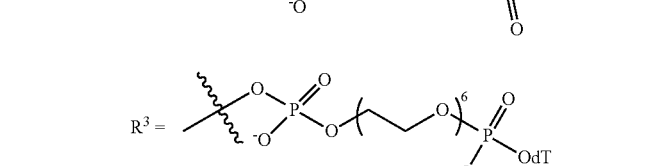 |
A = antibody

TABLE 2-continued

Exemplary Compounds of Structure I

| No. | MW. Found Calc. | Structure |
|---|---|---|
| I-29 | TBD | 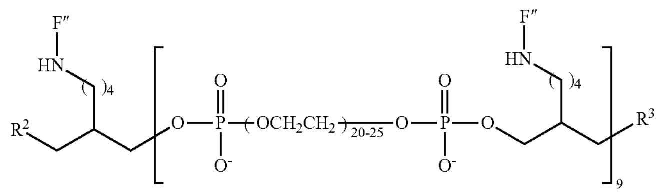 |
| I-30 | TBD | 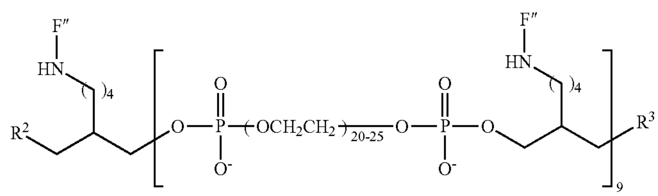 |
| I-31 | TBD | 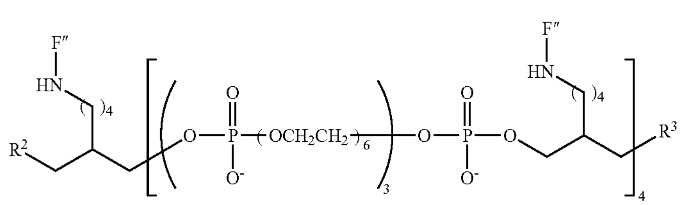 |

TABLE 2-continued

Exemplary Compounds of Structure I

| No. | MW. Found Calc. | Structure |
|---|---|---|
| I-32 | 7241.2 7238.2 | |
| I-33 | TBD | |

TABLE 2-continued
Exemplary Compounds of Structure I
| No. | MW. Found Calc. | Structure |
|---|---|---|
| I-34 | TBD | 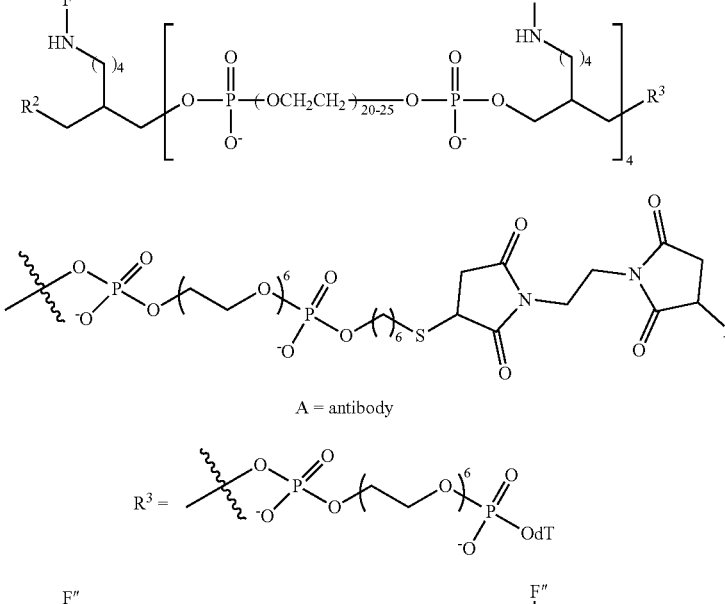 |
| I-35 | TBD | 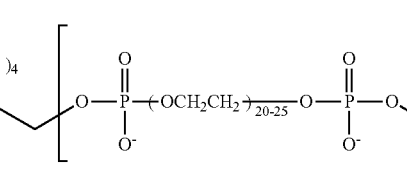 |
| I-36 | TBD | 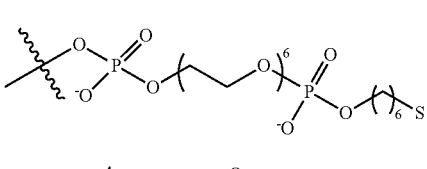 |

TABLE 2-continued

Exemplary Compounds of Structure I

| No. | MW. Found Calc. | Structure |
|---|---|---|
| I-37 | 6997.1 6997.0 | 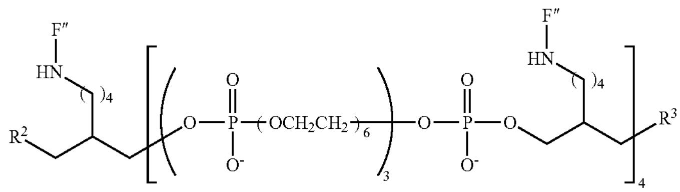 |
| I-38 | TBD | 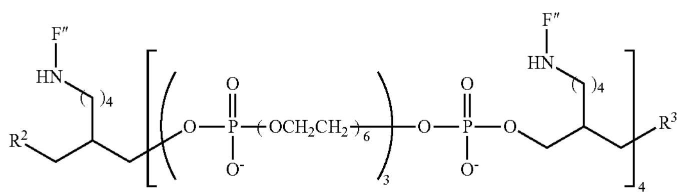 |
| I-39 | TBD | 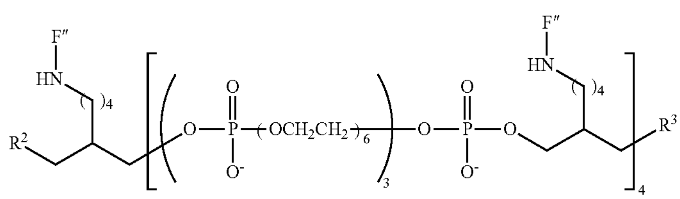 |

TABLE 2-continued

Exemplary Compounds of Structure I

| No. | MW. Found Calc. | Structure |
|---|---|---|
| I-40 | TBD | 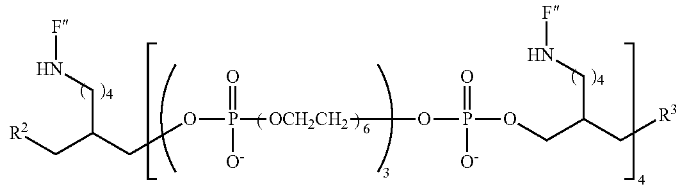 |
| I-41 | TBD | 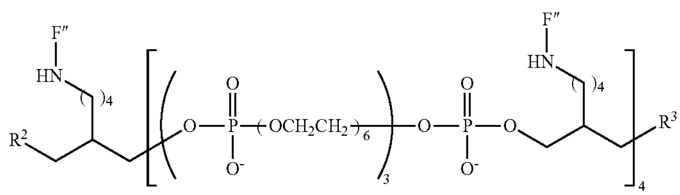 |
| I-42 | TBD | 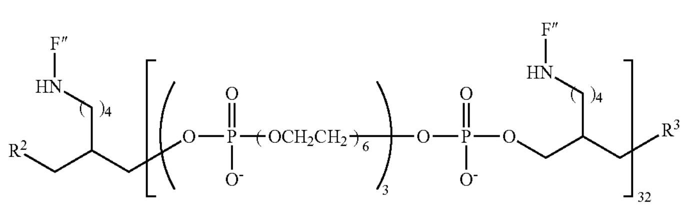 |

A = antibody

TABLE 2-continued
Exemplary Compounds of Structure I
| No. | MW. Found Calc. | Structure |
|---|---|---|
| | | 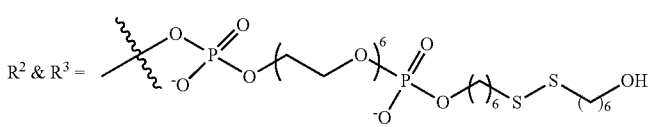 |
| I-43 | 3103.9 3103.6 | 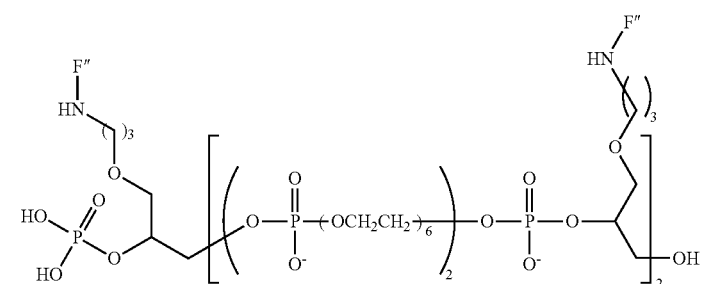 |
| I-44 | 5619.5 5619.8 | 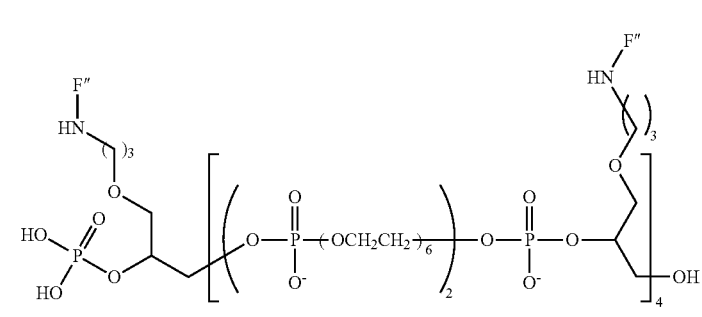 |
| I-45 | 15684.6 15681.5 | 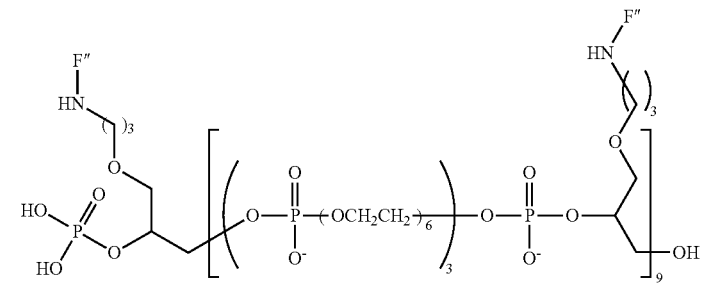 |
| | | 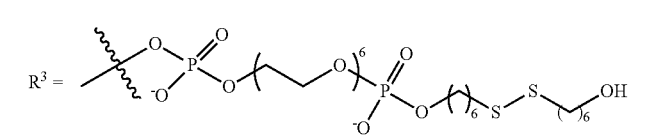 |
| I-46 | 6997.1 6997.0 | 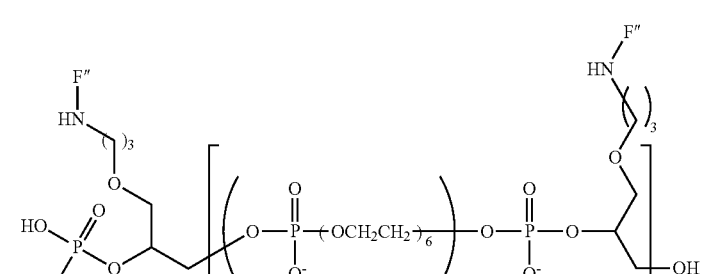 |

TABLE 2-continued

Exemplary Compounds of Structure I

| No. | MW. Found Calc. | Structure |
|---|---|---|
| I-47 | 11912.1 11910.1 | 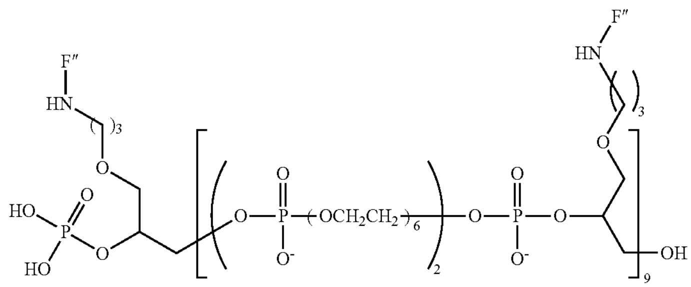 |
| I-48 | 9273.9 9272.0 | |
| I-49 | 16252.9 16250.0 | |

TABLE 2-continued

Exemplary Compounds of Structure I

| No. | MW. Found Calc. | Structure |
|---|---|---|
| I-50 | 17260.3 17260.0 | 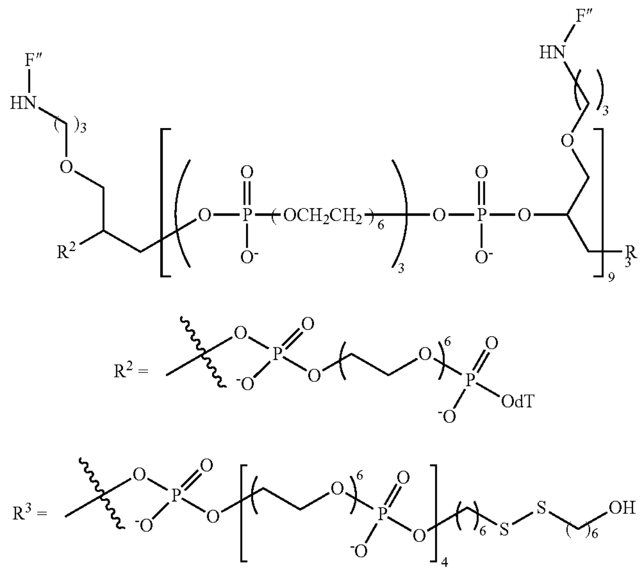 |
| I-51 | TBD | 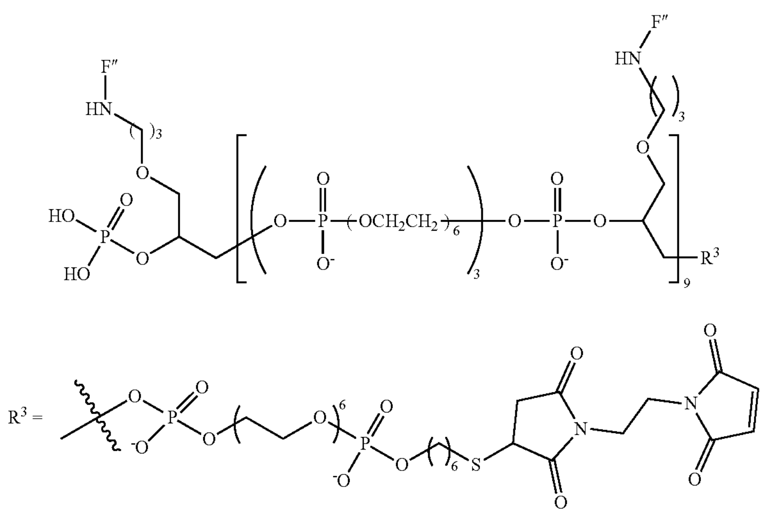 |
| I-52 | TBD | 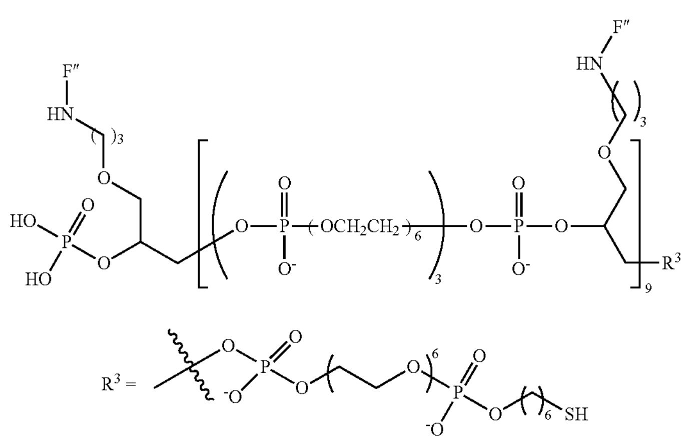 |

TABLE 2-continued
Exemplary Compounds of Structure I
| No. | MW. Found Calc. | Structure |
|---|---|---|
| I-53 | TBD | 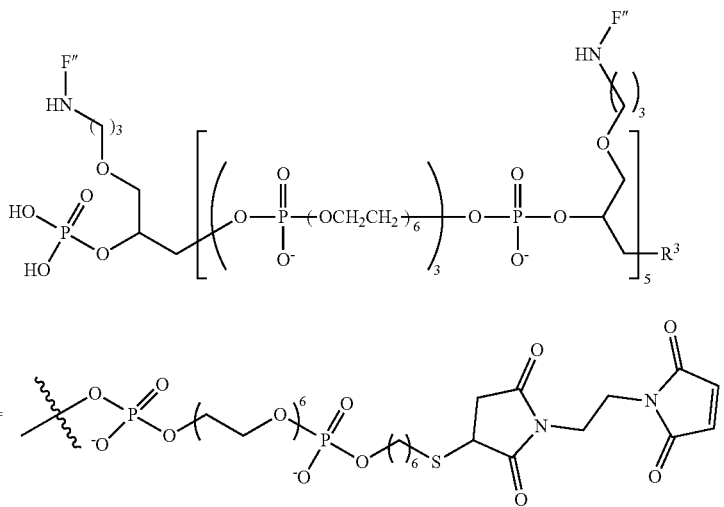 |
| I-54 | TBD | 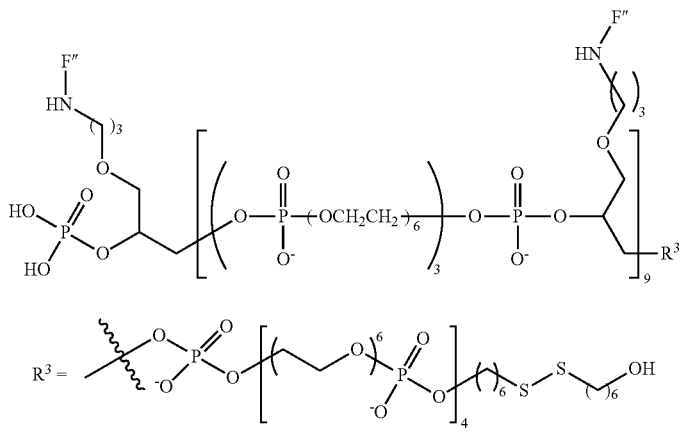 |
| I-55 | TBD | 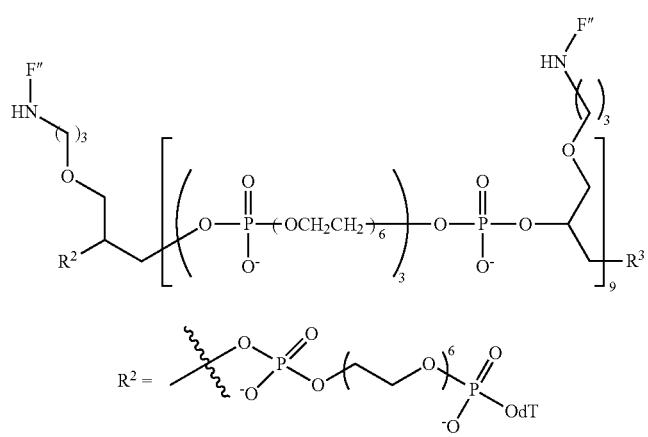 |

TABLE 2-continued
Exemplary Compounds of Structure I
| No. | MW. Found Calc. | Structure |
|---|---|---|
| I-56 | TBD | 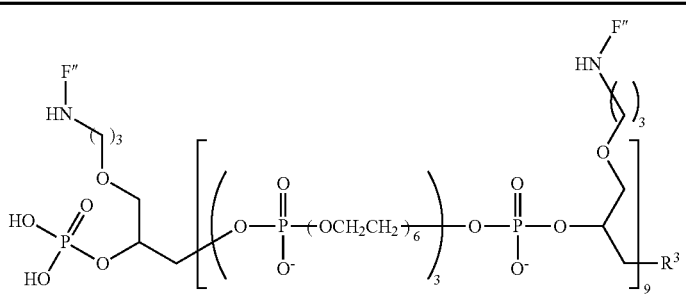 |
| I-57 | TBD | 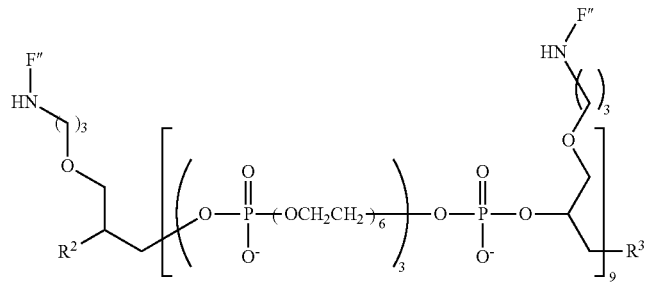 |
| I-58 | TBD | 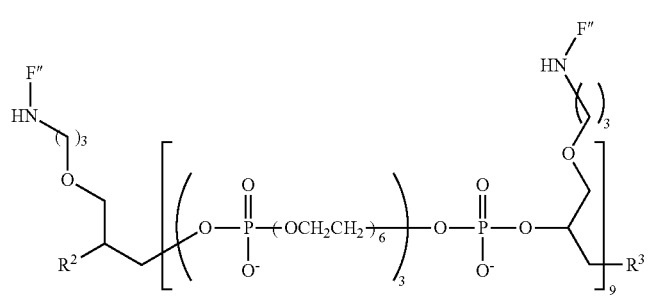 |

TABLE 2-continued

Exemplary Compounds of Structure I

| No. | MW. Found Calc. | Structure |
|---|---|---|

$R^2$ = [structure showing phosphate-PEG-phosphate-OdT linker]

$R^3$ = [structure showing phosphate-PEG-phosphate-alkyl-S-succinimide-ethyl-succinimide-antibody linker]

A = antibody

I-59  TBD

[structure of compound I-59 with HO-P(=O)(OH)-O-CH2-CH(O-...)-CH2-O-(CH2)3-NH-F″ groups and bracketed phosphate-PEG repeat units, with R³ substituent]

$R^3$ = [structure showing phosphate-PEG-phosphate-alkyl-S-succinimide-ethyl-succinimide-antibody linker]

A = antibody

I-60  TBD

[structure of compound I-60 with HO-P(=O)(OH)-O-CH2-CH(O-...)-CH2-O-(CH2)3-NH-F″ groups, bracketed phosphate-(OCH2CH2)n-phosphate repeat units, terminating in -OH]

n = about 23 such that PEG M.W. = about 1,000

*TBD = to be determined

As used in Table 2 and throughout the application R², R³, m, n and L' have the definitions provided for compounds of structure (I) unless otherwise indicated, and F, F' and F" refer to a fluorescein moiety having the following structures, respectively:

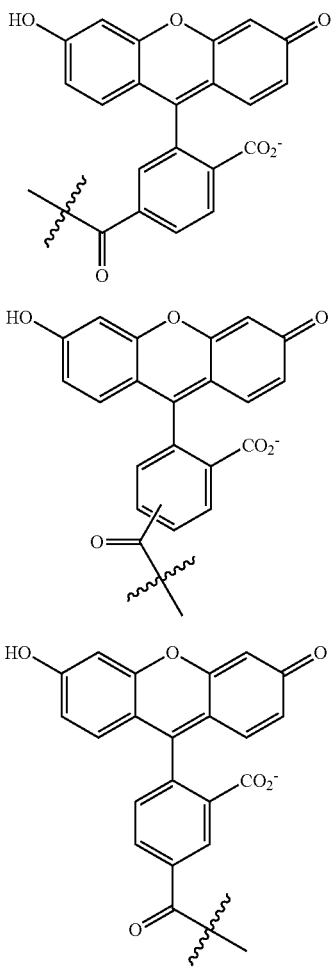

"dT" refers to the following structure:

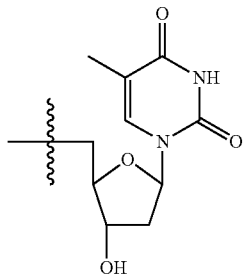

Some embodiments include any of the foregoing compounds, including the specific compounds provided in Table 2, conjugated to a targeting moiety, such as an antibody.

The present disclosure generally provides compositions comprising compounds having increased fluorescence emission relative to earlier known compounds and methods of using the same. Accordingly, certain embodiments are directed to a fluorescent compound comprising Y fluorescent moieties M, wherein the fluorescent compound has a peak fluorescence emission upon excitation with a predetermined wavelength of ultraviolet light of at least 85% of Y times greater than the peak fluorescence emission of a single M moiety upon excitation with the same wavelength of ultraviolet light, and wherein Y is an integer of 2 or more. Fluorescent compounds include compounds which emit a fluorescent signal upon excitation with light, such as ultraviolet light.

In some embodiments, the fluorescent compound has a peak fluorescence emission of at least 90% of Y times greater, 95% of Y times greater, 97% of Y times greater or 99% of Y times greater than the peak fluorescence emission of a single M moiety.

In some embodiments, Y is an integer from 2 to 100, for example 2-10.

In some embodiments, the Y M moiety have, independently, one of the following structures:

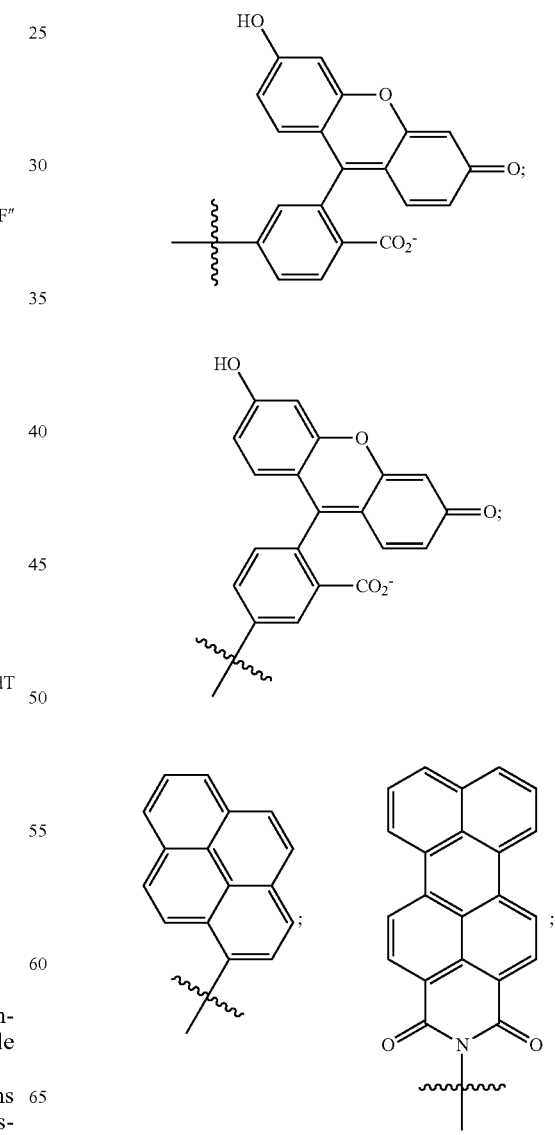

79
-continued
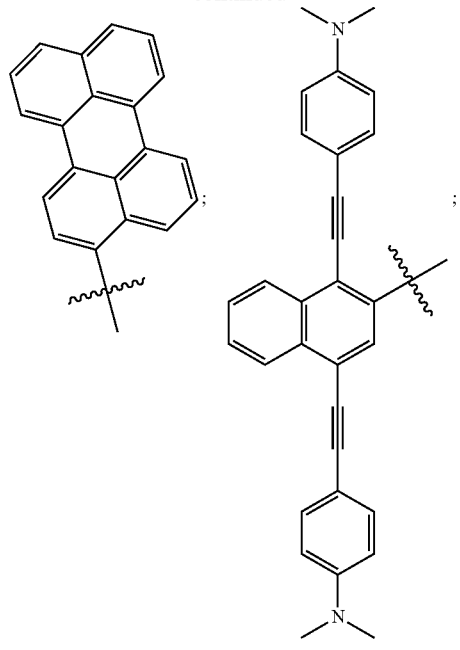
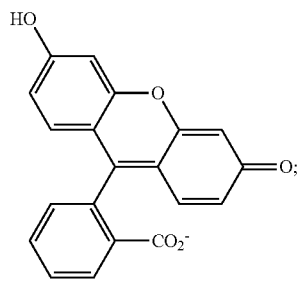
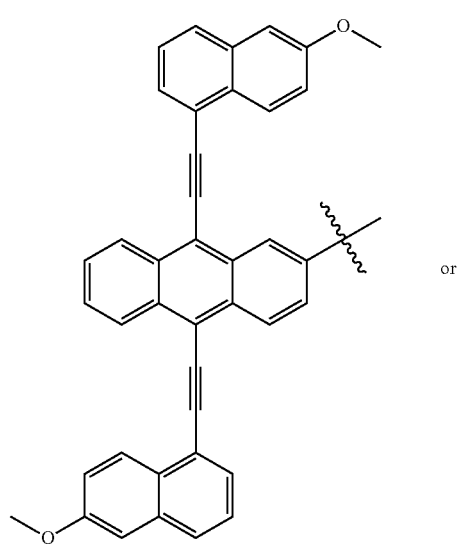  or
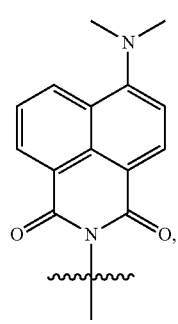
wherein ⌇ indicates a point of attachment to the fluorescent compound.
80
In other embodiments, the single M moiety has, independently, one of the following structures:
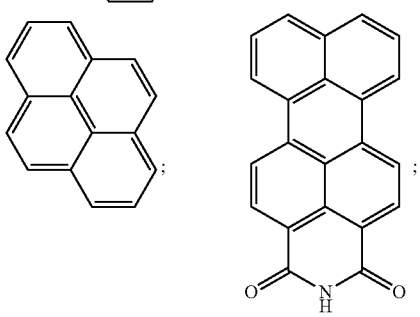
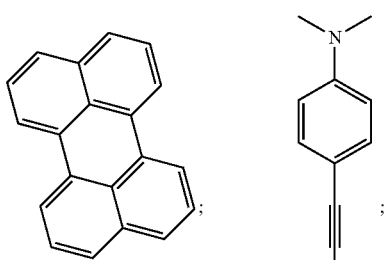

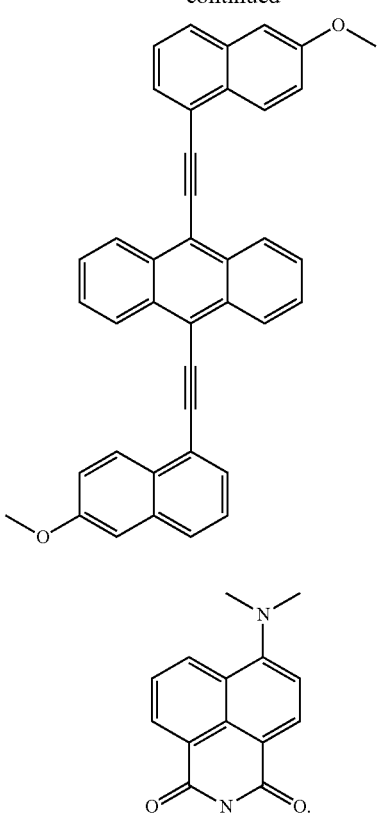

In more specific embodiments, the fluorescent compound comprises Y M moieties, independently having one of the following structures:

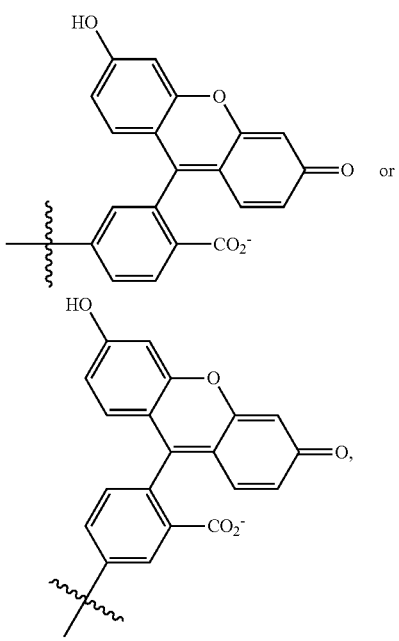

wherein ⁓ indicates a point of attachment to the fluorescent compound, and the single M moiety has the following structure:

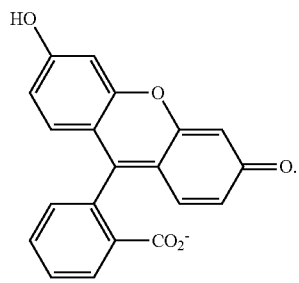

In other embodiments, the peak fluorescence emission is at a wavelength ranging from about 500 to about 550 nm.

In still more embodiments, the fluorescent compound comprises at least one ethylene oxide moiety.

Compositions comprising the fluorescent compound of any one of claims and an analyte are also provided.

The presently disclosed compounds are "tunable," meaning that by proper selection of the variables in any of the foregoing compounds, one of skill in the art can arrive at a compound having a desired and/or predetermined molar fluorescence (molar brightness). The tunability of the compounds allows the user to easily arrive at compounds having the desired fluorescence and/or color for use in a particular assay or for identifying a specific analyte of interest. Although all variables may have an effect on the molar fluorescence of the compounds, proper selection of M, $L^4$, m and n is believed to play an important role in the molar fluorescence of the compounds.

Accordingly, in one embodiment is provided a method for obtaining a compound having a desired molar fluorescence, the method comprising selecting an M moiety having a known fluorescence, preparing a compound of structure (I) comprising the M moiety, and selecting the appropriate variables for $L^4$, m and n to arrive at the desired molar fluorescence.

Molar fluorescence in certain embodiments can be expressed in terms of the fold increase or decrease relative to the fluorescence emission of the parent fluorophore (e.g., monomer). In some embodiments the molar fluorescence of the present compounds is 1.1×, 1.5×, 2×, 3×, 4×, 5×, 6×, 7×, 8×, 9× 10× or even higher relative to the parent fluorophore. Various embodiments include preparing compounds having the desired fold increase in fluorescence relative to the parent fluorophore by proper selection of $L^4$, m and n.

For ease of illustration, various compounds comprising phosphorous moieties (e.g., phosphate and the like) are depicted in the anionic state (e.g., —OPO(OH)O⁻, —OPO$_3^{2-}$). One of skill in the art will readily understand that the charge is dependent on pH and the uncharged (e.g., protonated or salt, such as sodium or other cation) forms are also included in the scope of embodiments of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention which exist in free base or acid form can be converted to their salts by treatment with the appropriate inorganic or organic base or acid by methods known to one skilled in the art. Salts of the compounds of the invention can be converted to their free base or acid form by standard techniques.

The following Reaction Schemes illustrate exemplary methods of making compounds of this invention. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Reaction Scheme I

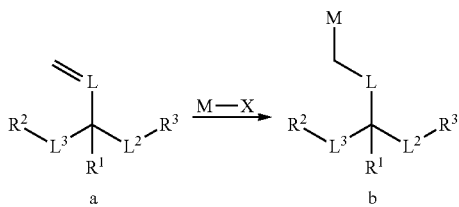

Reaction Scheme I illustrates an exemplary method for preparing an intermediate useful for preparation of compounds of structure (I), where R', $L^2$, $L^3$ and M are as defined above, $R^2$ and $R^3$ are as defined above or are protected variants thereof and L is an optional linker. Referring to Reaction Scheme 1, compounds of structure a can be purchased or prepared by methods well-known to those of ordinary skill in the art. Reaction of a with M-X, where x is a halogen such as bromo, under Suzuki coupling conditions known in the art results in compounds of structure b. Compounds of structure b can be used for preparation of compounds of structure (I) as described below.

Reaction Scheme II

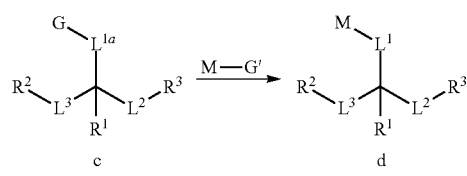

Reaction Scheme II illustrates an alternative method for preparation of intermediates useful for preparation of compounds of structure (I). Referring to reaction Scheme II, where $R^1$, $L^1$, $L^2$, $L^3$, G and M are as defined above, and $R^2$ and $R^3$ are as defined above, or are protected variants thereof, a compound of structure c, which can be purchased or prepared by well-known techniques, is reacted with M-G' to yield compounds of structure d. Here, G and G' represent functional groups having complementary reactivity (i.e., functional groups which react to form a covalent bond). G' may be pendant to M or a part of the structural backbone of M. G and G' may be any number of functional groups described herein, such as alkyne and azide, respectively, amine and activated ester, respectively or amine and isothiocyanate, respectively, and the like.

The compound of structure (I) may be prepared from one of structures b or d by reaction under well-known automated DNA synthesis conditions with a phosphoramidite compound having the following structure (e):

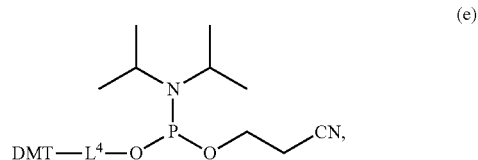

wherein A is as defined herein and each L is independently an optional linker.

DNA synthesis methods are well-known in the art. Briefly, two alcohol groups, for example $R^2$ and $R^3$ in intermediates b or d above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $R^3$) can be protected as a DMT group by reaction with DMT-Cl. A secondary alcohol (e.g., $R^2$) is then functionalized as a phosphoramidite by reaction with an appropriate reagent such as 2-cyanoethyl N,N-dissopropylchlorophosphoramidite. Methods for preparation of phosphoramidites and their oligomerization are well-known in the art and described in more detail in the examples.

Compounds of structure (I) are prepared by oligomerization of intermediates b or d and e according to the well-known phophoramidite chemistry described above. The desired number of m and n repeating units is incorporated into the molecule by repeating the phosphoramidite coupling the desired number of times.

In some other embodiments, the compounds have the following structure (II):

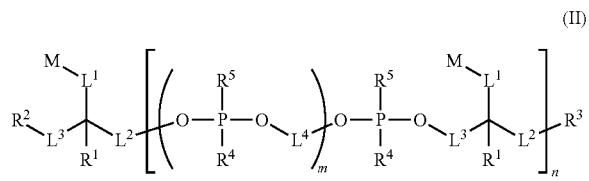

(II)

or a stereoisomer, tautomer or salt thereof, wherein:
M is, at each occurrence, independently a moiety comprising two or more carbon-carbon double bonds and at least one degree of conjugation;
$L^1$, $L^2$ and $L^3$ are, at each occurrence, independently an optional alkylene, alkenylene, alkynylene, heteroalkylene, heteroalkenylene, heteroalkynylene or heteroatomic linker;
$L^4$ is, at each occurrence, independently an alkylene, alkenylene, alkynylene, heteroalkylene, heteroalkenylene or heteroalkynylene linker;
$R^2$ is, at each occurrence, independently H, alkyl or alkoxy; $R^2$ and $R^3$ are each independently H, OH, SH, alkyl, alkoxy, alkylether, —OP(=$R_a$)($R_b$)$R_c$, Q, a linker comprising a covalent bond to Q, a linker comprising a covalent bond to an analyte molecule, a linker comprising a covalent bond to a solid support or a linker comprising a covalent bond to a further compound of structure (II), wherein: $R_a$ is O or S; $R_b$ is OH, SH, O$^-$, S$^-$, OR$_d$ or SR$_d$; $R_c$ is OH, SH, O$^-$, S$^-$, OR$_d$, SR$_d$, alkyl, alkoxy, alkylether, alkoxyalkylether, phosphate, thiophosphate, phosphoalkyl, thiophosphoalkyl, phosphoalkylether or thiophosphoalkylether;
$R^4$ is, at each occurrence, independently OH, SH, O$^-$, S$^-$, OR$_d$ or SR$_d$;
$R^5$ is, at each occurrence, independently oxo, thioxo or absent;
Q is a moiety comprising a reactive group capable of forming a covalent bond with an analyte molecule, a solid support or a complementary reactive group Q;
$R^d$ is a cation;
m is, at each occurrence, independently an integer of zero or greater, provided that at least one occurrence of m is an integer of three or greater; and
n is an integer of one or greater.

In some embodiments, m is, at each occurrence, independently an integer of three or greater.

In some embodiments, $L^1$, $L^2$ and $L^3$ are, at each occurrence, independently optional alkylene or heteroalkylene linkers.

In some other embodiments of the compound of structure (II):
M is, at each occurrence, independently a moiety comprising two or more carbon-carbon double bonds and at least one degree of conjugation;
$L^1$, $L^2$ and $L^3$ are, at each occurrence, independently optional alkylene or heteroalkylene linkers;
$L^4$ is, at each occurrence, independently an alkylene, alkenylene, alkynylene, heteroalkylene, heteroalkenylene or heteroalkynylene linker up to twenty atoms in length;

$R^1$ is, at each occurrence, independently H, alkyl or alkoxy;
$R^2$ and $R^3$ are each independently H, OH, —OP(=$R_a$)($R_b$)$R_c$, Q, a linker comprising a covalent bond to Q, a linker comprising a covalent bond to an analyte molecule or a linker comprising a covalent bond to a solid support, wherein: $R_a$ is O or S; $R_b$ is OH, SH, O$^-$, OR$_d$ or SR$_d$; $R_c$ is OH, SH, O$^-$, OR$_d$, SR$_d$, phosphate, thiophosphate, phosphoalkyl, thiophosphoalkyl, phosphoalkylether or thiophosphoalkylether;
$R^4$ is, at each occurrence, independently OH, SH, O$^-$, S$^-$, OR$_d$ or SR$_d$;
$R^5$ is, at each occurrence, independently oxo, thioxo or absent;
Q is a moiety capable of bonding with an analyte molecule or a solid support;
$R_d$ is a cation;
m is, at each occurrence, independently an integer of zero or greater, provided that at least one occurrence of m is an integer of three or greater; and
n is an integer of one or greater.

In some embodiments, the compound has the following structure (IIA):

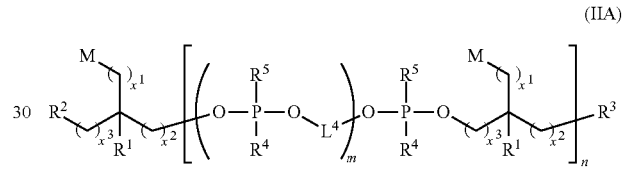

(IIA)

wherein $x^1$, $x^2$ and $x^3$ are, at each occurrence, independently an integer from 0 to 6.

The $L^4$ linker can be selected, along with other variables, to provide the desired fluorescence and/or color ("tune" the fluorescence and/or color). In some embodiments, $L^4$ is a linker up to 20 atoms in length, up to 13 atoms in length, for example up to 10 atoms in length or up to 6 atoms in length. In certain embodiments, $L^4$ does not include disulfide bonds. In other embodiments, $L^4$ is, at each occurrence, independently $C_1$-$C_6$ alkylene or $C_2$-$C_6$ alkynylene. In some embodiments, $L^4$ is a two-carbon linker.

In some other different embodiments, the compound has the following structure (JIB):

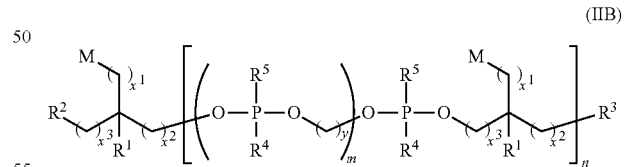

(IIB)

wherein:
$x^1$, $x^2$ and $x^3$ are, at each occurrence, independently an integer from 0 to 6; and
y is, at each occurrence, independently an integer from 1 to 6.

In certain embodiments of the foregoing y is 2. In other embodiments, $x^1$, $x^2$ and $x^3$ are each 1 at each occurrence. In some different embodiments, $x^2$ is 0 and $x^3$ is 1 at each occurrence.

In still other embodiments, $R^4$ is, at each occurrence, independently OH, O$^-$ or OR$_d$. It is understood that "OR$_d$"

and "$SR_d$" are intended to refer to $O^-$ and $S^-$ associated with a cation. For example, the disodium salt of a phosphate group may be represented as:

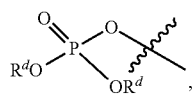

where $R^d$ is sodium ($Na^+$).

In further of the foregoing embodiments, $R^5$ is, at each occurrence, oxo.

In some other embodiments, the compound has one of the following structures (IIB') or (IIB"):

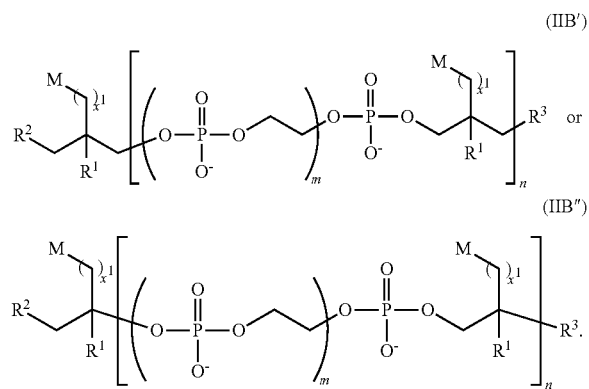

In any embodiments of the foregoing, $R^1$ is H.

In different embodiments, $R^2$ and $R^3$ are each independently OH or $-OP(=R_a)(R_b)R_c$. For example, in some embodiments $R^2$ and $R^3$ are each independently OH or $-OP(=R_a)(R_b)R_c$, wherein $R^a$ is O, $R_b$ is OH, $O^-$ or $OR^E$; $R_c$ is OH, $O^-$, $OR^d$, phosphate, thiophosphate, phosphoalkyl, thiophosphoalkyl, phosphoalkylether or thiophosphoalkylether; and $R^d$ is a counter ion.

In still other different embodiments, one of $R^2$ or $R^3$ is OH or $-OP(=R_a)(R_b)R_c$, and the other of $R^2$ or $R^3$ is Q or a linker comprising a covalent bond to Q. For example, in some embodiments one of $R^2$ or $R^3$ is OH or $-OP(=R_a)(R_b)R_c$, and the other of $R^2$ or $R^3$ is Q or a linker comprising a covalent bond to Q, wherein $R^a$ is O, $R_b$ is OH, $O^-$ or $OR^d$; $R_c$ is OH, $O^-$, $OR^d$, phosphate, thiophosphate, phosphoalkyl, thiophosphoalkyl, phosphoalkylether or thiophosphoalkylether; and $R^d$ is a counter ion.

In still other embodiments, Q is or comprises a moiety capable of bonding with an analyte molecule or a solid support. In certain embodiments, Q provides a means of connecting the compound of structure (II) to an analyte molecule or a solid support (e.g., by a covalent bond). For example, in some embodiments Q is or comprises a reactive group capable of forming a covalent bond with an analyte molecule or a solid support. In this regard the type of Q group and connectivity of the Q group to the remainder of the compound of structure (II) is not limited. In certain embodiments, the Q is a moiety which is not susceptible to hydrolysis under aqueous conditions, but is sufficiently reactive to form a bond with a corresponding group on an analyte molecule or solid support (e.g., an amine).

Certain embodiments of compounds of structure (II) comprise Q groups commonly employed in the field of bioconjugation. For example in some embodiments, Q is or comprises a nucleophilic reactive group, an electrophilic reactive group or a cycloaddition reactive group. In some more specific embodiments, Q is or comprises sulfhydryl, disulfide, activated ester, isothiocyanate, azide, alkyne, alkene, diene, dienophile, acid halide, sulfonyl halide, phosphine, α-haloamide, biotin, amino or a maleimide. In some embodiments, the activated ester is an N-succinimide ester, imidoester or polyflourophenyl ester. In other embodiments, the alkyne is an alkyl azide or acyl azide. Exemplary Q moieties are provided in Table 1 above.

It should be noted that in some embodiments, wherein Q is SH, the SH moiety will tend to form disulfide bonds with another sulfhydryl group on another compounds of structure (II). Accordingly, some embodiments include compounds of structure (II), which are in the form of disulfide dimers, the disulfide bond being derived from SH Q groups.

In some other embodiments, one of $R^2$ or $R^3$ is OH or $-OP(=R_a)(R_b)R_c$, and the other of $R^2$ or $R^3$ is a linker comprising a covalent bond to an analyte molecule or a linker comprising a covalent bond to a solid support. In some different embodiments, one of $R^2$ or $R^3$ is OH or $-OP(=R_a)(R_b)R_c$, and the other of $R^2$ or $R^3$ is a linker comprising a covalent bond to an analyte molecule or a linker comprising a covalent bond to a solid support, wherein $R^a$ is O, $R_b$ is OH, $O^-$ or $OR^d$; $R_c$ is OH, $O^-$, $OR^d$, phosphate, thiophosphate, phosphoalkyl, thiophosphoalkyl, phosphoalkylether or thiophosphoalkylether; and $R^d$ is a counter ion. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In still different embodiments, the solid support is a polymeric bead or nonpolymeric bead.

The value form is another variable that can be selected based on the desired fluorescence and/or color intensity. In some embodiments, m is, at each occurrence, independently an integer from 3 to 10. In other embodiments, m is, at each occurrence, independently an integer from 7 to 9.

The fluorescence intensity can also be tuned by selection of different values of n. In certain embodiments, n is an integer from 1 to 100. In other embodiments, n is an integer from 1 to 10.

M is selected based on the desired optical properties, for example based on a desired color and/or fluorescence emission wavelength. In some embodiments, M is the same at each occurrence; however, it is important to note that each occurrence of M need not be an identical M, and certain embodiments include compounds wherein M is not the same at each occurrence. M may be attached to the remainder of the molecule from any position (i.e., atom) on M. One of skill in the art will recognize means for attaching M to the remainder of molecule.

In some embodiments, M is a fluorescent or colored moiety. Any fluorescent and/or colored moiety known in the art and typically employed in colorimetric, UV, and/or fluorescent assays may be used. Examples of M moieties which are useful in various embodiments of the invention include: Xanthene derivatives (e.g., fluorescein, rhodamine, Oregon green, eosin or Texas red); Cyanine derivatives (e.g., Cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary M moieties include: Cyanine dyes, xanthate dyes (e.g., Hex, Vic, Nedd, Joe or Tet); Yakima yellow; Redmond red; tamra; texas red and Alexa Fluor® dyes.

In still other embodiments of any of the foregoing, M comprises three or more aryl or heteroaryl rings, or combinations thereof, for example four or more aryl or heteroaryl rings, or combinations thereof, or even five or more aryl or heteroaryl rings, or combinations thereof. In some embodiments, M comprises six aryl or heteroaryl rings, or combinations thereof. In further embodiments, the rings are fused. For example in some embodiments, M comprises three or more fused rings, four or more fused rings, five or more fused rings, or even six or more fused rings.

In some embodiments, M is cyclic. For example, in some embodiments M is carbocyclic. In other embodiment, M is heterocyclic. In still other embodiments of the foregoing, M, at each occurrence, independently comprises an aryl moiety. In some of these embodiments, the aryl moiety is multicyclic. In other more specific examples, the aryl moiety is a fused-multicyclic aryl moiety, for example which may comprise at least 3, at least 4, or even more than 4 aryl rings.

In other embodiments of any of the foregoing compounds of structure (II), M, at each occurrence, independently comprises at least one heteroatom. For example, in some embodiments, the heteroatom is nitrogen, oxygen or sulfur.

In still more embodiments of any of the foregoing, M, at each occurrence, independently comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, M, at each occurrence, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety. In other embodiments, M' is, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, M is, at each occurrence, independently a coumarin dye, resorufin dye, dipyrrometheneboron difluoride dye, ruthenium bipyridyl dye, energy transfer dye, thiazole orange dye, polymethine or N-aryl-1,8-naphthalimide dye.

In still more embodiments of any of the foregoing, M at each occurrence is the same. In other embodiments, each M is different. In still more embodiments, one or more M is the same and one or more M is different.

In some embodiments, M is pyrene, perylene, perylene monoimide or 6-FAM or derivative thereof. In some other embodiments, M' has one of the following structures:

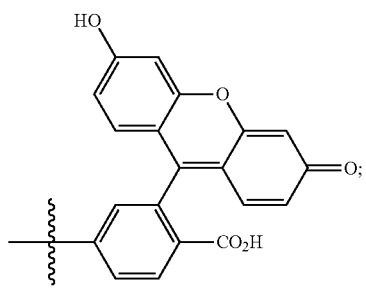

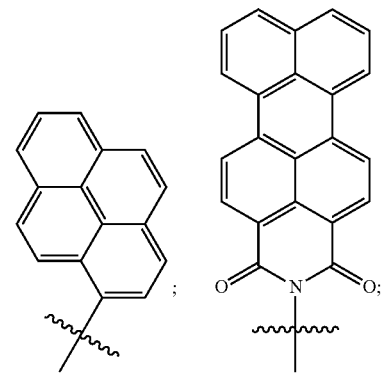

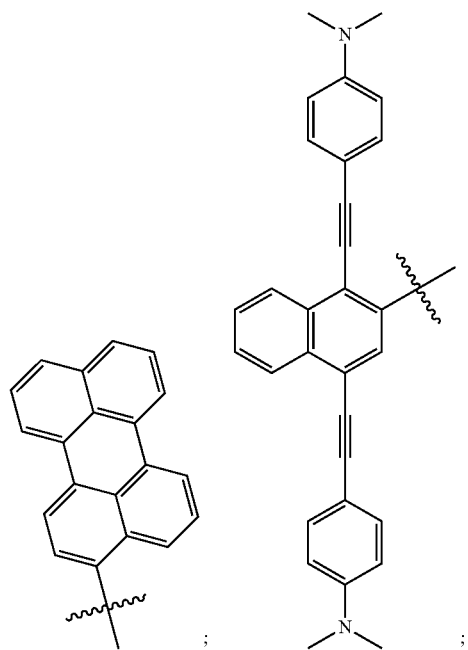

In some other embodiments, M¹ has the following structure:
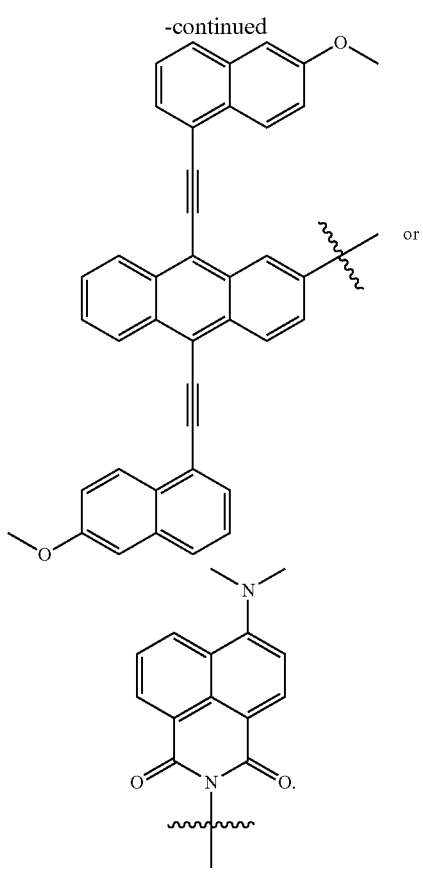
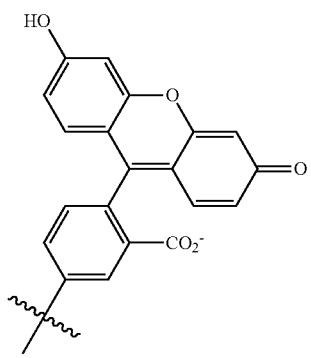
In some specific embodiments, the compound is a compound selected from Table 3:
TABLE 3
Exemplary Compounds
| Name | Structure |
| --- | --- |
| FC₃F | |
| FC₄F | |
| FC₅F | |

TABLE 3-continued

Exemplary Compounds

| Name | Structure |
|---|---|
| FC$_6$F | 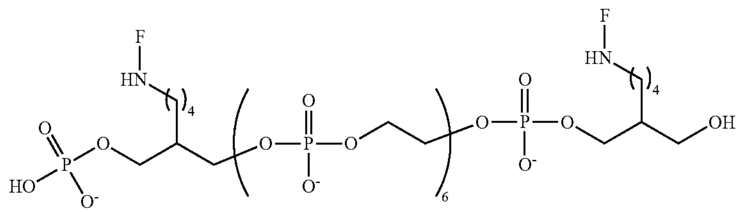 |
| FC$_7$F | 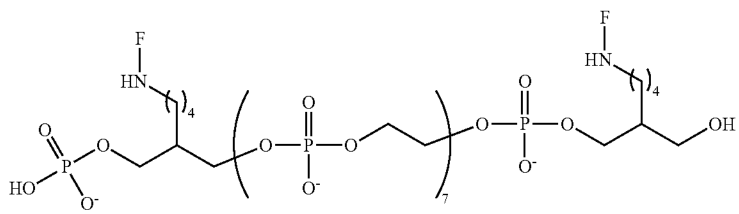 |
| FC$_8$F | 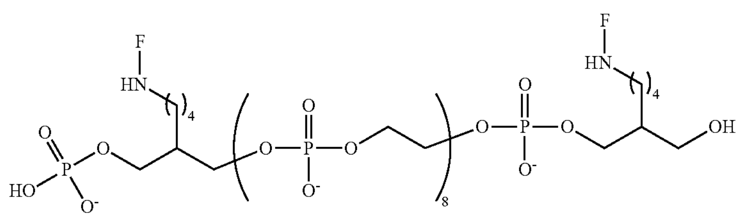 |
| FC$_9$F | 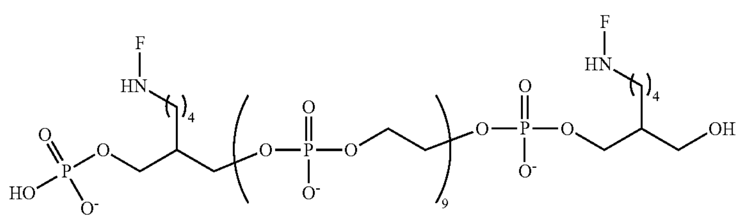 |
| YC$_3$Y | 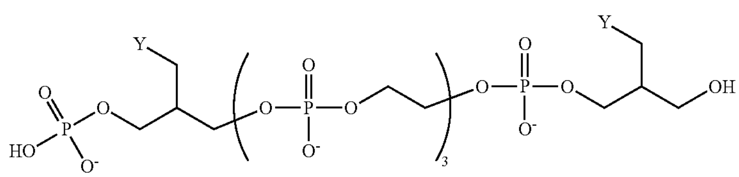 |
| YC$_4$Y | 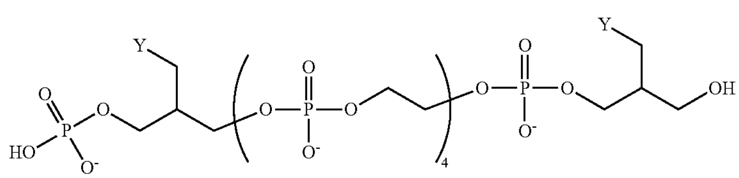 |
| YC$_5$Y | 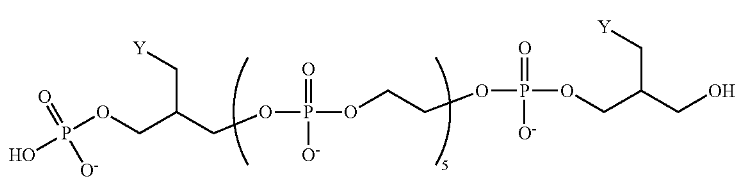 |

TABLE 3-continued
Exemplary Compounds
| Name | Structure |
|---|---|
| YC$_6$Y | 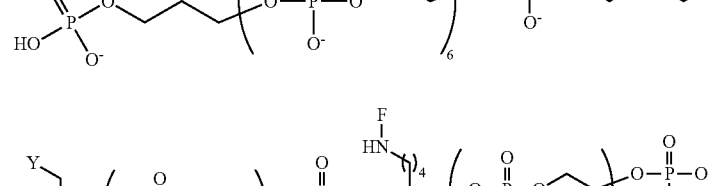 |
| YC$_3$FC$_3$Y | 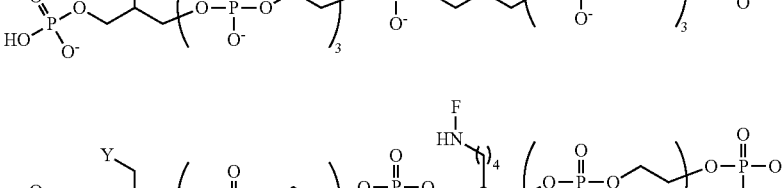 |
| YC$_4$FC$_4$Y | 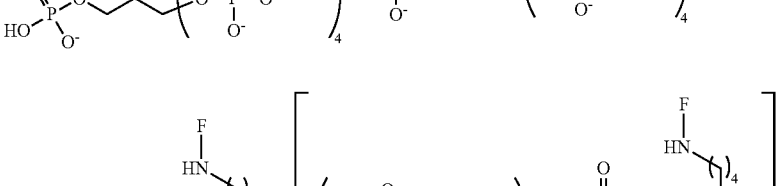 |
| F(C$_4$F)$_2$ | 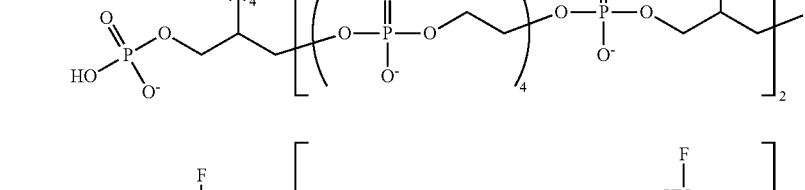 |
| F(C$_4$F)$_3$ | 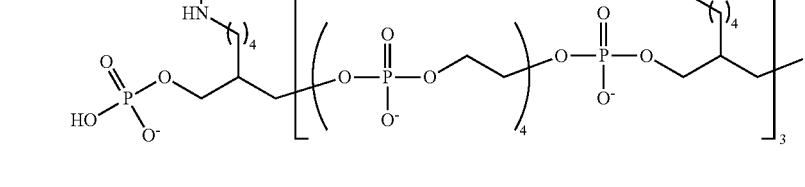 |
| F(C$_4$F)$_4$ | 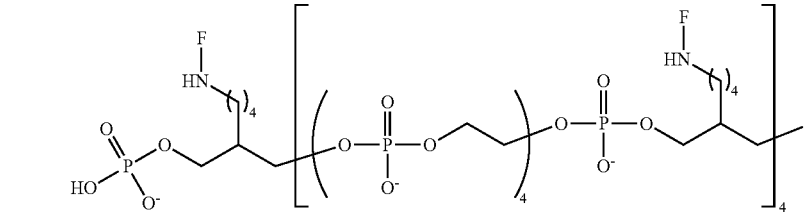 |
| F(C$_4$F)$_5$ | 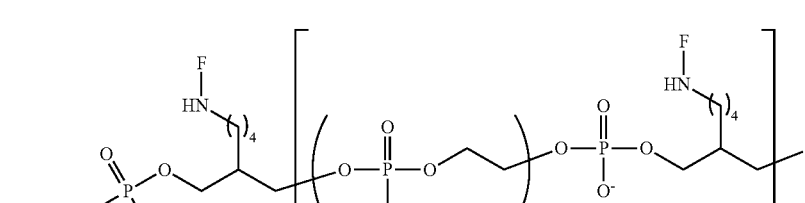 |

TABLE 3-continued

Exemplary Compounds

| Name | Structure |
|---|---|
| F(C₇F)₂ | (structure) |
| F(C₇F)₃ | (structure) |
| F(C₇F)₄ | (structure) |
| F(C₇F)₅ | (structure) |
| F(C₇F)₉ | (structure) |
| F(C₁₀F)₉ | (structure) |
| F(C₁₀F)₉SH | (structure) |

TABLE 3-continued

Exemplary Compounds

| Name | Structure |
|---|---|
| $EC_3E$ | (structure with subscript 3) |
| $EC_4E$ | (structure with subscript 4) |
| $EC_5E$ | (structure with subscript 5) |
| $EC_6E$ | (structure with subscript 6) |
| $EC_7E$ | (structure with subscript 7) |
| $EC_8E$ | (structure with subscript 8) |
| $EC_9E$ | (structure with subscript 9) |
| $EC_{10}E$ | (structure with subscript 10) |

TABLE 3-continued

Exemplary Compounds

| Name | Structure |
|---|---|
| E(C₆E)₂ | |
| E(C₇E)₂ | |
| E(C₈E)₂ | |
| E(C₉E)₂ | |
| EC₃F | |
| EC₄F | |
| EC₅F | |

TABLE 3-continued

Exemplary Compounds

| Name | Structure |
|---|---|
| EC$_6$F | 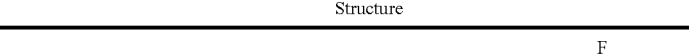 |

As used in Table 3, and throughout the application, F, E and Y refer to fluorescein, perylene and pyrene moieties, respectively, and have the following structures:

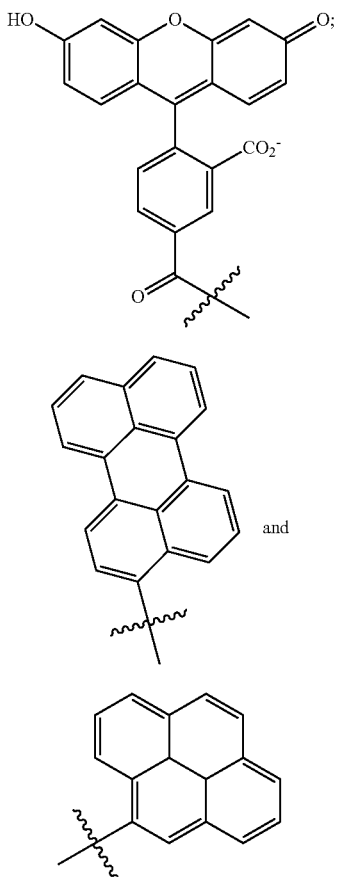

"F"

"E"

and

"Y"

The presently disclosed dye compounds are "tunable," meaning that by proper selection of the variables in any of the foregoing compounds, one of skill in the art can arrive at a compound having a desired and/or predetermined molar fluorescence (molar brightness). The tunability of the compounds allows the user to easily arrive at compounds having the desired fluorescence and/or color for use in a particular assay or for identifying a specific analyte of interest. Although all variables may have an effect on the molar fluorescence of the compounds, proper selection of M, m, n and $L^4$ is believed to play an important role in the molar fluorescence of the compounds. Accordingly, in one embodiment is provided a method for obtaining a compound having a desired molar fluorescence, the method comprising selecting an M moiety having a known fluorescence, preparing a compound of structure (II) comprising the M, and selecting the appropriate variables for m, n and $L^4$ to arrive at the desired molar fluorescence.

Molar fluorescence in certain embodiments can be expressed in terms of the fold increase or decrease relative to the fluorescence emission of the parent fluorophore (e.g., monomer). In some embodiments the molar fluorescence of the present compounds is 1.1×, 1.5×, 2×, 3×, 4×, 5×, 6×, 7×, 8×, 9× 10× or even higher relative to the parent fluorophore. Various embodiments include preparing compounds having the desired fold increase in fluorescence relative to the parent fluorophore by proper selection of m, n and $L^4$.

For ease of illustration, various compounds comprising phosphorous moieties (e.g., phosphate and the like) are depicted in the anionic state (e.g., —OPO(OH)O$^-$, —OPO$_3^{2-}$). One of skill in the art will readily understand that the charge is dependent on pH and the uncharged (e.g., protonated or salt, such as sodium or other cation) forms are also included in the scope of the invention.

It is understood that any embodiment of the compounds of structure (II), as set forth above, and any specific choice set forth herein for a $R^1$, $R^2$, $R^3$, $R^4$, $R^5$, $L^1$, $L^2$, $L^3$, $L^4$, M, m and n variable in the compounds of structure (II), as set forth above, may be independently combined with other embodiments and/or variables of the compounds of structure (II) to form embodiments of the inventions not specifically set forth above. In addition, in the event that a list of choices is listed for any particular R', $R^2$, $R^3$, $R^4$, $R^5$, $L^1$, $L^2$, $L^3$, $L^4$, M, m and n variable in a particular embodiment and/or claim, it is understood that each individual choice may be deleted from the particular embodiment and/or claim and that the remaining list of choices will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diaryalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention which exist in free base or acid form can be converted to their salts by treatment with the appropriate inorganic or organic base or acid by methods known to one skilled in the art. Salts of the compounds of the invention can be converted to their free base or acid form by standard techniques.

The following Reaction Schemes illustrate exemplary methods of making compounds of this invention. It is understood that one skilled in the art may be able to make these compounds by similar methods or by combining other methods known to one skilled in the art. It is also understood that one skilled in the art would be able to make, in a similar manner as described below, other compounds of structure (II) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Reaction Scheme I

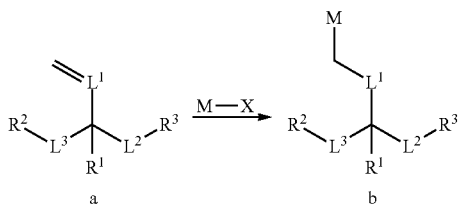

a         b

Reaction Scheme I illustrates an exemplary method for preparing an intermediate useful for preparation of compounds of structure (II), where $R^1$, $L^1$, $L^2$, $L^3$ and M are as defined above, and $R^2$ and $R^3$ are as defined above or are protected variants thereof. Referring to Reaction Scheme 1, compounds of structure a can be purchased or prepared by methods well-known to those of ordinary skill in the art. Reaction of a with M-X, where x is a halogen such as bromo, under Suzuki coupling conditions known in the art results in compounds of structure b. Compounds of structure b can be used for preparation of compounds of structure (II) as described below.

Reaction Scheme II

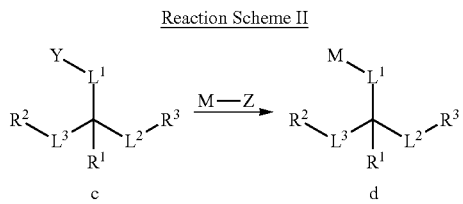

c         d

Reaction Scheme II illustrates an alternative method for preparation of compounds of intermediates useful for preparation of compounds of structure (II). Referring to reaction Scheme II, where $R^1$, $L^1$, $L^2$, $L^3$ and M are as defined above, and $R^2$ and $R^3$ are as defined above or are protected variants thereof, a compound of structure c, which can be purchased or prepared by well-known techniques, is reacted with M-Z to yield compounds of structure d. Here, Y and Z represent functional groups having complementary reactivity (i.e., functional groups which react to form a covalent bond). Z may be pendant to M or a part of the structural backbone of M, for example a cyclic anhydride. Y may be any number of functional groups, such as amino.

In certain embodiments, the compounds of structure I are oligomers comprising from 2-100 repeating units. Such oligomers can be prepared using methods analogous to well-known automated DNA synthesis methods. DNA synthesis methods are well-known in the art. Briefly, two alcohol groups, for example $R^2$ and $R^3$ in intermediates b or d above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $R^3$) can be protected as a DMT group by reaction with DMT-Cl. A secondary alcohol (e.g., $R^2$) is then functionalized as a phosphoramidite by reaction with an appropriate reagent such as 2-cyanoethyl N,N-dissopropylchlorophosphoramidite. Methods for preparation of phosphoramidites and their oligomerization are well-known in the art and described in more detail in the examples.

Oligomers of intermediates b or d are prepared according to the well-known phophoramidite chemistry described above. The desired number of m repeating units is incorporated into the molecule by repeating the phosphoramidite coupling the desired number of times with an appropriate intermediate, for example an intermediate having the following structure:

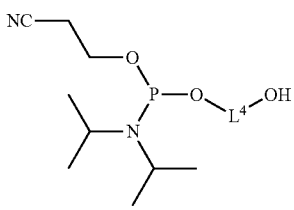

In embodiments, the dye compounds listed in Table 4 may be used in compositions and/or methods of the disclosure.

regarding synthetic methods). The UV and fluorescence properties were determined at 2 nM and pH 9.

TABLE 4

Dye Compounds

| Name | Structure | $\varepsilon_t^*$ |
|---|---|---|
| F | F—OH | 75k |
| FCF | 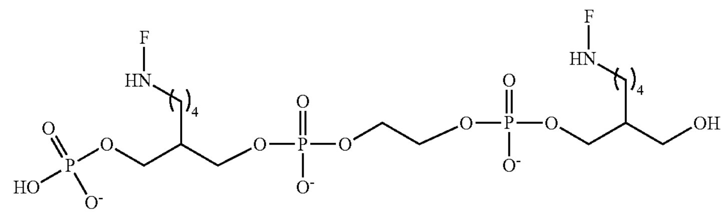 | 150k |
| F(CF)$_2$ | 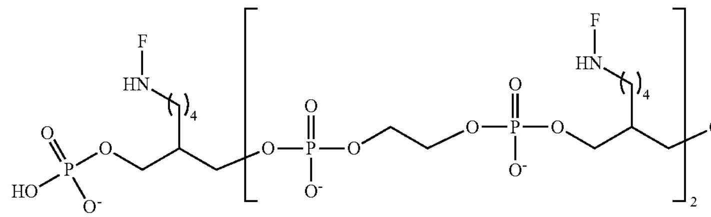 | 225k |
| F(CF)$_3$ | 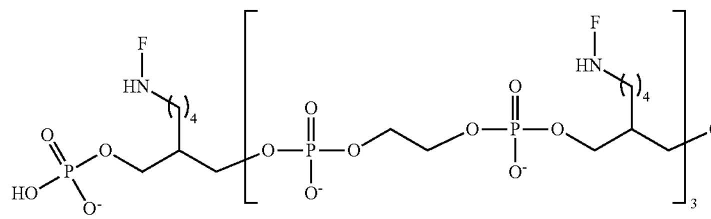 | 300k |
| F(CF)$_4$ | 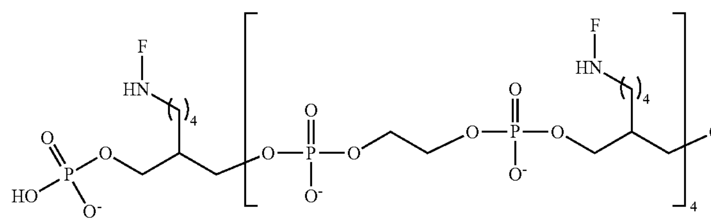 | 375k |
| F(CF)$_5$ | 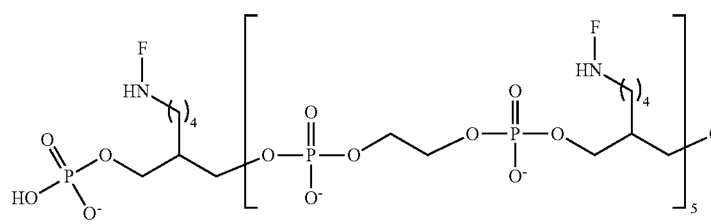 | 450k |
| F(CF)$_6$ | 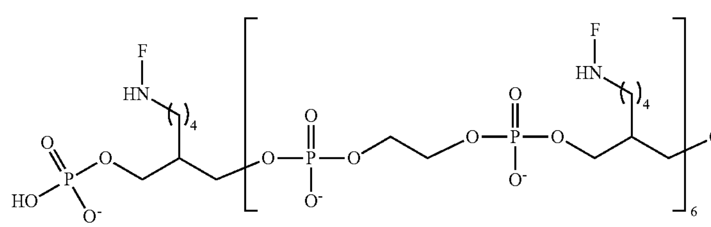 | 525k |

The dye compounds listed in Table 4 were prepared according to procedures known in the art (see, e.g., WO 2016/183185, incorporated by reference herein for the teachings $\varepsilon_t$=theoretical molar extinction coefficient In embodiments, the dye compounds listed in Table 5 may be used in compositions and/or methods of the disclosure.

The dye compounds listed in Table 5 were prepared according to procedures known in the art (see, e.g., WO 2016/183185, incorporated by reference herein for the teachings regarding synthetic methods).

TABLE 5

Dye Compounds

| Name | Structure | $\varepsilon_r{}^*$ |
|---|---|---|
| F | F—OH | 75k |
| FF | [structure] | 150k |
| FCF | [structure] | 150k |
| FC$_2$F | [structure] | 150k |
| FC$_3$F | [structure] | 150k |
| FC$_4$F | [structure] | 150k |
| FC$_5$F | [structure] | 150k |

TABLE 5-continued

Dye Compounds

| Name | Structure | $\varepsilon_t{}^*$ |
|---|---|---|
| $FC_6F$ | 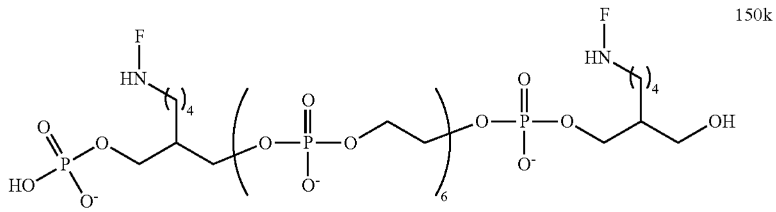 | 150k |
| $FC_7F$ | 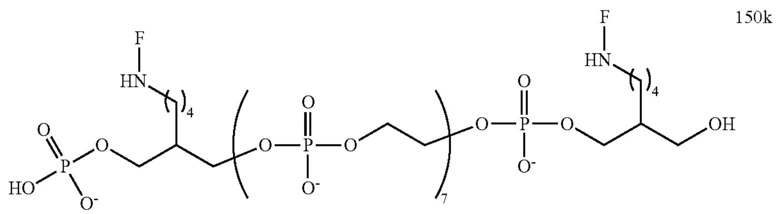 | 150k |
| $FC_8F$ | 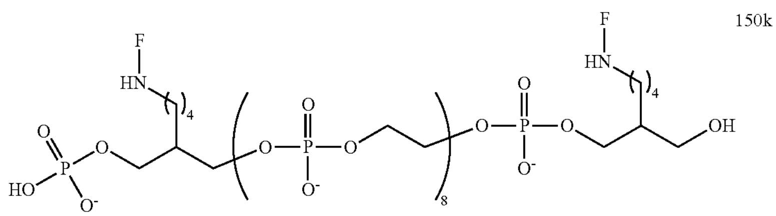 | 150k |
| $FC_9F$ | 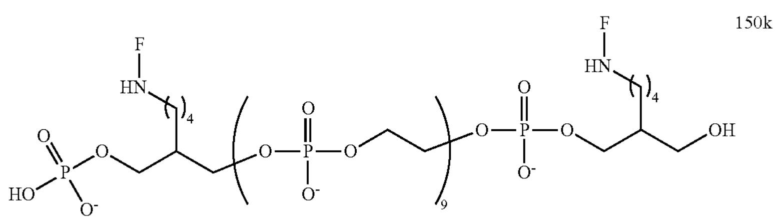 | 150k |

$\varepsilon_t$ and F are as defined above, and the "C linker" has the following structure:

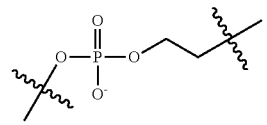

"C linker"

In embodiments, the dye compounds listed in Table 6 may be used in compositions and/or methods of the disclosure. The dye compounds listed in Table 6 were prepared according to procedures known in the art (see, e.g., WO 2016/183185, incorporated by reference herein for the teachings regarding synthetic methods). The UV and fluorescence properties were determined at 2 nM and pH 9.

TABLE 6

Dye Compounds

| Name | Structure | $\varepsilon_t^*$ |
|---|---|---|
| F | F—OH | 75k |
| FC$_4$F | 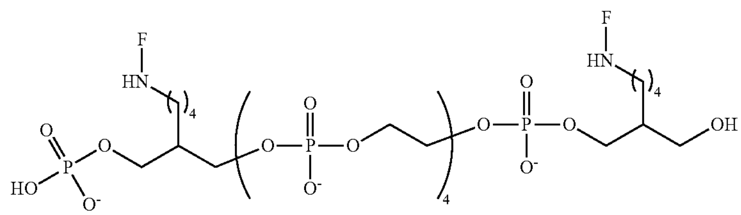 | 150k |
| F(C$_4$F)$_2$ | 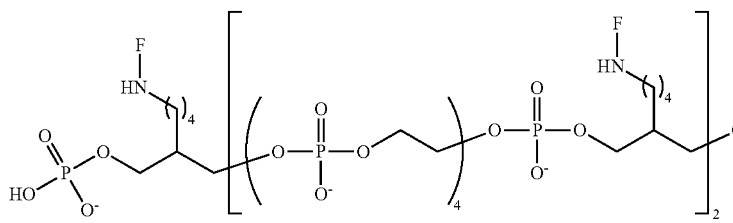 | 225k |
| F(C$_4$F)$_3$ | 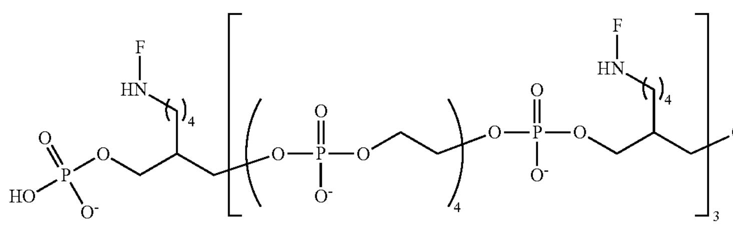 | 300k |
| F(C$_4$F)$_4$ | 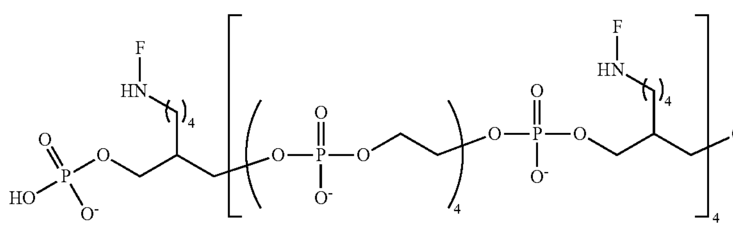 | 375k |
| F(C$_4$F)$_5$ | 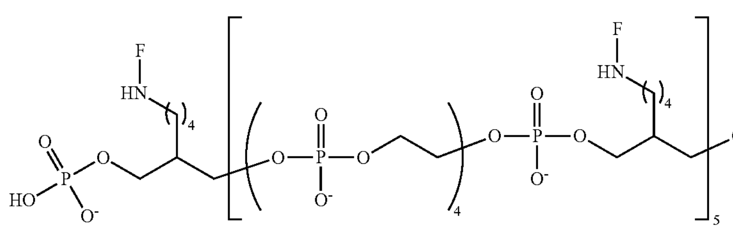 | 450k |

$\varepsilon_t$ and F are as defined above.

In embodiments, the dye compounds listed in Table 7 may be used in compositions and/or methods of the disclosure. The dye compounds listed in Table 7 were prepared according to procedures known in the art (see, e.g., WO 2016/183185, incorporated by reference herein for the teachings regarding synthetic methods). The UV and fluorescence properties were determined at 25 nM and pH 9.

TABLE 7

Dye Compounds

| Name | Structure | $\varepsilon_t{}^*$ |
|---|---|---|
| F | F—OH | 75k |
| FC$_7$F | 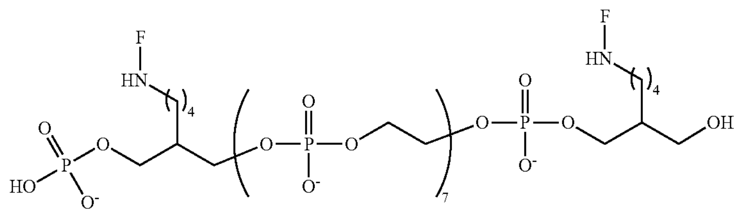 | 150k |
| F(C$_7$F)$_2$ | 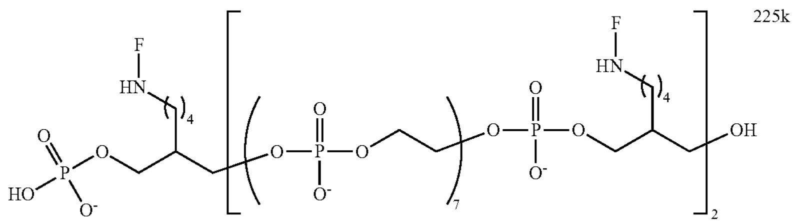 | 225k |
| F(C$_7$F)$_3$ | 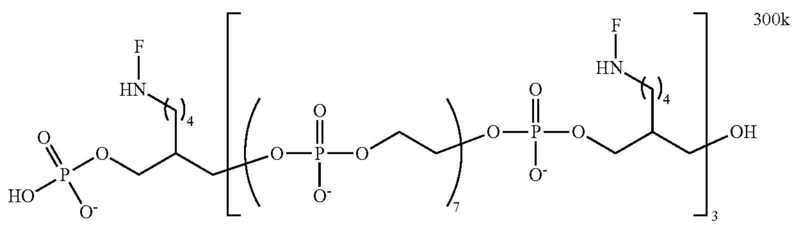 | 300k |
| F(C$_7$F)$_4$ | 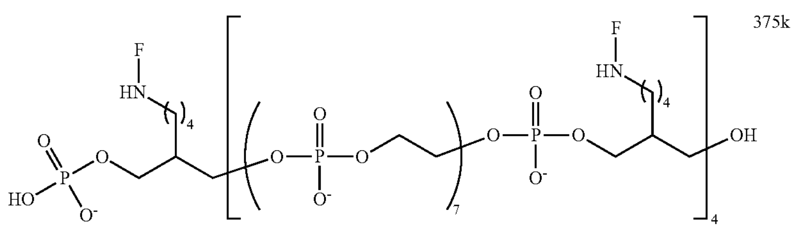 | 375k |
| F(C$_7$F)$_5$ | 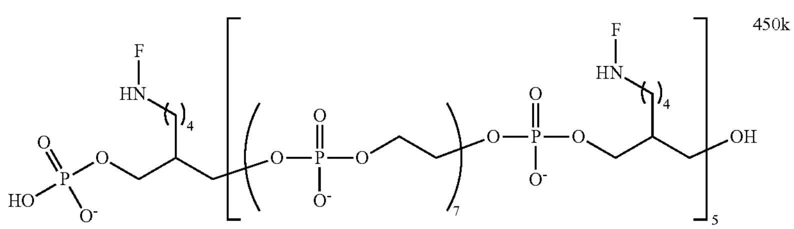 | 450k |

$\varepsilon_t$ and F are as defined above.

In embodiments, the dye compounds listed in Table 8 may be used in compositions and/or methods of the disclosure. The dye compounds listed in Table 8 were prepared according to procedures known in the art (see, e.g., WO 2016/183185, incorporated by reference herein for the teachings regarding synthetic methods). The UV and fluorescence properties were determined at 10 nM and pH 9.

TABLE 8

| Dye Compounds | |
|---|---|
| Name | Structure |
| F | F—OH |
| $FC_7F$ | (structure) |
| $F(C_7F)_2$ | (structure) |
| $F(C_7F)_3$ | (structure) |
| $F(C_7F)_4$ | (structure) |
| $F(C_7F)_5$ | (structure) |
| $F(C_7F)_9$ | (structure) |

F is as defined above.

In embodiments, the dye compounds listed in Table 9 may be used in compositions and/or methods of the disclosure. The dye compounds listed in Table 9 were prepared according to procedures known in the art (see, e.g., WO 2016/183185, incorporated by reference herein for the teachings regarding synthetic methods). The UV and fluorescence properties were determined at 50 nM and pH 9.

mercially available DNA synthesis reagents were purchased from Glen Research (Sterling, VA). Anhydrous pyridine, toluene, dichloromethane, diisopropylethyl amine, triethylamine, acetic acid, pyridine, and THF were purchased from Aldrich. All other chemicals were purchase from Aldrich or TCI and were used as is with no additional purification.

TABLE 9

Dye Compounds

| Name | Structure |
|---|---|
| E | (structure shown) |
| $E(C_6E)_2$ | (structure shown) |
| $E(C_7E)_2$ | (structure shown) |

E is as defined above.

The following examples are provided for purposes of illustration, not limitation.

EXAMPLES

General Methods

Mass spectral analysis was performed on a Waters/Micromass Quattro micro MS/MS system (in MS only mode) using MassLynx 4.1 acquisition software. Mobile phase used for LC/MS on dyes was 100 mM 1,1,1,3,3,3-hexafluoro-2-propanol (HFIP), 8.6 mM triethylamine (TEA), pH 8. Phosphoramidites and precursor molecules were also analyzed using a Waters Acquity UHPLC system with a 2.1 mm×50 mm Acquity BEH-C18 column held at 45° C., employing an acetonitrile/water mobile phase gradient. Molecular weights for monomer intermediates were obtained using tropylium cation infusion enhanced ionization on a Waters/Micromass Quattro micro MS/MS system (in MS only mode). Excitation and emission profiles experiments were recorded on a Cary Eclipse spectra photometer.

All reactions were carried out in oven dried glassware under a nitrogen atmosphere unless otherwise stated. Com-

Example 1

Synthesis of Dyes with Ethylene Glycol Spacer

Compounds with ethylene oxide linkers were prepared as followed:

The oligofluoroside constructs (i.e., compounds of structure (I)) were synthesized on an Applied Biosystems 394 DNA/RNA synthesizer on 1 μmol scale and possessed a 3'-phosphate group or 3'-$S_2$—$(CH_2)_6$—OH group or any of the other groups described herein. Synthesis was performed directly on CPG beads or on Polystyrene solid support using standard phopshoporamadite chemistry. The oligofluorosides were synthesized in the 3' to 5' direction using standard solid phase DNA methods, and coupling employed standard β-cyanoethyl phosphoramidite chemistry. Fluoroside phosphoramidite and spacers (e.g., hexaethyloxy-glycol phosphoramidite, triethyloxy-glycol phosphoramidite, polyethylene glycol phosphoramidite) and linker (e.g., 5'-amino-Modifier Phosphoramidite and thiol —Modifiers S2 Phosphoramidite) were dissolved in acetonitrile to make 0.1

M solutions, and were added in successive order using the following synthesis cycle: 1) removal of the 5'-dimethoxytrityl protecting group with dichloroacetic acid in dichloromethane, 2) coupling of the next phosphoramidite with activator reagent in acetonitrile, 3) oxidation of P(III) to form stable P(v) with iodine/pyridine/water, and 4) capping of any unreacted 5'-hydroxyl groups with acetic anhydride/1-methylimidizole/acetonitrile. The synthesis cycle was repeated until the full length oligofluoroside construct was assembled. At the end of the chain assembly, the monomethoxytrityl (MMT) group or dimethoxytrityl (DMT) group was removed with dichloroacetic acid in dichloromethane.

The compounds were provided on controlled-pore glass (CPG) support at 0.2 umol scale in a labeled Eppendorf tube. 400 $\mu$L of 20-30% NH$_4$OH was added and mixed gently. Open tubes were placed at 55° C. for ~5 minutes or until excess gases had been liberated, and then were closed tightly and incubated for 2 hrs (+/−15 min.). Tubes were removed from the heat block and allowed to reach room temperature, followed by centrifugation at 13,400 RPM for 30 seconds to consolidate the supernatant and solids. Supernatant was carefully removed and placed into a labeled tube, and then 150 $\mu$L acetonitrile was added to wash the support. After the wash was added to the tubes they were placed into a CentriVap apparatus at 40° C. until dried.

The products were characterized by ESI-MS (see Table 2), UV-absorbance, and fluorescence spectroscopy.

Example 2

Spectral Testing of Compounds

Dried compounds were reconstituted in 150 μL of 0.1M Na$_2$CO$_3$ buffer to make a ~1 mM stock. The concentrated stock was diluted 50× in 0.1×PBS and analyzed on a NanoDrop UV spectrometer to get an absorbance reading. Absorbance readings were used along with the extinction coefficient (75,000 M$^{-1}$ cm$^{-1}$ for each FAM unit) and Beer's Law to determine an actual concentration of the stock.

From the calculated stock concentrations, ~4 mL of a 5 μM solution was made in 0.1M Na$_2$CO$_3$ (pH 9) and analyzed in a 1×1 cm quartz cuvette on a Cary 60 UV spectrometer, using a spectral range of 300 nm to 700 nm, to gauge overall absorbance relative to the group. From these 5 μM solutions, a second dilution was made at either 50 nM or 25 nM (also in 0.1M Na$_2$CO$_3$, pH 9) for spectral analysis on a Cary Eclipse Fluorimeter. Excitation was set at 494 nm and emission spectra were collected from 499 to 700 nm.

Figure 1:
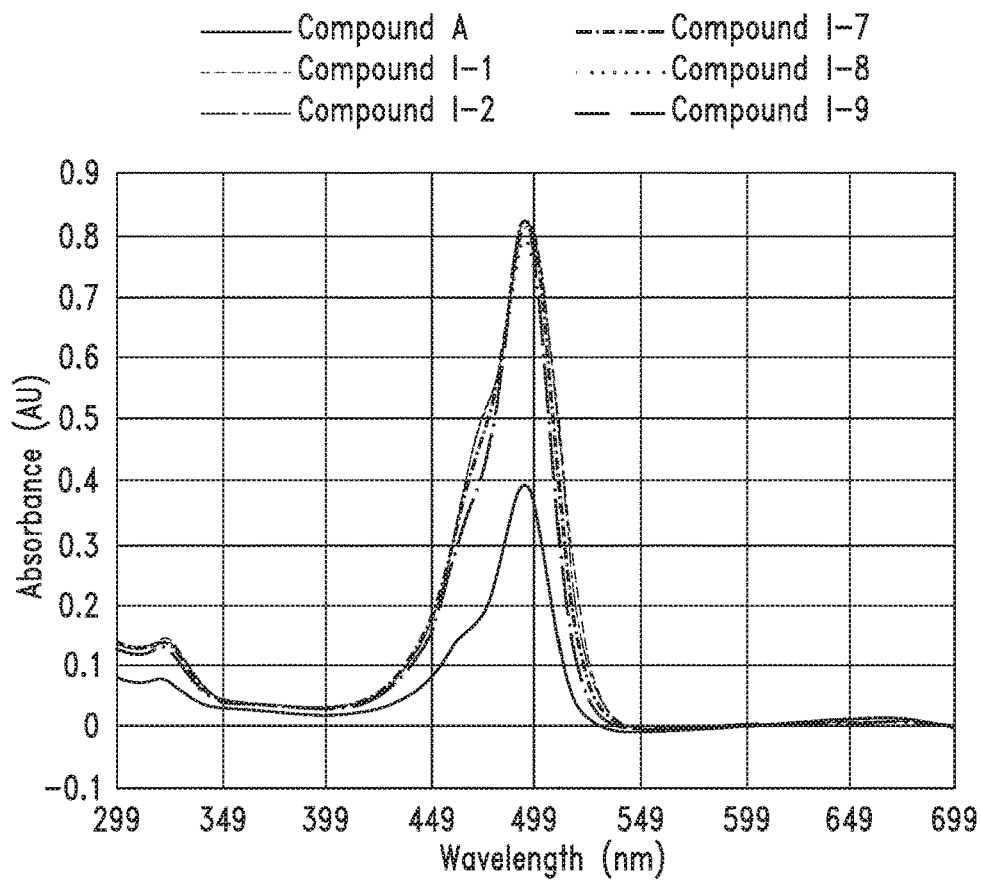
FIG. 1 provides UV absorbance spectra for representative compounds comprising a triethylene glycol spacer and a comparative compound at 5 μm and pH 9.
Figure 2:
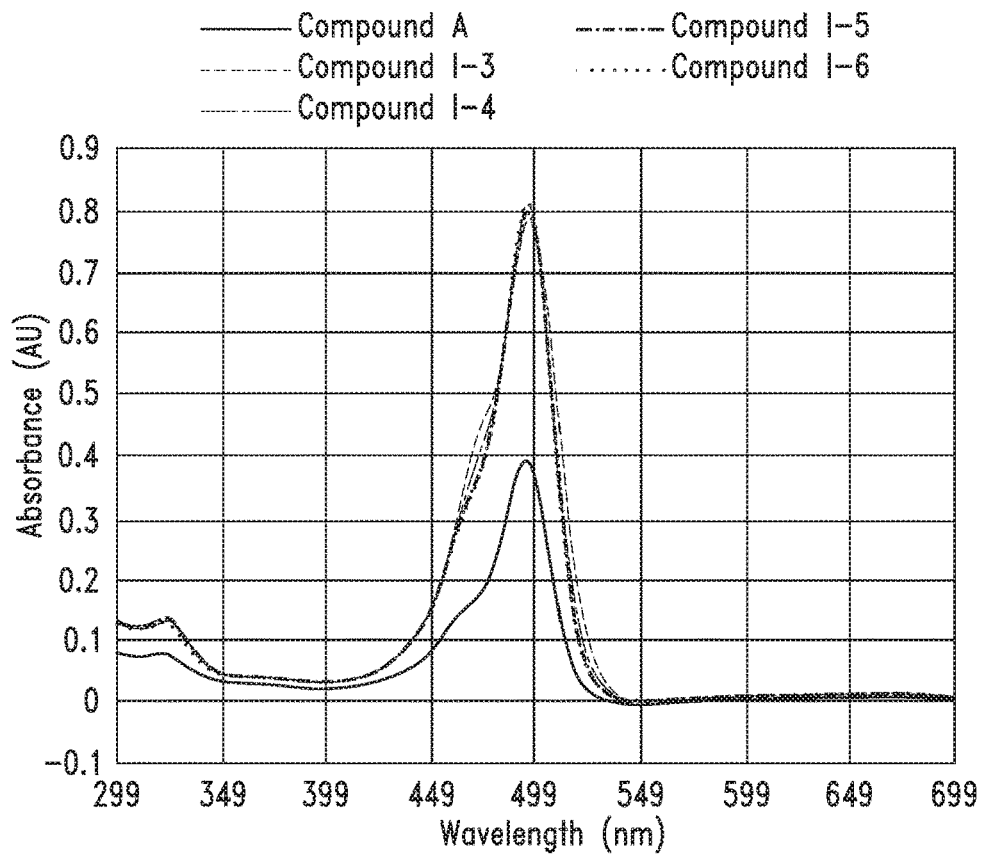
FIG. 2 is UV absorbance data for representative compounds comprising a hexaethylene glycol spacer and a comparative compound at 5 μm and pH 9.

FIG. 1 and FIG. 2 provide the UV absorbance of representative compounds of structure (I) and a comparative compound ("Compound A.") As seen in FIGS. 1 and 2, the UV extinction coefficient of representative compounds of structure (I) comprising two fluorescein moieties is approximately twice that of compound A.

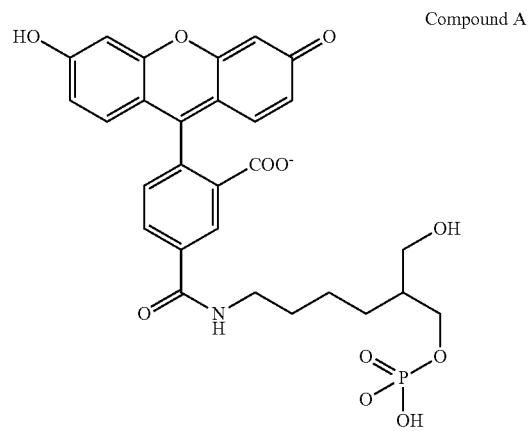

Compound A

Figure 3:
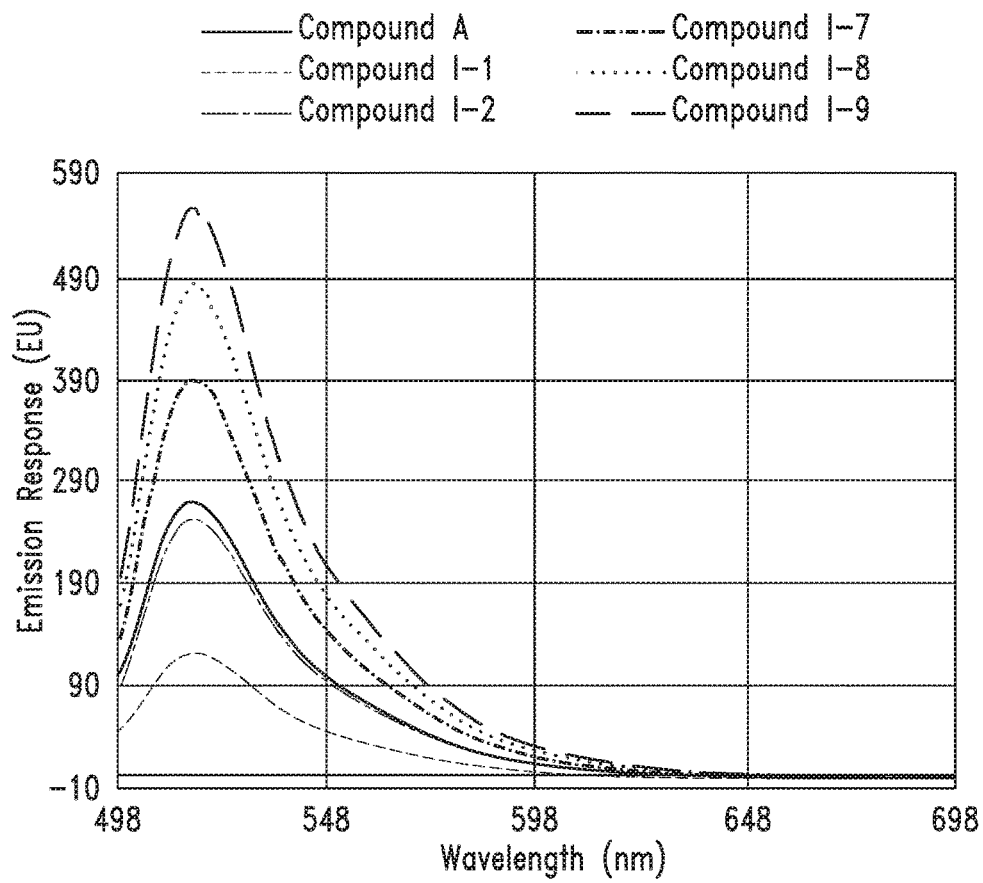
FIG. 3 is fluorescence emission spectra for representative compounds comprising a triethylene glycol spacer and a comparative compound at 50 nM and pH 9.
Figure 4:
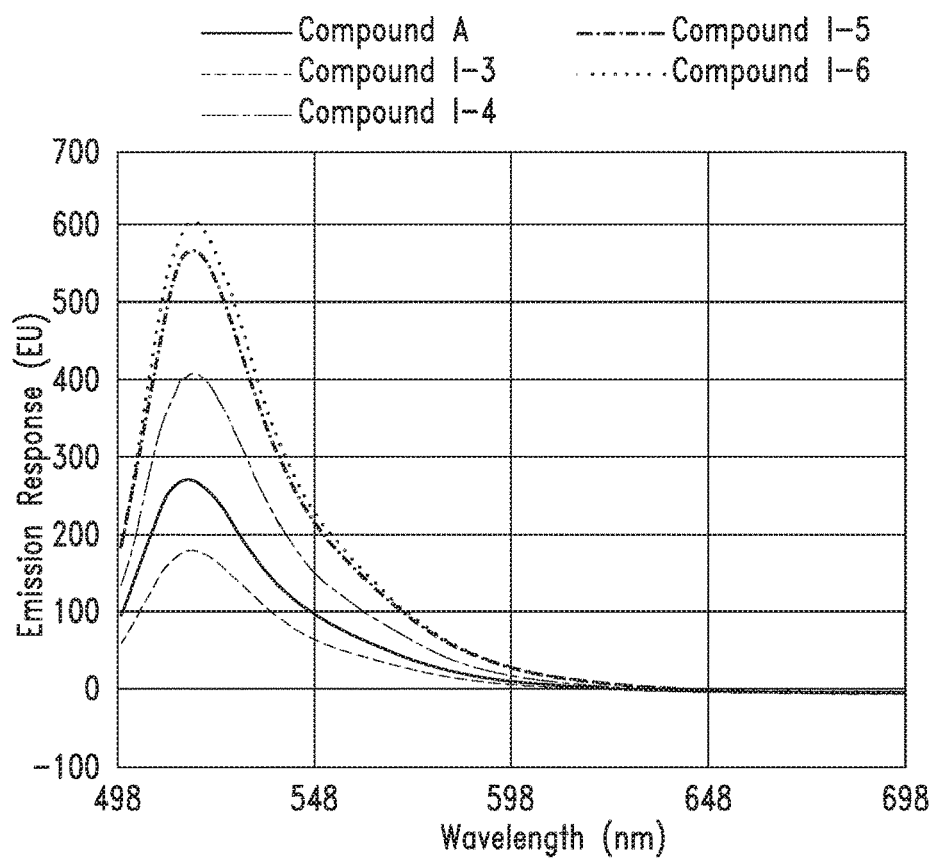
FIG. 4 presents fluorescence emission spectra for representative compounds comprising a hexaethylene glycol spacer and a comparative compound at 50 nM and pH 9.

The fluorescence emission spectra of representative compounds of structure (I) were also determined and compared to the emission spectrum of compound A. As demonstrated by the data in FIGS. 3 and 4, the fluorescence emission of representative compounds of structure (I) is higher than compound A, and the emission increases as the number of triethylene glycol or hexaethylene glycol units increases. While not wishing to be bound by theory, it is believed this unexpected increase in fluorescence emission is related to a decrease in internal quenching associated with the spatial distance provided by L$^4$.

Figure 5:
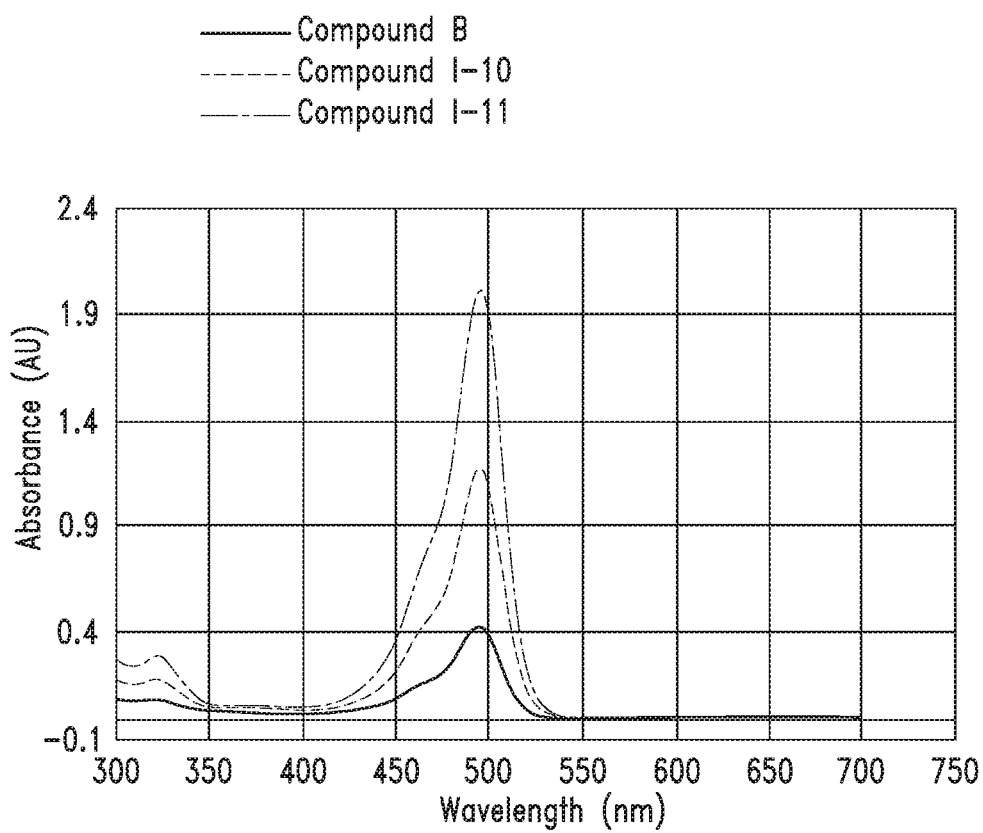
FIG. 5 is UV absorbance data at 5 μm for representative compounds comprising four hexaethylene glycol spacers and two or three fluorescein moieties relative to a comparative compound having a single fluorescein moiety.

Compounds I-10 and I-11 were tested to determine the effect of the number of M moieties on the UV absorbance and fluorescence emission of the compounds. FIG. 5 provides data comparing UV absorbance of compounds I-10 and I-11 to a comparative compound having a single M moiety ("Compound B") at 5 μm. At 5 uM, Compound B, which contains a single FAM unit absorbed at 0.43 AU, while compound I-10 (3 FAM units) absorbed at 1.17 AU and compound I-11 (5 FAM units) absorbed at 2.00 AU.

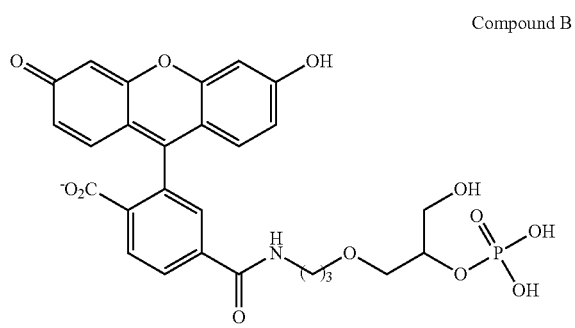

Compound B

Figure 6:
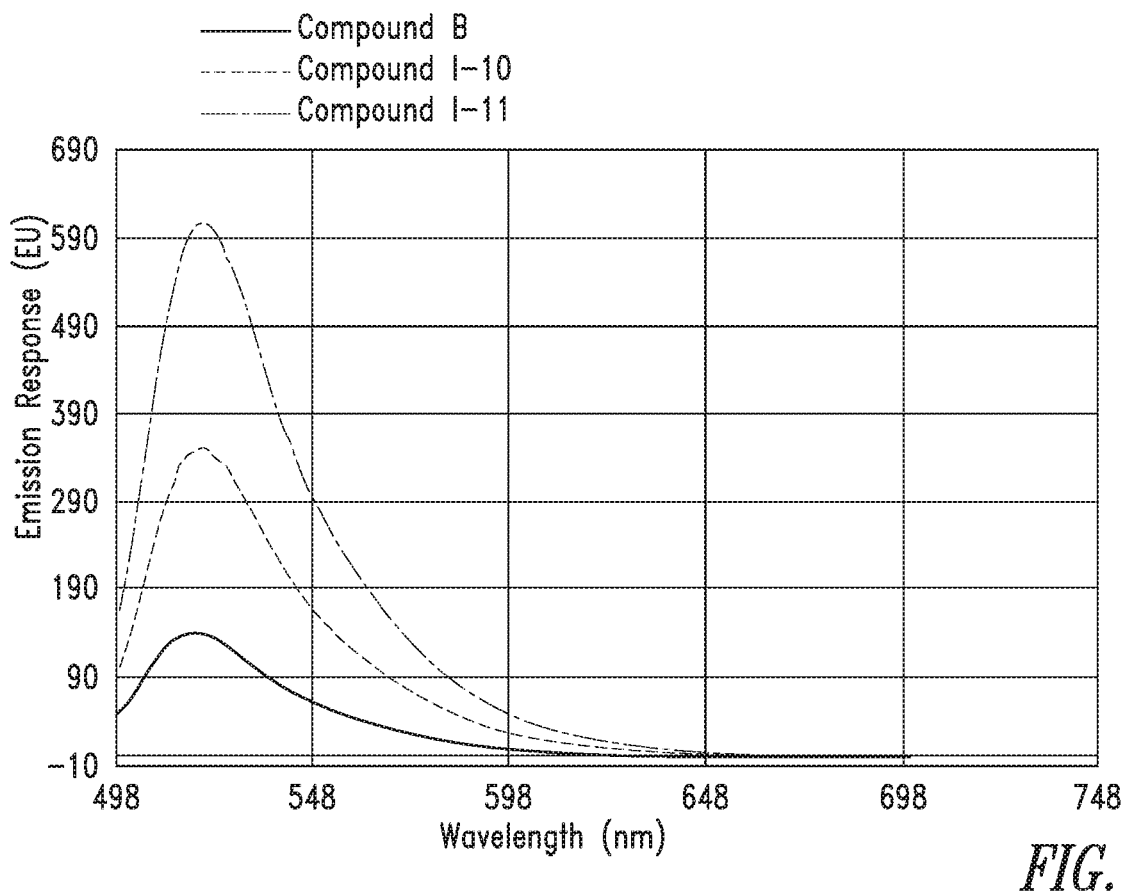
FIG. 6 is a graph of fluorescent emission data at 5 μm for representative compounds comprising four hexaethylene glycol spacers and two or three fluorescein moieties relative to a comparative compound having a single fluorescein moiety.

Fluorescence emission spectra for compounds I-10, I-11 and B at 25 nM are presented in FIG. 6. Rather than quenching (as more closely-spaced FAM units would do), compounds I-10 and I-11 showed emission responses that were increased by 2.5× and 4.3×, respectively, compared to the value of Compound B.

Example 3

Comparative Fluorescence Emission Response

Figure 7:
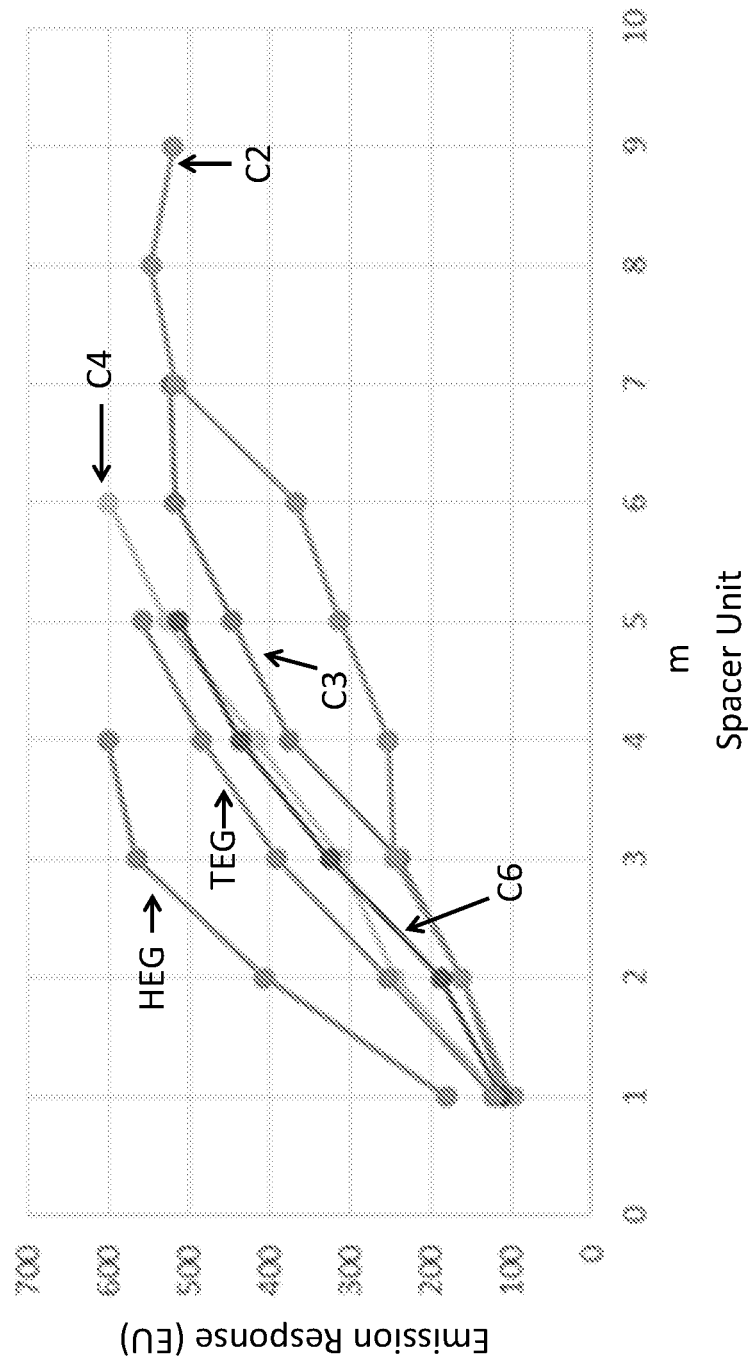
FIG. 7 shows comparative fluorescence emission response for illustrative compounds with various m values.

Compounds "HEG," "TEG," "C2," "C3," "C4" and "C6," wherein R$^2$ and R$^3$ are as defined for compound I-3 and m varied from 1 to 9, were prepared and their fluorescence emission spectra determined. Results are presented in FIG. 7. The data show that compounds according to embodiments of the present invention (i.e., HEG and TEG) have increased fluorescence emission with fewer repeating spacer moieties (i.e., lower values of m) relative to other dye compounds.

Figure 8:
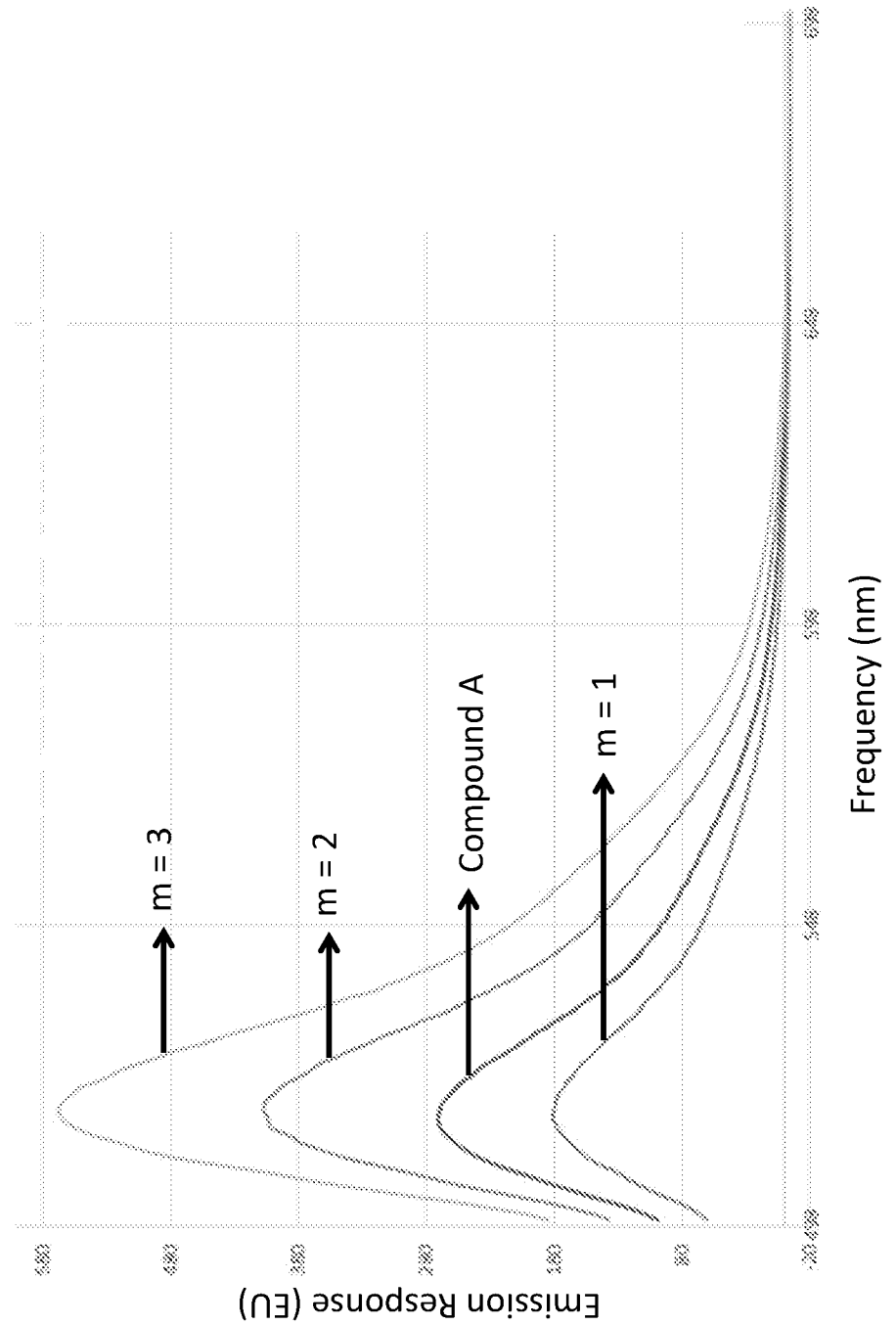
FIG. 8 provides data comparing fluorescence emission for the "HEG" compound, wherein m is 1, 2 or 3, relative to Compound A.

FIG. 8 provides data comparing fluorescence emission for the "HEG" compound, wherein m is 1, 2 or 3, relative to Compound A (50 nM, pH=9). The data show an increase in fluorescence emission for HEG relative to Compound A when m is greater than 2.

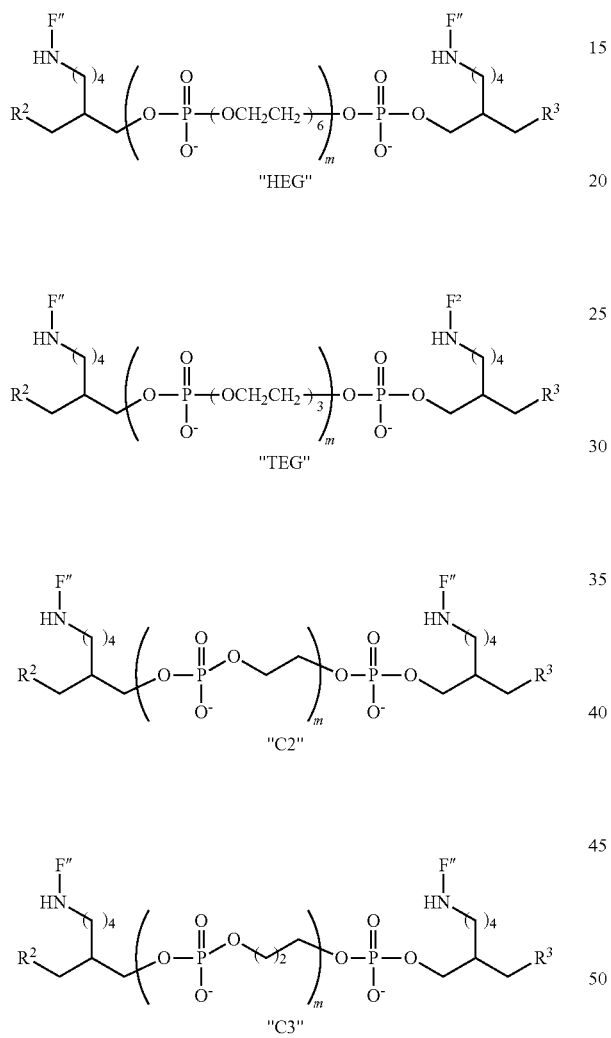

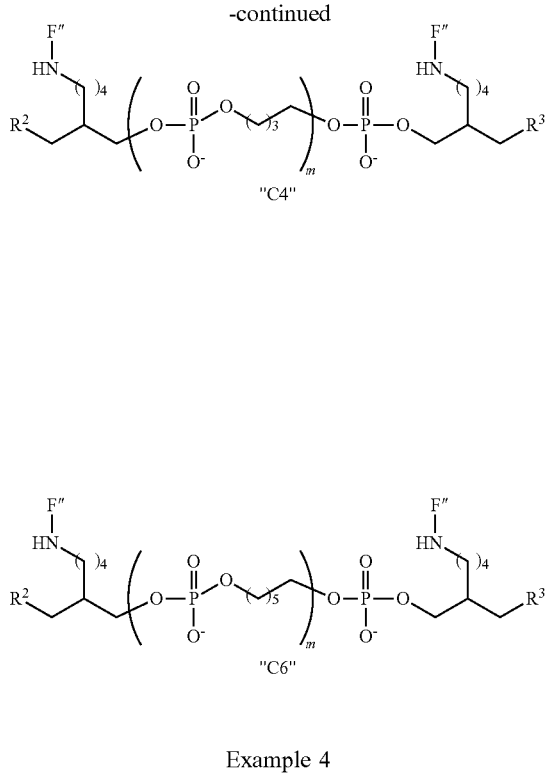

Example 4

Preparation of Representative Compounds

Figure 9:
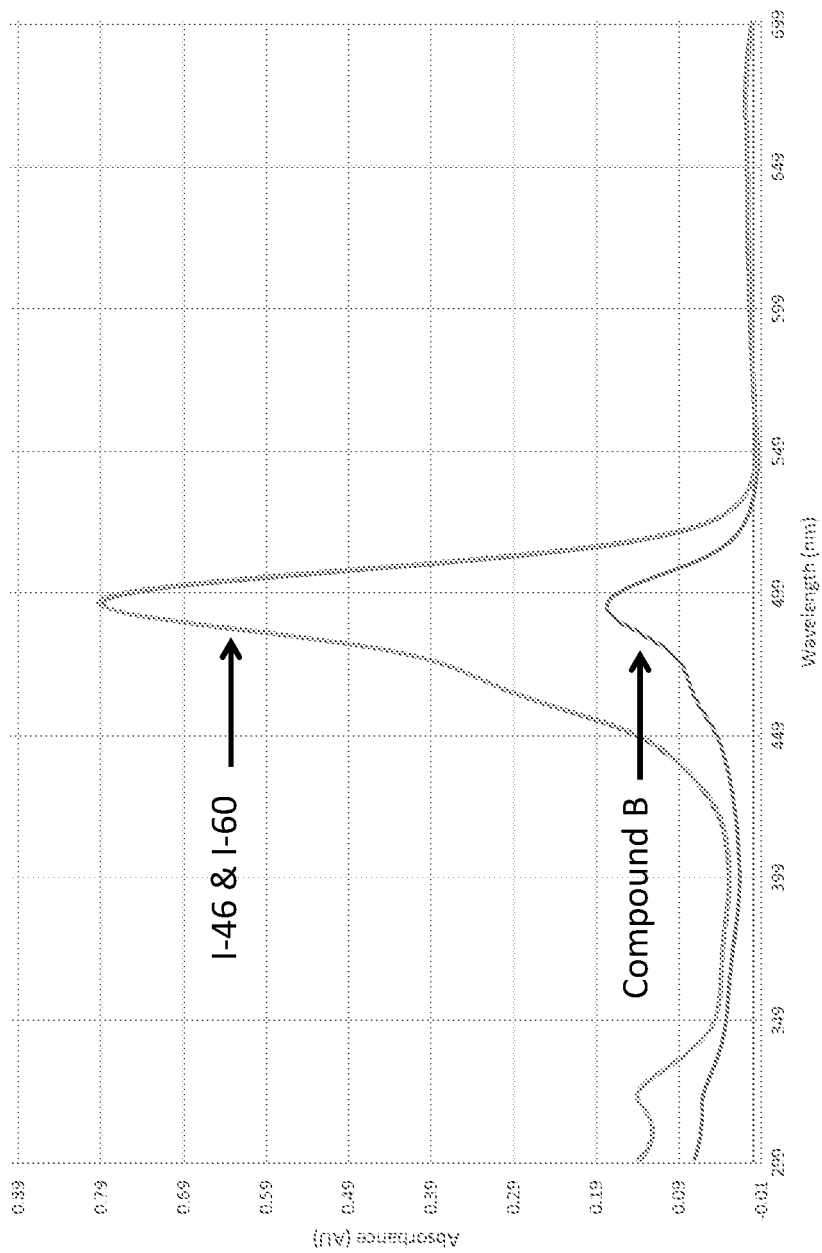
FIG. 9 provides absorbance data for compound I-32, compound I-46 and Compound B.

Compounds I-29, I-32 and representative analogues were prepared and tested to determine whether compounds wherein $L^4$ is a long linker (~1,000 dalton PEG) have similar properties to compounds with shorter $L^4$ linkers, but with multiple repeats (i.e., m is greater than 1). FIG. 9 provides UV absorbance data for compound I-60, compound I-46 and Compound B. The data show that compounds with long $L^4$ linkers have UV absorbance similar to those of compounds with multiple repeats of shorter linkers, and both compounds have increased absorbance relative to the control Compound B.

Example 5

Preparation of 99-Mer Dye

Compound I-42, having 33 fluorescein moieties was prepared using standard solid-phase oligonucleotide techniques as described herein. I-42 (represented by "A" in the below scheme) was trimerized as illustrated and described below to form a 99-mer dye.

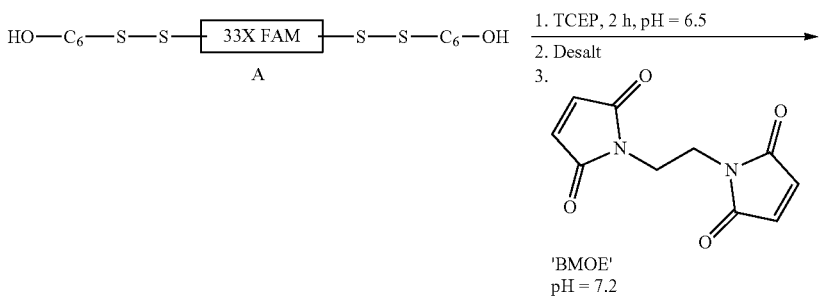

-continued

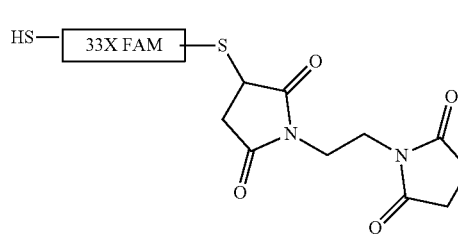

Figure 10:
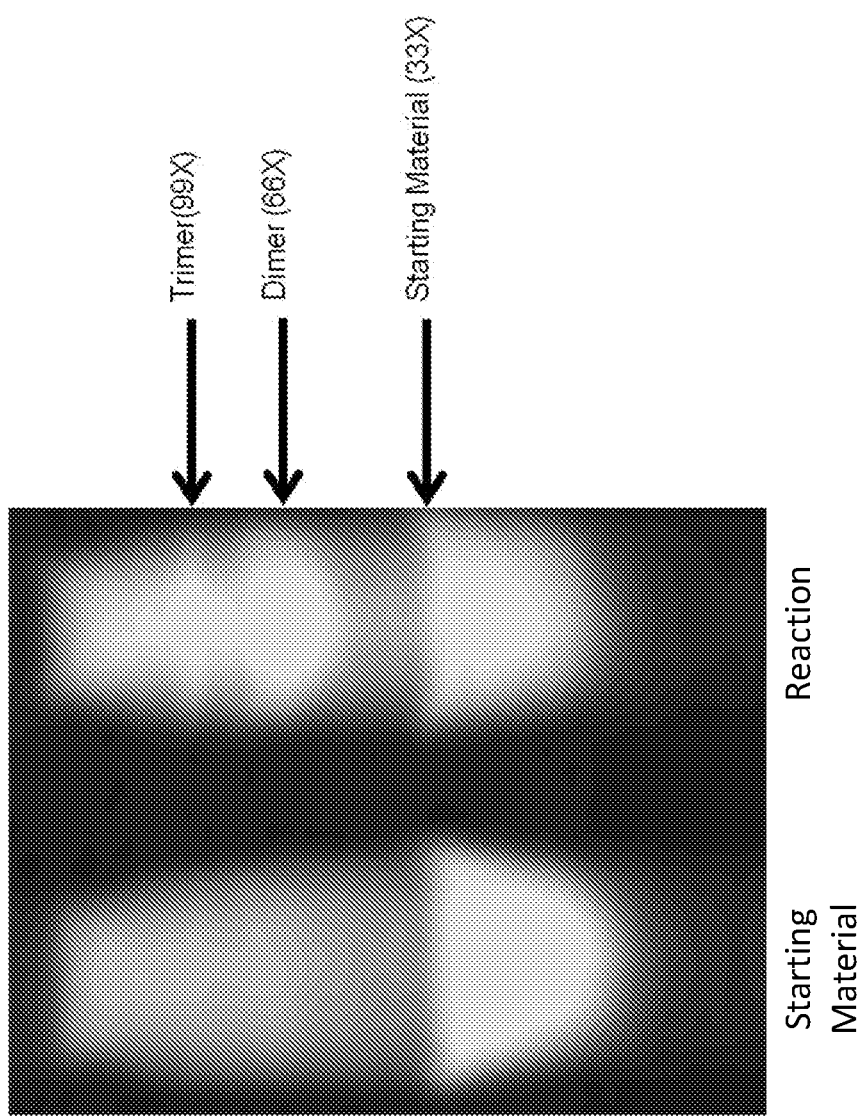
FIG. 10 shows the results of a reaction trimerizing compound I-42 as analyzed by PAGE.
Figure 11:
FIG. 11 diagrams the cations configurations in immunofluorescence methods.

In a 2004, polypropylene tube was placed sodium phosphate buffer (3.5 μL, 100 mM, pH=6.5) and a solution of I-42 bis-disulfide (5.5 μL, 0.18 mM in water). To this was added a solution tris(2-carboxyethyl)phosphine (TCEP, 1.0 μL, 10 mM in water). The tube was capped, vortexed and allowed to incubate at room temperature for 2 h. The mixture was desalted through micro Zeba Spin desalting columns (Pierce, Cat #89877). The desalted solution was treated with sodium phosphate buffer (2.0 μL, 500 mM, pH=7.2) and a DMSO solution of bismaleimidoethane (BMOE, 1.0 μL, 0.25 mM) and incubated overnight at room temperature. The reaction mixture was diluted with water (100 μL) and analyzed by PAGE (FIG. 10, Invitrogen EC6875, 10% TBE-Urea gel, 180V constant, electrophoresis halted with resolution of highest MW species completed, visualized by UV illumination (365 nm)).

Other oligomer dyes having any desired number of dye moieties are prepared in an analogous manner.

Example 6

General Flow Cytometry Methods

Unless otherwise noted, the following general procedures were used in the following Examples.

Lysis of whole blood:

Buffered Ammonium Chloride Method. For staining of live cells, ethylenediaminetetraacetate (EDTA) anticoagulated normal human blood is bulk lysed with Ammonium Chloride solution (ACK), 15 mL blood to 35 mL lyse for 15 min at room temperature (RT). The cells were washed twice with 50% Hank's Balanced Salt Solution (HBSS) and 50% 1% Fetal Bovine Serum (FBS) 1× Dulbecco's Phosphate-Buffered Saline (DPBS) with 0.02% sodium azide. The cells were then re-suspended to 100 μL/test/0.1-1×10e6 in donor plasma. Cells in plasma were added to pre-diluted antibodies for $V_f$ of 1004, 1% Bovine Serum Albumin (BSA) and 1×DPBS with 0.02% sodium azide in polypropylene 96 well HTS plates. After incubating for 45 min. at RT, the cells were washed twice with 50% HBSS and 50%-1% FBS 1×DPBS with 0.02% sodium azide.

Lyse/Fixation Method. Blood was lysed with 1.0 mL RBC lysing solution (ammonium chloride), 100-15 mL blood to 35 mL lyse for 15 min at RT. The cells were then washed twice with 50% HBSS and 50%-1% FBS 1×DPBS with 0.02% sodium azide. Cells were then re-suspended to 100 μL/test/1×10e6 in donor plasma. Pre-diluted antibodies were added in 1004, 1% BSA and 1×DPBS with 0.02% sodium azide. 1004, cells were added to 96 well polypropylene HTS plates (total 2004, test size). After incubation for 45 min. at RT the cells were washed twice with 50% HBSS and 50% 1% FBS 1×DPBS with 0.02% sodium azide.

Preparation of Antibody Conjugates:

Antibody conjugates were prepared by reacting a compound of structure (I) comprising a Q moiety having the following structure:

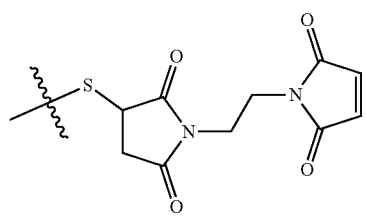 [SMILES: *SC1CC(=O)N(CCN2C(=O)C=CC2=O)C1=O]

with the desired antibody. The compound and antibody are thus conjugated by reaction of an S on the antibody with the Q moiety to form the following linking structure:

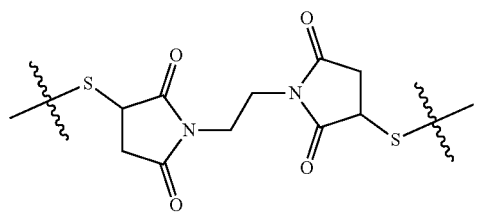 [SMILES: *SC1CC(=O)N(CCN2C(=O)CC(S*)C2=O)C1=O]

Antibody conjugates are indicated by the antibody name following by the compound number. For example, UCHT1-I-45 indicates a conjugate formed between compound I-45 and the UCHT1 antibody. If a referenced compound number does not include the above Q moiety in Table 2, it is understood that the Q moiety was installed and the conjugate prepared from the resulting compound having the Q moiety.

Dilution of Conjugates:

Antibodies were brought to RT. The antibody conjugates were diluted to concentrations in a range of 0.1-540 nM (8.0 micrograms or less per test) in a cell staining buffer (1×DPBS, 1% BSA, 0.02% sodium azide). In some examples, serial dilutions for each sample started at 269 nM antibody in cell staining buffer, and the antibody dilutions were kept protected from light until use. In other experiments, dilutions started at 4.0 μg antibody/test size, with the test size ranging from 100-200 μL. Titers were performed in two fold or four fold dilutions to generate binding curves. In some cases, 8.0 or 2.0 μg/test size were used in first well in a dilution series.

Flow Cytometry with Conjugate:

After physical characterization, the conjugates were tested for activity and functionality (antibody binding affinity and brightness of dye) and compared to reference antibody staining. Then the quality of resolution was determined by reviewing the brightness in comparison to auto-fluorescent negative controls, and other non-specific binding using the flow cytometer. Extensive studies of the mouse IgG1,k isotype control MOPC-21 conjugates were not included when testing I-45 because MOPC-21 non-specific binding was characterized during the testing of UCHT1-Compound C and UCHT1-I-45 in earlier tests. The I-45 conjugates were tested on Jurkat T cells, Ramos B cells, and a heterogeneous population of leukocytes in human blood or peripheral blood mononuclear cells (PBMC), and using polystyrene goat-anti-mouse Ig coated beads. Whole blood screening was the most routine for testing UCHT1 I-45 and its analogues. Bridging studies were implemented as new constructs were formed. Additional flow cytometry methods were used when testing conjugates (UCHT1-I-56, I-48, I-49, I-16, and I-21B) and compared to antibody conjugate references from Sony Biotechnology (UCHT1-FITC) and the key bridging references previously characterized (e.g. UCHT1-I-45, UCHT1-I-49) in most studies.

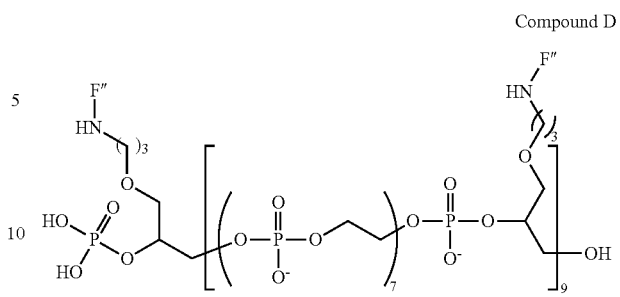

Compound D

Flow Cytometry Workflow:

Cells were cultured and observed for visual signs of metabolic stress for dye screening or off target binding (data not shown), or fresh healthy cells were used for conjugate screening. Cells were counted periodically to check cell density (1×10e5 and 1×10e6 viable cells/mL). Antibody conjugates were diluted (preferably in plate or tubes) before harvesting cells in stain buffer (DPBS, 0.1% BSA, 0.02% sodium azide). Cells with a viability range of 80-85% were used. The cells were washed twice by centrifuging and Compound C Perform Free Dye Flow Cytometry:

After molecular and physical characterization, the dyes were also tested for potential affinity to cells compared to a reference dye stain. Because dyes have the potential to also function as cellular probes and bind to cellular material, dyes can be generally screened against blood at high concentrations (>100 nM-to-10,000 nM) to ascertain specific characteristics. Expected or unexpected off target binding was then qualified by evaluating brightness and linearity upon dilution in comparison to auto-fluorescent negative controls, and other dye controls using the flow cytometer. Studies of Compound D (a Compound C free dye, but non-functionalized) was the positive control for bright off target binding of dyes and has been previously characterized when in conjugate form. The I-45 dyes were tested on heterogeneous population of leukocytes in human blood when cells are treated with lysis and fixation solution, and when the blood is aged, or when applied to PBMC monocyte populations. Bridging studies ranking the affinity (Compound D, I-45, I-49, and I-16) were performed for dye lot comparisons while including dyes from very early studies when characterizing Compound D.

washing cells with buffer to remove pH indicator, and to block cells with Ig and other proteins contained in FBS. The cell density was adjusted to test size in stain buffer. The cells were plated, one test per well, or dyes (pre-diluted) were applied to cells in plate. Then, the cells were incubated 45 min at 23° C. The cells were washed twice by centrifuging and washing cells with wash buffer, then aspirating the plate. The cells were re-suspended in acquisition buffer. 5000 intact cells were acquired by flow cytometry.

The fluorescence of the dyes was detected by 488 nM blue laser line by flow cytometry with peak emission (521 nM) detected using 525/50 bandpass filter. At least 1500 intact cells, with target acquisitions of 3000-5000 intact cells, were acquired by flow cytometry and analyzed to identify viable cells present in the cell preparation.

Data Analysis Methods:

Descriptive Statistics. The EC-800 software allows a user to collect numerous statistical data for each sample acquisition. Mean or Median Fluorescence Intensity (MFI) in the FL1-A channel was used to measure the brightness of an antibody-dye reagent when it was being interrogated by flow cytometry and when noise was reviewed. Other statistics were evaluated to determine dye characteristics and overall quality of the reagents including median Signal-to-Noise and absolute fluorescence (median or Geomean).

Histograms. The flow cytometry events were gated by size on forward versus side scatter (cell volume versus cell granularity). Those cells were then gated by fluorescent emission at 515 nm for Mean Fluorescence Intensity (MFI). The data collected are presented as dual parameter histograms plotted as number of events on the y-axis versus fluorescent intensity, which is represented on a log scale on the x-axis. The data may be summarized by affinity curves, or histograms of relative fluorescence intensity.

Binding Curves. MFI was chosen as it is the parameter that best measures the brightness of an antibody-dye reagent when it is being interrogated by FCM, this can be expressed as the geometric mean, median, or mean, and represent absolute fluorescence measurements. For comparison, where the noise can be highly characterized, a Signal-to-Noise ratio is reported as MFI, S/N.

Bi-Variate, Dual Parameter Histograms. In some cases, the FCM events were not gated in order to review qualitative outputs, and data are expressed by cell granularity (SSC) versus dye fluorescence. This method allows for the overall evaluation of all populations recovered in whole blood.

Example 7

Figure 14:
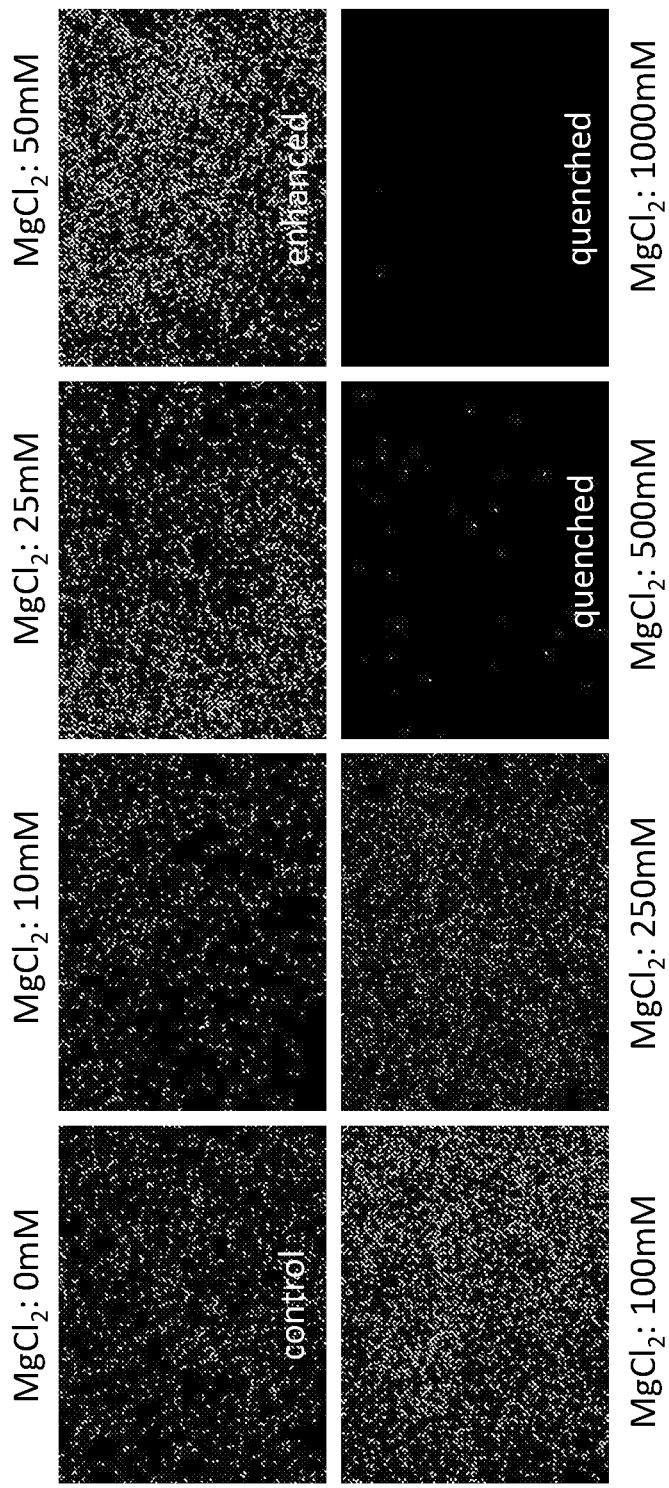
FIG. 14 shows first example results from fluorescence microscopy of fixed and permeabilized human PBMC. Extracellular and intracellular CD3 fluorescence resolution enhanced (and then quenched) by incubation with divalent cations, $MgCl_2$ Gradient, 10× I-16 UCHT1. The $MgCl_2$ titration (at pH 7.4) (range 0-1000 mM) was applied only during incubation with targeting moiety (10× I-16 UCHT1) for detection of surface and intracellular CD3, then washed with a buffer not containing cations.
Figure 15:
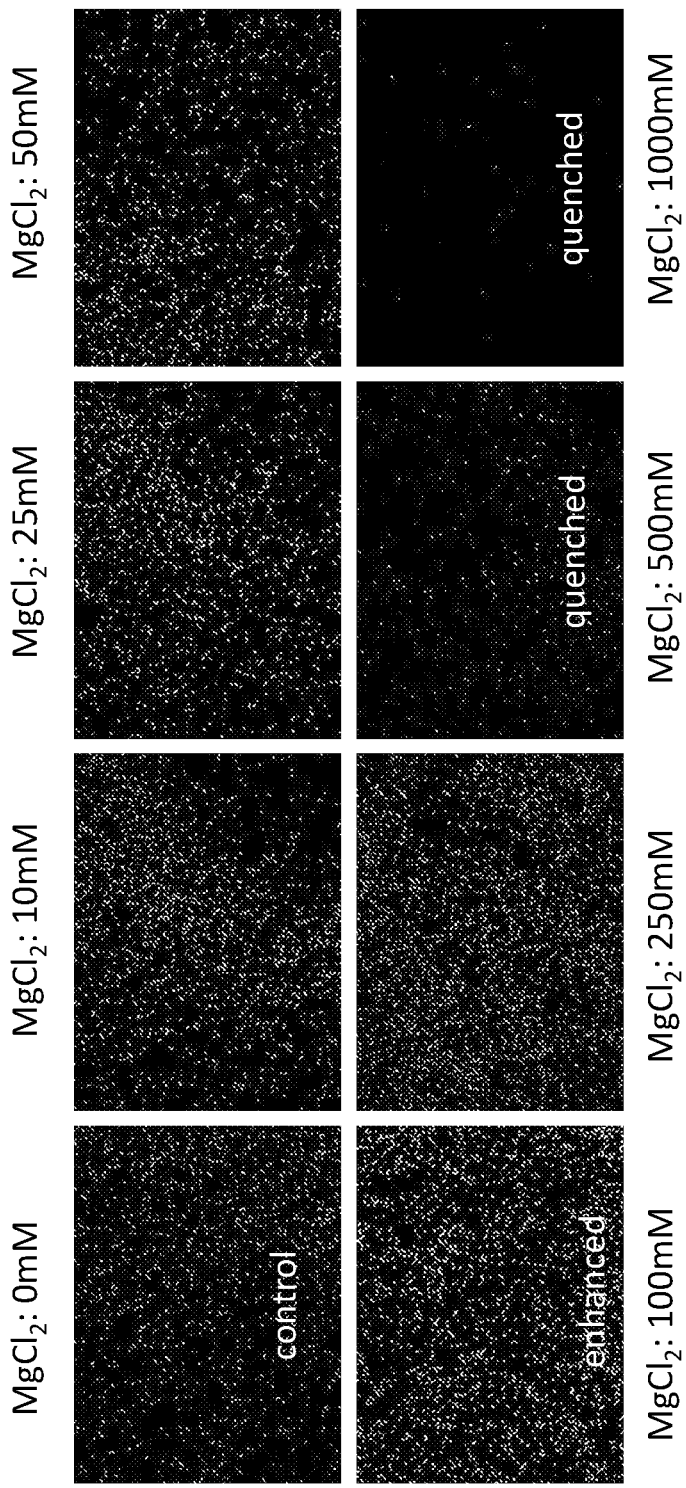
FIG. 15 shows fluorescence microscopy of fixed and permeabilized human PBMC. Extracellular and intracellular CD3 fluorescence resolution enhanced (and then quenched) by incubation with divalent cations, $MgCl_2$ Gradient, 5× I-32 UCHT1. $MgCl_2$ titration was applied (at pH 7.4) only during incubation with targeting moiety (5× I-32 UCHT1) for detection of surface and intracellular CD3, then washed with a buffer not containing cations.
Figure 16:
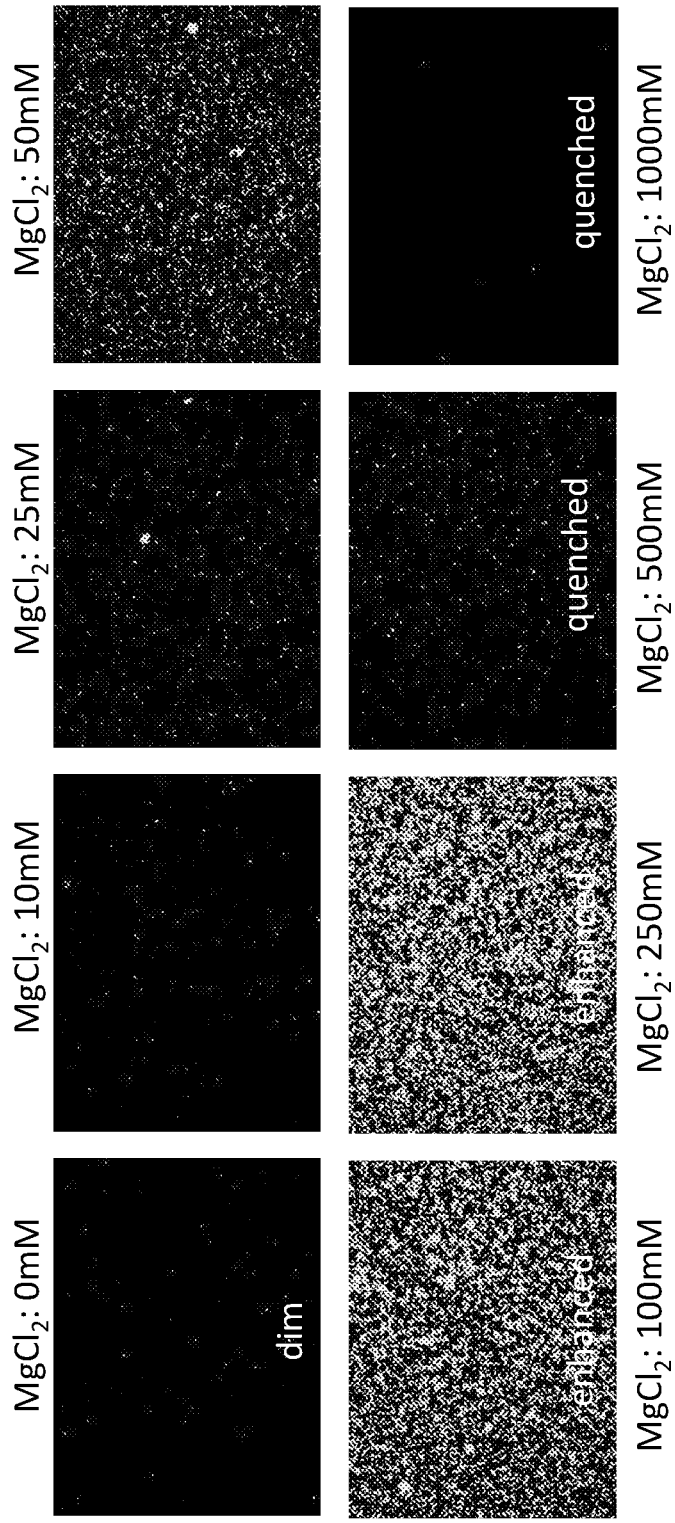
FIG. 16 shows results of the fluorescence microscopy of paraformaldehyde fixed Jurkat T cell, a cell line also specific for CD3. Extracellular CD3 fluorescence resolution enhanced (and then quenched) by incubation with divalent cations $MgCl_2$ Gradient, 10× I-16 UCHT1. The $MgCl_2$ titration (at pH 7.4) was applied during incubation with targeting moiety (10× I-16 UCHT1) for detection of surface and intracellular CD3, then washed with a buffer not containing cations.

Fixed PMBCS Stained with UCHT1-I-16 in $MgCl_2$ Gradient and Imaged by Microscopy PBMCs were fixed with 2% p.f. and washed and centrifuged 2× with 1×PBS. The cells were then incubated with permeabilization/blocking buffer. The cells were then incubated with 1% BSA 1×DPBS with mAbs, DAPI, and Biolegend CD14 antibody to co-stain Monocytes, 1 hr. UCHT1 is expected to label both surface, and intracellular CD3, and be accompanied by NSB of fixed proteins. In a black 96 flat well plate UCHT1-dye-antibody is incubated in $MgCl_2$ gradient (0-1000 mM). The cells are added to the antibody-$MgCl_2$ mixture and incubated for 1 hour. The cells are then washed twice with 1×PBS (without divalent cations). 10 ul Prolong Gold DAPI was added and incubated for 5 min. The cells were then washed 2× with 1×PBS. The cells were then plated in a clear 96 flat well plate, in 1×PBS, and imaged with 10× objective (100× total magnification). See FIGS. 13,14, and 15. Similar methods were also used with Jurkat T cells (FIG. 16).

Example 8

WBC or PBMC Stained with UCHT1-I-16 in $MgCl_2$ Gradient and Imaged by Microscopy.

150,000 to 200,000 paraformaldehyde fixed (at 2% in 1×DPBS for I-24 hours at 2-8° C.) and stored (2-8° C.<7 days) WBC or PBMC per well were stained with UCHT1-I-16 in magnesium chloride ($MgCl_2$) gradient. Cells were centrifuged at 2000 RPM (600 RCF) for 5 minutes, washed with 1×DPBS, centrifuged once again, and re-suspended in blocking buffer (1×DPBS+1% FBS+0.02% Sodium Azide). The cells were incubated in blocking buffer at RT for 40 minutes.

Separately, in a 1.5 mL Eppendorf tube, $MgCl_2$ was diluted in 1×PBS+1% FBS+0.02% Sodium Azide to desired concentration (0, 10, 25, 50, 100, 250, 500, or 1000 mM) and the UCHT1-I-16 (A4 fraction, Lot C0042 170105MFJ, 1.39 mg/mL, DOL 3.07) was added to each dilution at 0.7 μg or 1.0 μg. The mixed solution was incubated at RT for 40 minutes in the dark. After the 40 minute incubation, the cells were centrifuged, and the supernatant was removed. The cells were then re-suspended in each titration of the $MgCl_2$ solution. Samples were incubated for 45 minutes at RT in the dark. The cells were centrifuged at 600 RCF for 5 minutes and washed twice with 8004, of 1×DPBS. After washing, the cells were re-suspended in 1004, of 1×DPBS and placed in a 96-clear flat well plate for imaging. The images were taken using the MetaMorph™ imaging software at an exposure time of 500 ms using a 10× objective for a total magnification of 100×. Nikon filter cube 96311 B-2E/C was used for detection of fluorescein. Images were analyzed using ImageJ imaging software (by NIH). All images were processed the same way. Background subtraction was used, 50 pixels. Images were converted to 8-bit image and threshold of 14 was assigned. Cell counts and integrated intensity was analyzed per image and histograms were plotted using GraphPad™. Only PBMC data is shown in figures for clarity, but WBC experiments were performed prior to PBMC studies with similar results (data not shown).

Example 9

Evaluation of Antibodies in $MgCl_2$ Solutions for Specific Binding and Fluorescence Resolution by Flow Cytometry Antibodies were evaluated for specific binding and fluorescence resolution by flow cytometry in $MgCl_2$ solutions (pH 7.5). Jurkat cells were cultured according to instructions provided by ATCC and harvested live. Staining was performed when cells were applied to conjugated antibodies that had been stored in $MgCl_2$, incubated, washed, and acquired by flow cytometry.

Figure 17:
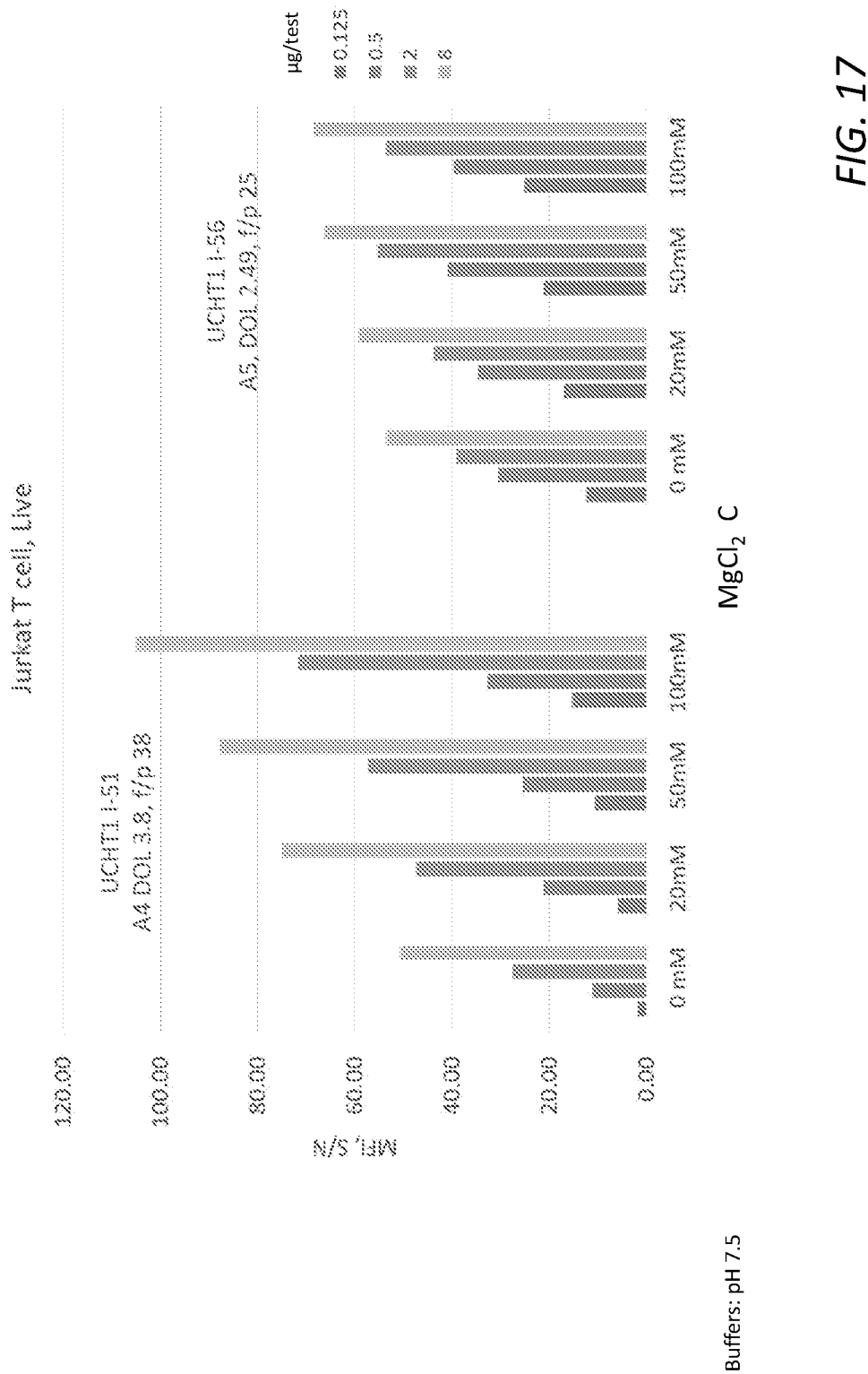
FIG. 17 shows flow cytometry results of live Jurkat T cells results of $MgCl_2$ titration (at pH 7.4) applied (0-100 mM) during incubation with targeting moiety (10× I-51 UCHT1 and 10× I-56 UCHT1) for detection of surface CD3, then washed with a buffer not containing cations. Extracellular CD3 fluorescence resolution was enhanced by incubation with divalent cations, $MgCl_2$ Gradient, 10× I-51 UCHT1 and 10× I-56 UCHT1. The cations concertation did not exceed 100 mM to preserve integrity of live cells.
Figure 18:
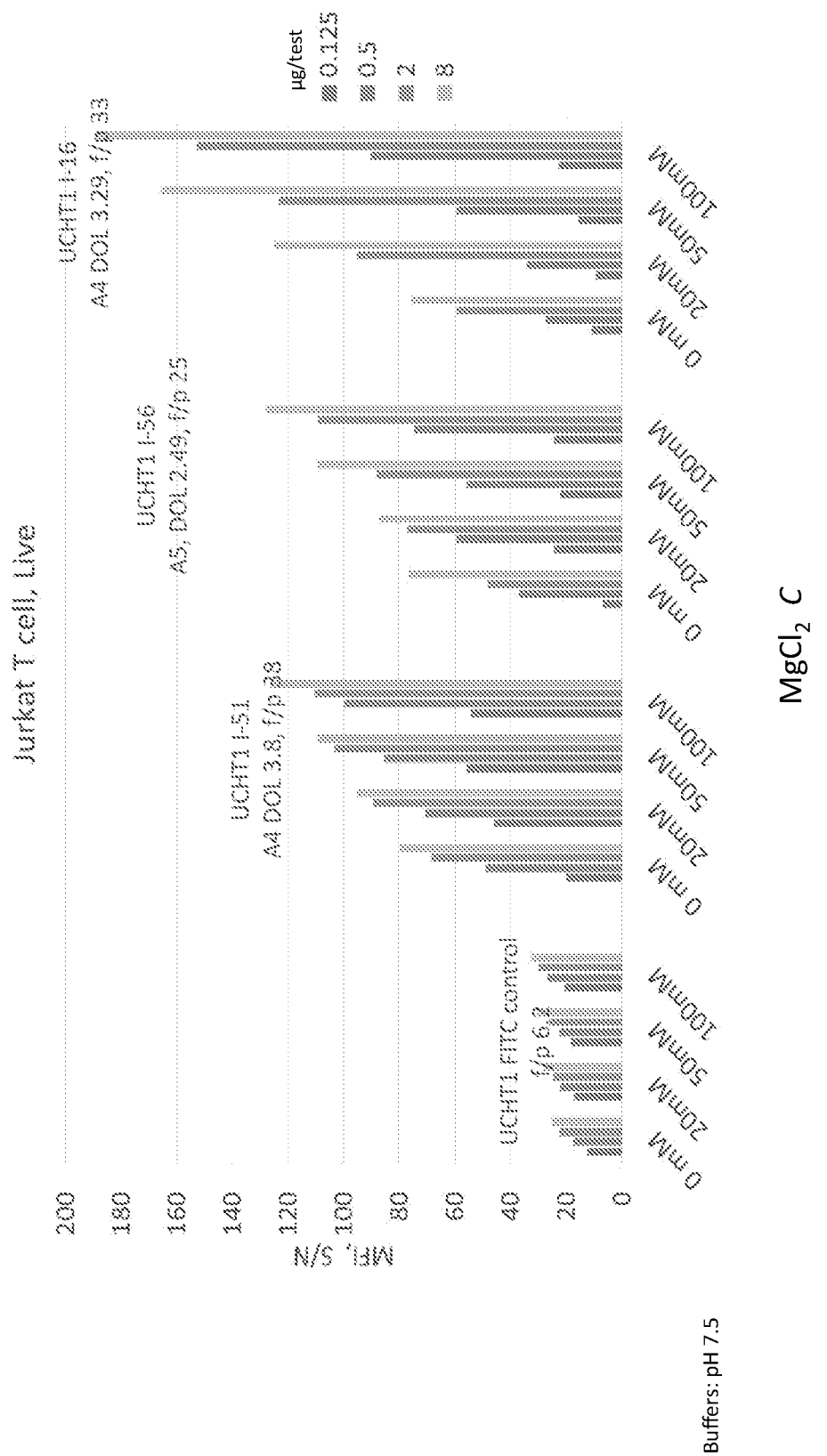
FIG. 18 shows repeat testing of flow cytometry of live Jurkat T cells results of $MgCl_2$ titration (at pH 7.4) applied (0-100 mM) during incubation with targeting moiety (10× I-51 UCHT1 and 10× I-56 UCHT1, 10× I-16 UCHT1) for detection of surface CD3, then washed with a buffer not containing cations. Extracellular CD3 fluorescence resolution was enhanced by incubation with divalent cations $MgCl_2$ Gradient, 10× I-51 UCHT1 and 10× I-56 UCHT1, 10× I-16 UCHT1. The cations concertation did not exceed 100 mM to preserve integrity of live cells.
Figure 19:
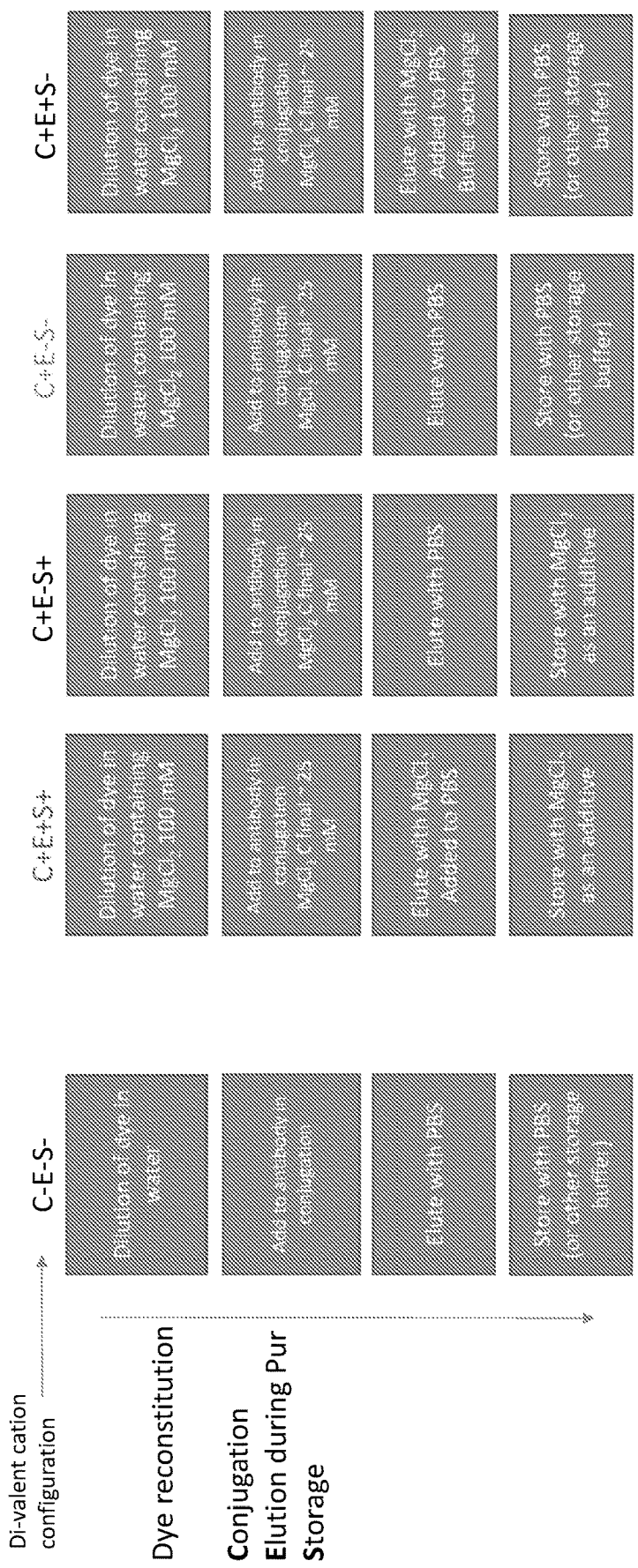
FIG. 19 outline of Cation Configurations as compared to New Methods for antibody conjugation (building the targeting moiety); for example, expressed as C−E−S− control vs. C+E+S+. In practice, this is re-suspending the maleimide activated moiety with water+0.1M $MgCl_2$) to include in conjugation of antibody, and during purification and elution, and storage in 0.1 $MgCl_2$.

$MgCl_2$ was diluted in 15 mL polypropylene tubes in 1×PBS to desired concentration (0, 10, 25, 50, or 100 nM) and pH measured and held constant to pH 7.5. Then 90 μl, $MgCl_2$ was distributed into each well of 96 well polypropylene plate. The antibodies were pre-treated with $MgCl_2$ solutions by adding antibody to the first well, serially diluted in respective concentrations of $MgCl_2$, and stored at 40 minutes at RT before use. UCHT1-I-51, -I-56, and -I-49 antibody fractions were diluted starting a series at 8.0 μg/test (C adjusted for $V_f$ of 100 μL). Cells were harvested from T-25 flasks, then washed and centrifuged (225 RCF) two times in 1% FBS Wash Buffer at RT to block cells with protein and treated with metabolic inhibitor sodium azide. The supernatant was removed after centrifugation. Cells were re-suspended to $1-3\times10^5$ cells/10 μL test in BSA Stain Buffer for incubation, then added to the $MgCl_2$, solution (for a 100 μL $V_f$ of 90 μL antibody and 10 μL cells), vortexed, and incubated at RT for 40 minutes in the dark. The mixture was centrifuged and washed with 1.6 mL BSA Stain Buffer two times at 225 RCF for 5 minutes, and the supernatant was removed. Cells were washed and centrifuged once more with 800 μL of 1×DPBS then re-suspended in 400 μL 1×DPBS containing 0.1% BSA and 0.02% sodium azide, and acquired by flow cytometry. Data was acquired and evaluated on the SONY EC-800 Flow Cytometry Analyzer, and exported to Microsoft Excel for descriptive analyses. The results of the comparison of I-51 and I-56 are shown in FIG. 17. The results of the comparison of I-51, I-56, and I-16 are shown in FIG. 18.

Example 10

Preparation of Phosphoramidites and Compounds

Exemplary compounds were prepared using standard solid-phase oligonucleotide synthesis protocols and a fluorescein-containing phosphoramidite having the following structure:

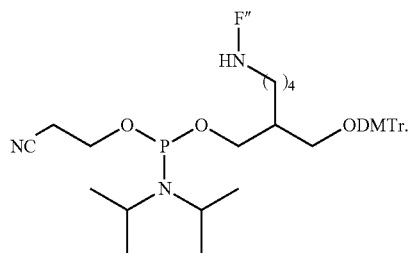

which was purchased from ChemGenes (Cat. #CLP-9780).

Exemplary linkers ($L^4$) were included in the compounds by coupling with a phosphoramidite having the following structure:

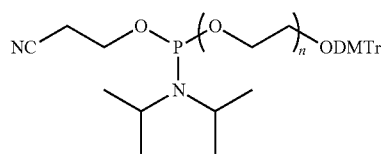

which is also commercially available.

Other exemplary compounds were prepared using a phosphoramidite prepared according to the following scheme:

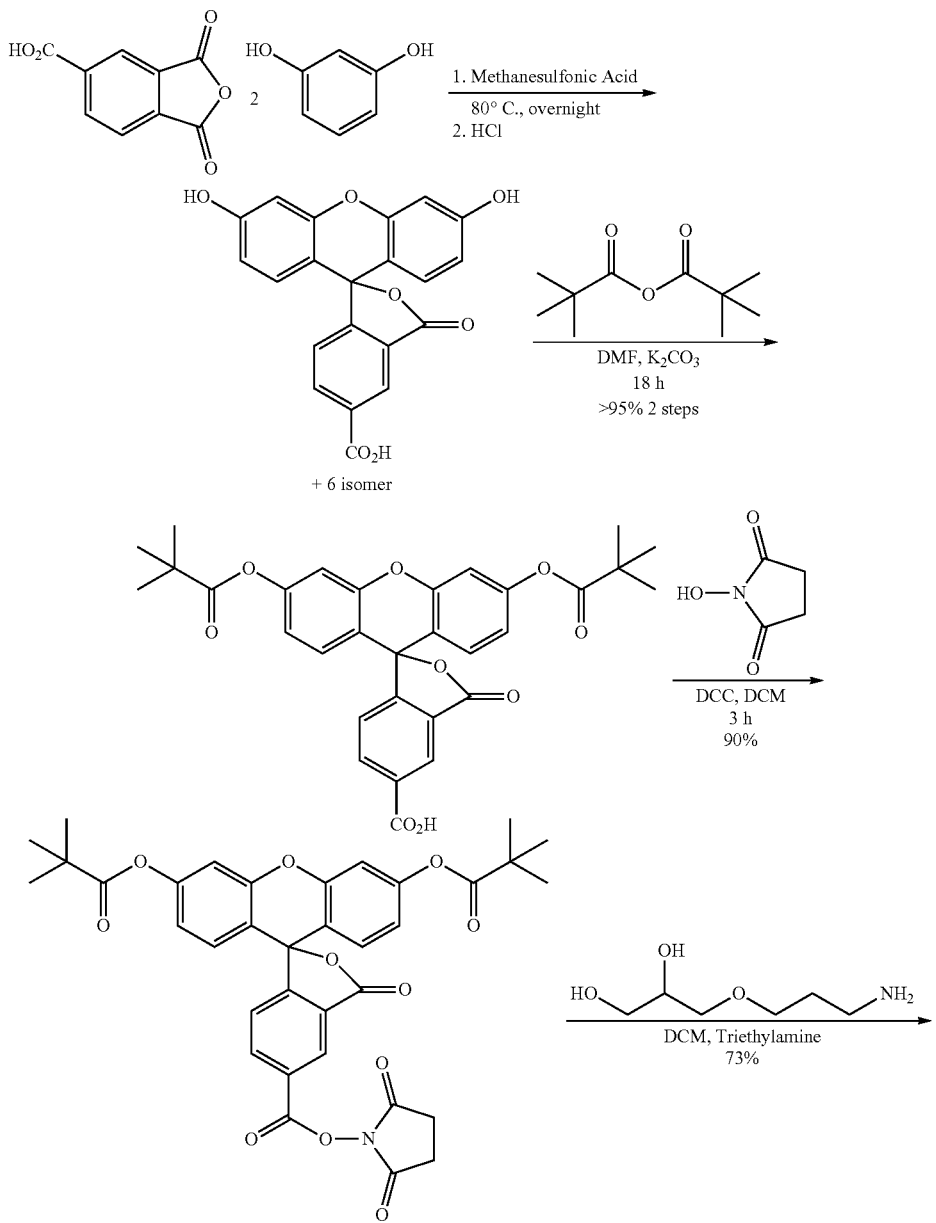

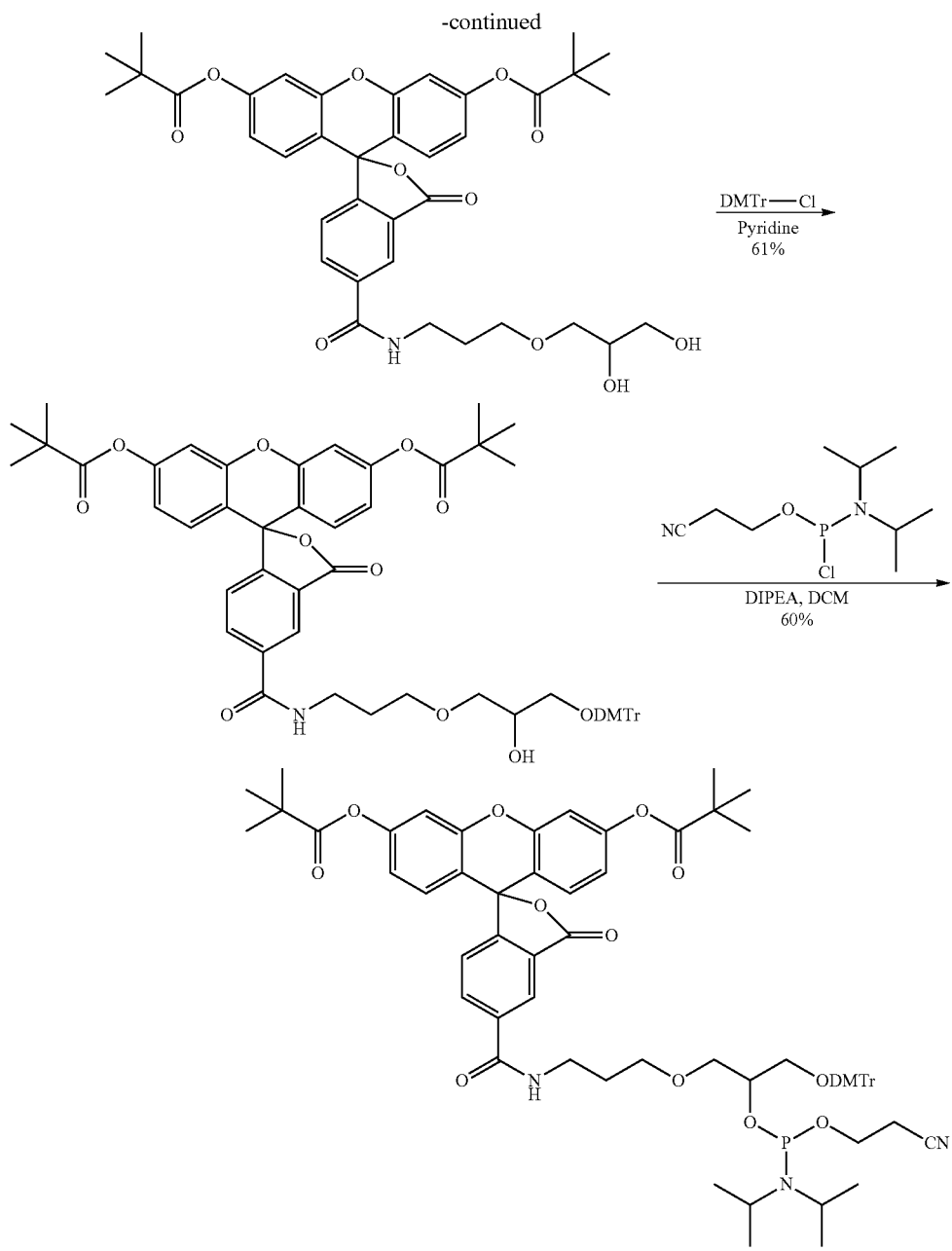

Final Deprotection produces the desired F‴ moiety. Other commercially available phosphoramidite reagents were employed as appropriate to install the various portions of the compounds. Q moieties having the following structure:

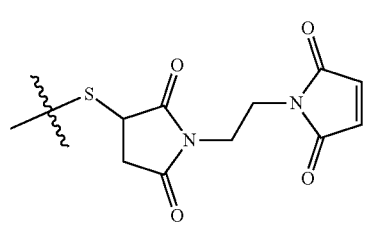 [SMILES: *SC1CC(=O)N(CCN2C(=O)C=CC2=O)C1=O]

were installed by reaction of:

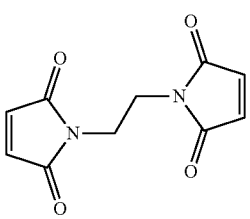 [SMILES: O=C1C=CC(=O)N1CCN1C(=O)C=CC1=O]

with a free sulfhydryl. Other Q moieties are installed in an analogous manner according to knowledge of one of ordinary skill in the art.

Example 11

Jurkat, Fresh, Live Cells. Comparing UCHT1 I-16 fractions, one without, and one with $MgCl_2$ and also comparing to I-21B and other references to the right (see FIG. 23). All antibodies were tested together on the same plate using same specimen. I-16 is evaluated for specific binding and fluorescence resolution by flow cytometry in $MgCl_2$ as applied during conjugation. $MgCl_2$ was applied only to UCHT1 I-16 during the conjugation at two stages: (1) When re-suspending the reaction with maleimide (water+0.1M $MgCl_2$) conjugation. (2) During purification and elution, and storage in 0.1 $MgCl_2$ in PBS. The antibodies were diluted into BSA stain buffer without any additional application of $MgCl_2$ to buffer containing cells. Flow Method: Jurkat T cells are cultured according instructions provided by American Type Culture Collection (ATCC) and harvested live. Briefly, staining is performed when cells are applied to conjugated antibodies, incubated, washed and then acquired by flow cytometry: Antibody fractions were diluted starting a series at 2.0 μg/test (C adjusted for $V_f$ of 100 μL). Cells were harvested from T-25 flasks, washed and centrifuged (225 RCF) two times in 1% FBS Wash Buffer at room temperature (RT) to block cells with protein and treat with metabolic inhibitor sodium azide. The supernatant removed after centrifugation. Cells re-suspended to $1-3\times10^5$ cells/100 μL test in BSA Stain Buffer for incubation, then added to antibodies, vortexed, and incubated at RT for 40 minutes in the dark. The mixture was centrifuged and washed with 1.6 mL BSA Stain Buffer two times at 225 RCF for 5 minutes, supernatant removed. Cells were washed and centrifuged once more with 800 μL of 1×DPBS then re-suspended in 400 μL 1×DPBS containing 0.1% BSA and 0.02% sodium azide, and acquired by flow cytometry. Data is acquired and evaluated on the SONY EC-800 Flow Cytometry Analyzer, and exported to Microsoft Excel for descriptive analyses. UCHT1 I-16 fraction A5 with a DOL of 2.47, f/p 25, showed equal or brighter fluorescence to UCHT1 I-21B, fraction A5, DOL 3.0, f/p 30. The addition of $MgCl_2$ during conjugation allows for the enhancement of UCHT1 I-16 in comparison to UCHT1 I-16, fraction A6, DOL 4.18, f/p 42, where $MgCl_2$ was not present. This finding is of practical significance, as it has been observed in previous experiments UCHT1 I-16 is dimmer than both I-51 and I-21B, but is brighter here when $MgCl_2$ is used to purify the antibody.

Example 12

Comparison of I-16 to Bb 515 and FITC by Flow Cytometry

In general, FIGS. 19, and 20-24 show results of three builds of conjugates with different configurations of cations with some differences in degree of labeling (DOL) and then tested by flow cytometry (as described before). Briefly, a comparison I-16 to I-21B, BB515, and FITC was performed. Extracellular staining of fresh blood or cells was stained, lysed, washed, then incubated 45 min at room temperature, then washed again.

Comparisons are in WBC on CD3+ T cells and Jurkat T cells (Jurkat T cell in FIG. 23) when labeling for human CD3 expression (as previously described). The UCHT1-I-16 or I-21A and I-57 were compared to UCHT1-BB515 and UCHT1-FITC. It was found UCHT1-I-16 is 1.7× brighter than UCHT1-BB515 and 5.7× brighter than UCHT1 FITC. As indicated above, $MgCl_2$, was present in different phases of the production process (e.g. conjugation, elution during purification, and or storage, abbreviated as in the example C+E+S+) See FIG. 19.

Figure 20A:
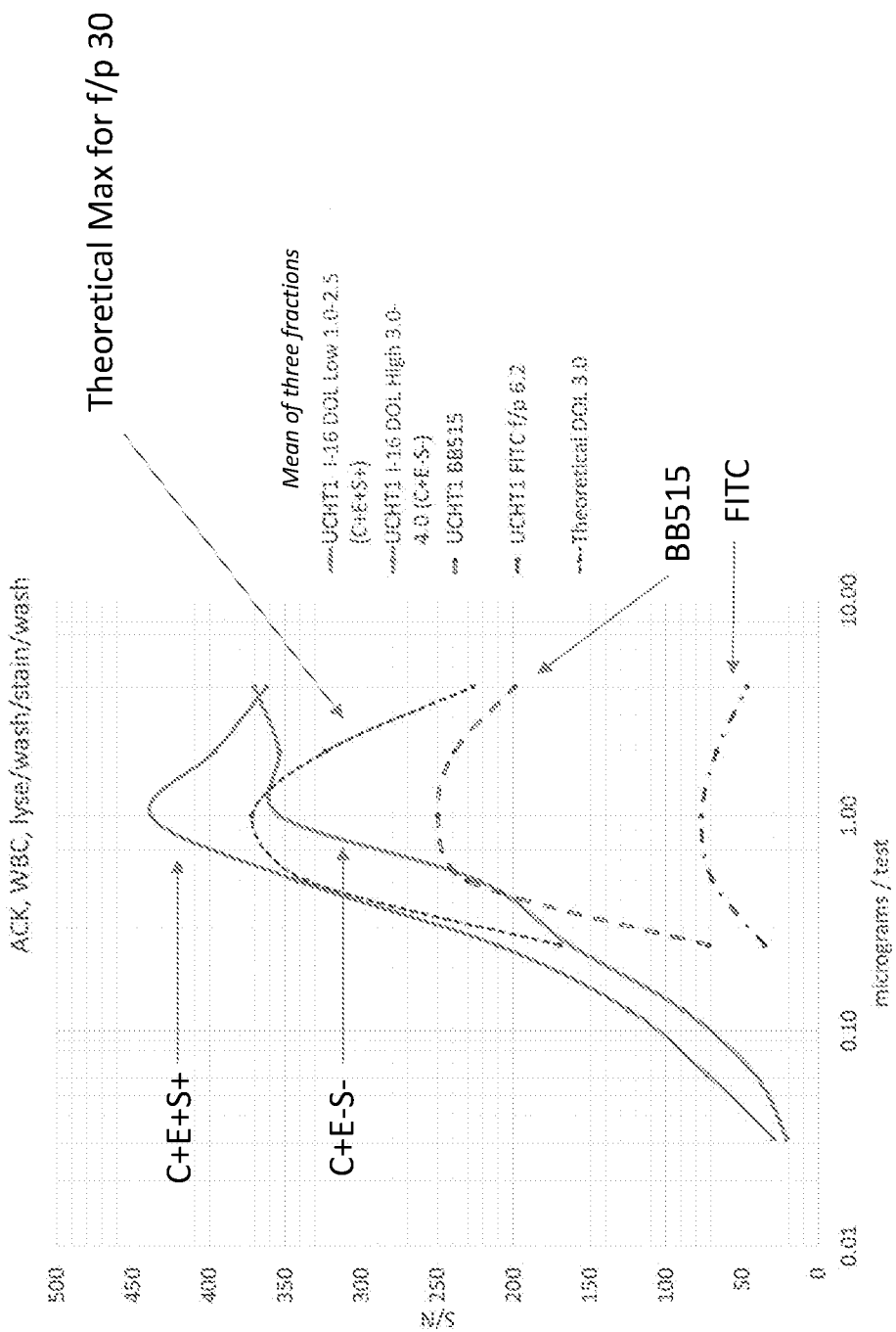
FIG. 20A shows example of summary of findings of signal enhancement as titration curves derived from human whole blood cell flow cytometry. CD3 fluorescence resolution in two configurations is shown. S/N is enhanced by inclusion of divalent cations when $MgCl_2$ included in conjugation process steps for 10× I-16 UCHT1. Results when potassium buffered ammonium chloride (ACK) red cell lysed whole blood cells (WBC) when $MgCl_2$ is included in the conjugation, elution (purification), and storage of the targeting moiety (10× I-16 UCHT1) for detection of surface CD3 are shown. Results were compared to BD Horizon Brilliant Blue 515™ UCHT1 and FITC UCHT1. The assay was incubated and washed with a buffer not containing cations.
Figure 20B:
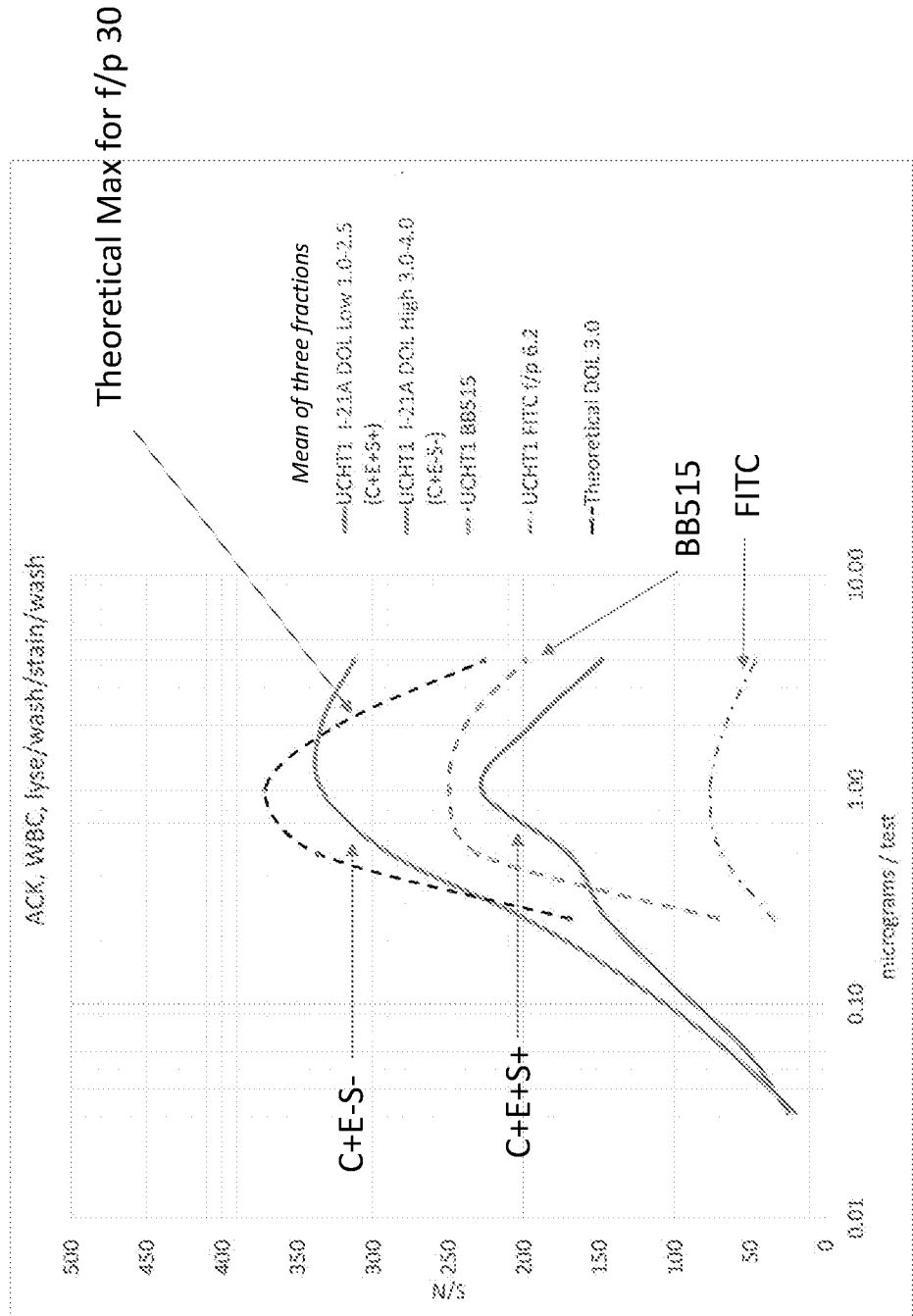
FIG. 20B shows example of summary of findings of signal enhancement as titration curves derived from human whole blood cell flow cytometry. CD3 fluorescence resolution in two configurations is shown. S/N is enhanced by inclusion of divalent cations when $MgCl_2$ included in conjugation process steps for 10× I-21A UCHT1. Results when potassium buffered ammonium chloride (ACK) red cell lysed whole blood cells (WBC) when $MgCl_2$ is included in the conjugation, elution (purification), and storage of the targeting moiety (10× I-21A UCHT1) for detection of surface CD3 are shown. Results were compared to BD Horizon Brilliant Blue 515™ UCHT1 and FITC UCHT1. The assay was incubated and washed with a buffer not containing cations.
Figure 21:
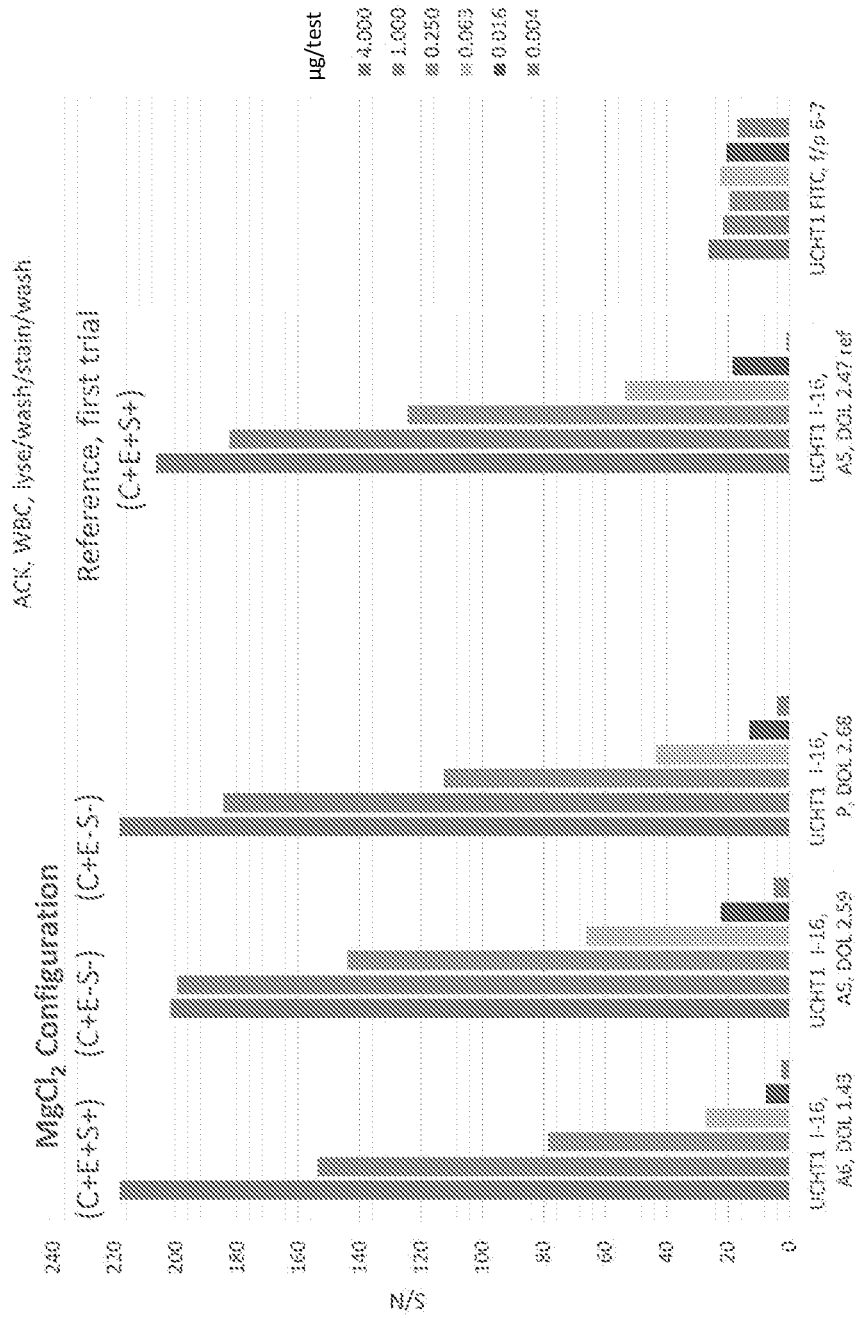

FIGS. 20A and 20B shows C+E+S+ is compared C+E−S− of UCHT1-I-16 and UCHT1-I-21A. While FIG. 21 demonstrates three conjugation runs of UCHT1-I-16 using configurations C+E+S+, C+E−S−, and C+E−S−, as compared to the first trial run of C+E+S+, conjugation positive control reference.

FIG. 22 show additional experimental procedures by flow cytometry applied to determine absolute fluorescence rather than signal to noise. A calibration curve was determined using populations of beads labeled with titration in equivalents of soluble fluorophore. The beads acquired in conditions same as acquisition of data by flow cytometry to identify channels of discrete equivalent levels of fluorophore. Evaluating the standard curve generated by beads, the data from similar experiments as in FIG. 21 were re-expressed by calculation using power linear regression. This way, the Molecular Equivalents of Soluble Fluorophore (MESF) estimates for the three process configurations could be determined for three lots. UCHT1-I-16 UCHT1-I-16, lots ($1^{st}\ 2^{nd}\ 3^{rd}$) of configurations C+E+S+, C+E−S−, C+E−S− respectively, then compared to BB515 (one lot) and FITC (two lots). This method demonstrates an absolute brightness of 8-10× brighter than FITC, and equivalent to BB515.

FIG. 23 shows UCHT1-I-16 (C+E+S+) as compared to other (C−E−S−) configurations as negative controls, I-51, I-21B, and I-16, and positive control reference FITC. The C+E+S+ configuration exceeds theoretical fluorescence levels in this case if comparing to a target f/p of 30, while the C−E−S− configurations are not as bright as theoretical would imply.

FIG. 24 show three lots tested A, B, and C showing two fractions from the conjugation. The theoretical S/N was exceeded by the C+E−S− configuration.

Overall, those conjugates containing cation in the configurations were brighter by flow cytometry than other conjugates, and elution and storage was observed to be of only slight advantage at high concentrations of targeting moiety during incubation. This was determined in different analyses methods using linear regressions between conjugate configurations but data is not shown here.

Example 13

Oligofluoroside Dyes are Demonstrated to be Ion Sensors and High Resolution by Flow Cytometry Upon Co-Application with Magnesium Productivity of an alternative reaction applied to bio-conjugation was tested. Water and 0.1 M magnesium chloride added during re-constitution from a lyophilized state of pre-maleimide activated dye and then applied to reductant treated antibody (TCEP) for bio-conjugation was hypothesized to improve antibody conjugates perhaps due to the same effects of charge shielding or Lewis acid coordination. As well, possibly from polyphosphate charge shielding prior to entering into the reaction with free sulfhydryl groups. In summary, conjugation trials show magnesium to be suitable for modifying ultrabright fluorophore polymers for further use in maleimide conjugation reactions and subsequent application of antibody conjugates for staining in an analytical procedure using Flow Cytometry (FCM).

Methods: Experiments were Guided by Three Approaches:

1) Choosing systems of magnesium inclusion in the process of UCHT1 antibody conjugation labeling to 10× dye while targeting a final dye on label (DOL) specification of less than 5.0

2) Choosing magnesium to be applied to antibody prior and during the staining method of CD3 antigen on cells. An interference study of ions on the analytical procedure.

3) Evaluating fluorescence emission of conjugates in solution.

The above represent three points of interrogation in the antibody development process that influence dye conformation and subsequent assay output. This system approach assumes the conjugation method 1) will alter how the dye interacts with antibody, 2) will improve targeting of the DOL (efficient labeling), and 3) improve fluorescence resolution by FCM (improve signal, and antibody affinity).

Conjugation method: The dye is re-suspended in water+ 0.1M $MgCl_2$ and then combined with the antibody and incubated for one hour at 0° C. (final $MgCl_2$ C ~25 mM). The conjugate is purified and eluted over a 10×300 nm Superdex 200 column using 1×PBS buffer. Fractions are collected in mirco-centrifuge vials. Some fractions are pooled, concentrated using 30k MWCO concentrators. Where elution and storage on magnesium is applied, the elution buffer included 0.1 M $MgCl_2$, and/or the storage buffer was spiked with $MgCl_2$ for a $C_f$ of 0.1 M. Concentration of conjugate is determined using Nano Drop 2000. The absorption values are recorded at 280 nm and 495 nm. A Correction Factor (OD280/OD495) of 0.19 for the 10× dye and the principles of Beer's law was used to determine fluorochrome to protein (f/p) ratio=(dye on label, DOL). For example a DOL of 3 is equivalent to an f/p of 30.

Fluorescence studies: Live Jurkat T cells, and/or potassium buffered ammonium chloride lysed (ACK) whole blood cells (WBC) and other WBC models were used to verify fluorescence resolution in FCM after a conjugate was produced. Studies with $MgCl_2$ at incubation with cells, and then washed away, was applied to monitor the immediate effects of addition of divalent cations to the assay. See, FIGS. 17 and 18. In contrast, spectral in solution studies were performed (in buffer only) to output absorption and emission spectra in the presence and absence of divalent cations. See, FIGS. 25B and 27B. Analogously, studies of final acquisition buffer (by FCM) were employed to represent the practical consequences of ion inclusion or exclusion during read when antibody was bound to cells. See, FIGS. 27A and 28.

Conjugation studies: In general, three lots were prepared in serial with different configurations and compared to previous material. Process improvements were investigated by incorporating $MgCl_2$ at different points into our standard maleimide UCHT1 (anti-CD3) bio-conjugation. Conjugation system equivalency and bridging studies were executed in serial steps to optimize resolution by FCM using our conjugation method previously established. See, FIGS. 21, 20B, 23, 24, and 25A. Magnesium was applied in the conjugation process in different conjugation systems for comparisons. Systems tested were (C+E+S+), (C+E−S−), (C+E−S+), (expressed in acronym as $C_{onjugation}+E_{lution}+S_{torage}+$). The f/p (Dye on Label) was targeted in each system based upon previous observations about TCEP and maleimide stoichiometry of the non-$MgCl_2$ maleimide reaction previously established in our laboratory to initial Degree of Labeling (DOL) of 2-4 equivalents higher than the target DOL to limit final DOL<5.0. In some experiments, dyes of other tether lengths (4×, 6×, 10×) were tested alongside the control tether length of 1× I-16. (Data not shown).

Data analyses of outputs of three systems are described using; dye on label efficiency [actual DOL/applied DOL at conjugation]*100, fluorescence intensity (relative emission) (FIG. 25A), signal-to-noise (SN) (median signal of CD3+ population/median noise CD3− population) by FCM, regression analyses of S/N between systems, and other performance parameters were evaluated (e.g. degree of nonspecific binding).

Additional quantification of FCM channels using FITC conjugated to bead standards (Bangs Laboratories) were used to measure Molecules of Equivalent Soluble Fluorochrome (MESF) output of 10×FAM UCHT1 I-16 by FCM. See, FIG. 22.

Results: Early studies indicated when $MgCl_2$ (0-100 mM) is present during antibody and antigen incubation, and washed off as continuing the FCM method, a signal enhancement effect was observed at 25-100 mM, particularly at high concentrations of antibody (dye), FIGS. 17 and 18. An additional preliminary study including $MgCl_2$ in all stages of conjugation: dye reconstitution, conjugation, elution, storage [symbolized as system (C+E+S+)] showed production of an ultrabright reference antibody of superior performance than previously observed without $MgCl_2$.

Presuming $MgCl_2$ will have a positive effect on brightness as observed in preliminary study, we therefore prepared additional lots (C+E+S+) while targeting a low DOL (i.e. 1-3) [theoretical dye to protein equivalents of 4.5:1] to avoid over conjugation and limit changes in antibody affinity with the expectation of creating a superior reagent. Again a bright S/N by flow cytometry resulted in a practical fluorescence output of about an f/p of 30 with DOLs ranging 1.4-2.7 (f/p 14-27). The S/N exceeded theoretical values as compared to FITC with an f/p 6.2 and exceeding a theoretical brightness factor of (30/6.2) of 4.8 greater than the FITC control.

An interim ion interference study was then performed using 1−16 (C+E−S−) vs. (C+E−S+) to potentially exclude elution as a condition in the process, and to see if storage is important. We demonstrated (C+E−S−) worked as expected (elution not necessary for high resolution) as compared to (C+E−S−), (C+E+S+), and a spiked formulation at storage (C+E−S+) used as the original reference test, FIG. 21. The results indicate it is of little additional benefit to signal at incubation with cells when residual amounts of magnesium are present during dilution of the stored material for FCM. These results taken together showed that at least including $MgCl_2$ at conjugation could be of practical benefit to performance while elution and storage can be set aside.

Therefore, it was assumed we could increase the DOL by the inclusion of magnesium in a simpler system (C+E−S−) using a theoretical dye to protein equivalents of 7:1. So additional lots were made using the configuration (C+E−S−) to target final high DOL (3-5) and spiked-in-storage fractions set aside also (C+E−S+) for later re-confirmation of storage effect (residual magnesium present during incubation). In general signal was retained, as expected for UCHT1-I-16. The storage and incubation signal enhancement was also re-confirmed as before, but is of little consequence to overall equivalency of systems (C+E−S−C+E−S+). A comparison of UCHT1 I-16 first and second lots in the same experiment again confirmed low DOL 1-3 reagents and inclusion of $MgCl_2$ assist in exceeding UCHT1 BB515 (BD Biosciences) SN results, and approximated the theoretical f/p of 30 based upon FITC controls for both systems.

A 3$^{rd}$ lot was produced using configuration C+E−S− at a theoretical dye to protein equivalents of 4.5:1. The system targeted a DOL like that of the first lot (final DOL range 1-3). Again, the UCHT1 I-16 with an enhancement was observed. The practical implication is the I-16 dye conjugate is higher resolution by FCM with about double the dye labeling efficiency prior to use of $MgCl_2$ (mean absolute labeling efficiency, before=24%, compared to three sets of conjugations with $MgCl_2$; 53%, 58%, 62%).

Downstream to simulate in solution application, absorption and emission spectra of conjugates in solution with PBS containing C of $MgCl_2$ (0-1000 mM) at pH 7.4 showed ion concentration dependent quenching, rather than enhancement of signal. Emission data in solution showed the conjugated dyes can be rank ordered by pre-quantified DOL (as determined by Nano Drop) as expected, but are quenched in solution in rank order by additives EDTA<$MgCl_2$<$CaCl_2$ and effected by a poly-cationic blocker in ways unique to the each construct and configuration. Data not shown. This observation was consistent with observations of quenching at sample acquisition by FCM using different resuspension buffers with or without magnesium. The addition of $MgCl_2$ present during fluorescence visualization of any method, as in FIGS. 27A, 27B, and 28, (either in solution, or during acquisition by FCM) showed signals were quenched. These observations are in contrast to the preliminary studies FCM where it was observed $MgCl_2$ enhanced signal/noise when present during incubation with cells, but subsequently washed off prior to sample acquisition. See, FIGS. 17 and 18.

Finally, to confirm preliminary studies with the lots made in the early serial experiments of different configurations, conjugates were made again in parallel on the same day, with identical materials, and identical purification procedures. Only the cation configurations were varied (C−E−S− control, and C+E−S−, C+E+S). Also, through previous experimental findings, the final f/p was targeted to be approximately the same across all conjugates (19.7 to 24.7) to eliminate confounding interpretations of degree of labeling. These conjugates were then tested by FCM. In general, this experiment confirmed the effect of adding $MgCl_2$ to the system was beneficial for producing a targeting moiety with more efficient fluorescence output. See, FIG. 25A.

Finally, $MgCl_2$ improves conjugation labeling efficiency when used to solubilize the activated dye prior to addition to conjugation reaction, thus supporting the quality relationship between early process inputs and efficient labeling and higher resolution fluorescence observed in later process outputs. These observations also support the first aim of the studies to verify productivity improvements could be achieved. See, FIG. 26. Additional quantification and characterization of dynamic range of the instrument of FCM channels and using Bangs™ beads FITC standards (Bangs Laboratories) to quantify Molecules of Equivalent Soluble Fluorescein (MESF) indicated the conjugate was 8-10× brighter than UCHT1 FITC f/p 6-7. This is brighter than can be reported by absolute S/N as determined by median signal-to-noise in FCM. See, FIG. 22.

Discussion: Originally polymers with high density charge were designed to be highly soluble in water, so when salts are introduced, conformational changes can be expected. This is probably the case with the lower charge density molecules of similar design (I-16), but to a lesser degree. This presents the common case that ions can lead to interference of the analytical procedure (in this case fluorescence and detection of CD3). Interferences that can be eliminated or controlled by chemical adaptations to the procedure, or to the reagent itself can be employed.

In summary, it is thought magnesium has the potential to positively alter the bio-conjugated dye and/or the antibody. Additionally, the polymers tested have have ion sensing properties, are weak divalent ion chelators, and are sensitive to differing buffer formulations of similar pH. The understanding, without being bound by theory, is that the dye is in favorable conformation for efficient conjugation when $MgCl_2$ is applied, limiting the alteration of antibody isoelectric point and improving antigen binding at lower concentrations. It is postulated $MgCl_2$ is charge shielding and stabilizing dyes under certain conditions, improving affinity of the antibody when used in conjugation, elution, storage, or during incubation, but quenches when observed in solution.

While more study is required, ideally, if these compounds can be ion and salt form stabilized (or charge neutralized) prior to application in assays without quenching, and without interaction with other poly-cations, utility of the dye and the making of a bioconjugate could be considerably improved. Presumably, FCM protocols, particularly whole blood lysed, where plasma, supplemented serum, blocks, or chelators are present during the stain/lyse/fix procedure, we can expect some interaction (or lack thereof) of the dye with ions. We have observed such interactions as loss of affinity (as expressed by affinity curves in titrations) and increased non-specific binding with fixed WBC and in fresh cells that undergo stain/lyse/fix/wash procedures. (Data not shown). Because divalent cations and polycations are present in blood plasma, particularly as released from lysed red cells, or in activated cells, or on cell surface, a similar ionic interaction could be expected. In effect, blocking with magnesium aimed at the dye, or a poly-backbone block aimed at target substrate could be suitable for protection against interfering factors in plasma and complex tissue. Additionally, a specific methodology identified to exploit the effect could also be implemented, particularly with harsh fix/perm methods (methanol) in immunohistochemistry, and dense tissue sections where a charge shielded, and non-linear more neutrally charged conformation is desirable for efficient diffusion through the intracellular matrix. Finally, high background and low signals due to any non-specific binding and quenching could also be potentially interrupted by a magnesium wash, or magnesium inclusion during incubation. This could be important in staining conditions that lead to strong ionic association with poly-cations present in fixed and permeabilized tissue. In fact, observations with 2.0% paraformaldehyde fixed, red cell lysed, and isolated whole blood cells, PBMC, and Jurkat T cells indicate an enhancement of S/N in cells incubated with UCHT1-I-16 and magnesium chloride. The results also show a biphasic effect; at a low concentration, the S/N is low, while enhanced at 100 mM-250 mM, and then quenched again at 1000 mM. Again confirming the ionic association is perturbing fluorescence intensity by expected conformational changes. FIGS. 13, 14, 15, and 16.

All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/645,121, filed Mar. 19, 2018, are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for forming a covalent conjugate of a polymeric dye and a targeting moiety, the method comprising preparing a mixture comprising the polymeric dye, the targeting moiety, and a magnesium salt, and allowing the mixture to age for a time and at a temperature sufficient to form the covalent conjugate, wherein:
   a) the polymeric dye comprises:
      i) two or more fluorescent or colored moieties;
      ii) at least one negatively charged phosphate group; and
      iii) a reactive group Q capable of forming a covalent bond with a complementary reactive group Q' on the targeting moiety,
      wherein each of the two or more fluorescent or colored moieties are joined to an adjacent fluorescent or colored moiety via a linker comprising the at least one negatively charged phosphate group; and
   b) the targeting moiety has affinity for a target analyte and comprises the complementary reactive group Q'.

2. A method for detecting a target analyte, the method comprising:
   a) associating a covalent conjugate with the target analyte to form an analyte-targeting moiety complex in the presence of a magnesium salt, the covalent conjugate comprising:
      i) a targeting moiety that has affinity for the target analyte and comprises a covalent bond to a polymeric dye;
      ii) the polymeric dye comprising:
         A) two or more fluorescent or colored moieties;
         B) at least one negatively charged phosphate group; and
         C) a covalent bond to the targeting moiety,
         wherein each of the two or more fluorescent or colored moieties are joined to an adjacent fluorescent or colored moiety via a linker comprising the at least one negatively charged phosphate group; and
   b) detecting a fluorescent or colored signal from the analyte-targeting moiety complex.

3. The method of claim 2, further comprising treating the analyte-targeting moiety complex with a wash solution comprising a magnesium salt.

4. A method for detecting a target analyte, the method comprising:
   a) associating a covalent conjugate with the target analyte to form an analyte-targeting moiety complex, the covalent conjugate comprising:
      i) a targeting moiety that has affinity for the target analyte and comprises a covalent bond to a polymeric dye; and
      ii) the polymeric dye comprising:
         A) two or more fluorescent or colored moieties;
         B) at least one negatively charged phosphate group; and
         C) a covalent bond to the targeting moiety,
         wherein each of the two or more fluorescent or colored moieties are joined to an adjacent fluorescent or colored moiety via a linker comprising the at least one negatively charged phosphate group;
   b) treating:
      i) the covalent conjugate and the target analyte with a magnesium salt during the associating the covalent conjugate and the target analyte; and/or
      ii) the analyte-targeting moiety complex with a wash solution comprising a magnesium salt after the associating the covalent conjugate and the target analyte; and
   c) detecting a fluorescent or colored signal from the analyte-targeting moiety complex.

5. The method of claim 2, further comprising substantially removing all of the magnesium salt from the analyte-targeting moiety complex before detecting the fluorescent or colored signal.

6. The method of claim 5, wherein the magnesium salt is removed from a buffer comprising the analyte-targeting moiety complex.

7. The method of claim 2, further comprising forming the covalent conjugate.

8. The method of claim 7, wherein the polymeric dye and a magnesium salt have been admixed to form a composition comprising the polymeric dye and the magnesium salt prior to forming the covalent conjugate.

9. The method of claim 8, further comprising aging the composition comprising the polymeric dye and the magnesium salt prior to forming the covalent conjugate.

10. The method of claim 7, wherein magnesium salts are substantially absent while forming the covalent conjugate.

11. A composition comprising a covalent conjugate and a magnesium salt, the covalent conjugate comprising:
    i) a targeting moiety comprising a covalent bond to a polymeric dye;
    ii) the polymeric dye comprising:
       a) two or more fluorescent or colored moieties;
       b) at least one negatively charged phosphate group; and
       c) a covalent bond to the targeting moiety,
       wherein each of the two or more fluorescent or colored moieties are joined to an adjacent fluorescent or colored moiety via a linker comprising the at least one negatively charged phosphate group.

12. The method of claim 2, wherein the magnesium salt is magnesium chloride.

13. The method of claim 2, further comprising purifying the covalent conjugate.

14. The method or composition of claim 13, wherein purifying comprises substantially removing all of the magnesium salt from the covalent conjugate.

15. The method of claim 2, wherein the covalent conjugate has a fluorescent extinction coefficient at least 1.1 times higher than a corresponding conjugate prepared in the absence of the magnesium salt.

16. The method of claim 2, wherein the targeting moiety is an antibody.

17. The method of claim 2, wherein the polymeric dye has the following structure (I):

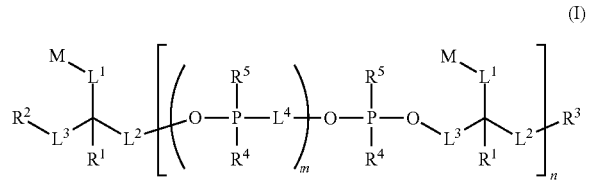

or a stereoisomer, salt or tautomer thereof, wherein:
M is, at each occurrence, independently a moiety comprising the fluorescent or colored moiety;
$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently an alkylene or alkylene oxide linker;

$R^1$ is, at each occurrence, independently H, alkyl or alkoxy;

$R^2$ and $R^3$ are each independently H, OH, SH, alkyl, alkoxy, alkylether, heteroalkyl, —OP($=R_a$)($R_b$)$R_c$, Q, or a protected form thereof, or L';

$R^4$ is, at each occurrence, independently OH, SH, O⁻, S⁻, $OR_d$ or $SR_d$;

$R^5$ is, at each occurrence, independently oxo, thioxo or absent;

$R_a$ is O or S;

$R_b$ is OH, SH, O⁻, S⁻, $OR_d$ or $SR_d$;

$R_c$ is OH, SH, O⁻, S⁻, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkyl ether;

$R_d$ is a counter ion;

L' is, at each occurrence, independently a linker comprising a covalent bond to Q, a linker comprising a covalent bond to the targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater, provided that at least one occurrence of m is an integer of one or greater, such that the compound includes at least one $L^4$; and n is an integer of one or greater.

18. The method claim 17, wherein the polymeric dye has the following structure (IA):

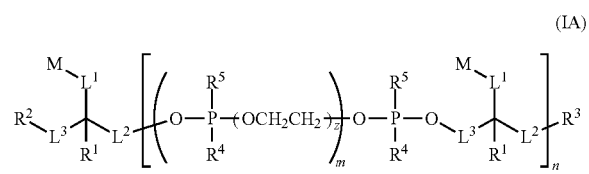

(IA)

wherein z is an integer from 2 to 100.

19. The method of claim 18, wherein the compound has the following structure (TB):

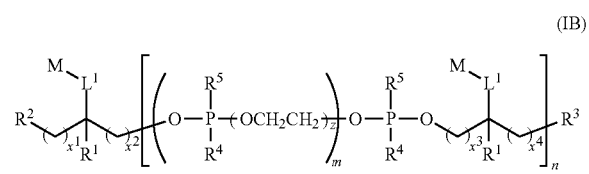

(IB)

wherein:

$x^1$, $x^2$, $x^3$ and $x^4$ are, at each occurrence, independently an integer from 0 to 6; and z is an integer from 2 to 100.

20. The method of claim 17, wherein L' comprises an alkylene oxide or phosphodiester moiety, or combinations thereof.

21. The method of claim 17, wherein Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group.

22. The method of claim 17, wherein M is, at each occurrence, independently a dimethylaminostilbene, quinacridone, fluorophenyl-dimethyl-BODIPY, bis-fluorophenyl-BODIPY, acridine, terrylene, sexiphenyl, porphyrin, benzopyrene, (fluorophenyl-dimethyl-difluorobora-diazaindacene)phenyl, (bis-fluorophenyl-difluorobora-diazaindacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety.

23. The method of claim 17, wherein the polymeric dye has one of the following structures:

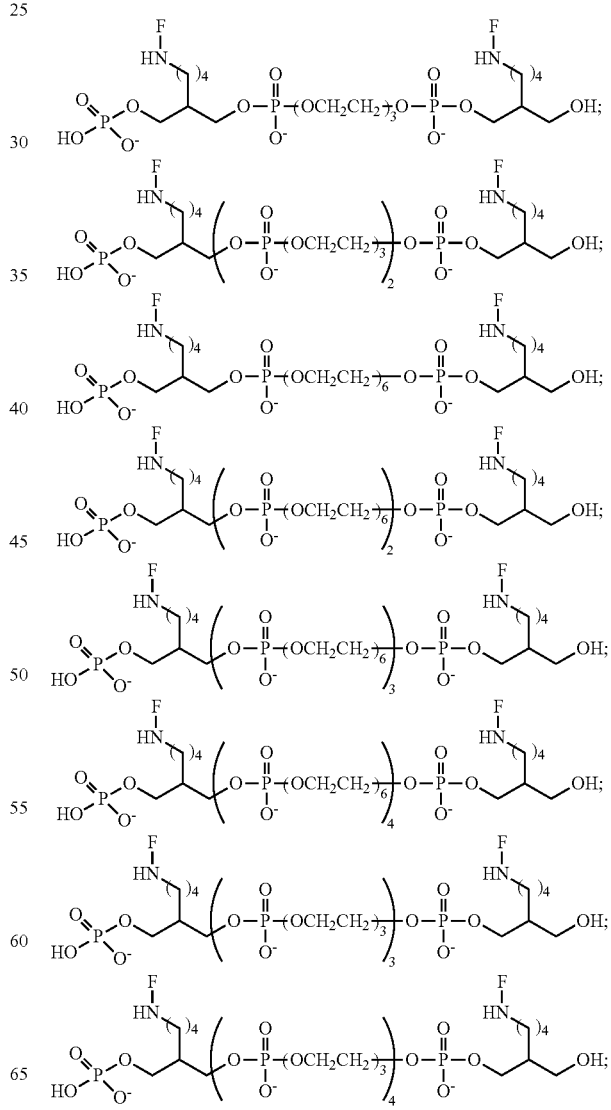

145
-continued
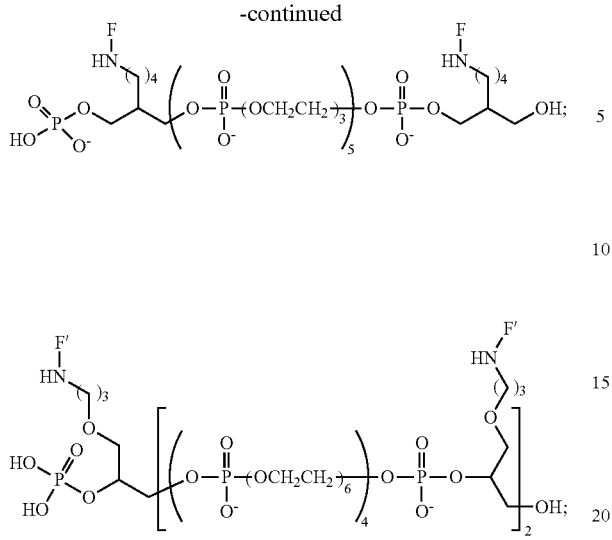
146
-continued
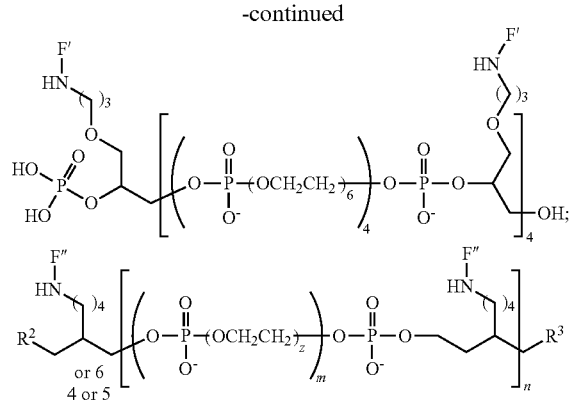
wherein:
z is an integer from 3 to 6,
m is an integer from 2 to 5, and
n is an integer from 1 to 10;
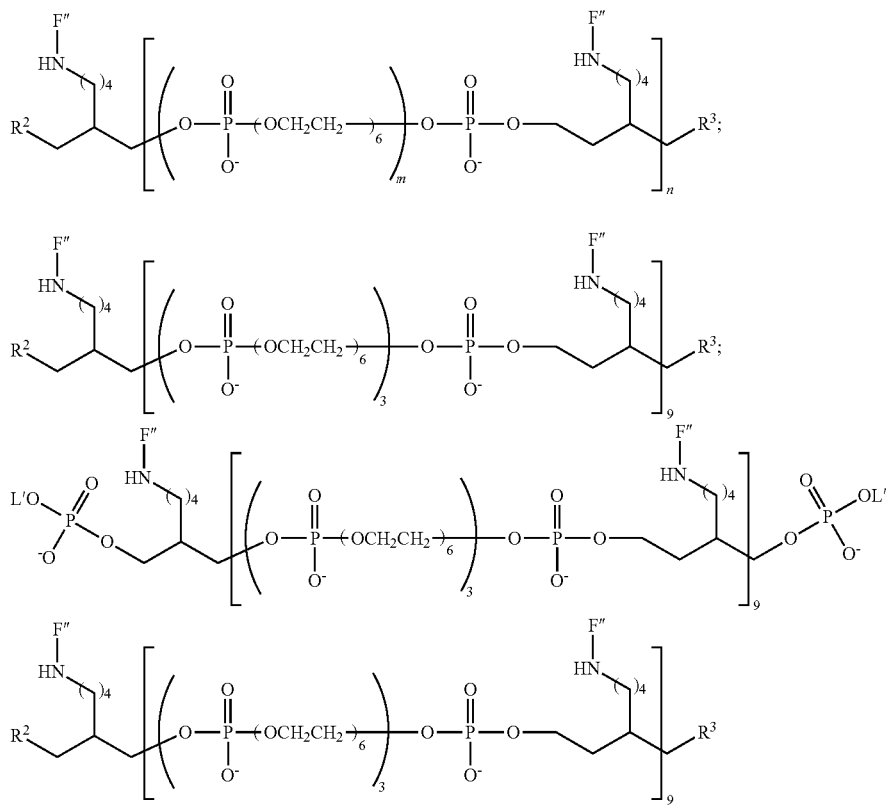
wherein:
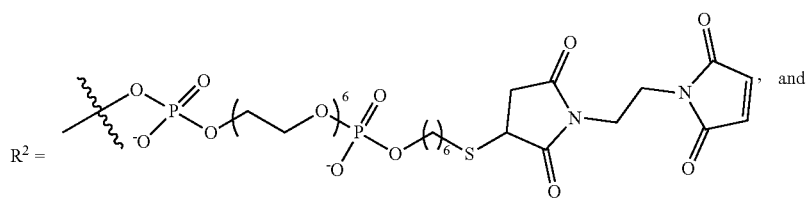

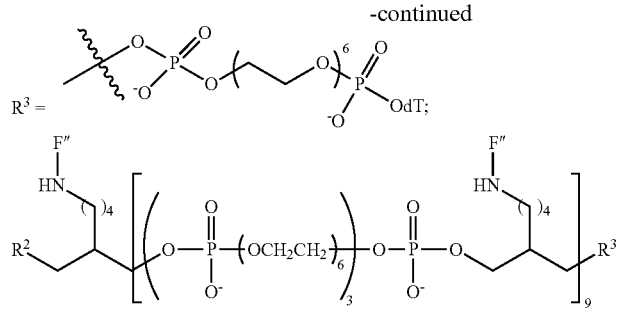
wherein:
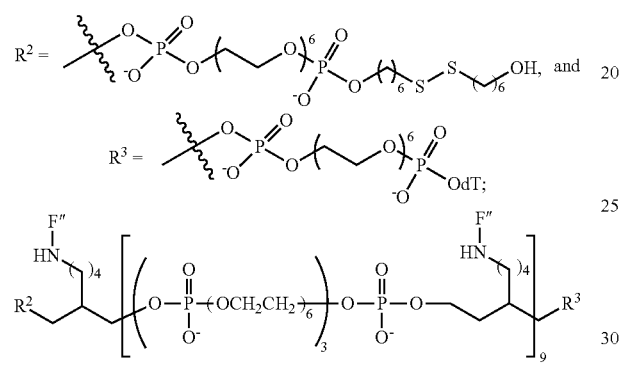
wherein:
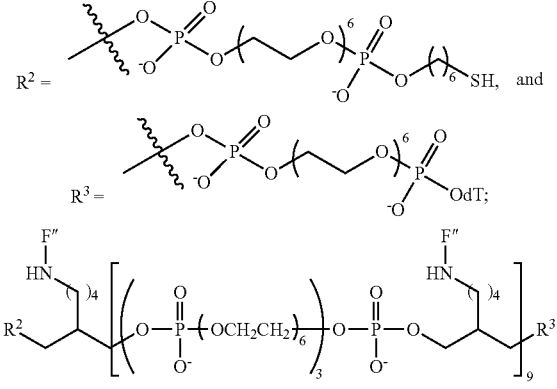
wherein:
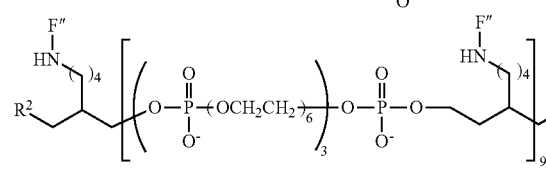
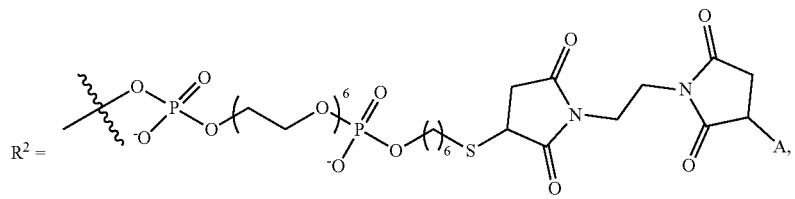
wherein A is an antibody, and
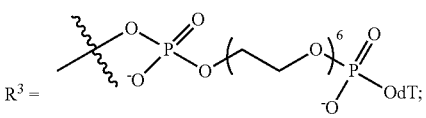
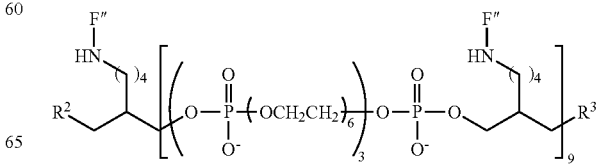

wherein:
$R^2 =$ 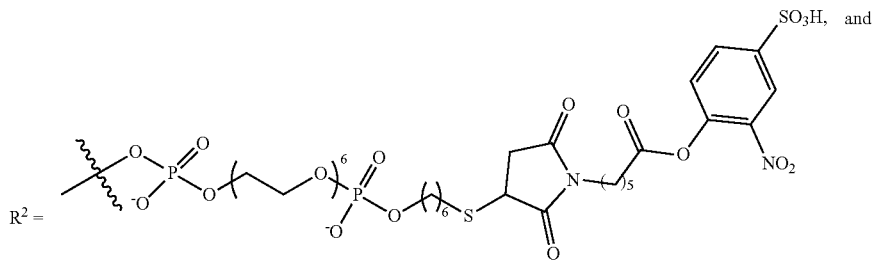
$R^3 =$ 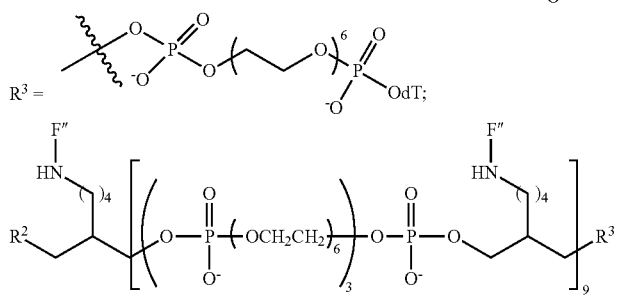
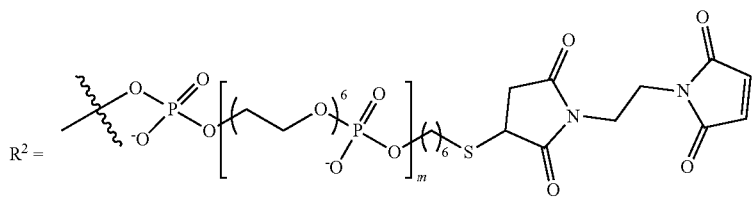
wherein:
$R^2 =$ 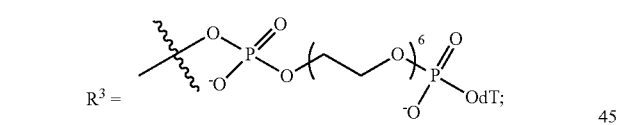
wherein m" is 4 or 10, and
$R^3 =$ 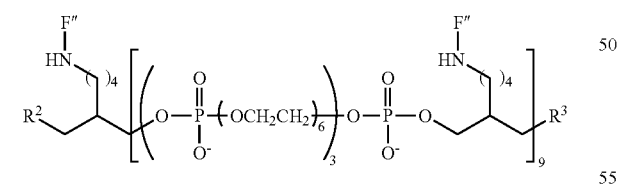
wherein:
$R^2 =$ 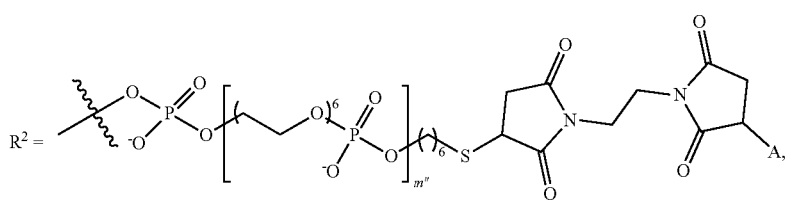

wherein m" is 4 or 10 and A is an antibody, and
$R^3 = $ 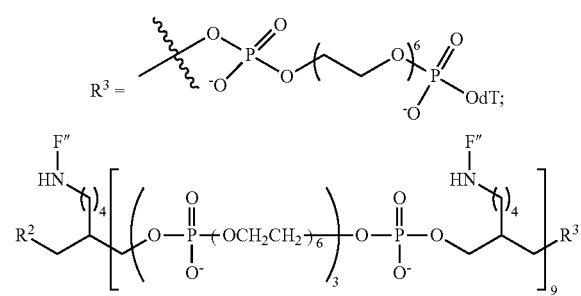
wherein:
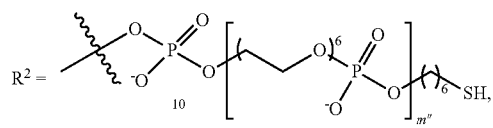
wherein m" is 4 or 10, and
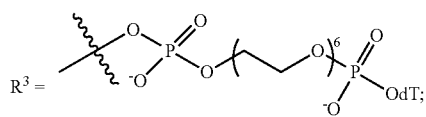
-continued
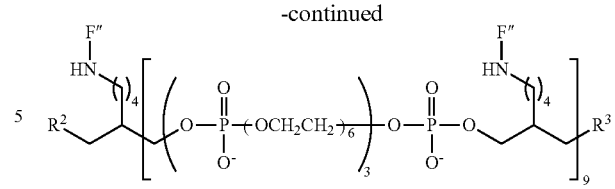
wherein:
$R^2 = $ 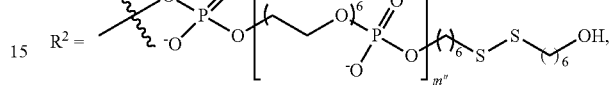
wherein m" is 4 or 10, and
$R^3 = $ 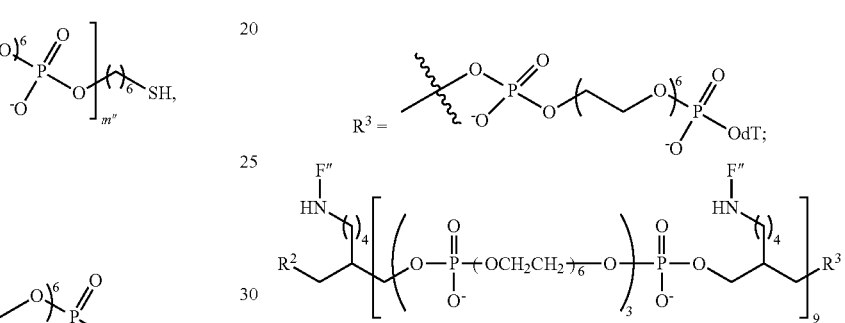
wherein:
$R^2 = $ 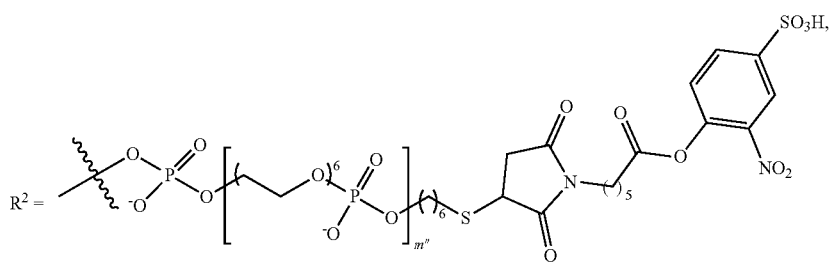
wherein m" is 4 or 10, and
$R^3 = $ 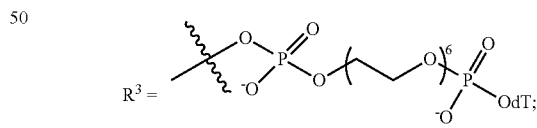
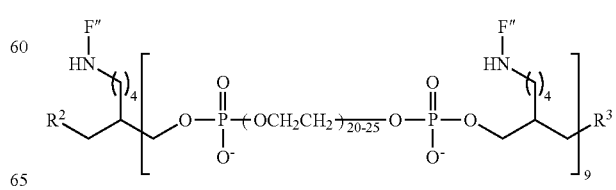

wherein:
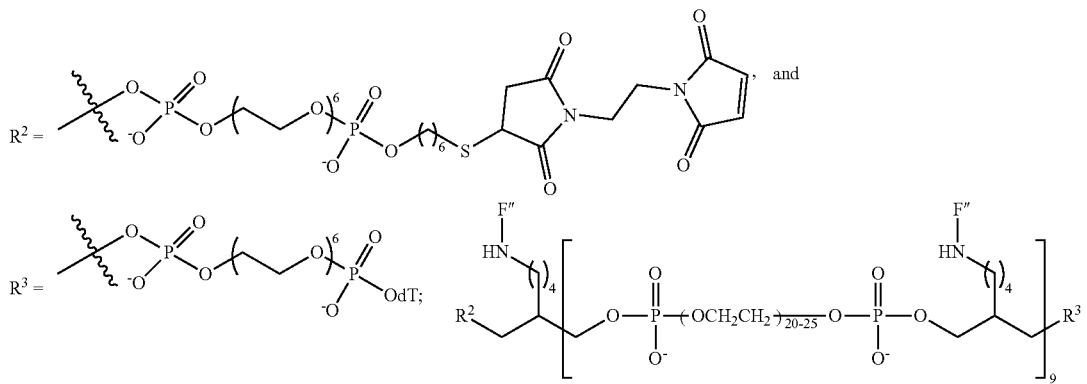
wherein:
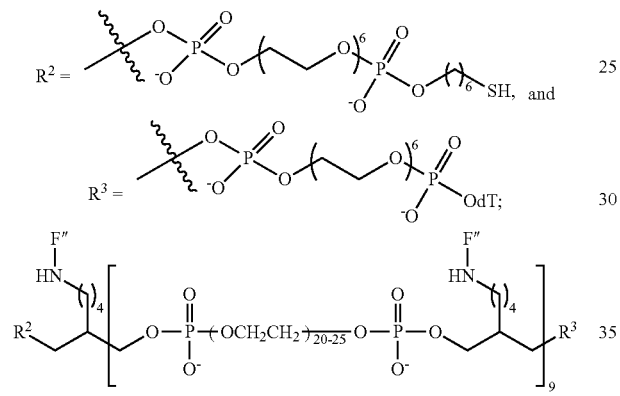
wherein:
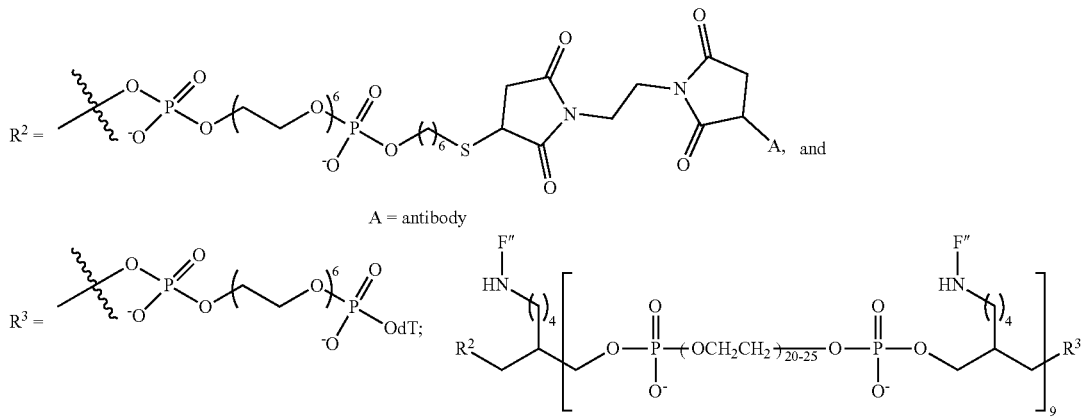
A = antibody
wherein:
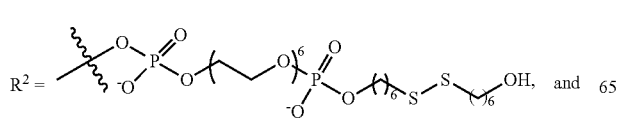

-continued
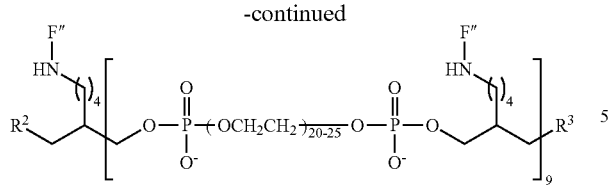
wherein:
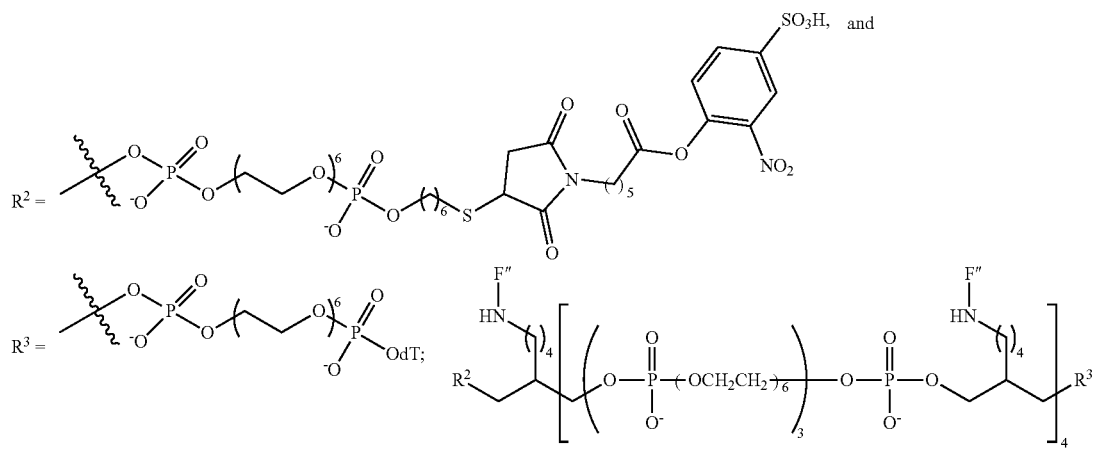
wherein:
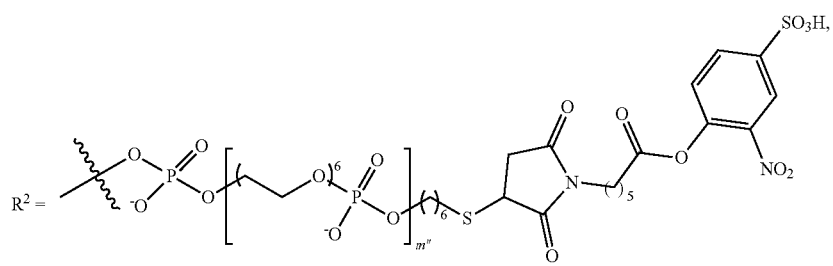
wherein m" is 4 or 10, and
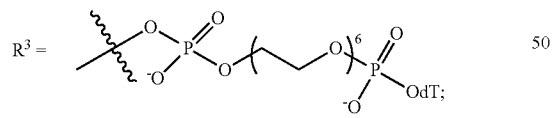
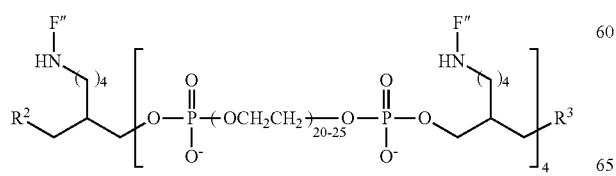

wherein:
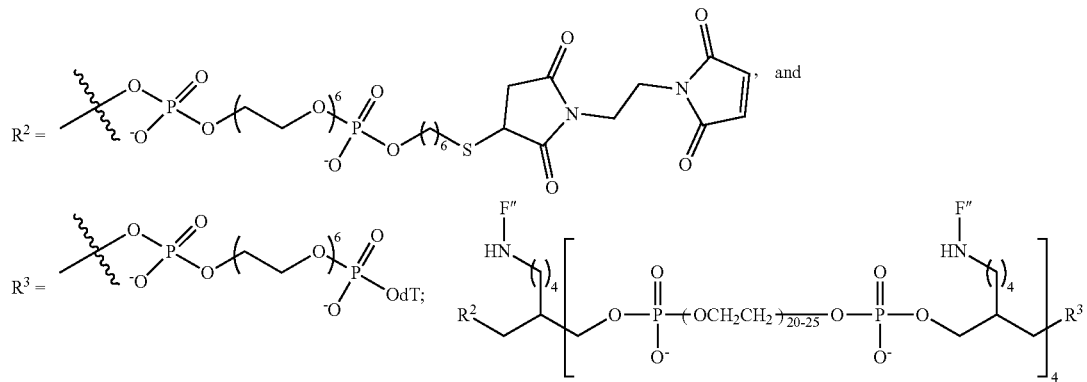
wherein:
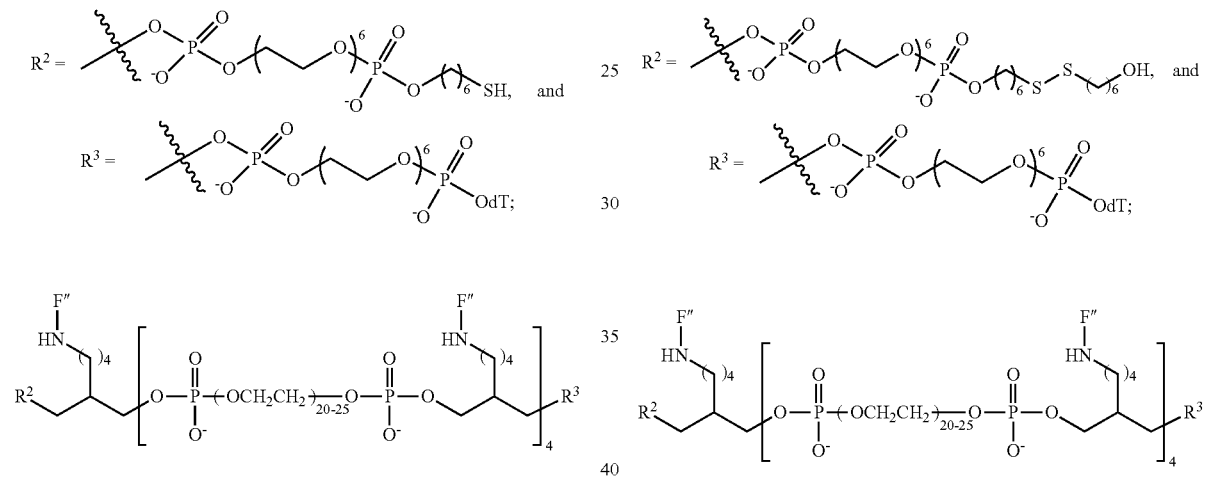
wherein:
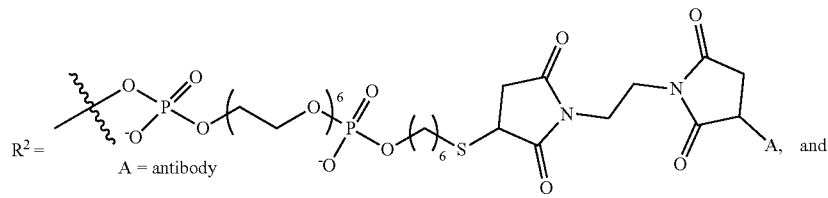
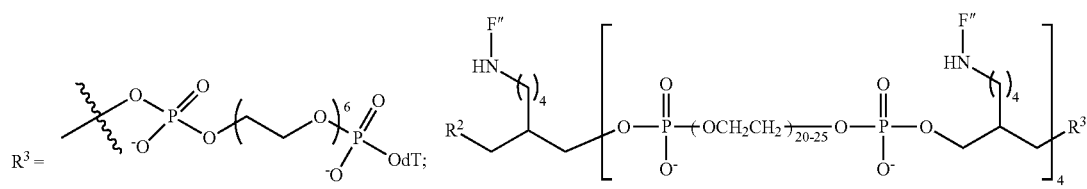

wherein:
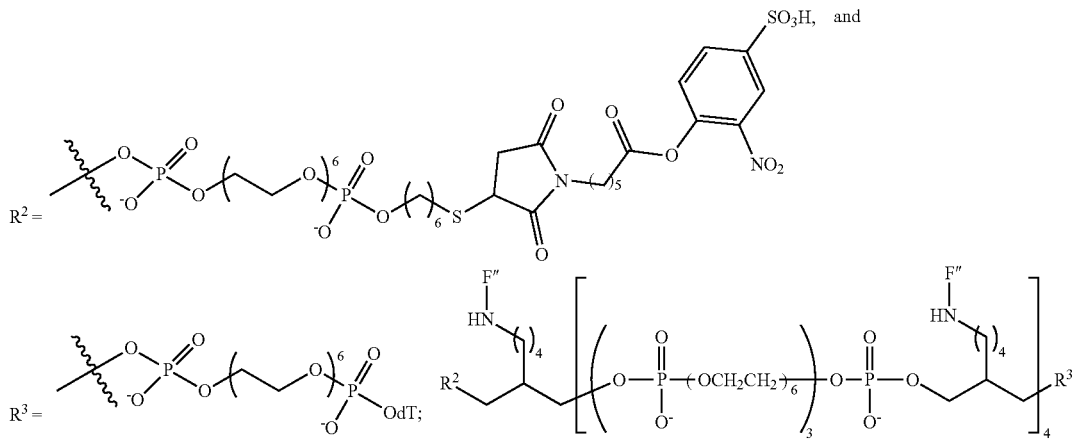
wherein:
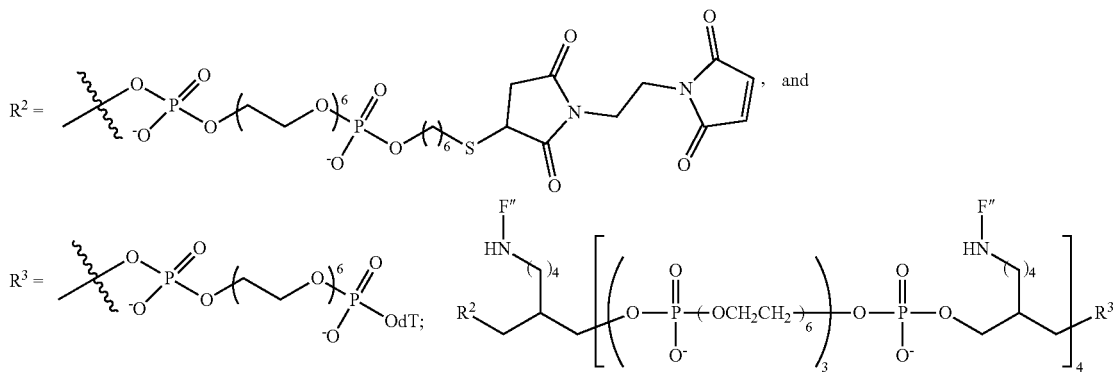
wherein:
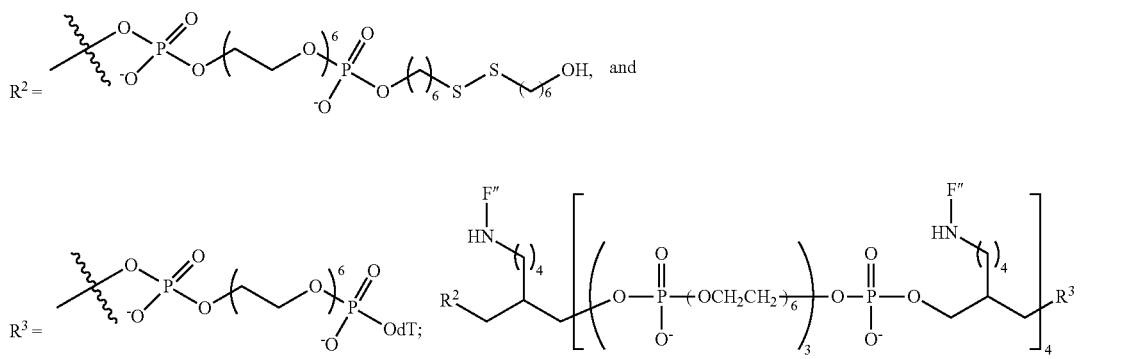
wherein:
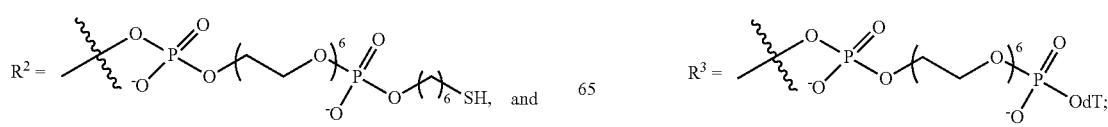

161
-continued
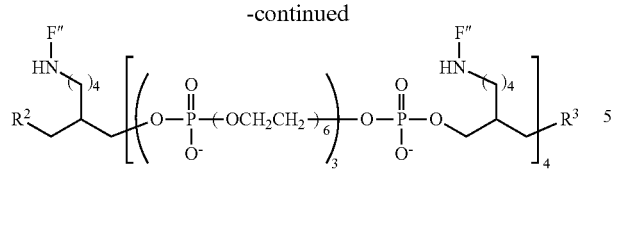
wherein:
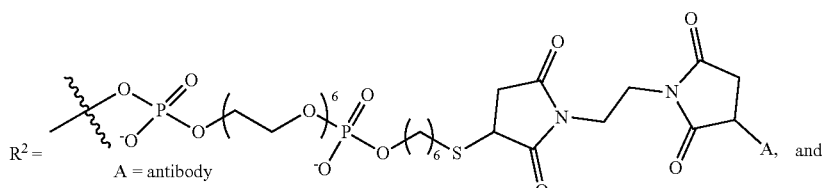
A = antibody
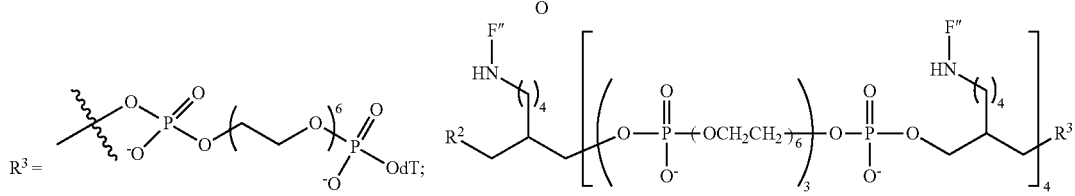
wherein:
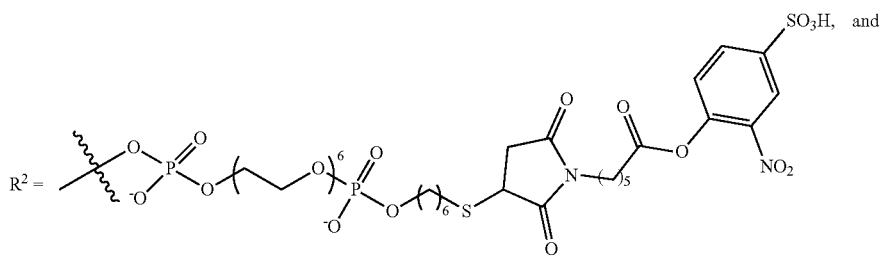
wherein:
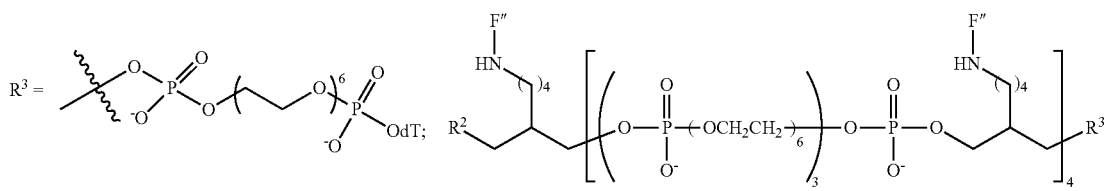
162
-continued
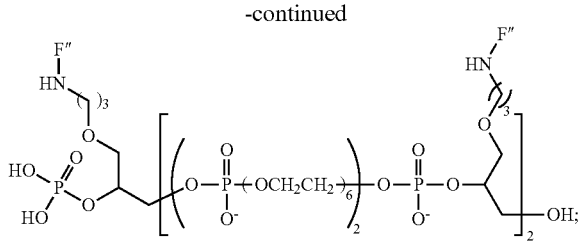
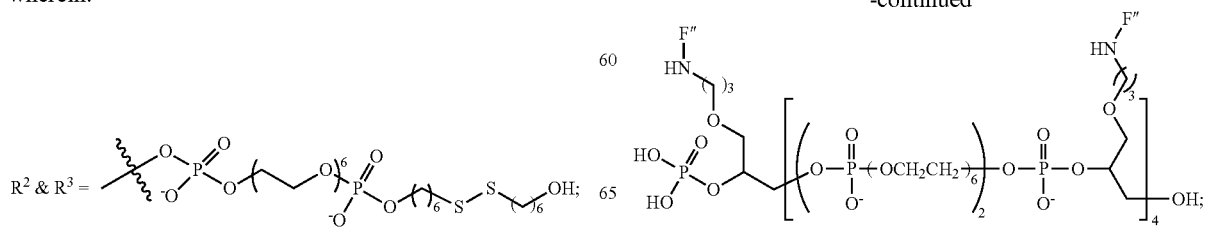

163
-continued
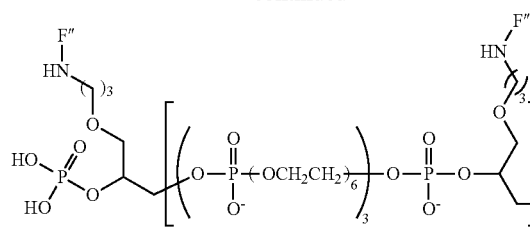
wherein:
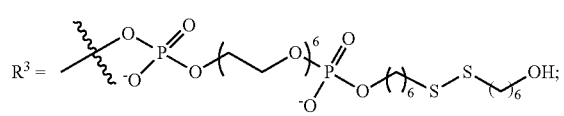
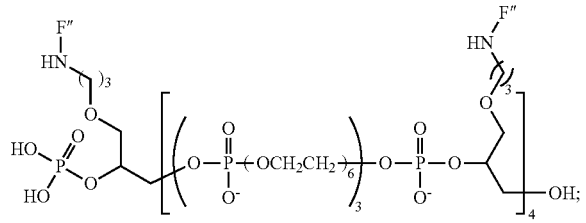
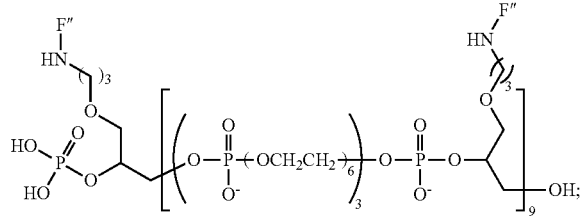
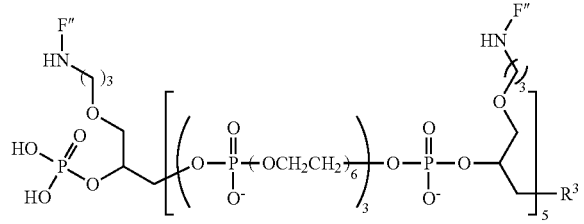
wherein:
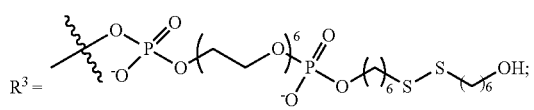
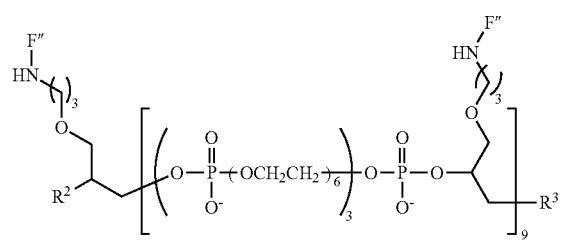
164
wherein:
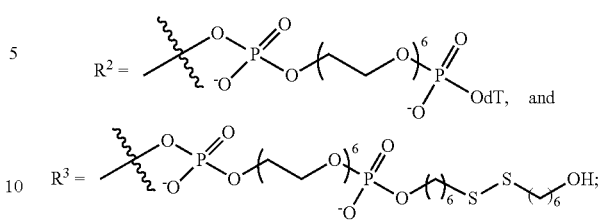
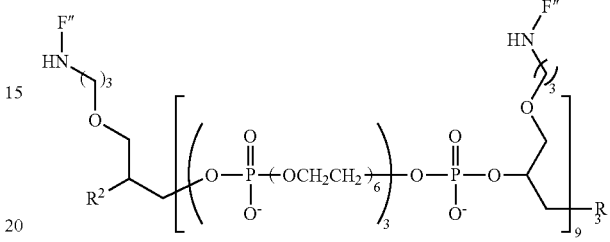
wherein:
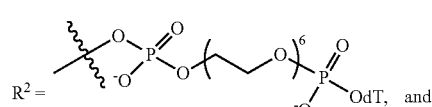
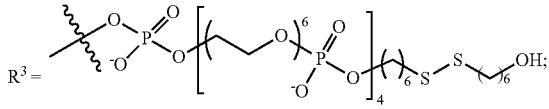
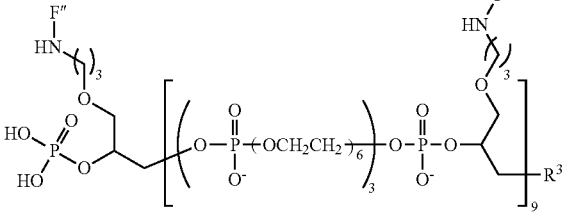
wherein:
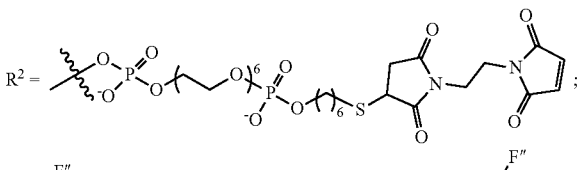
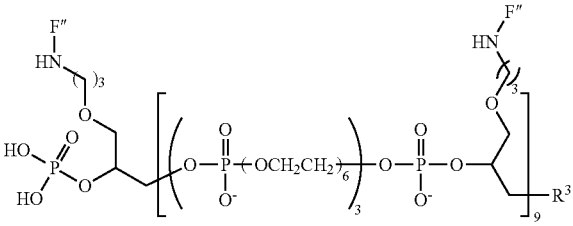
wherein:
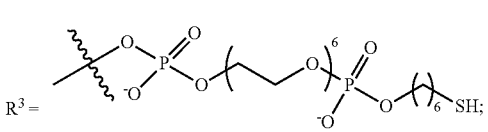

165
-continued
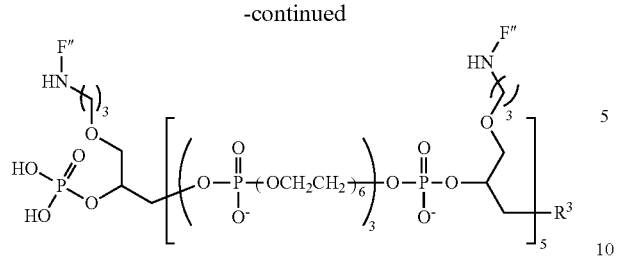
wherein:
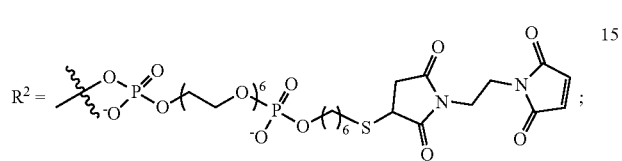
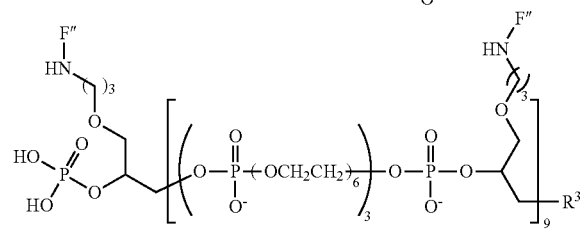
wherein:
R³ = 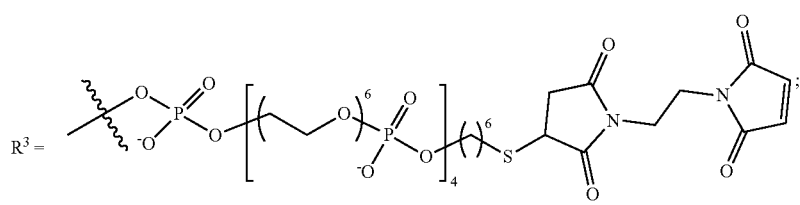
166
-continued
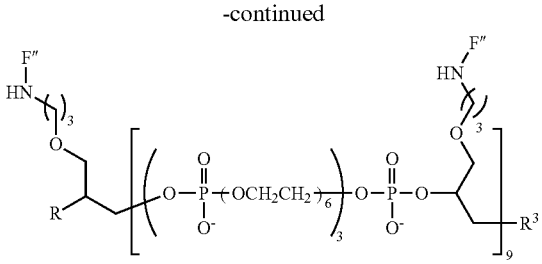
wherein:
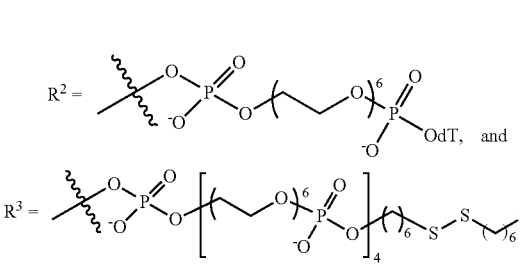
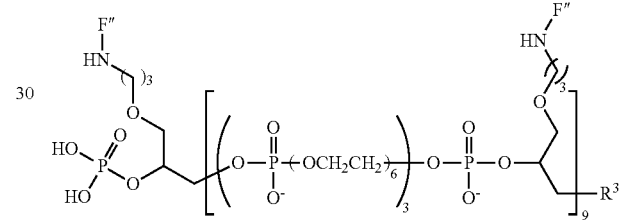
wherein:
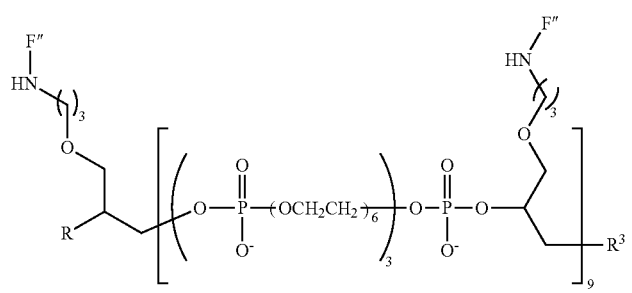

wherein:
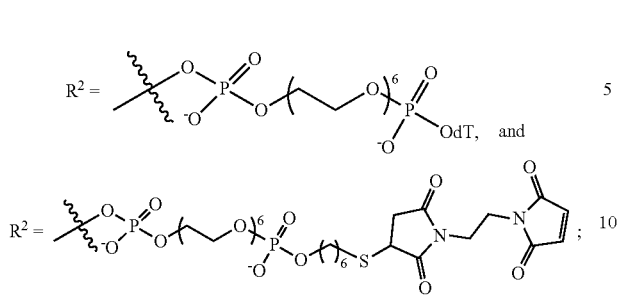
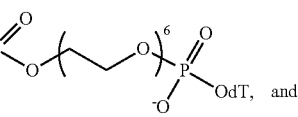
-continued
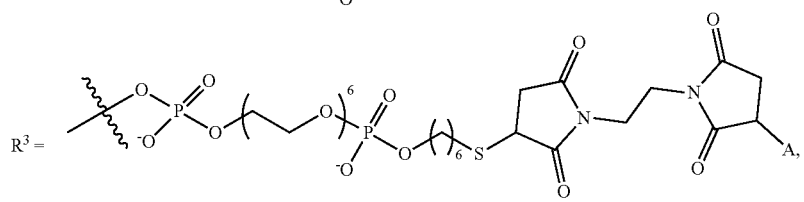
wherein:
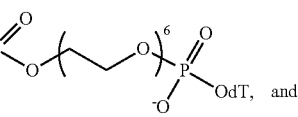
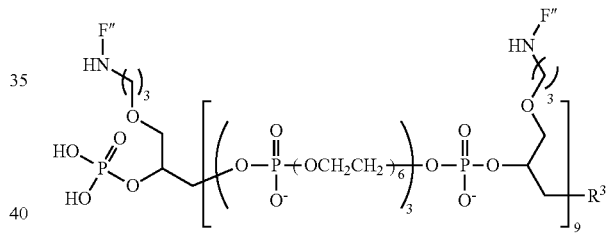
wherein A is an antibody;
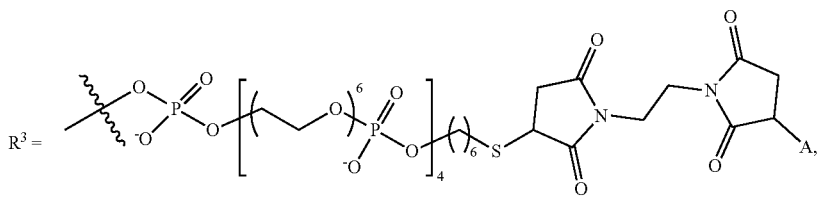
wherein:
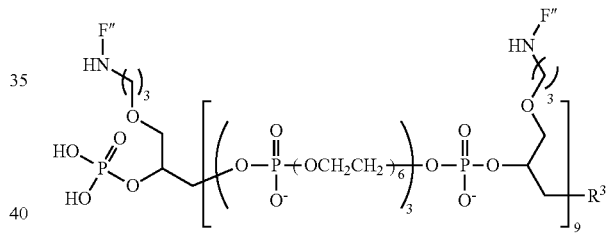
wherein A is an antibody; or
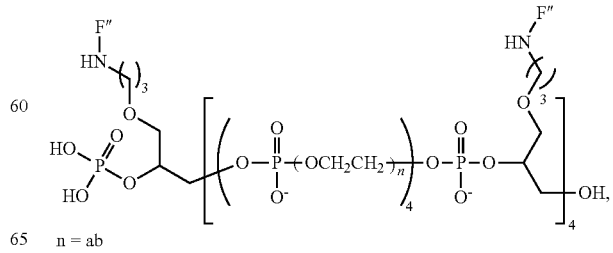
n = ab wherein n is 23, wherein:
F, F' and F" have the following structures, respectively:
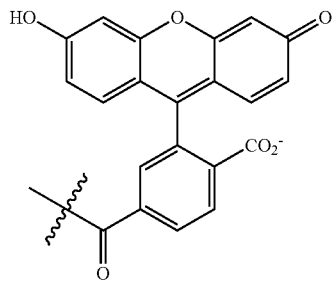
F
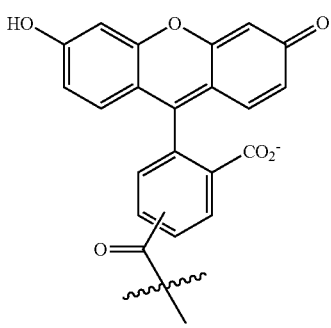
F'
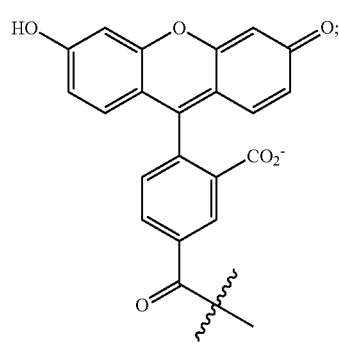
F"
and
dT has the following structure:
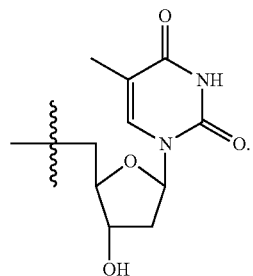
dT
* * * * *

UNITED STATES PATENT AND TRADEMARK OFFICE
CERTIFICATE OF CORRECTION

PATENT NO. : 11,874,280 B2  
APPLICATION NO. : 16/982341  
DATED : January 16, 2024  
INVENTOR(S) : Melissa Jackson et al.

Page 1 of 5

It is certified that error appears in the above-identified patent and that said Letters Patent is hereby corrected as shown below:

In the Claims:

Column 143, Claim 19, Line 57:
"structure (TB):" should read: --structure (IB):--.

Column 149, Claim 23, structure 4, above Line 40:

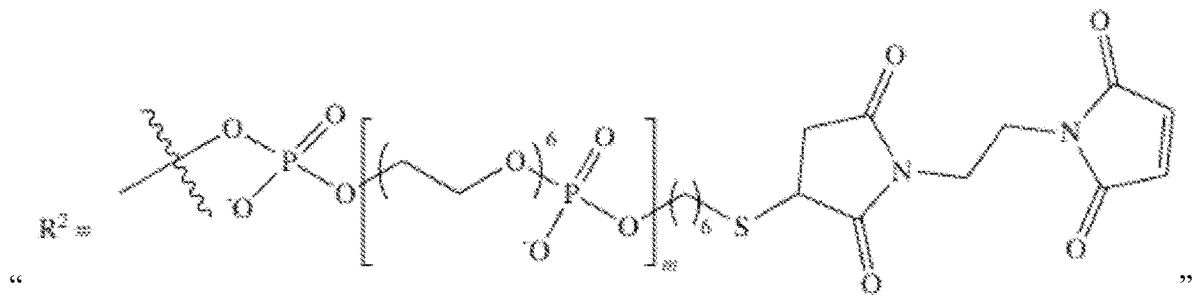

"

Should read:

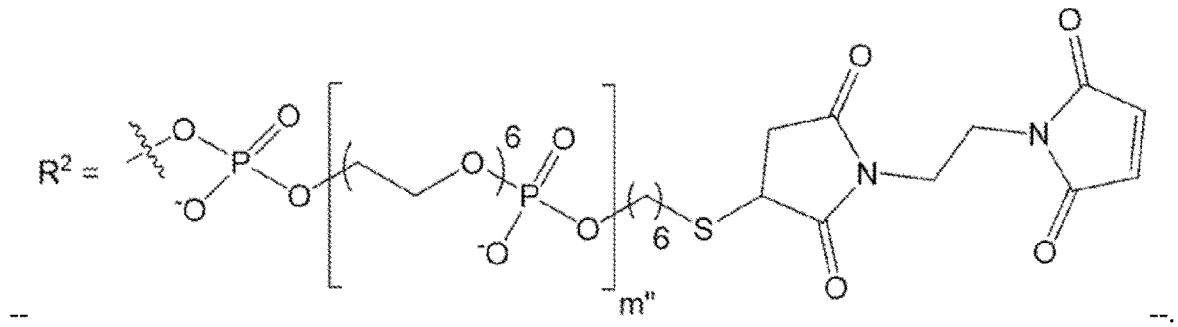

--                                                                                          --.

Signed and Sealed this  
Twenty-seventh Day of May, 2025

Coke Morgan Stewart  
*Acting Director of the United States Patent and Trademark Office*

Column 152, Claim 23, Lines 25-32, structure 4:
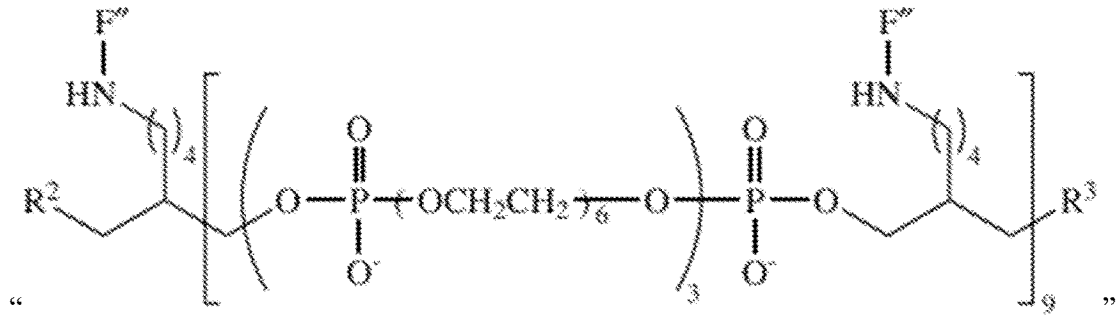
Should read:
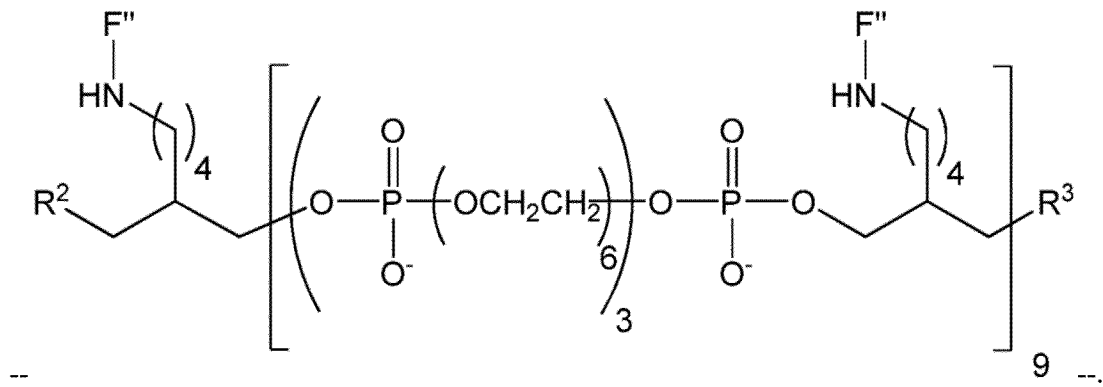
Columns 161-162, Claim 23, structure 8, above Line 60:
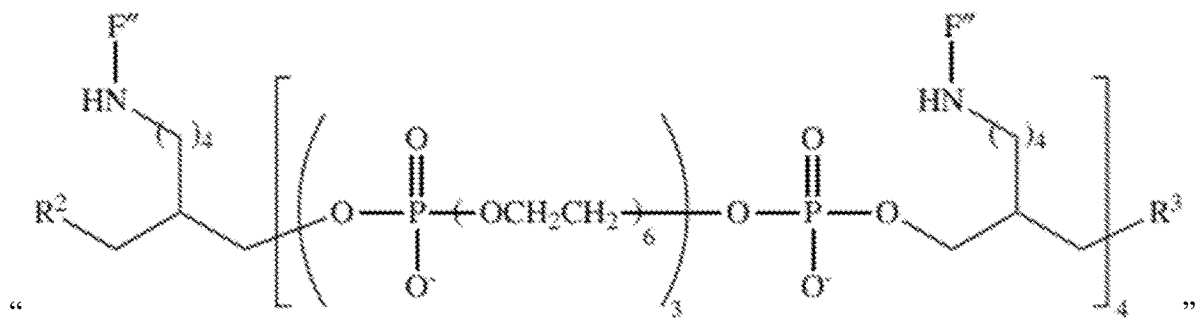
Should read:
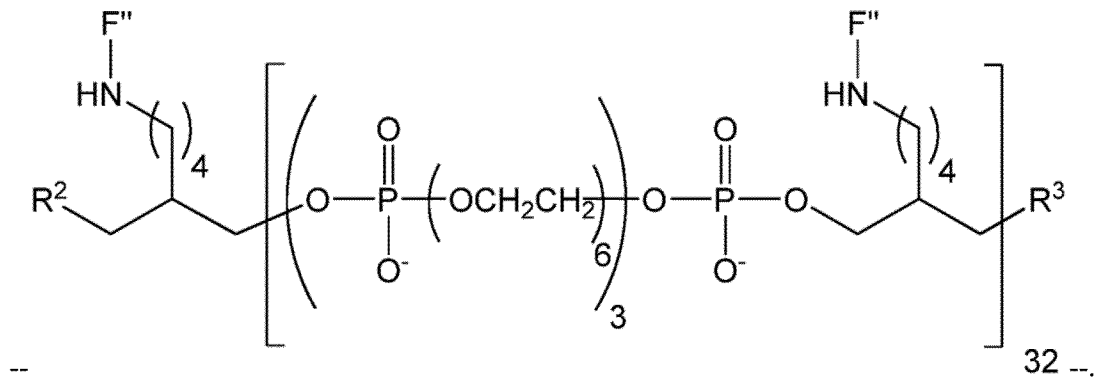

CERTIFICATE OF CORRECTION (continued)
U.S. Pat. No. 11,874,280 B2

Column 163, Claim 23, Structure 4, Lines 29-36:

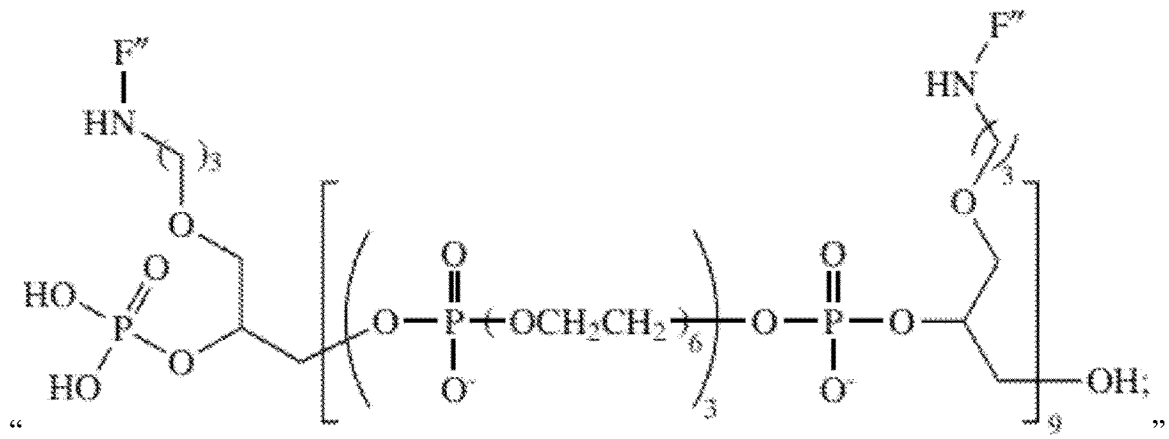

"                "

Should read:

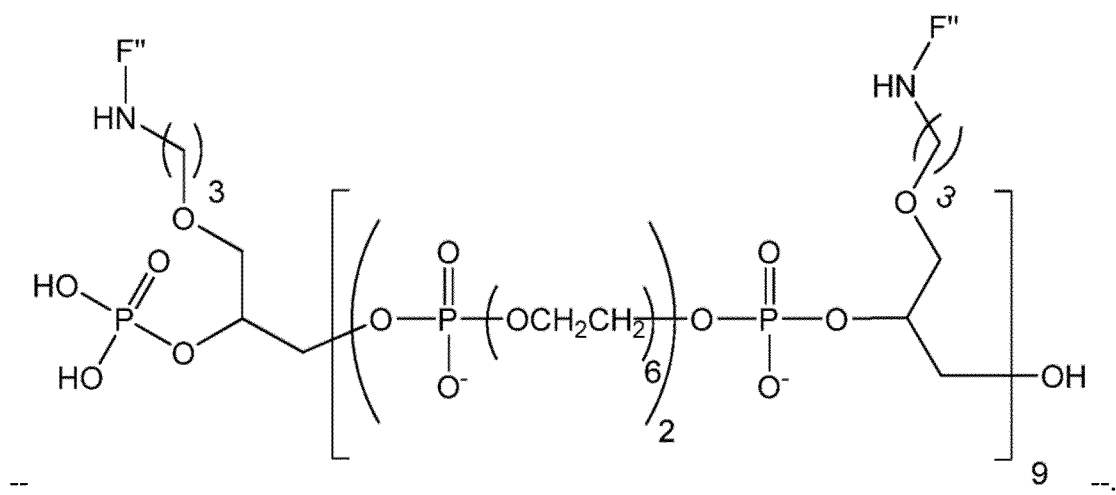

--                --.

Column 165, Claim 23, Lines 15-20, Structure 2:

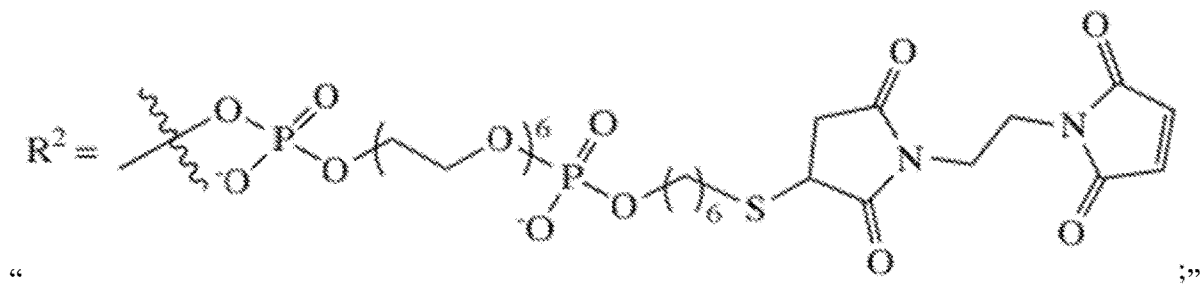

"                ;"

Should read:

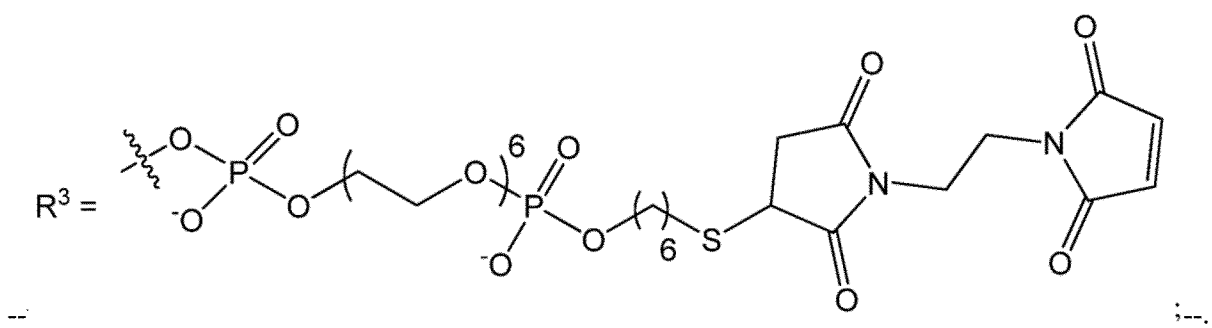
Column 166, Claim 23, Lines 1-10:
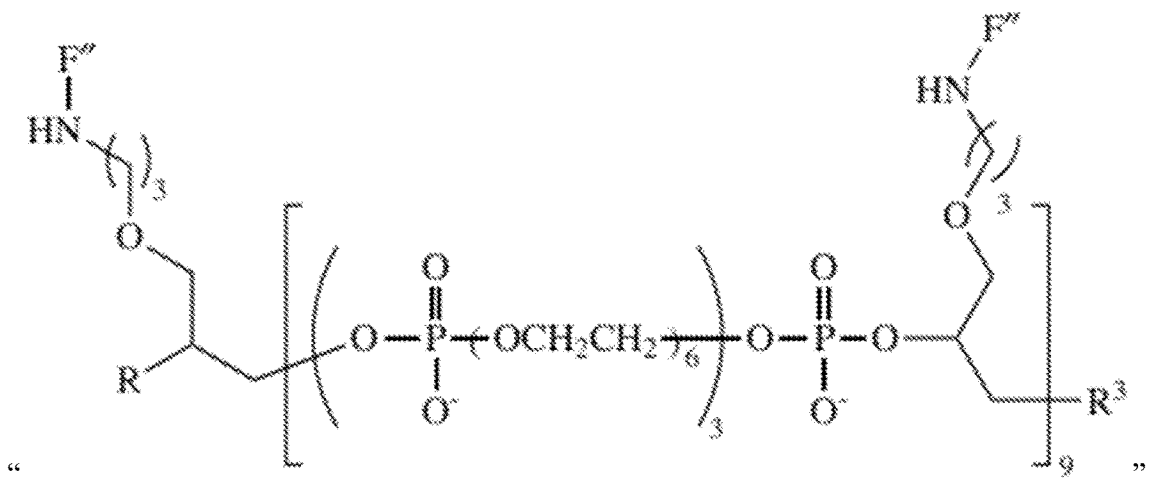
Should read:
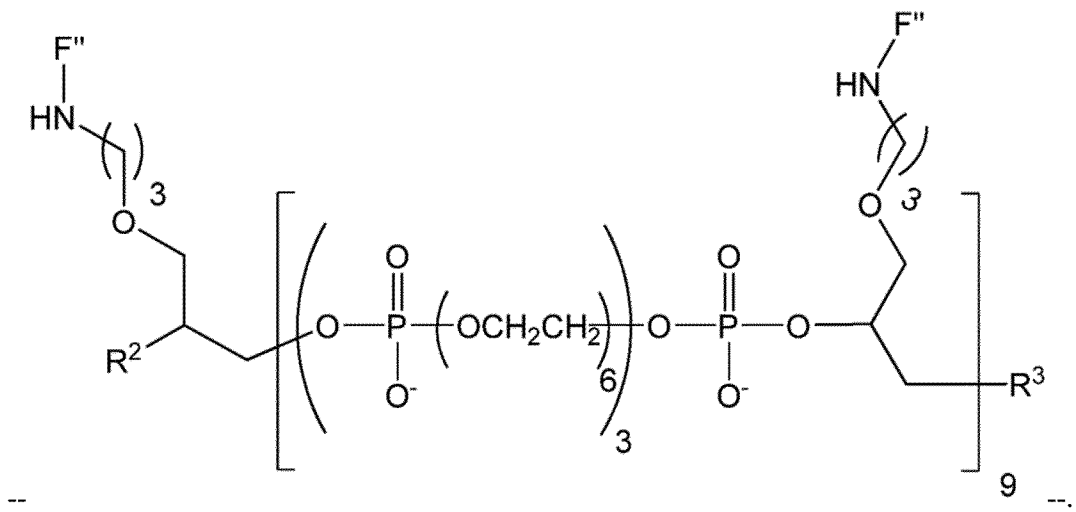
Columns 165-166, last structure on the page:

CERTIFICATE OF CORRECTION (continued)
U.S. Pat. No. 11,874,280 B2

Page 5 of 5

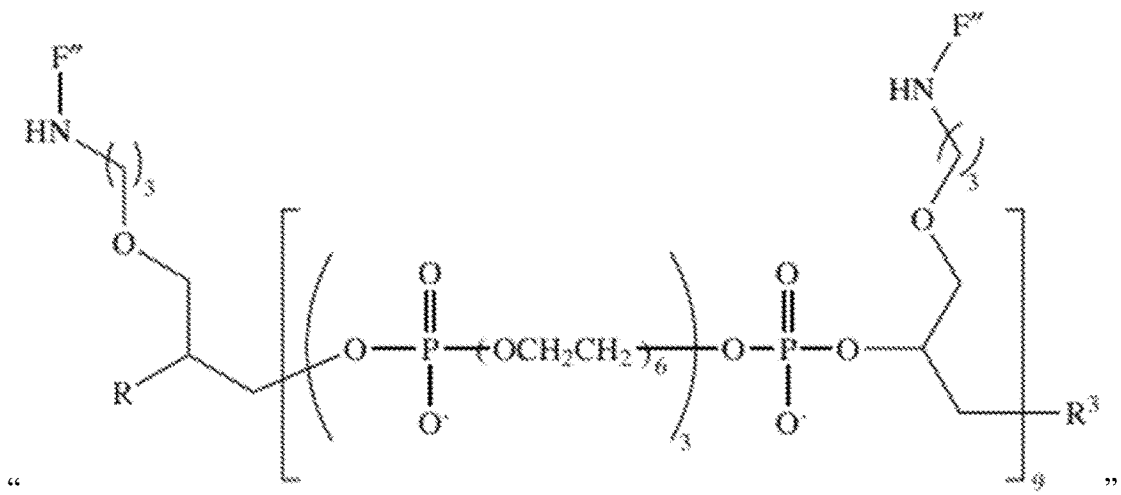

"

Should read:

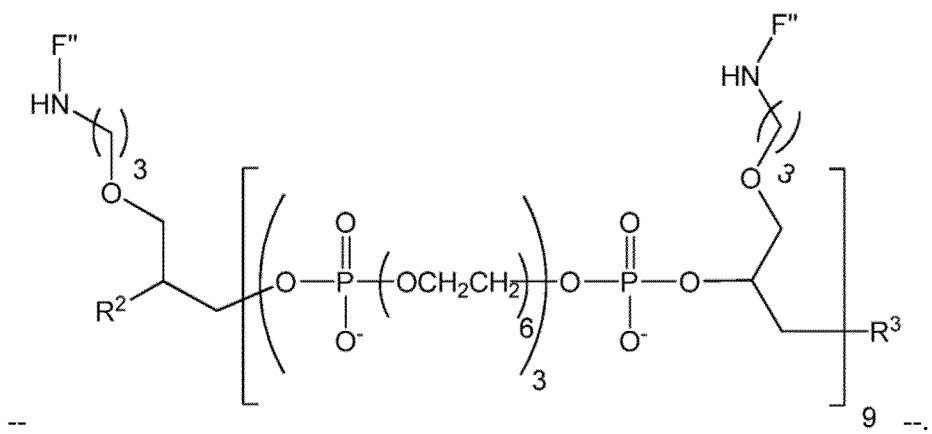

--

Column 167, Claim 23, Line 10, Structure 2:

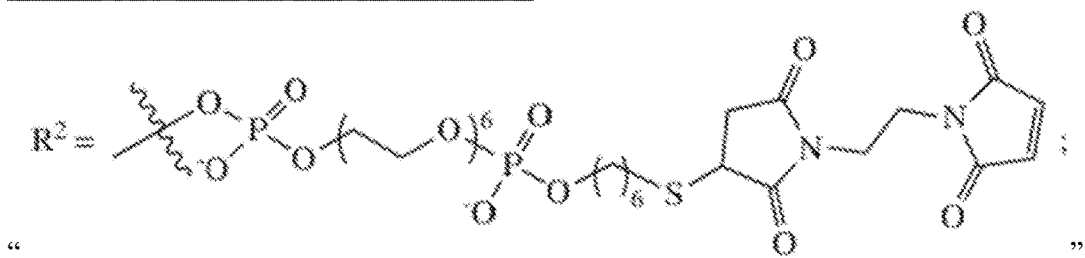

"

Should read:

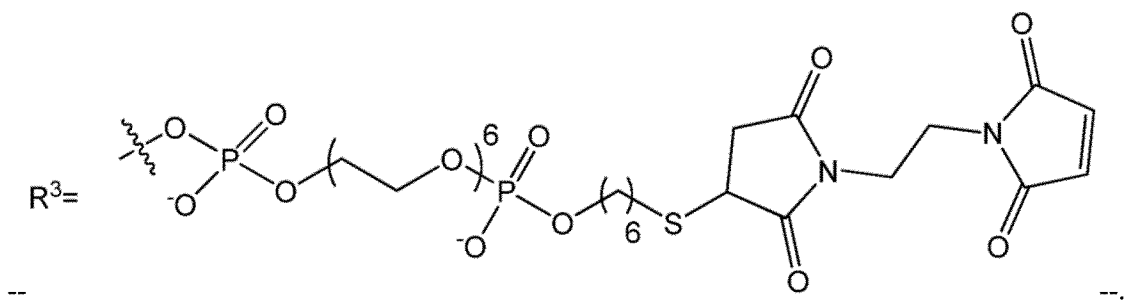

--